US008940501B2

(12) United States Patent
Ploegh et al.

(10) Patent No.: US 8,940,501 B2
(45) Date of Patent: Jan. 27, 2015

(54) METHODS FOR LIGATION AND USES THEREOF

(75) Inventors: Hidde L. Ploegh, Brookline, MA (US); John M. Antos, Everett, WA (US); Maximilian Wei-Lin Popp, Pittsford, NY (US); Carla Guimaraes, Boston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 158 days.

(21) Appl. No.: 13/145,644

(22) PCT Filed: Feb. 1, 2010

(86) PCT No.: PCT/US2010/000274
§ 371 (c)(1),
(2), (4) Date: Sep. 8, 2011

(87) PCT Pub. No.: WO2010/087994
PCT Pub. Date: Aug. 5, 2010

(65) Prior Publication Data
US 2011/0321183 A1    Dec. 29, 2011

Related U.S. Application Data

(60) Provisional application No. 61/148,787, filed on Jan. 30, 2009.

(51) Int. Cl.
*A01K 67/00* (2006.01)
*C07K 14/00* (2006.01)
*C12N 5/10* (2006.01)
*C12N 9/48* (2006.01)
*C12N 9/80* (2006.01)

(52) U.S. Cl.
CPC .. *C12N 9/48* (2013.01); *C12N 9/80* (2013.01); *A01K 2217/00* (2013.01)
USPC ............ 435/68.1; 800/13; 435/325; 530/300; 530/350

(58) Field of Classification Search
None
See application file for complete search history.

(56) References Cited

U.S. PATENT DOCUMENTS

| 4,469,863 | A | 9/1984 | Ts'o et al. |
|---|---|---|---|
| 4,816,567 | A | 3/1989 | Cabilly et al. |
| 5,096,815 | A | 3/1992 | Ladner et al. |
| 5,198,346 | A | 3/1993 | Ladner et al. |
| 5,223,409 | A | 6/1993 | Ladner et al. |
| 5,225,539 | A | 7/1993 | Winter |
| 5,283,433 | A | 2/1994 | Tsien |
| 5,296,703 | A | 3/1994 | Tsien |
| 5,403,484 | A | 4/1995 | Ladner et al. |
| 5,530,101 | A | 6/1996 | Queen et al. |
| 5,536,821 | A | 7/1996 | Agrawal et al. |
| 5,541,306 | A | 7/1996 | Agrawal et al. |
| 5,571,698 | A | 11/1996 | Ladner et al. |
| 5,585,089 | A | 12/1996 | Queen et al. |
| 5,614,622 | A | 3/1997 | Iyer et al. |
| 5,637,683 | A | 6/1997 | Usher et al. |
| 5,637,684 | A | 6/1997 | Cook et al. |
| 5,693,762 | A | 12/1997 | Queen et al. |
| 5,700,922 | A | 12/1997 | Cook |
| 5,707,622 | A | 1/1998 | Fong et al. |
| 5,717,083 | A | 2/1998 | Cook et al. |
| 5,719,262 | A | 2/1998 | Buchardt et al. |
| 5,739,308 | A | 4/1998 | Kandimalla et al. |
| 5,739,314 | A | 4/1998 | Roy et al. |
| 5,766,905 | A | 6/1998 | Studier et al. |
| 5,773,601 | A | 6/1998 | Agrawal |
| 5,859,205 | A | 1/1999 | Adair et al. |
| 5,886,165 | A | 3/1999 | Kandimalla et al. |
| 5,900,481 | A | 5/1999 | Lough et al. |
| 5,929,226 | A | 7/1999 | Padmapriya et al. |
| 5,955,599 | A | 9/1999 | Iyer et al. |
| 5,962,674 | A | 10/1999 | Iyer et al. |
| 5,977,296 | A | 11/1999 | Nielsen et al. |
| 5,990,296 | A | 11/1999 | Pastan et al. |
| 5,994,524 | A | 11/1999 | Matsushima et al. |
| 6,022,688 | A | 2/2000 | Jurinke et al. |
| 6,090,919 | A | 7/2000 | Cormack et al. |
| 6,099,842 | A | 8/2000 | Pastan et al. |
| 6,117,992 | A | 9/2000 | Iyer |
| 6,133,436 | A | 10/2000 | Koster et al. |
| 6,140,482 | A | 10/2000 | Iyer et al. |
| 6,245,894 | B1 | 6/2001 | Matsushima et al. |
| 6,261,776 | B1 | 7/2001 | Pirrung et al. |

(Continued)

FOREIGN PATENT DOCUMENTS

| WO | WO 96/34878 A1 | 11/1996 |
|---|---|---|
| WO | WO 98/28434 A1 | 7/1998 |
| WO | WO 01/14398 A1 | 3/2000 |
| WO | WO 00/56746 A2 | 9/2000 |
| WO | WO 00/62804 A2 | 10/2000 |

(Continued)

OTHER PUBLICATIONS

Mao, H. et al "Sortase-Mediated Protein Ligation: A New Method for Protein Engineering" (Feb. 10, 2004) J. Am. Chem. Soc. 126:2670-2671.*

(Continued)

*Primary Examiner* — Karlheinz R Skowronek
*Assistant Examiner* — Mindy Newman
(74) *Attorney, Agent, or Firm* — Wolf, Greenfield & Sacks; C. Hunter Baker; O. Tobias Brambrink

(57) ABSTRACT

The present invention relates to methods for ligation. The invention provides novel reagents and methods for ligating an acyl donor compound with an acyl acceptor compound. Provided acyl donor compounds comprise a transamidase recognition sequence that allows ligation with a nucleophilic acyl acceptor in the presence of transamidase. The invention further provides kits comprising acyl donor compounds and optionally comprising other reagents for ligation.

21 Claims, 58 Drawing Sheets

(56) References Cited

U.S. PATENT DOCUMENTS

| | | | |
|---|---|---|---|
| 6,316,003 | B1 | 11/2001 | Frankel et al. |
| 6,316,781 | B1 | 11/2001 | Nagle et al. |
| 6,342,221 | B1 | 1/2002 | Thorpe et al. |
| 6,379,974 | B1 | 4/2002 | Parce et al. |
| 6,429,025 | B1 | 8/2002 | Parce et al. |
| 6,440,722 | B1 | 8/2002 | Knapp et al. |
| 6,451,538 | B1 | 9/2002 | Cowsert |
| 6,451,602 | B1 | 9/2002 | Popoff et al. |
| 6,455,263 | B2 | 9/2002 | Payan |
| 6,455,307 | B1 | 9/2002 | McKay et al. |
| 6,455,308 | B1 | 9/2002 | Freier |
| 6,461,813 | B2 | 10/2002 | Lorens |
| 6,593,292 | B1 | 7/2003 | Rothbard et al. |
| 7,345,154 | B2 | 3/2008 | Cox |
| 7,524,831 | B2 | 4/2009 | Malcolm et al. |
| 7,531,630 | B2 | 5/2009 | Patten et al. |
| 7,592,010 | B2 | 9/2009 | Rosen et al. |
| 7,650,243 | B2 | 1/2010 | Gantier et al. |
| 2002/0192773 | A1 | 12/2002 | Walsh et al. |
| 2003/0022178 | A1 | 1/2003 | Schneewind et al. |
| 2003/0104622 | A1 | 6/2003 | Robbins et al. |
| 2003/0224490 | A1 | 12/2003 | Dessain et al. |
| 2007/0178112 | A1 | 8/2007 | Wang et al. |
| 2009/0088372 | A1 | 4/2009 | Roy et al. |

FOREIGN PATENT DOCUMENTS

| | | | |
|---|---|---|---|
| WO | WO 00/75372 | A1 | 12/2000 |
| WO | WO 01/18234 | A1 | 3/2001 |
| WO | WO 01/36486 | A2 | 5/2001 |
| WO | WO 03/020885 | A2 | 3/2003 |
| WO | WO 2005/012541 | A1 | 2/2005 |
| WO | WO 2005/051976 | A2 | 6/2005 |
| WO | WO 2005051976 | A2 * | 6/2005 |
| WO | WO 2005/086654 | A2 | 9/2005 |
| WO | WO 2007/108013 | A2 | 9/2007 |
| WO | WO 2010/087994 | A2 | 8/2010 |
| WO | WO 2011/133704 | A2 | 10/2011 |

OTHER PUBLICATIONS

Extended European Search Report for EP 10736161.0, mailed Nov. 30, 2012.
Invitation to Pay Additional Fees for PCT/US2010/000274, mailed Nov. 8, 2010.
International Search Report and Written Opinion for PCT/US2010/000274, mailed Dec. 22, 2010.
International Preliminary Report on Patentability for PCT/US2010/000274, mailed Aug. 11, 2011.
Genbank Submission; Accession No. AAD48437; Mazmanian et al.; Aug. 11, 1999. Updated Nov. 30, 2009 and Mar. 10, 2010.
Alexandrov et al., Intein-mediated synthesis of geranylgeranylated Rab7 protein in vitro. J Am Chem Soc. May 22, 2002;124(20):5648-9.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
Antos et al., A straight path to circular proteins. J Biol Chem. Jun. 5, 2009;284(23):16028-36. Epub Apr. 9, 2009.
Antos et al., Lipid modification of proteins through sortase-catalyzed transpeptidation. J Am Chem Soc. Dec. 3, 2008;130(48):16338-43.
Arnau et al., Current strategies for the use of affinity tags and tag removal for the purification of recombinant proteins. Protein Expr Purif. Jul. 2006;48(1):1-13. Epub Dec. 18, 2005.
Bader et al., Bioorganic synthesis of lipid-modified proteins for the study of signal transduction. Nature. Jan. 13, 2000;403(6766):223-6.
Barner-Kowollik et al., Mechanism and kinetics of dithiobenzoate-mediated RAFT polymerization. I. The current situation. J Polym Sci Part A: Polym Chem. Oct. 15, 2006;44(20):5809-31.

Barnett et al., Differential recognition of surface proteins in *Streptococcus pyogenes* by two sortase gene homologs. J Bacteriol. Apr. 2002;184(8):2181-91.
Baskin et al., Bioorthogonal click chemistry: Covalent labeling in living systems. QSAR Comb Sci. Dec. 2007;26(11-12):1211-9.
Baskin et al., Copper-free click chemistry for dynamic in vivo imaging. Proc Natl Acad Sci U S A. Oct. 23, 2007;104(43):16793-7. Epub Oct. 17, 2007.
Battioni et al., Preparation of functionalized polyhalogenated tetraaryl-porphyrins by selective substitution of the p-Fluorines of meso-tetra-(pentafluorophenyl)porphyrins. Tetrahed Lett. Jun. 17, 1991;32(25):2893-6.
Becer et al., Click chemistry beyond metal-catalyzed cycloaddition. Angew Chem Int Ed Engl. 2009;48(27):4900-8.
Becer et al., Clicking pentafluorostyrene copolymers: synthesis, nanoprecipitation, and glycosylation. Macromol. 2009;42(7):2387-94.
Benmohamed et al., Lipopeptide vaccines—yesterday, today, and tomorrow. Lancet Infect Dis. Jul. 2002;2(7):425-31.
Binder et al., 'Click' Chemistry in Polymer and Materials Science. Macromol Rapid Commun. Jan. 5, 2007;28(1):15-54.
Bitonti et al., Pulmonary delivery of an erythropoietin Fc fusion protein in non-human primates through an immunoglobulin transport pathway. Proc Natl Acad Sci U S A. Jun. 29, 2004;101(26):9763-8. Epub Jun. 21, 2004.
Blackman et al., Tetrazine ligation: fast bioconjugation based on inverse-electron-demand Diels-Alder reactivity. J Am Chem Soc. Oct. 15, 2008;130(41):13518-9. Epub Sep. 18, 2008.
Blomquist et al., Many-membered Carbon Rings. VII. Cyclooctyne. J Am Chem Soc. May 1953;75(9):2153-4.
Bock et al., CuI-catalyzed alkyne—azide "click" cycloadditions from a mechanistic and synthetic perspective. Eur J Org Chem. Jan. 2006;2006(1):51-68.
Boonyarattanakalin et al., Synthesis of an artificial cell surface receptor that enables oligohistidine affinity tags to func-tion as metal-dependent cell-penetrating peptides. J Am Chem Soc. Mar. 18, 2006;128(14):4917.
Boren et al., Ruthenium-catalyzed azide-alkyne cycloaddition: scope and mechanism. J Am Chem Soc. Jul. 16, 2008;130(28):8923-30. Epub Jun. 21, 2008.
Breydo et al., Nonpolar substitution at the C-terminus of the prion protein, a mimic of the glycosylphosphatidylinositol anchor, partially impairs amyloid fibril formation. Biochemistry. Jan. 23, 2007;46(3):852-61.
Campbell-Verduyn et al., Copper-free 'click': 1,3-dipolar cycloaddition of azides and arynes. Org Biomol Chem. Oct. 7, 2008;6(19):3461-3. Epub Aug. 13, 2008.
Campos et al., Development of thermal and photochemical strategies for thiol-ene click polymer functionalization. Macromol. 2008;41(19):7063-70.
Carell et al., A Novel Procedure for the Synthesis of Libraries Containing Small Organic Molecules. Angew Chem Int Ed Engl. 1994;33:2059-61.
Carell et al., A Solution-Phase Screening Procedure for the Isolation of Active Compounds from a Library of Molecules. Angew Chem Int Ed Engl. 1994;33:2061-4.
Chaiken et al., Identifying structure-function relationships in four-helix bundle cytokines: towards de novo mimetics design. Trends Biotechnol. Oct. 1996;14(10):369-75.
Chan et al., Convergent synthesis of 3-arm star polymers from RAFT-prepared poly(N,N-diethylacrylamide) via a thiol-ene click reaction. Chem Commun (Camb). Oct. 28, 2008;(40):495961. Epub Sep. 19, 2008.
Chan et al., Covalent attachment of proteins to solid supports and surfaces via Sortase-mediated ligation. PLoS One. Nov. 14, 2007;2(11):e1164.
Chassaing et al., "Click chemistry" in zeolites: copper(I) zeolites as new heterogeneous and ligand-free catalysts for the Huisgen [3+2] cycloaddition. Chemistry. 2008;14(22):6713-21.
Chen et al., Efficient synthesis and photodynamic activity of porphyrin-saccharide conjugates: targeting and incapacitating cancer cells. Biochemistry. Aug. 31, 2004;43(34):10918-29.

(56) References Cited

OTHER PUBLICATIONS

Chenoweth et al., Cyclooctyne-based reagents for uncatalyzed click chemistry: A computational survey. Org Biomol Chem. Dec. 21, 2009;7(24):5255-8. Epub Nov. 9, 2009.
Cho et al., an unnatural biopolymer. Science. Sep. 3, 1993;261(5126):1303-5.
Chudakov et al., Fluorescent proteins and their applications in imaging living cells and tissues. Physiol Rev. Jul. 2010;90(3):1103-63.
Clow et al., Immobilization of proteins to biacore sensor chips using *Staphylococcus aureus* sortase A. Biotechnol Lett. Sep. 2008;30(9):1603-7. Epub Apr. 15, 2008.
Codelli et al., Second-generation difluorinated cyclooctynes for copper-free click chemistry. J Am Chem Soc. Aug. 27, 2008;130(34):11486-93. Epub Aug. 5, 2008.
Comfort et al., A comparative genome analysis identifies distinct sorting pathways in gram-positive bacteria. Infect Immun. May 2004;72(5):2710-22.
Corey, Catalytic enantioselective Diels—Alder reactions: methods, mechanistic fundamentals, pathways, and applications. Angew Chem Int Ed Engl. May 17, 2002;41(10):1650-67.
Covic et al., Activation and inhibition of G protein-coupled receptors by cell-penetrating membrane-tethered peptides. Proc Natl Acad Sci U S A. Jan. 22, 2002;99(2):643-8.
Cui et al., Elimination of in vivo cleavage between target protein and intein in the intein-mediated protein purification systems. Protein Expr Purif. Nov. 2006;50(1):74-81. Epub Jun. 15, 2006.
Cull et al., Screening for receptor ligands using large libraries of peptides linked to the C terminus of the lac repressor. Proc Natl Acad Sci U S A. Mar. 1, 1992;89(5):1865-9.
Cwirla et al., Peptides on phage: a vast library of peptides for identifying ligands. Proc Natl Acad Sci U S A. Aug. 1990;87(16):6378-82.
Dag et al., Heterograft copolymers via double click reactions using one-pot technique. J Polym Sci Part A: Polym Chem. Oct. 15, 2008;46(20):6969-77.
Dag et al., Multiarm star block copolymers via Diels-Alder click reaction. J Polym Sci Part A: Polym Chem. Jan. 1, 2009;47(1):178-87.
Dag et al., Preparation of 3-arm star polymers (A3) via Diels—Alder click reaction. J Polym Sci Part A: Polym Chem. Jan. 1, 2008;46(1):302-13.
David et al., Facile, efficient routes to diverse protected thiols and to their deprotection and addition to create functional polymers by thiol-ene coupling. Macromolec. 2008;41(4):1151-61.
De Stgroth et al., Production of monoclonal antibodies: strategy and tactics. J Immunol Methods. 1980;35(1-2):1-21.
Devaraj et al., Tetrazine-based cycloadditions: application to pretargeted live cell imaging. Bioconjug Chem. Dec. 2008;19(12):2297-9.
Devlin et al., Random peptide libraries: a source of specific protein binding molecules. Science. Jul. 27, 1990;249(4967):404-6.
Dewitt et al., "Diversomers": an approach to nonpeptide, nonoligomeric chemical diversity. Proc Natl Acad Sci U S A. Aug. 1, 1993;90(15):6909-13.
Dondoni, The emergence of thiol-ene coupling as a click process for materials and bioorganic chemistry. Angew Chem Int Ed Engl. 2008;47(47):8995-7.
Dramsi et al., Sorting sortases: a nomenclature proposal for the various sortases of Gram-positive bacteria. Res Microbiol. Apr. 2005;156(3):289-97. Epub Jan. 28, 2005.
Duckworth et al., Selective labeling of proteins by using protein farnesyltransferase. Chembiochem. Jan. 2, 2007;8(1):98-105.
Durmaz et al., One-pot synthesis of ABC type triblock copolymers via in situ Click [3+2] and Diels—Alder [4+2] reactions. Macromol. 2007;40(2):191-8.
Durmaz et al., One-pot synthesis of star-block copolymers using double click reactions. J Polym Sci Part A: Polym Chem. Nov. 1, 2008;46(21):7091-100.

Eberl et al., Characterization of recombinant, membrane-attached full-length prion protein. J Biol Chem. Jun. 11, 2004;279(24):25058-65. Epub Mar. 18, 2004.
Erb et al., Recursive deconvolution of combinatorial chemical libraries. Proc Natl Acad Sci U S A. Nov. 22, 1994;91(24):11422-6.
Esposito et al., Enhancement of soluble protein expression through the use of fusion tags. Curr Opin Biotechnol. Aug. 2006;17(4):353-8. Epub Jun. 15, 2006.
Ess et al., Transition states of strain-promoted metal-free click chemistry: 1,3-dipolar cycloadditions of phenyl azide and cyclooctynes. Org Lett. Apr. 17, 2008;10(8):1633-6. Epub Mar. 26, 2008.
Evans, The rise of azide—alkyne 1,3-dipolar 'click' cycloaddition and its application to polymer science and surface modification. Australian J Chem. Jun. 18, 2007;60(6):384-95.
Feinberg et al., GFP Reconstitution Across Synaptic Partners (GRASP) defines cell contacts and synapses in living nervous systems. Neuron. Feb. 7, 2008;57(3):353-63.
Felici et al., Selection of antibody ligands from a large library of oligopeptides expressed on a multivalent exposition vector. J Mol Biol. Nov. 20, 1991;222(2):301-10.
Fodor et al., Multiplexed biochemical assays with biological chips. Nature. Aug. 5, 1993;364(6437):555-6.
Fournier et al., Clicking polymers: a straightforward approach to novel macromolecular architectures. Chem Soc Rev. Aug. 2007;36(8):1369-80. Epub May 3, 2007.
Gacal et al., Synthesis and characterization of polymeric thioxanthone photoinitiatiors via double click reactions. Macromol. 2008;41(7):2401-5.
Gallop et al., Applications of combinatorial technologies to drug discovery. 1. Background and peptide combinatorial libraries. J Med Chem. Apr. 29, 1994;37(9):1233-51.
Gauchet et al., Regio- and chemoselective covalent immobilization of proteins through unnatural amino acids. J Am Chem Soc. Jul. 26, 2006;128(29):9274-5.
Gierlich et al., Click chemistry as a reliable method for the high-density postsynthetic functionalization of alkyne-modified DNA. Org Lett. Aug. 17, 2006;8(17):3639-42.
Golas et al., Catalyst performance in "click" coupling reactions of polymers prepared by ATRP: Ligand and metal effects. Macromol. 2006;39(19):6451-7.
Gottlieb et al., Intein-mediated in vitro synthesis of lipidated Ras proteins. Chem Commun (Camb). Jan. 21, 2006;(3):260-2. Epub Nov. 28, 2005.
Gress et al., Thio-click modification of poly[2-(3-butenyl)-2-oxazoline]. Macromol. 2007;40(22):7928-33.
Grogan et al., Synthesis of lipidated green fluorescent protein and its incorporation in supported lipid bilayers. J Am Chem Soc. Oct. 19, 2005;127(41):14383-7.
Grünewald et al., Chemo- and regioselective peptide cyclization triggered by the N-terminal fatty acid chain length: the recombinant cyclase of the calcium-dependent antibiotic from *Streptomyces coelicolor*. Biochemistry. Mar. 16, 2004;43(10):2915-25.
Ha et al., Preparation of myristoylated Arf1 and Arf6. Methods Enzymol. 2005;404:164-74.
Hawker et al., The convergence of synthetic organic and polymer chemistries. Science. Aug. 19, 2005;309(5738):1200-5.
Heal et al., Site-specific N-terminal labelling of proteins in vitro and in vivo using N-myristoyl transferase and bioorthogonal ligation chemistry. Chem Commun (Camb). Jan. 28, 2008;(4):480-2. Epub Nov. 13, 2007.
Hicks et al., Synthesis and structural characterization of a mimetic membrane-anchored prion protein. FEBS J. Mar. 2006;273(6):1285-99.
Holmes et al., Isomerism in the Diels-Alder reaction. J Am Chem Soc. Jan. 1948;70(1):141-2.
Hornbeck, Enzyme-linked immunosorbent assays. Curr Protoc Immunol. 1991;11.2.1-22.
Hoyle et al., Thiol-enes: Chemistry of the past with promise for the future. J Polym Sci Part A: Polym Chem. Nov. 1, 2004;42(21):5301-38.
Hunkapiller et al., A microchemical facility for the analysis and synthesis of genes and proteins. Nature. Jul. 12-18, 1984;310(5973):105-11.

(56) References Cited

OTHER PUBLICATIONS

Hunter, New IL-12-family members: IL-23 and IL-27, cytokines with divergent functions. Nat Rev Immunol. Jul. 2005;5(7):521-31.

Inglis et al., Reversible addition fragmentation chain transfer (RAFT) and Hetero-Diels—Alder chemistry as a convenient conjugation tool for access to complex macromolecular designs. Macromol. 2008;41(12):4120-6.

Inglis et al., Ultrafast click conjugation of macromolecular building blocks at ambient temperature. Angew Chem Int Ed Engl. 2009;48(13):2411-4.

Jakobovits et al., From XenoMouse technology to panitumumab, the first fully human antibody product from transgenic mice. Nat Biotechnol. Oct. 2007;25(10):1134-43.

Jevsevar et al., PEGylation of therapeutic proteins. Biotechnol J. Jan. 2010;5(1):113-28.

Jobling et al., Construction and characterization of versatile cloning vectors for efficient delivery of native foreign proteins to the periplasm of *Escherichia coli*. Plasmid. 1997;38(3):158-73.

Johnson et al., Copper-free click chemistry for the in situ crosslinking of photodegradable star polymers. Chem Commun (Camb). Jul. 14, 2008;(26):3064-6. Epub Apr. 24, 2008.

Killops et al., Robust, efficient, and orthogonal synthesis of dendrimers via thiol-ene "click" chemistry. J Am Chem Soc. Apr. 16, 2008;130(15):5062-4. Epub Mar. 20, 2008.

Klaus et al., The three-dimensional high resolution structure of human interferon alpha-2a determined by heteronuclear NMR spectroscopy in solution. J Mol Biol. Dec. 12, 1997;274(4):661-75.

Köhler et al., Continuous cultures of fused cells secreting antibody of predefined specificity. Nature. Aug. 7, 1975;256(5517):495-7.

Kolb et al., Click Chemistry: Diverse Chemical Function from a Few Good Reactions. Angew Chem Int Ed Engl. Jun. 1, 2001;40(11):2004-2021.

Kolb et al., The growing impact of click chemistry on drug discovery. Drug Discov Today. Dec. 15, 2003;8(24):1128-37.

Kottani et al., Direct screening of solution phase combinatorial libraries encoded with externally sensitized photolabile tags. Proc Natl Acad Sci U S A. Sep. 19, 2006;103(38):13917-21. Epub Sep. 6, 2006.

Kruger et al., Analysis of the substrate specificity of the *Staphylococcus aureus* sortase transpeptidase SrtA. Biochemistry. Feb. 17, 2004;43(6):1541-51.

Ladmiral et al., Synthesis of neoglycopolymers by a combination of "click chemistry" and living radical polymerization. J Am Chem Soc. Apr. 12, 2006;128(14):4823-30.

Lam et al., A new type of synthetic peptide library for identifying ligand-binding activity. Nature. Nov. 7, 1991;354(6348):82-4.

Lam, Application of combinatorial library methods in cancer research and drug discovery. Anticancer Drug Des. Apr. 1997;12(3):145-67.

Laughlin et al., In vivo imaging of membrane-associated glycans in developing zebrafish. Science. May 2, 2008;320(5876):664-7.

Lautens et al., Transition Metal-Mediated Cycloaddition Reactions. Chem Rev. Feb. 1, 1996;96(1):49-92.

Li et al., 1,3-Dipolar cycloaddition of azides with electron-deficient alkynes under mild condition in water. Tetra Lett. Apr. 5, 2004;45(15):3143-6.

Li et al., End group transformations of RAFT-generated polymers with bismaleimides: Functional telechelics and modular block copolymers. J Polym Sci Part A: Polym Chem. Aug. 1, 2008;46(15):5093-100.

Luka et al., Expression and purification of glycine N-methyltransferases in *Escherichia coli*. Protein Expr Purif. Apr. 2003;28(2):280-6.

Lutz et al., Modular chemical tools for advanced macromolecular engineering. Polymer. Feb. 18, 2008;49(4):817-24.

Lutz, Copper-free azide-alkyne cycloadditions: new insights and perspectives. Angew Chem Int Ed Engl. 2008;47(12):2182-4.

Mao, A self-cleavable sortase fusion for one-step purification of free recombinant proteins. Protein Expr Purif. Sep. 2004;37(1):253-63.

Maresso et al., Surface protein IsdC and Sortase B are required for heme-iron scavenging of *Bacillus anthracis*. J Bacteriol. Dec. 2006;188(23):8145-52. Epub Sep. 29, 2006.

Mariscotti et al., The *Listeria monocytogenes* sortase-B recognizes varied amino acids at position 2 of the sorting motif. J Biol Chem. Mar. 6, 2009;284(10):6140-6. Epub Jan. 7, 2009.

Marraffini et al., Sortase C-mediated anchoring of BasI to the cell wall envelope of *Bacillus anthracis*. J Bacteriol. Sep. 2007;189(17):6425-36. Epub Jun. 22, 2007.

Martin et al., Non-natural cell surface receptors: synthetic peptides capped with N-cholesterylglycine efficiently deliver proteins into Mammalian cells. Bioconjug Chem. Jan.-Feb. 2003;14(1):67-74.

Mazmanian et al., An iron-regulated sortase anchors a class of surface protein during *Staphylococcus aureus* pathogenesis. Proc Natl Acad Sci U S A. Feb. 19, 2002;99(4):2293-8. Epub Feb. 5, 2002.

Moad et al., Toward living radical polymerization. Acc Chem Res. Sep. 2008;41(9):1133-42. Epub Aug. 14, 2008.

Mott et al., Four-helix bundle growth factors and their receptors: protein-protein interactions. Curr Opin Struct Biol. Feb. 1995;5(1):114-21.

Moyle et al., Self-adjuvanting lipopeptide vaccines. Curr Med Chem. 2008;15(5):506-16.

Muir, Semisynthesis of proteins by expressed protein ligation. Annu Rev Biochem. 2003;72:249-89. Epub Feb. 27, 2003.

Nelson et al., Myristoyl-based transport of peptides into living cells. Biochemistry. Dec. 25, 2007;46(51):14771-81. Epub Nov. 29, 2007.

Nicolaou et al., The Diels—Alder reaction in total synthesis. Angew Chem Int Ed Engl. May 17, 2002;41(10):1668-98.

Nilsson et al., Synthesis and thiol-ene photopolymerization of allyl-ether functionalized dendrimers. J Polym Sci Part A: Polym Chem. Feb. 15, 2008;46(4):1339-48.

Ning et al., Visualizing metabolically labeled glycoconjugates of living cells by copper-free and fast huisgen cycloadditions. Angew Chem Int Ed Engl. 2008;47(12):2253-5.

Ott et al., Post-modification of poly(pentafluorostyrene): a versatile "click" method to create well-defined multifunctional graft copolymers. Chem Commun (Camb). Aug. 14, 2008;(30):3516-8. Epub Jul. 3, 2008.

Pallen et al., An embarrassment of sortases—a richness of substrates? Trends Microbiol. Mar. 2001;9(3):97-102.

Parthasarathy et al., Sortase A as a novel molecular "stapler" for sequence-specific protein conjugation. Bioconjug Chem. Mar.-Apr. 2007;18(2):469-76. Epub Feb. 16, 2007.

Paulick et al., A chemical approach to unraveling the biological function of the glycosylphosphatidylinositol anchor. Proc Natl Acad Sci U S A. Dec. 18, 2007;104(51):20332-7. Epub Dec. 12, 2007.

Paulick et al., Synthetic analogues of glycosylphosphatidylinositol-anchored proteins and their behavior in supported lipid bilayers. J Am Chem Soc. Sep. 19, 2007;129(37):11543-50. Epub Aug. 23, 2007.

Pellois et al., A ligation and photorelease strategy for the temporal and spatial control of protein function in living cells. Angew Chem Int Ed Engl. Sep. 5, 2005;44(35):5713-7.

Popp et al., Sortagging: a versatile method for protein labeling. Nat Chem Biol. Nov. 2007;3(11):707-8. Epub Sep. 23, 2007.

Popp et al., Substrate filtering by the active site crossover loop in UCHL3 revealed by sortagging and gain-of-function mutations. J Biol Chem. Feb. 6, 2009;284(6):3593-602. Epub Dec. 1, 2008.

Pounder et al., Metal free thiol-maleimide 'Click' reaction as a mild functionalisation strategy for degradable polymers. Chem Commun (Camb). Nov. 7, 2008;(41):5158-60. Epub Sep. 29, 2008.

Pritz et al., Synthesis of biologically active peptide nucleic acid-peptide conjugates by sortase-mediated ligation. J Org Chem. May 11, 2007;72(10):3909-12. Epub Apr. 14, 2007.

Pritz et al., Synthesis of protein mimics with nonlinear backbone topology by a combined recombinant, enzymatic, and chemical synthesis strategy. Angew Chem Int Ed Engl. 2008;47(19):3642-5.

Race et al., Crystal structure of *Streptococcus pyogenes* sortase A: implications for sortase mechanism. J Biol Chem. Mar. 13, 2009;284(11):6924-33. Epub Jan. 6, 2009.

(56) References Cited

OTHER PUBLICATIONS

Reulen et al., Protein-liposome conjugates using cysteine-lipids and native chemical ligation. Bioconjug Chem. Mar.-Apr. 2007;18(2):590-6. Epub Feb. 22, 2007.

Robinson et al., Structure of the brain-derived neurotrophic factor/neurotrophin 3 heterodimer. Biochemistry. Apr. 4, 1995;34(13):4139-46.

Robinson et al., The structures of the neurotrophin 4 homodimer and the brain-derived neurotrophic factor/neurotrophin 4 heterodimer reveal a common Trk-binding site. Protein Sci. Dec. 1999;8(12):2589-97.

Rodenko et al., Class I major histocompatibility complexes loaded by a periodate trigger. J Am Chem Soc. Sep. 2, 2009;131(34):12305-13.

Rodionov et al., Mechanism of the ligand-free CuI-catalyzed azide-alkyne cycloaddition reaction. Angew Chem Int Ed Engl. Apr. 8, 2005;44(15):2210-5.

Saha et al., Cu-FeCl3-mediated one-pot multicomponent reaction leading to N-Aryl- and N-alkyltriazoles in water. Sinlett. 2007;10:1591-4.

Samantaray et al., Peptide-sugar ligation catalyzed by transpeptidase sortase: a facile approach to neoglycoconjugate synthesis. J Am Chem Soc. Feb. 20, 2008;130(7):2132-3. Epub Jan. 30, 2008.

Samaroo et al., Efficient microwave-assisted synthesis of amine-substituted tetrakis(pentafluorophenyl)porphyrin. Org Lett. Oct. 26, 2006;8(22):4985-8.

Samaroo et al., meso-Tetra(pentafluorophenyl)porphyrin as an efficient platform for combinatorial synthesis and the selection of new photodynamic therapeutics using a cancer cell line. J Comb Chem. Nov.-Dec. 2007;9(6):998-1011. Epub Sep. 15, 2007.

Sawoo et al., A new bio-active surface for protein immobilisation via copper-free 'click' between azido SAM and alkynyl Fischer carbene complex. Chem Commun (Camb). Dec. 7, 2008;(45):59579. Epub Oct. 9, 2008.

Scott et al., Searching for peptide ligands with an epitope library. Science. Jul. 27, 1990;249(4967):386-90.

Sharpless et al., Just click it: Undergraduate procedures for the copper(I)-catalyzed formation of 1,2,3-triazoles from azides and terminal acetylenes. J Chem Ed. 2005;82(12):1833-6.

Sheff et al., Transferrin receptor recycling in the absence of perinuclear recycling endosomes. J Cell Biol. Mar. 4, 2002;156(5):797-804. Epub Mar. 4, 2002.

Shi et al., Benzyne click chemistry: synthesis of benzotriazoles from benzynes and azides. Org Lett. Jun. 19, 2008;10(12):2409-12. Epub May 14, 2008.

Sinnwell et al., An atom-efficient conjugation approach to well-defined block copolymers using RAFT chemistry and hetero Diels-Alder cycloaddition. Chem Commun (Camb). May 7, 2008;(17):2052-4. Epub Feb. 20, 2008.

Sletten et al., A hydrophilic azacyclooctyne for Cu-free click chemistry. Org Lett. Jul. 17, 2008;10(14):3097-9. Epub Jun. 13, 2008.

Song et al., A photoinducible 1,3-dipolar cycloaddition reaction for rapid, selective modification of tetrazole-containing proteins. Angew Chem Int Ed Engl. 2008;47(15):2832-5.

Song et al., Selective functionalization of a genetically encoded alkene-containing protein via "photoclick chemistry" in bacterial cells. J Am Chem Soc. Jul. 30, 2008;130(30):9654-5. Epub Jul. 2, 2008.

Spain et al., Recent advances in the synthesis of well-defined glycopolymers. J Polym Sci Part A: Polym chem. Jun. 1, 2007;45(11):2059-72.

Stanford et al., One-pot synthesis of α,ω-chain end functional, stereoregular, star-shaped poly(lactide). Macromol. 2009;42(1):141-7.

Stewart et al., Cell-penetrating peptides as delivery vehicles for biology and medicine. Org Biomol Chem. Jul. 7, 2008;6(13):2242-55. Epub Apr. 15, 2008.

Sun et al., Selective disruption of early/recycling endosomes: release of disulfide-linked cargo mediated by a N-alkyl-3beta-cholesterylamine-capped peptide. J Am Chem Soc. Aug. 6, 2008;130(31):10064-5. Epub Jul. 10, 2008.

Tan et al., Improving the intein-mediated, site-specific protein biotinylation strategies both in vitro and in vivo. Bioorg Med Chem Lett. Dec. 20, 2004;14(24):6067-70.

Tanaka et al., Site-specific protein modification on living cells catalyzed by Sortase. Chembiochem. Mar. 25, 2008;9(5):802-7.

Ten Brummelhuis et al., Thiol—ene modification of 1,2-polybutadiene using uv light or sunlight. Macromol. 2008;41(24):9946-7.

Ton-That et al., Anchoring of surface proteins to the cell wall of Staphylococcus aureus. Sortase catalyzed in vitro transpeptidation reaction using LPXTG peptide and NH(2)-Gly(3) substrates. J Biol Chem. Mar. 31, 2000;275(13):9876-81.

Ton-That et al., Protein sorting to the cell wall envelope of Gram-positive bacteria. Biochim Biophys Acta. Nov. 11, 2004;1694(1-3):269-78.

Ton-That et al., Purification and characterization of sortase, the transpeptidase that cleaves surface proteins of Staphylococcus aureus at the LPXTG motif. Proc Natl Acad Sci U S A. Oct. 26, 1999;96(22):12424-9.

Torchilin, Recent advances with liposomes as pharmaceutical carriers. Nat Rev Drug Discov. Feb. 2005;4(2):145-60.

Tornøe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.

Tsien, The green fluorescent protein. Annu Rev Biochem. 1998;67:509-44.

Urbani et al., Convergent synthesis of second generation AB-type miktoarm dendrimers using "click" chemistry catalyzed by copper wire. Macrol. 2008;41(4):1057-60.

Van Berkel et al., Application of metal-free triazole formation in the synthesis of cyclic RGD-DTPA conjugates. Chembiochem. Jul. 21, 2008;9(11):1805-15.

Van Berkel et al., Metal-free triazole formation as a tool for bioconjugation. Chembiochem. Sep. 3, 2007;8(13):1504-8.

Wang et al., Bioconjugation by copper(I)-catalyzed azide-alkyne [3+2] cycloaddition. J Am Chem Soc. Mar. 19, 2003;125(11):3192-3.

Witczak et al., A click chemistry approach to glycomimetics: Michael addition of 2,3,4,6-tetra-O-acetyl-1-thio-beta-D-glucopyranose to 4-deoxy-1,2-O-isopropylidene-L-glycero-pent-4-enopyranos-3-ulose—a convenient route to novel 4-deoxy-(1→5)-5-C-thiodisaccharides. Carbohydr Res. Sep. 3, 2007;342(12-13):1929-33. Epub Jun. 9, 2007.

Zacharias et al., Partitioning of lipid-modified monomeric GFPs into membrane microdomains of live cells. Science. May 3, 2002;296(5569):913-6.

Zhao et al., An efficient on-column expressed protein ligation strategy: application to segmental triple labeling of human apolipoprotein E3. Protein Sci. Apr. 2008;17(4):736-47. Epub Feb. 27, 2008.

Zou et al., Cu-free cycloaddition for identifying catalytic active adenylation domains of nonribosomal peptide synthetases by phage display. Bioorg Med Chem Lett. Oct. 15, 2008;18(20):5664-7. Epub Aug. 28, 2008.

Zuckermann et al., Discovery of nanomolar ligands for 7-transmembrane G-protein-coupled receptors from a diverse N-(substituted)glycine peptoid library. J Med Chem. Aug. 19, 1994;37(17):2678-85.

Zumbuehl et al., An amphotericin B-fluorescein conjugate as a powerful probe for biochemical studies of the membrane. Angew Chem Int Ed Engl. Oct. 4, 2004;43(39):5181-5.

* cited by examiner

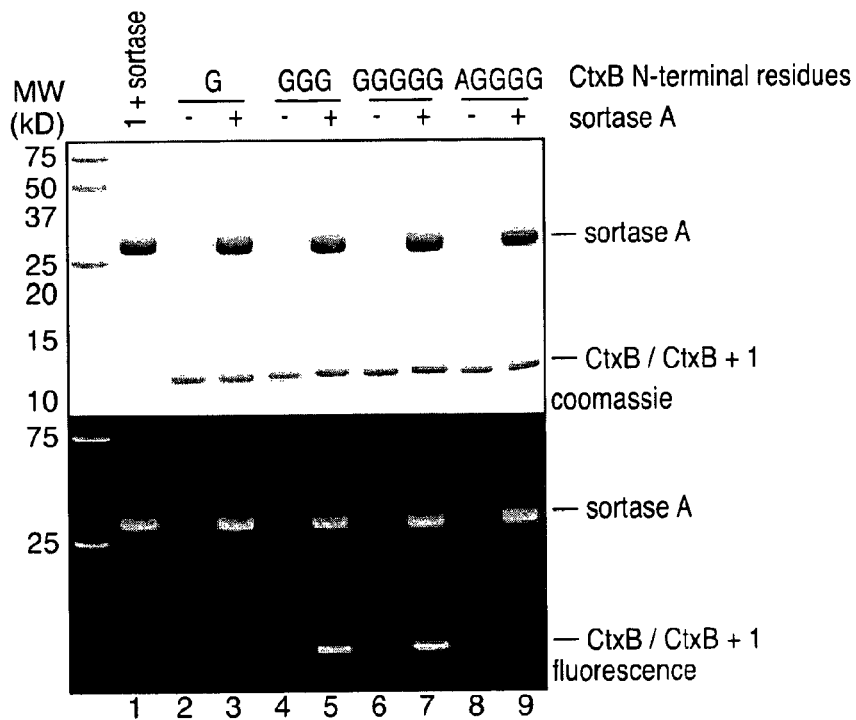
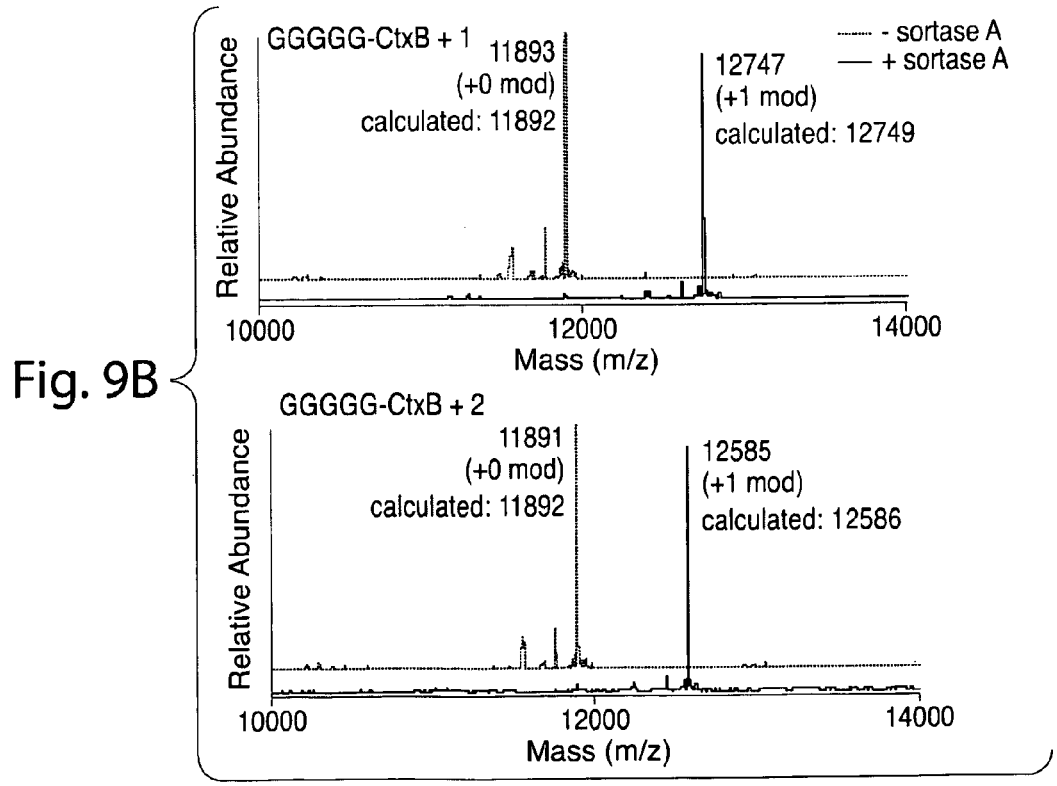
Fig. 9A
Fig. 9B

RP-HPLC 2-chol

ESI-MS for Lipidated Triglycine Nucleophiles

| Nucleophile | $[M+H]^+$ calc | $[M+H]^+$ obs |
|---|---|---|
| 1-ad | 493.3 | 493.6 |
| 1-C12 | 499.4 | 499.5 |
| 1-C14 | 527.4 | 527.6 |
| 1-C16 | 555.4 | 555.6 |
| 1-C18 | 583.5 | 583.6 |
| 1-C20 | 611.5 | 611.6 |
| 1-C22 | 639.5 | 639.7 |
| 1-C24 | 667.5 | 667.7 |
| 2-chol | 915.6 | 915.6 |

| eGFP Conjugate | absorbance (488 nm) | yield (%) |
|---|---|---|
| eGFP-GGG | 0.112 | 93 |
| eGFP-1-ad | 0.104 | 87 |
| eGFP-1-C12 | 0.104 | 87 |
| eGFP-1-C14 | 0.086 | 72 |
| eGFP-1-C16 | 0.077 | 64 |
| eGFP-1-C18 | 0.069 | 57 |
| eGFP-1-C20 | 0.079 | 66 |
| eGFP-1-C-22 | 0.100 | 83 |
| eGFP-1-C24 | 0.101 | 84 |
| eGFP-2-chol | 0.105 | 87 |

C-Terminal Transpeptidation Tolerates a Range of Nucleophiles

Nucleophile: cholesterol

Substrate: eGFP-LPETG-His$_6$

Uptake of cholesterol modified eGFP

C-Terminal Transpeptidation Tolerates a Range of Nucleophiles

Nucleophile: crosslinker/biotin

Substrate: H-2K$^b$-LPETG-AP(biotin)

Crosslinking MHC I / β$_2$m

C-Terminal Transpeptidation Tolerates a Range of Nucleophiles

Nucleophile: fluorophore

TAMRA

Substrate: CD40L-LPETG-HA

Cell Surface Labeling

ATGggcggat gtgatctgcc tcaaacccac agcctgggta gcaggaggac cttgatgctc
ctggcacaga tgaggagaat ctctcttttc tcctgcttga aggacagaca tgactttgga
tttccccagg aggagtttgg caaccagttc caaaaggctg aaaccatccc tgtcctccat
gagatgatcc agcagatctt caatctcttc agcacaaagg actcatctgc tgcttgggat
gagaccctcc tagacaaatt ctacactgaa ctctaccagc agctgaatga cctggaagcc
tgtgtgatac aggggtggg ggtgacagag actccctga aagagaagaa atacagccct
gctgtgagga aatacttcca aagaatcact ctctatctga aagagaagaa atacagccct
tgtgcctggg aggttgtcag agcagaaatc atgagatctt tttctttgtc aacaaacttg
caagaaagtt taagaagtaa gga gga tta cca gag aca gga gga ggc agc
catcatcatc atcattga (SEQ ID NO: 1)

MGGCDLPQTHSLGSRRTLMLLAQMRRISLFSCLKDRHDFGFPQEEFGNQFQKAETIPV
LHEMIQQIFNLFSTKDSSAAWDETLLDKFYTELYQQLNDLEACVIQGVGVTETPLMKEDS
ILAVRKYFQRITLYLKEKKYSPCAWEVVRAEIMRSFSLSTNLQESLRSKEG*GLPETGGGS*
HHHHHH (SEQ ID NO: 2)

Fig. 38

Circular Interferonα2 Sequence

Protein:

FGPQEEFGN QFQKAETIPV LHEMIQQIFN LFSTKDSSAA WDETLLDKFY
TELYQQLNDL EACVIQGVGV TETPLMKEDS ILAVRKYFQR ITLYLKEKKY
SPCAWEVVRA EIMRSFSLST NLQESLRSKE GGLPETGGCD LPQTHSLGSR
RTLMLLAQMR RISLFSCLKD RHD

Junction Peptides Identified after chymotrypsin digestion and MS/MS analysis

Protein Coverage:

| Sequence | MH+ | % Mass | AA | % AA |
|---|---|---|---|---|
| SKEGGLPETGGCDLPQTH | 1825.84 | 9.16 | 128 - 145 | 10.40 |
| SKEGGLPETGGCDLPQTHSLGSR | 2326.11 | 11.67 | 128 - 150 | 13.29 |
| EGGLPETGGCDLPQTH | 1610.71 | 8.08 | 130 - 145 | 9.25 |
| EGGLPETGGCDLPQTHSLGSR | 2110.98 | 10.59 | 130 - 150 | 12.14 |

Fig. 39B

SEQUENCE LISTING

```
<160> NUMBER OF SEQ ID NOS: 220

<210> SEQ ID NO 1
<211> LENGTH: 555
<212> TYPE: DNA
<213> ORGANISM: ARTIFICIAL SEQUENCE
<220> FEATURE:
<223> OTHER INFORMATION: Synthetic Polynucleotide

<400> SEQUENCE: 1
atgggcggat gtgatctgcc tcaaacccac agcctgggta gcaggaggac cttgatgctc      60
ctggcacaga tgaggagaat ctctcttttc tcctgcttga aggacagaca tgactttgga     120
tttccccagg aggagtttgg caaccagttc caaaaggctg aaaccatccc tgtcctccat     180
gagatgatcc agcagatctt caatctcttc agcacaaagg actcatctgc tgcttgggat     240
gagaccctcc tagacaaatt ctacactgaa ctctaccagc agctgaatga cctggaagcc     300
tgtgtgatac agggggtggg ggtgacagag actcccctga tgaaggagga ctccattctg     360
gctgtgagga aatacttcca aagaatcact ctctatctga aagagaagaa atacagccct     420
tgtgcctggg aggttgtcag agcagaaatc atgagatctt tttctttgtc aacaaacttg     480
caagaaagtt taagaagtaa ggaaggagga ttaccagaga caggaggagg cagccatcat     540
catcatcatc attga                                                      555

<210> SEQ ID NO 2
<211> LENGTH: 184
<212> TYPE: PRT
<213> ORGANISM: ARTIFICIAL SEQUENCE
<220> FEATURE:
<223> OTHER INFORMATION: Synthetic Polypeptide

<400> SEQUENCE: 2

Met Gly Gly Cys Asp Leu Pro Gln Thr His Ser Leu Gly Ser Arg Arg
1               5                   10                  15

Thr Leu Met Leu Leu Ala Gln Met Arg Arg Ile Ser Leu Phe Ser Cys
            20                  25                  30

Leu Lys Asp Arg His Asp Phe Gly Phe Pro Gln Glu Glu Phe Gly Asn
        35                  40                  45

Gln Phe Gln Lys Ala Glu Thr Ile Pro Val Leu His Glu Met Ile Gln
    50                  55                  60

Gln Ile Phe Asn Leu Phe Ser Thr Lys Asp Ser Ser Ala Ala Trp Asp
65                  70                  75                  80

Glu Thr Leu Leu Asp Lys Phe Tyr Thr Glu Leu Tyr Gln Gln Leu Asn
                85                  90                  95

Asp Leu Glu Ala Cys Val Ile Gln Gly Val Gly Val Thr Glu Thr Pro
            100                 105                 110

Leu Met Lys Glu Asp Ser Ile Leu Ala Val Arg Lys Tyr Phe Gln Arg
        115                 120                 125
```

```
Ile Thr Leu Tyr Leu Lys Glu Lys Lys Tyr Ser Pro Cys Ala Trp Glu
    130                 135                 140

Val Val Arg Ala Glu Ile Met Arg Ser Phe Ser Leu Ser Thr Asn Leu
145                 150                 155                 160

Gln Glu Ser Leu Arg Ser Lys Glu Gly Gly Leu Pro Glu Thr Gly Gly
                165                 170                 175

Gly Ser His His His His His His
            180

<210> SEQ ID NO 3
<211> LENGTH: 23
<212> TYPE: PRT
<213> ORGANISM: ARTIFICIAL SEQUENCE
<220> FEATURE:
<223> OTHER INFORMATION: Synthetic Polypeptide

<400> SEQUENCE: 3

Met Val Pro Cys Thr Leu Leu Leu Leu Ala Ala Ala Leu Ala Pro
1               5                   10                  15

Thr Gln Thr Arg Ala Gly Gly
            20

<210> SEQ ID NO 4
<211> LENGTH: 63
<212> TYPE: DNA
<213> ORGANISM: ARTIFICIAL SEQUENCE
<220> FEATURE:
<223> OTHER INFORMATION: Synthetic Polynucleotide

<400> SEQUENCE: 4
atggtaccgt gcacgctgct cctgctgttg gcggccgccc tggctccgac tcagacccgc        60
gcg                                                                     63

<210> SEQ ID NO 5
<211> LENGTH: 9
<212> TYPE: PRT
<213> ORGANISM: ARTIFICIAL SEQUENCE
<220> FEATURE:
<223> OTHER INFORMATION: Synthetic Polypeptide

<400> SEQUENCE: 5

Thr Thr Cys Cys Gly Leu Arg Gln Tyr
1               5

<210> SEQ ID NO 6
<211> LENGTH: 255
<212> TYPE: PRT
<213> ORGANISM: ARTIFICIAL SEQUENCE
<220> FEATURE:
<223> OTHER INFORMATION: Synthetic Polypeptide

<400> SEQUENCE: 6

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
                20                  25                  30

Glu Lys Trp Ile Val Thr Ala Ala His Cys Val Glu Glu Thr Thr Gly
            35                  40                  45

Val Lys Ile Thr Val Val Ala Gly Glu His Asn Ile Glu Glu Thr Glu
        50                  55                  60

His Thr Glu Gln Lys Arg Asn Val Ile Arg Ile Ile Pro His His Asn
65                  70                  75                  80
```

```
Tyr Asn Asn Ala Ala Ala Ala Ala Ile Asn Lys Tyr Asn His
                85                  90                  95

Asp Ile Ala Leu Leu Glu Leu Asp Glu Pro Leu Val Leu Asn Ser Tyr
            100                 105                 110

Val Thr Pro Ile Cys Ile Ala Asp Lys Glu Tyr Thr Thr Thr Asn Asn
            115                 120                 125

Asn Ile Ile Ile Phe Leu Lys Phe Gly Ser Gly Tyr Val Ser Gly Trp
130                 135                 140

Gly Arg Val Phe His Lys Gly Arg Ser Ala Leu Val Leu Gln Tyr Leu
145                 150                 155                 160

Arg Val Pro Leu Val Asp Arg Ala Thr Cys Leu Arg Ser Thr Lys Phe
                165                 170                 175

Thr Ile Tyr Asn Asn Met Phe Cys Ala Gly Gly Phe His Glu Gly
            180                 185                 190

Gly Gly Arg Arg Asp Ser Cys Gln Gly Asp Ser Gly Pro His Val
            195                 200                 205

Thr Glu Val Glu Gly Thr Ser Phe Leu Thr Gly Ile Ile Ser Trp Gly
    210                 215                 220

Glu Glu Cys Ala Ala Met Met Lys Gly Lys Tyr Gly Ile Tyr Thr Lys
225                 230                 235                 240

Val Ser Arg Tyr Val Asn Trp Ile Lys Glu Lys Thr Lys Leu Thr
                245                 250                 255

<210> SEQ ID NO 7
<211> LENGTH: 57
<212> TYPE: PRT
<213> ORGANISM: ARTIFICIAL SEQUENCE
<220> FEATURE:
<223> OTHER INFORMATION: Synthetic Polypeptide

<400> SEQUENCE: 7

Met Thr Cys Asn Ile Lys Asn Gly Arg Cys Glu Gln Phe Cys Lys Asn
1               5                   10                  15

Ser Ala Asp Asn Lys Val Val Cys Ser Cys Thr Glu Gly Tyr Arg Leu
            20                  25                  30

Ala Glu Asn Gln Lys Ser Cys Glu Pro Ala Val Pro Phe Pro Cys Gly
        35                  40                  45

Arg Val Ser Val Ser Gln Thr Ser Lys
    50                  55

<210> SEQ ID NO 8
<211> LENGTH: 496
<212> TYPE: PRT
<213> ORGANISM: ARTIFICIAL SEQUENCE
<220> FEATURE:
<223> OTHER INFORMATION: Synthetic Polypeptide

<400> SEQUENCE: 8

Glu Phe Ala Arg Pro Cys Ile Pro Lys Ser Phe Gly Tyr Ser Ser Val
1               5                   10                  15

Val Cys Val Cys Asn Ala Thr Tyr Cys Asp Ser Phe Asp Pro Pro Ala
            20                  25                  30

Leu Gly Thr Phe Ser Arg Tyr Glu Ser Thr Arg Ser Gly Arg Arg Met
        35                  40                  45

Glu Leu Ser Met Gly Pro Ile Gln Ala Asn His Thr Gly Thr Gly Leu
    50                  55                  60

Leu Leu Thr Leu Gln Pro Glu Gln Lys Phe Gln Lys Val Lys Gly Phe
```

-continued

```
                65                  70                  75                  80
Gly Gly Ala Met Thr Asp Ala Ala Leu Asn Ile Leu Ala Leu Ser
                        85                  90                  95
Pro Pro Ala Gln Asn Leu Leu Leu Lys Ser Tyr Phe Ser Glu Glu Gly
                    100                 105                 110
Ile Gly Tyr Asn Ile Ile Arg Val Pro Met Ala Ser Cys Asp Phe Ser
                    115                 120                 125
Ile Arg Thr Tyr Thr Tyr Ala Asp Thr Pro Asp Asp Phe Gln Leu His
                130                 135                 140
Asn Phe Ser Leu Pro Glu Glu Asp Thr Lys Leu Lys Ile Pro Leu Ile
145                 150                 155                 160
His Arg Ala Leu Gln Leu Ala Gln Arg Pro Val Ser Leu Leu Ala Ser
                    165                 170                 175
Pro Trp Thr Ser Pro Thr Trp Leu Lys Thr Asn Gly Ala Val Asn Gly
                180                 185                 190
Lys Gly Ser Leu Lys Gly Gln Pro Gly Asp Ile Tyr His Gln Thr Trp
                    195                 200                 205
Ala Arg Tyr Phe Val Lys Phe Leu Asp Ala Tyr Ala Glu His Lys Leu
                210                 215                 220
Gln Phe Trp Ala Val Thr Ala Glu Asn Glu Pro Ser Ala Gly Leu Leu
225                 230                 235                 240
Ser Gly Tyr Pro Phe Gln Cys Leu Gly Phe Thr Pro Glu His Gln Arg
                    245                 250                 255
Asp Phe Ile Ala Arg Asp Leu Gly Pro Thr Leu Ala Asn Ser Thr His
                260                 265                 270
His Asn Val Arg Leu Leu Met Leu Asp Asp Gln Arg Leu Leu Leu Pro
                275                 280                 285
His Trp Ala Lys Val Val Leu Thr Asp Pro Glu Ala Ala Lys Tyr Val
                290                 295                 300
His Gly Ile Ala Val His Trp Tyr Leu Asp Phe Leu Ala Pro Ala Lys
305                 310                 315                 320
Ala Thr Leu Gly Glu Thr His Arg Leu Phe Pro Asn Thr Met Leu Phe
                    325                 330                 335
Ala Ser Glu Ala Cys Val Gly Ser Lys Phe Trp Glu Gln Ser Val Arg
                340                 345                 350
Leu Gly Ser Trp Asp Arg Gly Met Gln Tyr Ser His Ser Ile Ile Thr
                355                 360                 365
Asn Leu Leu Tyr His Val Val Gly Trp Thr Asp Trp Asn Leu Ala Leu
                370                 375                 380
Asn Pro Glu Gly Gly Pro Asn Trp Val Arg Asn Phe Val Asp Ser Pro
385                 390                 395                 400
Ile Ile Val Asp Ile Thr Lys Asp Thr Phe Tyr Lys Gln Pro Met Phe
                    405                 410                 415
Tyr His Leu Gly His Phe Ser Lys Phe Ile Pro Glu Gly Ser Gln Arg
                420                 425                 430
Val Gly Leu Val Ala Ser Gln Lys Asn Asp Leu Asp Ala Val Ala Leu
                435                 440                 445
Met His Pro Asp Gly Ser Ala Val Val Val Leu Asn Arg Ser Ser
                450                 455                 460
Lys Asp Val Pro Leu Thr Ile Lys Asp Pro Ala Val Gly Phe Leu Glu
465                 470                 475                 480
Thr Ile Ser Pro Gly Tyr Ser Ile His Thr Tyr Leu Trp His Arg Gln
                    485                 490                 495
```

<210> SEQ ID NO 9
<211> LENGTH: 390
<212> TYPE: PRT
<213> ORGANISM: ARTIFICIAL SEQUENCE
<220> FEATURE:
<223> OTHER INFORMATION: Synthetic Polypeptide

<400> SEQUENCE: 9

```
Leu Asp Asn Gly Leu Ala Arg Thr Pro Thr Met Gly Trp Leu His Trp
1               5                   10                  15

Glu Arg Phe Met Cys Asn Leu Asp Cys Gln Glu Pro Asp Ser Cys
            20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
        210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
        290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365
```

```
Thr Ser Arg Leu Arg Ser His Ile Asn Pro Thr Gly Thr Val Leu Leu
    370                 375                 380

Gln Leu Glu Asn Thr Met
385                 390

<210> SEQ ID NO 10
<211> LENGTH: 479
<212> TYPE: PRT
<213> ORGANISM: ARTIFICIAL SEQUENCE
<220> FEATURE:
<223> OTHER INFORMATION: Synthetic Polypeptide

<400> SEQUENCE: 10

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
                20                  25                  30

Gln Leu Ala Ala Gly Gly Leu Arg Phe Thr Asp Phe Tyr Val Pro Val
            35                  40                  45

Ser Leu Pro Ser Arg Ala Ala Leu Leu Thr Gly Arg Leu Pro Val Arg
    50                  55                  60

Met Gly Met Tyr Pro Gly Val Leu Val Pro Ser Ser Arg Gly Gly Leu
65                  70                  75                  80

Pro Leu Glu Glu Val Thr Val Ala Glu Val Leu Ala Ala Arg Gly Tyr
                85                  90                  95

Leu Thr Gly Met Ala Gly Lys Trp His Leu Gly Val Gly Pro Glu Gly
            100                 105                 110

Ala Phe Leu Pro Pro His Gln Gly Phe His Arg Phe Leu Gly Ile Pro
        115                 120                 125

Tyr Ser His Asp Gln Gly Pro Cys Gln Asn Leu Thr Cys Phe Pro Pro
    130                 135                 140

Ala Thr Pro Cys Asp Gly Gly Cys Asp Gln Gly Leu Val Pro Ile Pro
145                 150                 155                 160

Leu Leu Ala Asn Leu Ser Val Glu Ala Gln Pro Pro Trp Leu Pro Gly
                165                 170                 175

Leu Glu Ala Arg Tyr Met Ala Phe Ala His Asp Leu Met Ala Asp Ala
            180                 185                 190

Gln Arg Gln Asp Arg Pro Phe Phe Leu Tyr Tyr Ala Ser His His Thr
        195                 200                 205

His Tyr Pro Gln Phe Ser Gly Gln Ser Phe Ala Glu Arg Ser Gly Arg
    210                 215                 220

Gly Pro Phe Gly Asp Ser Leu Met Glu Leu Asp Ala Ala Val Gly Thr
225                 230                 235                 240

Leu Met Thr Ala Ile Gly Asp Leu Gly Leu Leu Glu Glu Thr Leu Val
                245                 250                 255

Ile Phe Thr Ala Asp Asn Gly Pro Glu Thr Met Arg Met Ser Arg Gly
            260                 265                 270

Gly Cys Ser Gly Leu Leu Arg Cys Gly Lys Gly Thr Thr Tyr Glu Gly
        275                 280                 285

Gly Val Arg Glu Pro Ala Leu Ala Phe Trp Pro Gly His Ile Ala Pro
    290                 295                 300

Gly Val Thr His Glu Leu Ala Ser Ser Leu Asp Leu Leu Pro Thr Leu
305                 310                 315                 320

Ala Ala Leu Ala Gly Ala Pro Leu Pro Asn Val Thr Leu Asp Gly Phe
                325                 330                 335
```

```
Asp Leu Ser Pro Leu Leu Gly Thr Gly Lys Ser Pro Arg Gln Ser
            340                 345                 350

Leu Phe Phe Tyr Pro Ser Tyr Pro Asp Glu Val Arg Gly Val Phe Ala
            355                 360                 365

Val Arg Thr Gly Lys Tyr Lys Ala His Phe Phe Thr Gln Gly Ser Ala
370                 375                 380

His Ser Asp Thr Thr Ala Asp Pro Ala Cys His Ala Ser Ser Ser Leu
385                 390                 395                 400

Thr Ala His Glu Pro Pro Leu Leu Tyr Asp Leu Ser Lys Asp Pro Gly
            405                 410                 415

Glu Asn Tyr Asn Leu Leu Gly Ala Thr Pro Glu Val Leu Gln Ala Leu
            420                 425                 430

Lys Gln Leu Gln Leu Leu Lys Ala Gln Leu Asp Ala Ala Val Thr Phe
            435                 440                 445

Gly Pro Ser Gln Val Ala Arg Gly Glu Asp Pro Ala Leu Gln Ile Cys
            450                 455                 460

Cys His Pro Gly Cys Thr Pro Arg Pro Ala Cys Cys His Cys Pro
465                 470                 475

<210> SEQ ID NO 11
<211> LENGTH: 474
<212> TYPE: PRT
<213> ORGANISM: ARTIFICIAL SEQUENCE
<220> FEATURE:
<223> OTHER INFORMATION: Synthetic Polypeptide

<400> SEQUENCE: 11

Ser Arg Pro Pro His Leu Val Phe Leu Leu Ala Asp Asp Leu Gly Trp
1               5                   10                  15

Asn Asp Val Gly Phe His Gly Ser Arg Ile Arg Thr Pro His Leu Asp
            20                  25                  30

Ala Leu Ala Ala Gly Gly Val Leu Leu Asp Asn Tyr Tyr Thr Gln Pro
        35                  40                  45

Leu Thr Pro Ser Arg Ser Gln Leu Leu Thr Gly Arg Tyr Gln Ile Arg
    50                  55                  60

Thr Gly Leu Gln His Gln Ile Ile Trp Pro Cys Gln Pro Ser Cys Val
65                  70                  75                  80

Pro Leu Asp Glu Lys Leu Leu Pro Gln Leu Leu Lys Glu Ala Gly Tyr
                85                  90                  95

Thr Thr His Met Val Gly Lys Trp His Leu Gly Met Tyr Arg Lys Glu
            100                 105                 110

Cys Leu Pro Thr Arg Arg Gly Phe Asp Thr Tyr Phe Gly Tyr Leu Leu
        115                 120                 125

Gly Ser Glu Asp Tyr Tyr Ser His Glu Arg Cys Thr Leu Ile Asp Ala
    130                 135                 140

Leu Asn Val Thr Arg Cys Ala Leu Asp Phe Arg Asp Gly Glu Glu Val
145                 150                 155                 160

Ala Thr Gly Tyr Lys Asn Met Tyr Ser Thr Asn Ile Phe Thr Lys Arg
                165                 170                 175

Ala Ile Ala Leu Ile Thr Asn His Pro Pro Glu Lys Pro Leu Phe Leu
            180                 185                 190

Tyr Leu Ala Leu Gln Ser Val His Glu Pro Leu Gln Val Pro Glu Glu
        195                 200                 205

Tyr Leu Lys Pro Tyr Asp Phe Ile Gln Asp Lys Asn Arg His His Tyr
    210                 215                 220
```

```
Ala Gly Met Val Ser Leu Met Asp Glu Ala Val Gly Asn Val Thr Ala
225                 230                 235                 240

Ala Leu Lys Ser Ser Gly Leu Trp Asn Asn Thr Val Phe Ile Phe Ser
            245                 250                 255

Thr Asp Asn Gly Gly Gln Thr Leu Ala Gly Gly Asn Asn Trp Pro Leu
        260                 265                 270

Arg Gly Arg Lys Trp Ser Leu Trp Glu Gly Val Arg Gly Val Gly
    275                 280                 285

Phe Val Ala Ser Pro Leu Leu Lys Gln Lys Gly Val Lys Asn Arg Glu
290                 295                 300

Leu Ile His Ile Ser Asp Trp Leu Pro Thr Leu Val Lys Leu Ala Arg
305                 310                 315                 320

Gly His Thr Asn Gly Thr Lys Pro Leu Asp Gly Phe Asp Val Trp Lys
                325                 330                 335

Thr Ile Ser Glu Gly Ser Pro Ser Pro Arg Ile Glu Leu Leu His Asn
                340                 345                 350

Ile Asp Pro Asn Phe Val Asp Ser Ser Pro Cys Ser Ala Phe Asn Thr
            355                 360                 365

Ser Val His Ala Ala Ile Arg His Gly Asn Trp Lys Leu Leu Thr Gly
370                 375                 380

Tyr Pro Gly Cys Gly Tyr Trp Phe Pro Pro Ser Gln Tyr Asn Val
385                 390                 395                 400

Ser Glu Ile Pro Ser Ser Asp Pro Pro Thr Lys Thr Leu Trp Leu Phe
                405                 410                 415

Asp Ile Asp Arg Asp Pro Glu Glu Arg His Asp Leu Ser Arg Glu Tyr
            420                 425                 430

Pro His Ile Val Thr Lys Leu Leu Ser Arg Leu Gln Phe Tyr His Lys
        435                 440                 445

His Ser Val Pro Val Tyr Phe Pro Ala Gln Asp Pro Arg Cys Asp Pro
    450                 455                 460

Lys Ala Thr Gly Val Trp Gly Pro Trp Met
465                 470

<210> SEQ ID NO 12
<211> LENGTH: 492
<212> TYPE: PRT
<213> ORGANISM: ARTIFICIAL SEQUENCE
<220> FEATURE:
<223> OTHER INFORMATION: Synthetic Polypeptide

<400> SEQUENCE: 12

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
            20                  25                  30

Gln Pro Gly Cys Ser Val Leu Asp Glu Ala Phe Gln Arg Tyr Arg Asp
        35                  40                  45

Leu Leu Phe Gly Thr Leu Glu Lys Asn Val Leu Val Ser Val Val
    50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                85                  90                  95

Trp Gly Ala Leu Arg Gly Leu Glu Thr Phe Ser Gln Leu Val Trp Lys
            100                 105                 110
```

-continued

Ser Ala Glu Gly Thr Phe Phe Ile Asn Lys Thr Glu Ile Glu Asp Phe
            115                 120                 125

Pro Arg Phe Pro His Arg Gly Leu Leu Asp Thr Ser Arg His Tyr
130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190

Pro Val Thr His Ile Tyr Thr Ala Gln Asp Val Lys Glu Val Ile Glu
            195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
            260                 265                 270

Ser Ser Val Phe Pro Asp Phe Tyr Leu His Leu Gly Gly Asp Glu Val
            275                 280                 285

Asp Phe Thr Cys Trp Lys Ser Asn Pro Glu Ile Gln Asp Phe Met Arg
290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                325                 330                 335

Trp Gln Glu Val Phe Asp Asn Lys Val Lys Ile Gln Pro Asp Thr Ile
            340                 345                 350

Ile Gln Val Trp Arg Glu Asp Ile Pro Val Asn Tyr Met Lys Glu Leu
            355                 360                 365

Glu Leu Val Thr Lys Ala Gly Phe Arg Ala Leu Leu Ser Ala Pro Trp
370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
            420                 425                 430

Leu Val Pro Arg Leu Trp Pro Arg Ala Gly Ala Val Ala Glu Arg Leu
            435                 440                 445

Trp Ser Asn Lys Leu Thr Ser Asp Leu Thr Phe Ala Tyr Glu Arg Leu
450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 13
<211> LENGTH: 492
<212> TYPE: PRT
<213> ORGANISM: ARTIFICIAL SEQUENCE
<220> FEATURE:

<223> OTHER INFORMATION: Synthetic Polypeptide

<400> SEQUENCE: 13

```
Leu Trp Pro Trp Pro Gln Asn Phe Gln Thr Ser Asp Gln Arg Tyr Val
1               5                   10                  15
Leu Tyr Pro Asn Asn Phe Gln Phe Gln Tyr Asp Val Ser Ser Ala Ala
            20                  25                  30
Gln Pro Gly Cys Ser Val Leu Asp Glu Ala Phe Gln Arg Tyr Arg Asp
        35                  40                  45
Leu Leu Phe Gly Thr Leu Glu Lys Asn Val Leu Val Ser Val Val
50                  55                  60
Thr Pro Gly Cys Asn Gln Leu Pro Thr Leu Ser Val Glu Asn Tyr
65                  70                  75                  80
Thr Leu Thr Ile Asn Asp Asp Gln Cys Leu Leu Ser Glu Thr Val
                    85                  90                  95
Trp Gly Ala Leu Arg Gly Leu Glu Thr Phe Ser Gln Leu Val Trp Lys
            100                 105                 110
Ser Ala Glu Gly Thr Phe Phe Ile Asn Lys Thr Glu Ile Glu Asp Phe
            115                 120                 125
Pro Arg Phe Pro His Arg Gly Leu Leu Leu Asp Thr Ser Arg His Tyr
130                 135                 140
Leu Pro Leu Ser Ser Ile Leu Asp Thr Leu Asp Val Met Ala Tyr Asn
145                 150                 155                 160
Lys Leu Asn Val Phe His Trp His Leu Val Asp Asp Pro Ser Phe Pro
                165                 170                 175
Tyr Glu Ser Phe Thr Phe Pro Glu Leu Met Arg Lys Gly Ser Tyr Asn
            180                 185                 190
Pro Val Thr His Ile Tyr Thr Ala Gln Asp Val Lys Glu Val Ile Glu
            195                 200                 205
Tyr Ala Arg Leu Arg Gly Ile Arg Val Leu Ala Glu Phe Asp Thr Pro
210                 215                 220
Gly His Thr Leu Ser Trp Gly Pro Gly Ile Pro Gly Leu Leu Thr Pro
225                 230                 235                 240
Cys Tyr Ser Gly Ser Glu Pro Ser Gly Thr Phe Gly Pro Val Asn Pro
                245                 250                 255
Ser Leu Asn Asn Thr Tyr Glu Phe Met Ser Thr Phe Phe Leu Glu Val
            260                 265                 270
Ser Ser Val Phe Pro Asp Phe Tyr Leu His Leu Gly Gly Asp Glu Val
        275                 280                 285
Asp Phe Thr Cys Trp Lys Ser Asn Pro Glu Ile Gln Asp Phe Met Arg
290                 295                 300
Lys Lys Gly Phe Gly Glu Asp Phe Lys Gln Leu Glu Ser Phe Tyr Ile
305                 310                 315                 320
Gln Thr Leu Leu Asp Ile Val Ser Ser Tyr Gly Lys Gly Tyr Val Val
                325                 330                 335
Trp Gln Glu Val Phe Asp Asn Lys Val Lys Ile Gln Pro Asp Thr Ile
            340                 345                 350
Ile Gln Val Trp Arg Glu Asp Ile Pro Val Asn Tyr Met Lys Glu Leu
        355                 360                 365
Glu Leu Val Thr Lys Ala Gly Phe Arg Ala Leu Leu Ser Ala Pro Trp
370                 375                 380
Tyr Leu Asn Arg Ile Ser Tyr Gly Pro Asp Trp Lys Asp Phe Tyr Val
385                 390                 395                 400
```

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
            420                 425                 430

Leu Val Pro Arg Leu Trp Pro Arg Ala Gly Ala Val Ala Glu Arg Leu
        435                 440                 445

Trp Ser Asn Lys Leu Thr Ser Asp Leu Thr Phe Ala Tyr Glu Arg Leu
    450                 455                 460

Ser His Phe Arg Cys Glu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 14
<211> LENGTH: 480
<212> TYPE: PRT
<213> ORGANISM: ARTIFICIAL SEQUENCE
<220> FEATURE:
<223> OTHER INFORMATION: Synthetic Polypeptide

<400> SEQUENCE: 14

Pro Ala Leu Trp Pro Leu Pro Leu Ser Val Lys Met Thr Pro Asn Leu
1               5                   10                  15

Leu His Leu Ala Pro Glu Asn Phe Tyr Ile Ser His Ser Pro Asn Ser
            20                  25                  30

Thr Ala Gly Pro Ser Cys Thr Leu Leu Glu Glu Ala Phe Arg Arg Tyr
        35                  40                  45

His Gly Tyr Ile Phe Gly Thr Gln Val Gln Gln Leu Leu Val Ser Ile
    50                  55                  60

Thr Leu Gln Ser Glu Cys Asp Ala Phe Pro Asn Ile Ser Ser Asp Glu
65                  70                  75                  80

Ser Tyr Thr Leu Leu Val Lys Glu Pro Val Ala Val Leu Lys Ala Asn
                85                  90                  95

Arg Val Trp Gly Ala Leu Arg Gly Leu Glu Thr Phe Ser Gln Leu Val
            100                 105                 110

Tyr Gln Asp Ser Tyr Gly Thr Phe Thr Ile Asn Glu Ser Thr Ile Ile
        115                 120                 125

Asp Ser Pro Arg Phe Ser His Arg Gly Ile Leu Ile Asp Thr Ser Arg
    130                 135                 140

His Tyr Leu Pro Val Lys Ile Ile Leu Lys Thr Leu Asp Ala Met Ala
145                 150                 155                 160

Phe Asn Lys Phe Asn Val Leu His Trp His Ile Val Asp Asp Gln Ser
                165                 170                 175

Phe Pro Tyr Gln Ser Ile Thr Phe Pro Glu Leu Ser Asn Lys Gly Ser
            180                 185                 190

Tyr Ser Leu Ser His Val Tyr Thr Pro Asn Asp Val Arg Met Val Ile
        195                 200                 205

Glu Tyr Ala Arg Leu Arg Gly Ile Arg Val Leu Pro Glu Phe Asp Thr
    210                 215                 220

Pro Gly His Thr Leu Ser Trp Gly Lys Gly Gln Lys Asp Leu Leu Thr
225                 230                 235                 240

Pro Cys Tyr Ser Asp Ser Phe Gly Pro Ile Asn Pro Thr Leu Asn Thr
                245                 250                 255

Thr Tyr Ser Phe Leu Thr Thr Phe Phe Lys Glu Ile Ser Glu Val Phe
            260                 265                 270

```
Pro Asp Gln Phe Ile His Leu Gly Gly Asp Glu Val Glu Phe Lys Cys
            275                 280                 285

Trp Glu Ser Asn Pro Lys Ile Gln Asp Phe Met Arg Gln Lys Gly Phe
    290                 295                 300

Gly Thr Asp Phe Lys Lys Leu Glu Ser Phe Tyr Ile Gln Lys Val Leu
305                 310                 315                 320

Asp Ile Ile Ala Thr Ile Asn Lys Gly Ser Ile Val Trp Gln Glu Val
                325                 330                 335

Phe Asp Asp Lys Ala Lys Leu Ala Pro Gly Thr Ile Val Glu Val Trp
            340                 345                 350

Lys Asp Ser Ala Tyr Pro Glu Glu Leu Ser Arg Val Thr Ala Ser Gly
        355                 360                 365

Phe Pro Val Ile Leu Ser Ala Pro Trp Tyr Leu Asp Leu Ile Ser Tyr
    370                 375                 380

Gly Gln Asp Trp Arg Lys Tyr Tyr Lys Val Glu Pro Leu Asp Phe Gly
385                 390                 395                 400

Gly Thr Gln Lys Gln Lys Gln Leu Phe Ile Gly Gly Glu Ala Cys Leu
                405                 410                 415

Trp Gly Glu Tyr Val Asp Ala Thr Asn Leu Thr Pro Arg Leu Trp Pro
            420                 425                 430

Arg Ala Ser Ala Val Gly Glu Arg Leu Trp Ser Ser Lys Asp Val Arg
        435                 440                 445

Asp Met Asp Asp Ala Tyr Asp Arg Leu Thr Arg His Arg Cys Arg Met
    450                 455                 460

Val Glu Arg Gly Ile Ala Ala Gln Pro Leu Tyr Ala Gly Tyr Cys Asn
465                 470                 475                 480

<210> SEQ ID NO 15
<211> LENGTH: 481
<212> TYPE: PRT
<213> ORGANISM: ARTIFICIAL SEQUENCE
<220> FEATURE:
<223> OTHER INFORMATION: Synthetic Polypeptide

<400> SEQUENCE: 15

Pro Ala Leu Trp Pro Leu Pro Leu Ser Val Lys Met Thr Pro Asn Leu
1               5                   10                  15

Leu His Leu Ala Pro Glu Asn Phe Tyr Ile Ser His Ser Pro Asn Ser
            20                  25                  30

Thr Ala Gly Pro Ser Cys Thr Leu Leu Glu Glu Ala Phe Arg Arg Tyr
        35                  40                  45

His Gly Tyr Ile Phe Gly Thr Gln Val Gln Gln Leu Leu Val Ser Ile
    50                  55                  60

Thr Leu Gln Ser Glu Cys Asp Ala Phe Pro Asn Ile Ser Ser Asp Glu
65                  70                  75                  80

Ser Tyr Thr Leu Leu Val Lys Glu Pro Val Ala Val Leu Lys Ala Asn
            85                  90                  95

Arg Val Trp Gly Ala Leu Arg Gly Leu Glu Thr Phe Ser Gln Leu Val
            100                 105                 110

Tyr Gln Asp Ser Tyr Gly Thr Phe Thr Ile Asn Glu Ser Thr Ile Ile
        115                 120                 125

Asp Ser Pro Arg Phe Ser His Arg Gly Ile Leu Ile Asp Thr Ser Arg
    130                 135                 140

His Tyr Leu Pro Val Lys Ile Ile Leu Lys Thr Leu Asp Ala Met Ala
145                 150                 155                 160
```

-continued

```
Phe Asn Lys Phe Asn Val Leu His Trp His Ile Val Asp Asp Gln Ser
            165                 170                 175

Phe Pro Tyr Gln Ser Ile Thr Phe Pro Glu Leu Ser Asn Lys Gly Ser
        180                 185                 190

Tyr Ser Leu Ser His Val Tyr Thr Pro Asn Asp Val Arg Met Val Ile
        195                 200                 205

Glu Tyr Ala Arg Leu Arg Gly Ile Arg Val Leu Pro Glu Phe Asp Thr
    210                 215                 220

Pro Gly His Thr Leu Ser Trp Gly Lys Gly Gln Lys Asp Leu Leu Thr
225                 230                 235                 240

Pro Cys Tyr Ser Leu Asp Ser Phe Gly Pro Ile Asn Pro Thr Leu Asn
                245                 250                 255

Thr Thr Tyr Ser Phe Leu Thr Thr Phe Phe Lys Glu Ile Ser Glu Val
            260                 265                 270

Phe Pro Asp Gln Phe Ile His Leu Gly Gly Asp Glu Val Glu Phe Lys
        275                 280                 285

Cys Trp Glu Ser Asn Pro Lys Ile Gln Asp Phe Met Arg Gln Lys Gly
        290                 295                 300

Phe Gly Thr Asp Phe Lys Lys Leu Glu Ser Phe Tyr Ile Gln Lys Val
305                 310                 315                 320

Leu Asp Ile Ile Ala Thr Ile Asn Lys Gly Ser Ile Val Trp Gln Glu
                325                 330                 335

Val Phe Asp Asp Lys Ala Lys Leu Ala Pro Gly Thr Ile Val Glu Val
            340                 345                 350

Trp Lys Asp Ser Ala Tyr Pro Glu Glu Leu Ser Arg Val Thr Ala Ser
            355                 360                 365

Gly Phe Pro Val Ile Leu Ser Ala Pro Trp Tyr Leu Asp Leu Ile Ser
    370                 375                 380

Tyr Gly Gln Asp Trp Arg Lys Tyr Tyr Lys Val Glu Pro Leu Asp Phe
385                 390                 395                 400

Gly Gly Thr Gln Lys Gln Lys Gln Leu Phe Ile Gly Gly Glu Ala Cys
                405                 410                 415

Leu Trp Gly Glu Tyr Val Asp Ala Thr Asn Leu Thr Pro Arg Leu Trp
            420                 425                 430

Pro Arg Ala Ser Ala Val Gly Glu Arg Leu Trp Ser Ser Lys Asp Val
            435                 440                 445

Arg Asp Met Asp Asp Ala Tyr Asp Arg Leu Thr Arg His Arg Cys Arg
            450                 455                 460

Met Val Glu Arg Gly Ile Ala Ala Gln Pro Leu Tyr Ala Gly Tyr Cys
465                 470                 475                 480

Asn
```

<210> SEQ ID NO 16
<211> LENGTH: 492
<212> TYPE: PRT
<213> ORGANISM: ARTIFICIAL SEQUENCE
<220> FEATURE:
<223> OTHER INFORMATION: Synthetic Polypeptide

<400> SEQUENCE: 16

```
Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
            20                  25                  30

Gln Pro Gly Cys Ser Val Leu Asp Glu Ala Phe Gln Arg Tyr Arg Asp
```

```
                35                  40                  45
Leu Leu Phe Gly Thr Leu Glu Lys Asn Val Leu Val Ser Val Val
 50                  55                  60

Thr Pro Gly Cys Asn Gln Leu Pro Thr Leu Glu Ser Val Glu Asn Tyr
 65                  70                  75                  80

Thr Leu Thr Ile Asn Asp Asp Gln Cys Leu Leu Ser Glu Thr Val
                 85                  90                  95

Trp Gly Ala Leu Arg Gly Leu Glu Thr Phe Ser Gln Leu Val Trp Lys
                100                 105                 110

Ser Ala Glu Gly Thr Phe Phe Ile Asn Lys Thr Glu Ile Glu Asp Phe
                115                 120                 125

Pro Arg Phe Pro His Arg Gly Leu Leu Leu Asp Thr Ser Arg His Tyr
                130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
                180                 185                 190

Pro Val Thr His Ile Tyr Thr Ala Gln Asp Val Lys Glu Val Ile Glu
                195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
                260                 265                 270

Ser Ser Val Phe Pro Asp Phe Tyr Leu His Leu Gly Gly Asp Glu Val
                275                 280                 285

Asp Phe Thr Cys Trp Lys Ser Asn Pro Glu Ile Gln Asp Phe Met Arg
290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                325                 330                 335

Trp Gln Glu Val Phe Asp Asn Lys Val Lys Ile Gln Pro Asp Thr Ile
                340                 345                 350

Ile Gln Val Trp Arg Glu Asp Ile Pro Val Asn Tyr Met Lys Glu Leu
                355                 360                 365

Glu Leu Val Thr Lys Ala Gly Phe Arg Ala Leu Leu Ser Ala Pro Trp
                370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
                420                 425                 430

Leu Val Pro Arg Leu Trp Pro Arg Ala Gly Ala Val Ala Glu Arg Leu
                435                 440                 445

Trp Ser Asn Lys Leu Thr Ser Asp Leu Thr Phe Ala Tyr Glu Arg Leu
                450                 455                 460
```

```
Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 17
<211> LENGTH: 307
<212> TYPE: PRT
<213> ORGANISM: ARTIFICIAL SEQUENCE
<220> FEATURE:
<223> OTHER INFORMATION: Synthetic Polypeptide

<400> SEQUENCE: 17

Val Pro Trp Phe Pro Arg Thr Ile Gln Glu Leu Asp Arg Phe Ala Asn
1               5                   10                  15

Gln Ile Leu Ser Tyr Gly Ala Glu Leu Asp Ala Asp His Pro Gly Phe
            20                  25                  30

Lys Asp Pro Val Tyr Arg Ala Arg Arg Lys Gln Phe Ala Asp Ile Ala
        35                  40                  45

Tyr Asn Tyr Arg His Gly Gln Pro Ile Pro Arg Val Glu Tyr Met Glu
    50                  55                  60

Glu Glu Lys Lys Thr Trp Gly Thr Val Phe Lys Thr Leu Lys Ser Leu
65                  70                  75                  80

Tyr Lys Thr His Ala Cys Tyr Glu Tyr Asn His Ile Phe Pro Leu Leu
                85                  90                  95

Glu Lys Tyr Cys Gly Phe His Glu Asp Asn Ile Pro Gln Leu Glu Asp
            100                 105                 110

Val Ser Gln Phe Leu Gln Thr Cys Thr Gly Phe Arg Leu Arg Pro Val
        115                 120                 125

Ala Gly Leu Leu Ser Ser Arg Asp Phe Leu Gly Leu Ala Phe Arg
    130                 135                 140

Val Phe His Cys Thr Gln Tyr Ile Arg His Gly Ser Lys Pro Met Tyr
145                 150                 155                 160

Thr Pro Glu Pro Asp Ile Cys His Glu Leu Leu Gly His Val Pro Leu
                165                 170                 175

Phe Ser Asp Arg Ser Phe Ala Gln Phe Ser Gln Glu Ile Gly Leu Ala
            180                 185                 190

Ser Leu Gly Ala Pro Asp Glu Tyr Ile Glu Lys Leu Ala Thr Ile Tyr
        195                 200                 205

Trp Phe Thr Val Glu Phe Gly Leu Cys Lys Gln Gly Asp Ser Ile Lys
    210                 215                 220

Ala Tyr Gly Ala Gly Leu Leu Ser Ser Phe Gly Glu Leu Gln Tyr Cys
225                 230                 235                 240

Leu Ser Glu Lys Pro Lys Leu Leu Pro Leu Glu Leu Glu Lys Thr Ala
                245                 250                 255

Ile Gln Asn Tyr Thr Val Thr Glu Phe Gln Pro Leu Tyr Tyr Val Ala
            260                 265                 270

Glu Ser Phe Asn Asp Ala Lys Glu Lys Val Arg Asn Phe Ala Ala Thr
        275                 280                 285

Ile Pro Arg Pro Phe Ser Val Arg Tyr Asp Pro Tyr Thr Gln Arg Ile
    290                 295                 300

Glu Val Leu
305

<210> SEQ ID NO 18
```

<211> LENGTH: 452
<212> TYPE: PRT
<213> ORGANISM: ARTIFICIAL SEQUENCE
<220> FEATURE:
<223> OTHER INFORMATION: Synthetic Polypeptide

<400> SEQUENCE: 18

```
Ala Pro Asp Gln Asp Glu Ile Gln Arg Leu Pro Gly Leu Ala Lys Gln
1               5                   10                  15

Pro Ser Phe Arg Gln Tyr Ser Gly Tyr Leu Lys Ser Ser Gly Ser Lys
            20                  25                  30

His Leu His Tyr Trp Phe Val Glu Ser Gln Lys Asp Pro Glu Asn Ser
        35                  40                  45

Pro Val Val Leu Trp Leu Asn Gly Gly Pro Gly Cys Ser Ser Leu Asp
    50                  55                  60

Gly Leu Leu Thr Glu His Gly Pro Phe Leu Val Gln Pro Asp Gly Val
65                  70                  75                  80

Thr Leu Glu Tyr Asn Pro Tyr Ser Trp Asn Leu Ile Ala Asn Val Leu
                85                  90                  95

Tyr Leu Glu Ser Pro Ala Gly Val Gly Phe Ser Tyr Ser Asp Asp Lys
            100                 105                 110

Phe Tyr Ala Thr Asn Asp Thr Glu Val Ala Gln Ser Asn Phe Glu Ala
        115                 120                 125

Leu Gln Asp Phe Phe Arg Leu Phe Pro Glu Tyr Lys Asn Asn Lys Leu
    130                 135                 140

Phe Leu Thr Gly Glu Ser Tyr Ala Gly Ile Tyr Ile Pro Thr Leu Ala
145                 150                 155                 160

Val Leu Val Met Gln Asp Pro Ser Met Asn Leu Gln Gly Leu Ala Val
                165                 170                 175

Gly Asn Gly Leu Ser Ser Tyr Glu Gln Asn Asp Asn Ser Leu Val Tyr
            180                 185                 190

Phe Ala Tyr Tyr His Gly Leu Leu Gly Asn Arg Leu Trp Ser Ser Leu
        195                 200                 205

Gln Thr His Cys Cys Ser Gln Asn Lys Cys Asn Phe Tyr Asp Asn Lys
    210                 215                 220

Asp Leu Glu Cys Val Thr Asn Leu Gln Glu Val Ala Arg Ile Val Gly
225                 230                 235                 240

Asn Ser Gly Leu Asn Ile Tyr Asn Leu Tyr Ala Pro Cys Ala Gly Gly
                245                 250                 255

Val Pro Ser His Phe Arg Tyr Glu Lys Asp Thr Val Val Gln Asp
            260                 265                 270

Leu Gly Asn Ile Phe Thr Arg Leu Pro Leu Lys Arg Met Trp His Gln
        275                 280                 285

Ala Leu Leu Arg Ser Gly Asp Lys Val Arg Met Asp Pro Pro Cys Thr
    290                 295                 300

Asn Thr Thr Ala Ala Ser Thr Tyr Leu Asn Asn Pro Tyr Val Arg Lys
305                 310                 315                 320

Ala Leu Asn Ile Pro Glu Gln Leu Pro Gln Trp Asp Met Cys Asn Phe
                325                 330                 335

Leu Val Asn Leu Gln Tyr Arg Arg Leu Tyr Arg Ser Met Asn Ser Gln
            340                 345                 350

Tyr Leu Lys Leu Leu Ser Ser Gln Lys Tyr Gln Ile Leu Leu Tyr Asn
        355                 360                 365

Gly Asp Val Asp Met Ala Cys Asn Phe Met Gly Asp Glu Trp Phe Val
    370                 375                 380
```

```
Asp Ser Leu Asn Gln Lys Met Glu Val Gln Arg Arg Pro Trp Leu Val
385                 390                 395                 400

Lys Tyr Gly Asp Ser Gly Glu Gln Ile Ala Gly Phe Val Lys Glu Phe
                405                 410                 415

Ser His Ile Ala Phe Leu Thr Ile Lys Gly Ala Gly His Met Val Pro
            420                 425                 430

Thr Asp Lys Pro Leu Ala Ala Phe Thr Met Phe Ser Arg Phe Leu Asn
        435                 440                 445

Lys Gln Pro Tyr
    450

<210> SEQ ID NO 19
<211> LENGTH: 145
<212> TYPE: PRT
<213> ORGANISM: ARTIFICIAL SEQUENCE
<220> FEATURE:
<223> OTHER INFORMATION: Synthetic Polypeptide

<400> SEQUENCE: 19

Leu Pro Gln Ser Phe Leu Leu Lys Cys Leu Glu Gln Val Arg Lys Ile
1               5                   10                  15

Gln Gly Asp Gly Ala Ala Leu Gln Glu Lys Leu Cys Ala Thr Tyr Lys
            20                  25                  30

Leu Cys His Pro Glu Glu Leu Val Leu Leu Gly His Ser Leu Gly Ile
        35                  40                  45

Pro Trp Ala Pro Leu Leu Ala Gly Cys Leu Ser Gln Leu His Ser Gly
    50                  55                  60

Leu Phe Leu Tyr Gln Gly Leu Leu Gln Ala Leu Glu Gly Ile Ser Pro
65                  70                  75                  80

Glu Leu Gly Pro Thr Leu Asp Thr Leu Gln Leu Asp Val Ala Asp Phe
                85                  90                  95

Ala Thr Thr Ile Trp Gln Gln Met Glu Glu Leu Gly Met Met Pro Ala
            100                 105                 110

Phe Ala Ser Ala Phe Gln Arg Arg Ala Gly Gly Val Leu Val Ala Ser
        115                 120                 125

His Leu Gln Ser Phe Leu Glu Val Ser Tyr Arg Val Leu Arg His Leu
    130                 135                 140

Ala
145

<210> SEQ ID NO 20
<211> LENGTH: 105
<212> TYPE: PRT
<213> ORGANISM: ARTIFICIAL SEQUENCE
<220> FEATURE:
<223> OTHER INFORMATION: Synthetic Polypeptide

<400> SEQUENCE: 20

Glu His Val Asn Ala Ile Gln Glu Ala Arg Arg Leu Leu Asn Leu Ser
1               5                   10                  15

Arg Asp Thr Ala Ala Glu Met Asn Glu Thr Val Glu Val Ile Ser Glu
            20                  25                  30

Met Phe Asp Leu Gln Glu Pro Thr Cys Leu Gln Thr Arg Leu Glu Leu
        35                  40                  45

Tyr Lys Gln Gly Leu Arg Gly Ser Leu Thr Lys Leu Lys Gly Pro Leu
    50                  55                  60

Thr Met Met Ala Ser His Tyr Lys Gln His Cys Pro Pro Thr Pro Glu
```

```
                65                  70                  75                  80
Thr Ser Cys Ala Thr Gln Ile Ile Thr Phe Glu Ser Phe Lys Glu Asn
                    85                  90                  95
Leu Lys Asp Phe Leu Leu Val Ile Pro
                100                 105

<210> SEQ ID NO 21
<211> LENGTH: 165
<212> TYPE: PRT
<213> ORGANISM: ARTIFICIAL SEQUENCE
<220> FEATURE:
<223> OTHER INFORMATION: Synthetic Polypeptide

<400> SEQUENCE: 21

Cys Asp Leu Pro Gln Thr His Ser Leu Gly Ser Arg Arg Thr Leu Met
1               5                  10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 22
<211> LENGTH: 166
<212> TYPE: PRT
<213> ORGANISM: ARTIFICIAL SEQUENCE
<220> FEATURE:
<223> OTHER INFORMATION: Synthetic Polypeptide

<400> SEQUENCE: 22

Met Ser Tyr Asn Leu Leu Gly Phe Leu Gln Arg Ser Ser Asn Phe Gln
1               5                  10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95
```

```
His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 23
<211> LENGTH: 242
<212> TYPE: PRT
<213> ORGANISM: ARTIFICIAL SEQUENCE
<220> FEATURE:
<223> OTHER INFORMATION: Synthetic Polypeptide

<400> SEQUENCE: 23

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30

Ile Leu Lys Asn Trp Lys Glu Glu Ser Asp Arg Lys Ile Met Gln Ser
        35                  40                  45

Gln Ile Val Ser Phe Tyr Phe Lys Leu Phe Lys Asn Phe Lys Asp Asp
    50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Arg Asp Asp Phe Glu Lys Leu
            85                  90                  95

Thr Asn Tyr Ser Val Thr Asp Leu Asn Val Gln Arg Lys Ala Ile Asp
            100                 105                 110

Glu Leu Ile Gln Val Met Ala Glu Leu Gly Ala Asn Val Ser Gly Glu
        115                 120                 125

Phe Val Lys Glu Ala Glu Asn Leu Lys Lys Tyr Phe Asn Asp Asn Gly
    130                 135                 140

Thr Leu Phe Leu Gly Ile Leu Lys Asn Trp Lys Glu Glu Ser Asp Arg
145                 150                 155                 160

Lys Ile Met Gln Ser Gln Ile Val Ser Phe Tyr Phe Lys Leu Phe Lys
                165                 170                 175

Asn Phe Lys Asp Asp Gln Ser Ile Gln Lys Ser Val Glu Thr Ile Lys
            180                 185                 190

Glu Asp Met Asn Val Lys Phe Phe Asn Ser Asn Lys Lys Lys Arg Asp
        195                 200                 205

Asp Phe Glu Lys Leu Thr Asn Tyr Ser Val Thr Asp Leu Asn Val Gln
    210                 215                 220

Arg Lys Ala Ile His Glu Leu Ile Gln Val Met Ala Glu Leu Ser Pro
225                 230                 235                 240

Ala Ala

<210> SEQ ID NO 24
<211> LENGTH: 122
<212> TYPE: PRT
<213> ORGANISM: ARTIFICIAL SEQUENCE
<220> FEATURE:
<223> OTHER INFORMATION: Synthetic Polypeptide
```

<400> SEQUENCE: 24

```
Ser Thr Lys Lys Thr Gln Leu Gln Leu Glu His Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Phe Lys Phe Tyr Met Pro Lys Lys Ala Thr Glu Leu
        35                  40                  45

Lys His Leu Gln Cys Leu Glu Glu Leu Lys Pro Leu Glu Glu Val
    50                  55                  60

Leu Asn Leu Ala Gln Asn Phe His Leu Arg Pro Arg Asp Leu Ile Ser
65                  70                  75                  80

Asn Ile Asn Val Ile Val Leu Glu Leu Lys Gly Phe Met Cys Glu Tyr
                85                  90                  95

Ala Asp Glu Thr Ala Thr Ile Val Glu Phe Leu Asn Arg Trp Ile Thr
            100                 105                 110

Phe Cys Gln Ser Ile Ile Ser Thr Leu Thr
            115                 120
```

```
<210> SEQ ID NO 25
<211> LENGTH: 152
<212> TYPE: PRT
<213> ORGANISM: ARTIFICIAL SEQUENCE
<220> FEATURE:
<223> OTHER INFORMATION: Synthetic Polypeptide
```

<400> SEQUENCE: 25

```
Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser
145                 150
```

```
<210> SEQ ID NO 26
<211> LENGTH: 148
<212> TYPE: PRT
<213> ORGANISM: ARTIFICIAL SEQUENCE
<220> FEATURE:
<223> OTHER INFORMATION: Synthetic Polypeptide
```

<400> SEQUENCE: 26

```
Asp Lys Pro Val Ala His Val Val Ala Asn Pro Gln Ala Glu Gly Gln
1               5                   10                  15
```

```
Leu Gln Trp Ser Asn Arg Arg Ala Asn Ala Leu Leu Ala Asn Gly Val
         20                  25                  30

Glu Leu Arg Asp Asn Gln Leu Val Pro Ile Glu Gly Leu Phe Leu
         35                  40                  45

Ile Tyr Ser Gln Val Leu Phe Lys Gly Gln Gly Cys Pro Ser Thr His
 50                  55                  60

Val Leu Leu Thr His Thr Ile Ser Arg Ile Ala Val Ser Tyr Gln Thr
 65                  70                  75                  80

Lys Val Asn Leu Leu Ser Ala Ile Lys Ser Pro Cys Gln Arg Glu Thr
                 85                  90                  95

Pro Glu Gly Ala Glu Ala Lys Pro Trp Tyr Glu Pro Ile Tyr Leu Gly
                100                 105                 110

Gly Val Phe Gln Leu Glu Lys Gly Asp Arg Leu Ser Ala Glu Ile Asn
                115                 120                 125

Arg Pro Asp Tyr Leu Asp Phe Ala Glu Ser Gly Gln Val Tyr Phe Gly
                130                 135                 140

Ile Ile Ala Leu
145

<210> SEQ ID NO 27
<211> LENGTH: 144
<212> TYPE: PRT
<213> ORGANISM: ARTIFICIAL SEQUENCE
<220> FEATURE:
<223> OTHER INFORMATION: Synthetic Polypeptide

<400> SEQUENCE: 27

Lys Pro Ala Ala His Leu Ile Gly Asp Pro Ser Lys Gln Asn Ser Leu
 1               5                  10                  15

Leu Trp Arg Ala Asn Thr Asp Arg Ala Phe Leu Gln Asp Gly Phe Ser
                 20                  25                  30

Leu Ser Asn Asn Ser Leu Leu Val Pro Thr Ser Gly Ile Tyr Phe Val
                 35                  40                  45

Tyr Ser Gln Val Val Phe Ser Gly Lys Ala Tyr Ser Pro Lys Ala Thr
 50                  55                  60

Ser Ser Pro Leu Tyr Leu Ala His Glu Val Gln Leu Phe Ser Ser Gln
 65                  70                  75                  80

Tyr Pro Phe His Val Pro Leu Leu Ser Ser Gln Lys Met Val Tyr Pro
                 85                  90                  95

Gly Leu Gln Glu Pro Trp Leu His Ser Met Tyr His Gly Ala Ala Phe
                100                 105                 110

Gln Leu Thr Gln Gly Asp Gln Leu Ser Thr His Thr Asp Gly Ile Pro
                115                 120                 125

His Leu Val Leu Ser Pro Ser Thr Val Phe Phe Gly Ala Phe Ala Leu
                130                 135                 140

<210> SEQ ID NO 28
<211> LENGTH: 166
<212> TYPE: PRT
<213> ORGANISM: ARTIFICIAL SEQUENCE
<220> FEATURE:
<223> OTHER INFORMATION: Synthetic Polypeptide

<400> SEQUENCE: 28

Ala Pro Pro Arg Leu Ile Cys Asp Ser Arg Val Leu Glu Arg Tyr Leu
 1               5                  10                  15

Leu Glu Ala Lys Glu Ala Glu Lys Ile Thr Thr Gly Cys Ala Glu His
```

```
            20                  25                  30

Cys Ser Leu Asn Glu Lys Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Lys Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Asn Ser Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 29
<211> LENGTH: 21
<212> TYPE: PRT
<213> ORGANISM: ARTIFICIAL SEQUENCE
<220> FEATURE:
<223> OTHER INFORMATION: Synthetic Polypeptide

<400> SEQUENCE: 29

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 30
<211> LENGTH: 29
<212> TYPE: PRT
<213> ORGANISM: ARTIFICIAL SEQUENCE
<220> FEATURE:
<223> OTHER INFORMATION: Synthetic Polypeptide

<400> SEQUENCE: 30

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 31
<211> LENGTH: 166
<212> TYPE: PRT
<213> ORGANISM: ARTIFICIAL SEQUENCE
<220> FEATURE:
<223> OTHER INFORMATION: Synthetic Polypeptide

<400> SEQUENCE: 31

Phe Pro Thr Ile Pro Leu Ser Arg Leu Ala Asp Asn Ala Trp Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Ile His Ser Phe Trp Trp Asn Pro
        35                  40                  45
```

```
Gln Thr Ser Leu Cys Pro Ser Glu Ser Ile Pro Thr Pro Ser Asn Lys
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Ala Leu Leu Lys Asn Tyr Gly Leu Leu Tyr Cys Phe Asn Lys Asp
    130                 135                 140

Met Ser Lys Val Ser Thr Tyr Leu Arg Thr Val Gln Cys Arg Ser Val
145                 150                 155                 160

Glu Gly Ser Cys Gly Phe
                165

<210> SEQ ID NO 32
<211> LENGTH: 242
<212> TYPE: PRT
<213> ORGANISM: ARTIFICIAL SEQUENCE
<220> FEATURE:
<223> OTHER INFORMATION: Synthetic Polypeptide

<400> SEQUENCE: 32

Cys His His Arg Ile Cys His Cys Ser Asn Arg Val Phe Leu Cys Gln
1               5                   10                  15

Glu Ser Lys Val Thr Glu Ile Pro Ser Asp Leu Pro Arg Asn Ala Ile
                20                  25                  30

Glu Leu Arg Phe Val Leu Thr Lys Leu Arg Val Ile Gln Lys Gly Ala
            35                  40                  45

Phe Ser Gly Phe Gly Asp Leu Glu Lys Ile Glu Ile Ser Gln Asn Asp
    50                  55                  60

Val Leu Glu Val Ile Glu Ala Asp Val Phe Ser Asn Leu Pro Lys Leu
65                  70                  75                  80

His Glu Ile Arg Ile Glu Lys Ala Asn Asn Leu Leu Tyr Ile Asn Pro
                85                  90                  95

Glu Ala Phe Gln Asn Leu Pro Asn Leu Gln Tyr Leu Leu Ile Ser Asn
                100                 105                 110

Thr Gly Ile Lys His Leu Pro Asp Val His Lys Ile His Ser Leu Gln
            115                 120                 125

Lys Val Leu Leu Asp Ile Gln Asp Asn Ile Asn Ile His Thr Ile Glu
    130                 135                 140

Arg Asn Ser Phe Val Gly Leu Ser Phe Glu Ser Val Ile Leu Trp Leu
145                 150                 155                 160

Asn Lys Asn Gly Ile Gln Glu Ile His Asn Cys Ala Phe Asn Gly Thr
                165                 170                 175

Gln Leu Asp Glu Leu Asn Leu Ser Asp Asn Asn Asn Leu Glu Glu Leu
                180                 185                 190

Pro Asn Asp Val Phe His Gly Ala Ser Gly Pro Val Ile Leu Asp Ile
            195                 200                 205

Ser Arg Thr Arg Ile His Ser Leu Pro Ser Tyr Gly Leu Glu Asn Leu
    210                 215                 220

Lys Lys Leu Arg Ala Arg Ser Thr Tyr Asn Leu Lys Lys Leu Pro Thr
225                 230                 235                 240
```

Leu Glu

<210> SEQ ID NO 33
<211> LENGTH: 130
<212> TYPE: PRT
<213> ORGANISM: ARTIFICIAL SEQUENCE
<220> FEATURE:
<223> OTHER INFORMATION: Synthetic Polypeptide

<400> SEQUENCE: 33

```
Ile Gln Lys Val Gln Asp Asp Thr Lys Thr Leu Ile Lys Thr Ile Val
1               5                   10                  15

Thr Arg Ile Asn Asp Ile Leu Asp Phe Ile Pro Gly Leu His Pro Ile
            20                  25                  30

Leu Thr Leu Ser Lys Met Asp Gln Thr Leu Ala Val Tyr Gln Gln Ile
        35                  40                  45

Leu Thr Ser Met Pro Ser Arg Asn Val Ile Gln Ile Ser Asn Asp Leu
    50                  55                  60

Glu Asn Leu Arg Asp Leu Leu His Val Leu Ala Phe Ser Lys Ser Cys
65                  70                  75                  80

His Leu Pro Glu Ala Ser Gly Leu Glu Thr Leu Asp Ser Leu Gly Gly
                85                  90                  95

Val Leu Glu Ala Ser Gly Tyr Ser Thr Glu Val Val Ala Leu Ser Arg
            100                 105                 110

Leu Gln Gly Ser Leu Gln Asp Met Leu Trp Gln Leu Asp Leu Ser Pro
        115                 120                 125

Gly Cys
    130
```

<210> SEQ ID NO 34
<211> LENGTH: 62
<212> TYPE: PRT
<213> ORGANISM: ARTIFICIAL SEQUENCE
<220> FEATURE:
<223> OTHER INFORMATION: Synthetic Polypeptide

<400> SEQUENCE: 34

```
Pro Glu Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Arg Ala Pro Gln Thr Gly Ile Val Asp Glu Cys Cys Phe
        35                  40                  45

Arg Ser Cys Asp Leu Arg Arg Leu Glu Met Tyr Cys Ala Pro
    50                  55                  60
```

<210> SEQ ID NO 35
<211> LENGTH: 125
<212> TYPE: PRT
<213> ORGANISM: ARTIFICIAL SEQUENCE
<220> FEATURE:
<223> OTHER INFORMATION: Synthetic Polypeptide

<400> SEQUENCE: 35

```
Met Tyr Arg Ser Ala Phe Ser Val Gly Leu Glu Thr Arg Val Thr Val
1               5                   10                  15

Pro Asn Val Pro Ile Arg Phe Thr Lys Ile Phe Tyr Asn Gln Gln Asn
            20                  25                  30

His Tyr Asp Gly Ser Thr Gly Lys Phe Tyr Cys Asn Ile Pro Gly Leu
```

```
                35                  40                  45
Tyr Tyr Phe Ser Tyr His Ile Thr Val Tyr Met Lys Asp Val Lys Val
     50                  55                  60
Ser Leu Phe Lys Lys Asp Lys Ala Val Leu Phe Thr Tyr Asp Gln Tyr
 65                  70                  75                  80
Gln Glu Asn Val Asp Gln Ala Ser Gly Ser Val Leu Leu His Leu Glu
                 85                  90                  95
Val Gly Asp Gln Val Trp Leu Gln Val Tyr Tyr Ala Asp Asn Val Asn
                100                 105                 110
Asp Ser Thr Phe Thr Gly Phe Leu Leu Tyr His Asp Thr
                115                 120                 125

<210> SEQ ID NO 36
<211> LENGTH: 111
<212> TYPE: PRT
<213> ORGANISM: ARTIFICIAL SEQUENCE
<220> FEATURE:
<223> OTHER INFORMATION: Synthetic Polypeptide

<400> SEQUENCE: 36

Met Tyr Arg Ser Ala Phe Ser Val Gly Leu Pro Asn Val Pro Ile Arg
 1               5                  10                  15
Phe Thr Lys Ile Phe Tyr Asn Gln Gln Asn His Tyr Asp Gly Ser Thr
             20                  25                  30
Gly Lys Phe Tyr Cys Asn Ile Pro Gly Leu Tyr Tyr Phe Ser Tyr His
         35                  40                  45
Ile Thr Val Tyr Met Lys Asp Val Lys Val Ser Leu Phe Lys Lys Asp
     50                  55                  60
Lys Val Leu Phe Thr Tyr Asp Gln Tyr Gln Glu Lys Val Asp Gln Ala
 65                  70                  75                  80
Ser Gly Ser Val Leu Leu His Leu Glu Val Gly Asp Gln Val Trp Leu
                 85                  90                  95
Gln Val Tyr Asp Ser Thr Phe Thr Gly Phe Leu Leu Tyr His Asp
                100                 105                 110

<210> SEQ ID NO 37
<211> LENGTH: 102
<212> TYPE: PRT
<213> ORGANISM: ARTIFICIAL SEQUENCE
<220> FEATURE:
<223> OTHER INFORMATION: Synthetic Polypeptide

<400> SEQUENCE: 37

Met Tyr Arg Ser Ala Phe Ser Val Gly Leu Glu Thr Arg Val Thr Val
 1               5                  10                  15
Pro Ile Arg Phe Thr Lys Ile Phe Tyr Asn Gln Gln Asn His Tyr Asp
             20                  25                  30
Gly Ser Thr Gly Lys Phe Tyr Cys Asn Ile Pro Gly Leu Tyr Tyr Phe
         35                  40                  45
Ser Tyr His Ile Thr Val Asp Val Lys Val Ser Leu Phe Lys Lys Asp
     50                  55                  60
Lys Ala Val Leu Phe Thr Gln Ala Ser Gly Ser Val Leu Leu His Leu
 65                  70                  75                  80
Glu Val Gly Asp Gln Val Trp Leu Gln Asn Asp Ser Thr Phe Thr Gly
                 85                  90                  95
Phe Leu Leu Tyr His Asp
                100
```

<210> SEQ ID NO 38
<211> LENGTH: 693
<212> TYPE: PRT
<213> ORGANISM: ARTIFICIAL SEQUENCE
<220> FEATURE:
<223> OTHER INFORMATION: Synthetic Polypeptide

<400> SEQUENCE: 38

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ala Ala Ser Ala Arg Ala Trp Pro Lys Met
    210                 215                 220

His Thr Val Asn Gly Tyr Val Asn Arg Ser Leu Pro Gly Leu Ile Gly
225                 230                 235                 240

Cys His Arg Lys Ser Val Tyr Trp His Val Ile Gly Met Gly Thr Thr
                245                 250                 255

Pro Glu Val His Ser Ile Phe Leu Glu Gly His Thr Phe Leu Val Arg
            260                 265                 270

Asn His Arg Gln Ala Ser Leu Glu Ile Ser Pro Ile Thr Phe Leu Thr
        275                 280                 285

Ala Gln Thr Leu Leu Met Asp Leu Gly Gln Phe Leu Leu Phe Cys His
    290                 295                 300

Ile Ser Ser His Gln His Asp Gly Met Glu Ala Tyr Val Lys Val Asp
305                 310                 315                 320

Ser Cys Pro Glu Glu Pro Gln Phe Asp Asp Asn Ser Pro Ser Phe
                325                 330                 335

Ile Gln Ile Arg Ser Val Ala Lys Lys His Pro Lys Thr Trp Val His
            340                 345                 350

Tyr Ile Ala Ala Glu Glu Glu Asp Trp Asp Tyr Ala Pro Leu Val Leu
        355                 360                 365
```

```
Ala Pro Asp Asp Arg Ser Tyr Lys Ser Gln Tyr Leu Asn Asn Gly Pro
    370                 375                 380

Gln Arg Ile Gly Arg Lys Tyr Lys Lys Val Arg Phe Met Ala Tyr Thr
385                 390                 395                 400

Asp Glu Thr Phe Lys Thr Arg Glu Ala Ile Gln His Glu Ser Gly Ile
            405                 410                 415

Leu Gly Pro Leu Leu Tyr Gly Glu Val Gly Asp Thr Leu Leu Ile Ile
        420                 425                 430

Phe Lys Asn Gln Ala Ser Arg Pro Tyr Asn Ile Tyr Pro His Gly Ile
    435                 440                 445

Thr Asp Val Arg Pro Leu Tyr Ser Arg Arg Leu Pro Lys Gly Val Lys
450                 455                 460

His Leu Lys Asp Phe Pro Ile Leu Pro Gly Glu Ile Phe Lys Tyr Lys
465                 470                 475                 480

Trp Thr Val Thr Val Glu Asp Gly Pro Thr Lys Ser Asp Pro Arg Cys
            485                 490                 495

Leu Thr Arg Tyr Tyr Ser Ser Phe Val Asn Met Glu Arg Asp Leu Ala
        500                 505                 510

Ser Gly Leu Ile Gly Pro Leu Leu Ile Cys Tyr Lys Glu Ser Val Asp
    515                 520                 525

Gln Arg Gly Asn Gln Ile Met Ser Asp Lys Arg Asn Val Ile Leu Phe
530                 535                 540

Ser Val Phe Asp Glu Asn Arg Ser Trp Tyr Leu Thr Glu Asn Ile Gln
545                 550                 555                 560

Arg Phe Leu Pro Asn Pro Ala Gly Val Gln Leu Glu Asp Pro Glu Phe
            565                 570                 575

Gln Ala Ser Asn Ile Met His Ser Ile Asn Gly Tyr Val Phe Asp Ser
        580                 585                 590

Leu Gln Leu Ser Val Cys Leu His Glu Val Ala Tyr Trp Tyr Ile Leu
    595                 600                 605

Ser Ile Gly Ala Gln Thr Asp Phe Leu Ser Val Phe Phe Ser Gly Tyr
610                 615                 620

Thr Phe Lys His Lys Met Val Tyr Glu Asp Thr Leu Thr Leu Phe Pro
625                 630                 635                 640

Phe Ser Gly Glu Thr Val Phe Met Ser Met Glu Asn Pro Gly Leu Trp
            645                 650                 655

Ile Leu Gly Cys His Asn Ser Asp Phe Arg Asn Arg Gly Met Thr Ala
        660                 665                 670

Leu Leu Lys Val Ser Ser Cys Asp Lys Asn Thr Gly Asp Tyr Tyr Glu
    675                 680                 685

Asp Ser Tyr Glu Asp
    690

<210> SEQ ID NO 39
<211> LENGTH: 644
<212> TYPE: PRT
<213> ORGANISM: ARTIFICIAL SEQUENCE
<220> FEATURE:
<223> OTHER INFORMATION: Synthetic Polypeptide

<400> SEQUENCE: 39

Arg Ser Phe Gln Lys Lys Thr Arg His Tyr Phe Ile Ala Ala Val Glu
1               5                   10                  15

Arg Leu Trp Asp Tyr Gly Met Ser Ser Pro His Val Leu Arg Asn
            20                  25                  30
```

```
Arg Ala Gln Ser Gly Ser Val Pro Gln Phe Lys Lys Val Phe Gln
             35                  40                  45
Glu Phe Thr Asp Gly Ser Phe Thr Gln Pro Leu Tyr Arg Gly Glu Leu
 50                  55                  60
Asn Glu His Leu Gly Leu Leu Gly Pro Tyr Ile Arg Ala Glu Val Glu
 65                  70                  75                  80
Asp Asn Ile Met Val Thr Phe Arg Asn Gln Ala Ser Arg Pro Tyr Ser
             85                  90                  95
Phe Tyr Ser Ser Leu Ile Ser Tyr Glu Glu Asp Gln Arg Gln Gly Ala
            100                 105                 110
Glu Pro Arg Lys Asn Phe Val Lys Pro Asn Glu Thr Lys Thr Tyr Phe
            115                 120                 125
Trp Lys Val Gln His His Met Ala Pro Thr Lys Asp Glu Phe Asp Cys
            130                 135                 140
Lys Ala Trp Ala Tyr Ser Ser Asp Val Asp Leu Glu Lys Asp Val His
145                 150                 155                 160
Ser Gly Leu Ile Gly Pro Leu Leu Val Cys His Thr Asn Thr Leu Asn
                    165                 170                 175
Pro Ala His Gly Arg Gln Val Thr Val Gln Glu Phe Ala Leu Phe Phe
                    180                 185                 190
Thr Ile Phe Asp Glu Thr Lys Ser Trp Tyr Phe Thr Glu Asn Met Glu
            195                 200                 205
Arg Asn Cys Arg Ala Pro Cys Asn Ile Gln Met Glu Asp Pro Thr Phe
            210                 215                 220
Lys Glu Asn Tyr Arg Phe His Ala Ile Asn Gly Tyr Ile Met Asp Thr
225                 230                 235                 240
Leu Pro Gly Leu Val Met Ala Gln Asp Gln Arg Ile Arg Trp Tyr Leu
                    245                 250                 255
Leu Ser Met Gly Ser Asn Glu Asn Ile His Ser Ile His Phe Ser Gly
                    260                 265                 270
His Val Phe Thr Val Arg Lys Lys Glu Glu Tyr Lys Met Ala Leu Tyr
            275                 280                 285
Asn Leu Tyr Pro Gly Val Phe Glu Thr Val Glu Met Leu Pro Ser Lys
            290                 295                 300
Ala Gly Ile Trp Arg Val Glu Cys Leu Ile Gly Glu His Leu His Ala
305                 310                 315                 320
Gly Met Ser Thr Leu Phe Leu Val Tyr Ser Asn Lys Cys Gln Thr Pro
                    325                 330                 335
Leu Gly Met Ala Ser Gly His Ile Arg Asp Phe Gln Ile Thr Ala Ser
                    340                 345                 350
Gly Gln Tyr Gly Gln Trp Ala Pro Lys Leu Ala Arg Leu His Tyr Ser
            355                 360                 365
Gly Ser Ile Asn Ala Trp Ser Thr Lys Glu Pro Phe Ser Trp Ile Lys
            370                 375                 380
Val Asp Leu Leu Ala Pro Met Ile Ile His Gly Ile Lys Thr Gln Gly
385                 390                 395                 400
Ala Arg Gln Lys Phe Ser Ser Leu Tyr Ile Ser Gln Phe Ile Ile Met
                    405                 410                 415
Tyr Ser Leu Asp Gly Lys Lys Trp Gln Thr Tyr Arg Gly Asn Ser Thr
                    420                 425                 430
Gly Thr Leu Met Val Phe Phe Gly Asn Val Asp Ser Ser Gly Ile Lys
            435                 440                 445
His Asn Ile Phe Asn Pro Pro Ile Ile Ala Arg Tyr Ile Arg Leu His
```

```
                450                 455                 460
Pro Thr His Tyr Ser Ile Arg Ser Thr Leu Arg Met Glu Leu Met Gly
465                 470                 475                 480

Cys Asp Leu Asn Ser Cys Ser Met Pro Leu Gly Met Glu Ser Lys Ala
                485                 490                 495

Ile Ser Asp Ala Gln Ile Thr Ala Ser Ser Tyr Phe Thr Asn Met Phe
                500                 505                 510

Ala Thr Trp Ser Pro Ser Lys Ala Arg Leu His Leu Gln Gly Arg Ser
                515                 520                 525

Asn Ala Trp Arg Pro Gln Val Asn Asn Pro Lys Glu Trp Leu Gln Val
                530                 535                 540

Asp Phe Gln Lys Thr Met Lys Val Thr Gly Val Thr Thr Gln Gly Val
545                 550                 555                 560

Lys Ser Leu Leu Thr Ser Met Tyr Val Lys Glu Phe Leu Ile Ser Ser
                565                 570                 575

Ser Gln Asp Gly His Gln Trp Thr Leu Phe Phe Gln Asn Gly Lys Val
                580                 585                 590

Lys Val Phe Gln Gly Asn Gln Asp Ser Phe Thr Pro Val Val Asn Ser
                595                 600                 605

Leu Asp Pro Pro Leu Leu Thr Arg Tyr Leu Arg Ile His Pro Gln Ser
                610                 615                 620

Trp Val His Gln Ile Ala Leu Arg Met Glu Val Leu Gly Cys Glu Ala
625                 630                 635                 640

Gln Asp Leu Tyr

<210> SEQ ID NO 40
<211> LENGTH: 578
<212> TYPE: PRT
<213> ORGANISM: ARTIFICIAL SEQUENCE
<220> FEATURE:
<223> OTHER INFORMATION: Synthetic Polypeptide

<400> SEQUENCE: 40

Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
                20                  25                  30

Glu Asp His Val Lys Leu Val Asn Glu Val Thr Glu Phe Ala Lys Thr
                35                  40                  45

Cys Val Ala Asp Glu Ser Ala Glu Asn Cys Asp Lys Ser Leu His Thr
        50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
                100                 105                 110

Arg Pro Glu Val Asp Val Met Cys Thr Ala Phe His Asp Asn Glu Glu
                115                 120                 125

Thr Phe Leu Lys Lys Tyr Leu Tyr Glu Ile Ala Arg Arg His Pro Tyr
                130                 135                 140

Phe Tyr Ala Pro Glu Leu Leu Phe Phe Ala Lys Arg Tyr Lys Ala Ala
145                 150                 155                 160

Phe Thr Glu Cys Cys Gln Ala Ala Asp Lys Ala Ala Cys Leu Leu Pro
                165                 170                 175
```

```
Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
        195                 200                 205

Ala Trp Ala Val Ala Arg Leu Ser Gln Arg Phe Pro Lys Ala Glu Phe
    210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
    290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
        355                 360                 365

Val Phe Asp Glu Phe Lys Pro Leu Val Glu Glu Pro Gln Asn Leu Ile
    370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415

Pro Thr Leu Val Glu Val Ser Arg Asn Leu Gly Lys Val Gly Ser Lys
            420                 425                 430

Cys Cys Lys His Pro Glu Ala Lys Arg Met Pro Cys Ala Glu Asp Tyr
        435                 440                 445

Leu Ser Val Val Leu Asn Gln Leu Cys Val Leu His Glu Lys Thr Pro
    450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
                485                 490                 495

Glu Phe Asn Ala Glu Thr Phe Thr Phe His Ala Asp Ile Cys Thr Leu
            500                 505                 510

Ser Glu Lys Glu Arg Gln Ile Lys Lys Gln Thr Ala Leu Val Glu Leu
        515                 520                 525

Val Lys His Lys Pro Lys Ala Thr Lys Glu Gln Leu Lys Ala Val Met
    530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala
```

```
<210> SEQ ID NO 41
<211> LENGTH: 303
<212> TYPE: PRT
<213> ORGANISM: ARTIFICIAL SEQUENCE
<220> FEATURE:
<223> OTHER INFORMATION: Synthetic Polypeptide

<400> SEQUENCE: 41

Ile Lys Gly Gly Leu Phe Ala Asp Ile Ala Ser His Pro Trp Gln Ala
1               5                   10                  15

Ala Ile Phe Ala Lys His His Arg Arg Gly Gly Glu Arg Phe Leu Cys
            20                  25                  30

Gly Gly Ile Leu Ile Ser Ser Cys Trp Ile Leu Ser Ala Ala His Cys
        35                  40                  45

Phe Gln Gln Gln Gln Gln Glu Glu Glu Glu Arg Arg Arg Arg
    50                  55                  60

Phe Phe Phe Phe Phe Pro Pro Pro Pro Pro His His Leu Thr Val
65                  70                  75                  80

Ile Leu Gly Arg Thr Tyr Arg Val Val Pro Gly Glu Glu Glu Gln Lys
                85                  90                  95

Phe Glu Val Glu Lys Tyr Ile Val His Lys Glu Phe Asp Asp Asp Thr
            100                 105                 110

Tyr Asp Asn Asp Ile Ala Leu Leu Gln Leu Lys Ser Ser Ser Ser Ser
        115                 120                 125

Asp Asp Asp Asp Ser Ser Ser Ser Ser Ser Ser Ser Ser Arg
    130                 135                 140

Arg Arg Arg Arg Cys Ala Gln Glu Ser Ser Val Val Arg Thr Val Cys
145                 150                 155                 160

Leu Pro Pro Ala Asp Leu Gln Leu Pro Asp Trp Thr Glu Cys Glu Leu
                165                 170                 175

Ser Gly Tyr Gly Lys His Glu Ala Leu Ser Pro Phe Tyr Ser Glu Arg
            180                 185                 190

Leu Lys Glu Ala His Val Arg Leu Tyr Pro Ser Ser Arg Cys Thr Thr
        195                 200                 205

Thr Ser Ser Ser Gln Gln Gln His Leu Leu Asn Arg Thr Val Thr Asp
    210                 215                 220

Asn Met Leu Cys Ala Gly Asp Thr Thr Thr Arg Arg Arg Ser Ser Ser
225                 230                 235                 240

Asn Asn Asn Leu His Asp Ala Cys Gln Gly Asp Ser Gly Gly Pro Leu
                245                 250                 255

Val Cys Leu Asn Asp Gly Arg Met Thr Leu Val Gly Ile Ile Ser Trp
            260                 265                 270

Gly Leu Gly Cys Gly Gly Gln Gln Lys Asp Val Pro Gly Val Tyr Thr
        275                 280                 285

Lys Val Thr Asn Tyr Leu Asp Trp Ile Arg Asp Asn Met Arg Pro
    290                 295                 300

<210> SEQ ID NO 42
<211> LENGTH: 578
<212> TYPE: PRT
<213> ORGANISM: ARTIFICIAL SEQUENCE
<220> FEATURE:
<223> OTHER INFORMATION: Synthetic Polypeptide

<400> SEQUENCE: 42

Ser Glu Val Ala His Arg Phe Lys Asp Leu Gly Glu Glu Asn Phe Lys
1               5                   10                  15
```

-continued

Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
        35                  40                  45

Cys Val Ala Asp Glu Ser Ala Glu Asn Cys Asp Lys Ser Leu His Thr
50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
        115                 120                 125

Thr Phe Leu Lys Lys Tyr Leu Tyr Glu Ile Ala Arg Arg His Pro Tyr
130                 135                 140

Phe Tyr Ala Pro Glu Leu Leu Phe Phe Ala Lys Arg Tyr Lys Ala Ala
145                 150                 155                 160

Phe Thr Glu Cys Cys Gln Ala Ala Asp Lys Ala Ala Cys Leu Leu Pro
                165                 170                 175

Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
        195                 200                 205

Ala Trp Ala Val Ala Arg Leu Ser Gln Arg Phe Pro Lys Ala Glu Phe
210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
        355                 360                 365

Val Phe Asp Glu Phe Lys Pro Leu Val Glu Glu Pro Gln Asn Leu Ile
370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415

Pro Thr Leu Val Glu Val Ser Arg Asn Leu Gly Lys Val Gly Ser Lys
            420                 425                 430

Cys Cys Lys His Pro Glu Ala Lys Arg Met Pro Cys Ala Glu Asp Tyr

```
                435                 440                 445
Leu Ser Val Val Leu Asn Gln Leu Cys Val Leu His Glu Lys Thr Pro
    450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
                485                 490                 495

Glu Phe Asn Ala Glu Thr Phe Thr Phe His Ala Asp Ile Cys Thr Leu
                500                 505                 510

Ser Glu Lys Glu Arg Gln Ile Lys Lys Gln Thr Ala Leu Val Glu Leu
            515                 520                 525

Val Lys His Lys Pro Lys Ala Thr Lys Glu Gln Leu Lys Ala Val Met
    530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala

<210> SEQ ID NO 43
<211> LENGTH: 141
<212> TYPE: PRT
<213> ORGANISM: ARTIFICIAL SEQUENCE
<220> FEATURE:
<223> OTHER INFORMATION: Synthetic Polypeptide

<400> SEQUENCE: 43

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
                20                  25                  30

Phe Leu Ser Phe Pro Thr Thr Lys Thr Tyr Phe Pro His Phe Asp Leu
            35                  40                  45

Ser His Gly Ser Ala Gln Val Lys Gly His Gly Lys Lys Val Ala Asp
        50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
                100                 105                 110

Leu Pro Ala Glu Phe Thr Pro Ala Val His Ala Ser Leu Asp Lys Phe
            115                 120                 125

Leu Ala Ser Val Ser Thr Val Leu Thr Ser Lys Tyr Arg
        130                 135                 140

<210> SEQ ID NO 44
<211> LENGTH: 146
<212> TYPE: PRT
<213> ORGANISM: ARTIFICIAL SEQUENCE
<220> FEATURE:
<223> OTHER INFORMATION: Synthetic Polypeptide

<400> SEQUENCE: 44

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
```

```
                    20                  25                  30
Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
        50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 45
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 45

Leu Pro Xaa Thr Gly
1               5

<210> SEQ ID NO 46
<211> LENGTH: 11
<212> TYPE: PRT
<213> ORGANISM: ARTIFICIAL SEQUENCE
<220> FEATURE:
<223> OTHER INFORMATION: Synthetic Polypeptide

<400> SEQUENCE: 46

Leu Pro Glu Thr Gly His His His His His
1               5                   10

<210> SEQ ID NO 47
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 47

Leu Pro Arg Thr
1

<210> SEQ ID NO 48
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 48
```

Leu Pro Arg Thr
1

<210> SEQ ID NO 49
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 49

Gly Gly Gly Gly Gly
1               5

<210> SEQ ID NO 50
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 50

Leu Pro Arg Thr
1

<210> SEQ ID NO 51
<211> LENGTH: 11
<212> TYPE: PRT
<213> ORGANISM: ARTIFICIAL SEQUENCE
<220> FEATURE:
<223> OTHER INFORMATION: Synthetic Polypeptide

<400> SEQUENCE: 51

Leu Pro Glu Thr Gly His His His His His His
1               5                   10

<210> SEQ ID NO 52
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 52

Gly Glu Phe Ala Pro Lys
1               5

<210> SEQ ID NO 53
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 53

Leu Pro Glu Thr
1

<210> SEQ ID NO 54
<211> LENGTH: 16
<212> TYPE: PRT
<213> ORGANISM: ARTIFICIAL SEQUENCE
<220> FEATURE:
<223> OTHER INFORMATION: Synthetic Polypeptide

<400> SEQUENCE: 54

Gly Gly Gly Gly Gly Leu Pro Glu Thr Gly His His His His His His

```
                1               5                  10                 15
```

<210> SEQ ID NO 55
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 55

Leu Pro Glu Thr Gly
1               5

<210> SEQ ID NO 56
<211> LENGTH: 12
<212> TYPE: PRT
<213> ORGANISM: ARTIFICIAL SEQUENCE
<220> FEATURE:
<223> OTHER INFORMATION: Synthetic Polypeptide

<400> SEQUENCE: 56

Gly His His His His His His Leu Pro Ser Thr Gly
1               5                  10

<210> SEQ ID NO 57
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 57

Leu Pro Ser Thr
1

<210> SEQ ID NO 58
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 58

Leu Pro Glu Thr Gly Gly
1               5

<210> SEQ ID NO 59
<211> LENGTH: 8
<212> TYPE: PRT
<213> ORGANISM: ARTIFICIAL SEQUENCE
<220> FEATURE:
<223> OTHER INFORMATION: Synthetic Polypeptide

<400> SEQUENCE: 59

Gly Ser His His His His His His
1               5

<210> SEQ ID NO 60
<211> LENGTH: 8
<212> TYPE: PRT
<213> ORGANISM: ARTIFICIAL SEQUENCE
<220> FEATURE:
<223> OTHER INFORMATION: Synthetic Polypeptide

<400> SEQUENCE: 60

Gly Gly Leu Pro Glu Thr Gly Gly
1               5

<210> SEQ ID NO 61
<211> LENGTH: 8
<212> TYPE: PRT
<213> ORGANISM: ARTIFICIAL SEQUENCE
<220> FEATURE:
<223> OTHER INFORMATION: Synthetic Polypeptide

<400> SEQUENCE: 61

Gly Gly Leu Pro Glu Thr Gly Gly
1               5

<210> SEQ ID NO 62
<211> LENGTH: 14
<212> TYPE: PRT
<213> ORGANISM: ARTIFICIAL SEQUENCE
<220> FEATURE:
<223> OTHER INFORMATION: Synthetic Polypeptide

<400> SEQUENCE: 62

Gly Gly Leu Pro Glu Thr Gly Gly His His His His His His
1               5                   10

<210> SEQ ID NO 63
<211> LENGTH: 12
<212> TYPE: PRT
<213> ORGANISM: ARTIFICIAL SEQUENCE
<220> FEATURE:
<223> OTHER INFORMATION: Synthetic Polypeptide

<400> SEQUENCE: 63

Leu Pro Glu Thr Gly Gly His His His His His His
1               5                   10

<210> SEQ ID NO 64
<211> LENGTH: 8
<212> TYPE: PRT
<213> ORGANISM: ARTIFICIAL SEQUENCE
<220> FEATURE:
<223> OTHER INFORMATION: Synthetic Polypeptide

<400> SEQUENCE: 64

Leu Pro Glu Thr Gly Gly Gly Lys
1               5

<210> SEQ ID NO 65
<211> LENGTH: 12
<212> TYPE: PRT
<213> ORGANISM: ARTIFICIAL SEQUENCE
<220> FEATURE:
<223> OTHER INFORMATION: Synthetic Polypeptide

<400> SEQUENCE: 65

Leu Pro Glu Thr Gly Gly His His His His His His
1               5                   10

<210> SEQ ID NO 66
<211> LENGTH: 21
<212> TYPE: PRT
<213> ORGANISM: ARTIFICIAL SEQUENCE
<220> FEATURE:
<223> OTHER INFORMATION: Synthetic Polypeptide

<400> SEQUENCE: 66

Leu Pro Glu Thr Ala Ala Gly Lys Gly Leu Pro Glu Thr Gly Gly His
1               5                   10                  15

His His His His His
            20

<210> SEQ ID NO 67
<211> LENGTH: 21
<212> TYPE: PRT
<213> ORGANISM: ARTIFICIAL SEQUENCE
<220> FEATURE:
<223> OTHER INFORMATION: Synthetic Polypeptide

<400> SEQUENCE: 67

Leu Pro Glu Thr Ala Ala Gly Lys Gly Leu Pro Glu Thr Gly Gly His
1               5                   10                  15

His His His His His
            20

<210> SEQ ID NO 68
<211> LENGTH: 16
<212> TYPE: PRT
<213> ORGANISM: ARTIFICIAL SEQUENCE
<220> FEATURE:
<223> OTHER INFORMATION: Synthetic Polypeptide

<400> SEQUENCE: 68

Leu Pro Glu Thr Ala Ala Gly Lys Gly Leu Pro Glu Thr Gly Gly Gly
1               5                   10                  15

<210> SEQ ID NO 69
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 69

Leu Pro Lys Thr
1

<210> SEQ ID NO 70
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 70

Leu Pro Ile Thr
1

<210> SEQ ID NO 71
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 71

Leu Pro Asp Thr
1

<210> SEQ ID NO 72
<211> LENGTH: 4
<212> TYPE: PRT
<213> ORGANISM: ARTIFICIAL SEQUENCE
<220> FEATURE:
<223> OTHER INFORMATION: Synthetic Polypeptide

```
<400> SEQUENCE: 72

Ser Pro Lys Thr
1

<210> SEQ ID NO 73
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 73

Leu Ala Glu Thr
1

<210> SEQ ID NO 74
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 74

Leu Ala Ala Thr
1

<210> SEQ ID NO 75
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 75

Leu Ala Glu Thr
1

<210> SEQ ID NO 76
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 76

Leu Ala Ser Thr
1

<210> SEQ ID NO 77
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 77

Leu Ala Glu Thr
1

<210> SEQ ID NO 78
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 78
```

Leu Pro Leu Thr
1

<210> SEQ ID NO 79
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 79

Leu Ser Arg Thr
1

<210> SEQ ID NO 80
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 80

Val Pro Asp Thr
1

<210> SEQ ID NO 81
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 81

Ile Pro Gln Thr
1

<210> SEQ ID NO 82
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 82

Tyr Pro Arg Arg
1

<210> SEQ ID NO 83
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 83

Leu Pro Met Thr
1

<210> SEQ ID NO 84
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 84

Leu Pro Leu Thr
1

<210> SEQ ID NO 85
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 85

Leu Ala Phe Thr
1

<210> SEQ ID NO 86
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 86

Leu Pro Gln Thr
1

<210> SEQ ID NO 87
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 87

Asn Ser Lys Thr
1

<210> SEQ ID NO 88
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 88

Asn Pro Gln Thr
1

<210> SEQ ID NO 89
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 89

Asn Ala Lys Thr
1

<210> SEQ ID NO 90
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 90

Asn Pro Gln Ser

```
<210> SEQ ID NO 91
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 91

Leu Pro Lys Thr Gly
1               5

<210> SEQ ID NO 92
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 92

Leu Pro Ala Thr Gly
1               5

<210> SEQ ID NO 93
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 93

Leu Pro Asn Thr Gly
1               5

<210> SEQ ID NO 94
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 94

Leu Pro Xaa Ala Gly
1               5

<210> SEQ ID NO 95
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 95

Leu Pro Asn Ala Gly
1               5

<210> SEQ ID NO 96
<211> LENGTH: 5
<212> TYPE: PRT
<213> ORGANISM: ARTIFICIAL SEQUENCE
<220> FEATURE:
<223> OTHER INFORMATION: Synthetic Polypeptide
```

```
<400> SEQUENCE: 96

Leu Pro Asn Thr Ala
1               5

<210> SEQ ID NO 97
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 97

Leu Gly Xaa Thr Gly
1               5

<210> SEQ ID NO 98
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 98

Leu Gly Ala Thr Gly
1               5

<210> SEQ ID NO 99
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 99

Ile Pro Xaa Thr Gly
1               5

<210> SEQ ID NO 100
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 100

Ile Pro Asn Thr Gly
1               5

<210> SEQ ID NO 101
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 101

Ile Pro Glu Thr Gly
1               5
```

```
<210> SEQ ID NO 102
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be Gln or Lys
<220> FEATURE:
<221> NAME/KEY: misc_feature
<222> LOCATION: (4)..(4)
<223> OTHER INFORMATION: Xaa can be Thr or Ser
<220> FEATURE:
<221> NAME/KEY: misc_feature
<222> LOCATION: (5)..(5)
<223> OTHER INFORMATION: Xaa can be Asn, Gly or Ser

<400> SEQUENCE: 102

Asn Pro Xaa Xaa Xaa
1               5

<210> SEQ ID NO 103
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 103

Asn Pro Gln Thr Asn
1               5

<210> SEQ ID NO 104
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 104

Asn Pro Lys Thr Gly
1               5

<210> SEQ ID NO 105
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 105

Asn Ser Lys Thr Ala
1               5

<210> SEQ ID NO 106
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 106

Asn Pro Gln Thr Gly
1               5

<210> SEQ ID NO 107
<211> LENGTH: 5
```

```
<212> TYPE: PRT
<213> ORGANISM: ARTIFICIAL SEQUENCE
<220> FEATURE:
<223> OTHER INFORMATION: Synthetic Polypeptide

<400> SEQUENCE: 107

Asn Ala Lys Thr Asn
1               5

<210> SEQ ID NO 108
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 108

Asn Pro Gln Ser Ser
1               5

<210> SEQ ID NO 109
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be Glu, Ala, Ser or His

<400> SEQUENCE: 109

Asn Ala Xaa Thr Gly
1               5

<210> SEQ ID NO 110
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 110

Leu Pro Xaa Thr Ala
1               5

<210> SEQ ID NO 111
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 111

Leu Ala Xaa Thr Gly
1               5

<210> SEQ ID NO 112
<211> LENGTH: 6
<212> TYPE: PRT
<213> ORGANISM: ARTIFICIAL SEQUENCE
```

```
<220> FEATURE:
<223> OTHER INFORMATION: Synthetic Polypeptide

<400> SEQUENCE: 112

Gln Val Pro Thr Gly Val
1               5

<210> SEQ ID NO 113
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Ala or Ser

<400> SEQUENCE: 113

Leu Pro Xaa Thr Xaa
1               5

<210> SEQ ID NO 114
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 114

Leu Pro Ser Thr Ser
1               5

<210> SEQ ID NO 115
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 115

Leu Pro Lys Thr Gly
1               5

<210> SEQ ID NO 116
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 116

Leu Pro Ile Thr Gly
1               5

<210> SEQ ID NO 117
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 117

Leu Pro Asp Thr Ala
```

```
1               5

<210> SEQ ID NO 118
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 118

Ser Pro Lys Thr Gly
1               5

<210> SEQ ID NO 119
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 119

Leu Ala Glu Thr Gly
1               5

<210> SEQ ID NO 120
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 120

Leu Ala Ala Thr Gly
1               5

<210> SEQ ID NO 121
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 121

Leu Ala His Thr Gly
1               5

<210> SEQ ID NO 122
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 122

Leu Ala Ser Thr Gly
1               5

<210> SEQ ID NO 123
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 123

Leu Ala Glu Thr Gly
1               5
```

```
<210> SEQ ID NO 124
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 124

Leu Pro Leu Thr Gly
1               5

<210> SEQ ID NO 125
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 125

Leu Ser Arg Thr Gly
1               5

<210> SEQ ID NO 126
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 126

Val Pro Asp Thr Gly
1               5

<210> SEQ ID NO 127
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 127

Ile Pro Gln Thr Gly
1               5

<210> SEQ ID NO 128
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 128

Tyr Pro Arg Arg Gly
1               5

<210> SEQ ID NO 129
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 129

Leu Pro Met Thr Gly
1               5
```

<210> SEQ ID NO 130
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 130

Leu Pro Leu Thr Gly
1               5

<210> SEQ ID NO 131
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 131

Leu Ala Phe Thr Gly
1               5

<210> SEQ ID NO 132
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 132

Leu Pro Gln Thr Ser
1               5

<210> SEQ ID NO 133
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 133

Asn Pro Gln Ser
1

<210> SEQ ID NO 134
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 134

Leu Pro Ser Thr
1

<210> SEQ ID NO 135
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 135

Asn Ser Lys Thr
1

```
<210> SEQ ID NO 136
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 136

Asn Pro Gln Thr
1

<210> SEQ ID NO 137
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 137

Asn Ala Lys Thr
1

<210> SEQ ID NO 138
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 138

Leu Pro Ile Thr
1

<210> SEQ ID NO 139
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 139

Leu Ala Glu Thr
1

<210> SEQ ID NO 140
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be Asp, Glu, Ala, Asn, Gln, Lys or Arg

<400> SEQUENCE: 140

Leu Pro Xaa Thr Ala
1               5

<210> SEQ ID NO 141
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be Asp, Glu, Ala, Asn, Gln, Lys or Arg
```

```
<400> SEQUENCE: 141

Leu Pro Xaa Thr Gly
1               5

<210> SEQ ID NO 142
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 142

Leu Pro Glu Thr Ala
1               5

<210> SEQ ID NO 143
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 143

Gly Thr Xaa Pro Leu
1               5

<210> SEQ ID NO 144
<211> LENGTH: 6
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 144

Gly Gly Thr Xaa Pro Leu
1               5

<210> SEQ ID NO 145
<211> LENGTH: 7
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 145

Gly Gly Thr Xaa Pro Leu Gly
1               5

<210> SEQ ID NO 146
<211> LENGTH: 8
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
```

```
<222> LOCATION: (4)..(4)
<223> OTHER INFORMATION: Xaa can be any naturally occurring amino acid

<400> SEQUENCE: 146

Gly Gly Thr Xaa Pro Leu Gly Gly
1               5

<210> SEQ ID NO 147
<211> LENGTH: 12
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 147

Leu Pro Xaa Thr Gly Gly His His His His His His
1               5                   10

<210> SEQ ID NO 148
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 148

Leu Pro Xaa Thr Ala
1               5

<210> SEQ ID NO 149
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 149

Leu Val Pro Arg Gly
1               5

<210> SEQ ID NO 150
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 150

Leu Val Pro Arg Gly Gly
1               5

<210> SEQ ID NO 151
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 151

Leu Val Pro Arg Gly Ser
```

```
1               5

<210> SEQ ID NO 152
<211> LENGTH: 8
<212> TYPE: PRT
<213> ORGANISM: ARTIFICIAL SEQUENCE
<220> FEATURE:
<223> OTHER INFORMATION: Synthetic Polypeptide

<400> SEQUENCE: 152

Leu Glu Val Leu Phe Gln Gly Pro
1               5

<210> SEQ ID NO 153
<211> LENGTH: 8
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be Val, Ala or Thr

<400> SEQUENCE: 153

Leu Glu Xaa Leu Phe Gln Gly Pro
1               5

<210> SEQ ID NO 154
<211> LENGTH: 15
<212> TYPE: PRT
<213> ORGANISM: ARTIFICIAL SEQUENCE
<220> FEATURE:
<223> OTHER INFORMATION: Synthetic Polypeptide

<400> SEQUENCE: 154

Leu Pro Glu Thr Ala Ala Gly Lys Gly Leu Pro Glu Thr Gly Gly
1               5                   10                  15

<210> SEQ ID NO 155
<211> LENGTH: 9
<212> TYPE: PRT
<213> ORGANISM: ARTIFICIAL SEQUENCE
<220> FEATURE:
<223> OTHER INFORMATION: Synthetic Polypeptide

<400> SEQUENCE: 155

Ala Ala Gly Lys Gly Leu Pro Glu Thr
1               5

<210> SEQ ID NO 156
<211> LENGTH: 15
<212> TYPE: PRT
<213> ORGANISM: ARTIFICIAL SEQUENCE
<220> FEATURE:
<223> OTHER INFORMATION: Synthetic Polypeptide

<400> SEQUENCE: 156

Gly Gly Thr Glu Pro Leu Gly Lys Gly Ala Ala Thr Glu Pro Leu
1               5                   10                  15

<210> SEQ ID NO 157
<211> LENGTH: 11
<212> TYPE: PRT
<213> ORGANISM: ARTIFICIAL SEQUENCE
<220> FEATURE:
<223> OTHER INFORMATION: Synthetic Polypeptide
```

<400> SEQUENCE: 157

Leu Pro Glu Thr Gly His His His His His His
1               5                   10

<210> SEQ ID NO 158
<211> LENGTH: 29
<212> TYPE: DNA
<213> ORGANISM: ARTIFICIAL SEQUENCE
<220> FEATURE:
<223> OTHER INFORMATION: Synthetic Polynucleotide

<400> SEQUENCE: 158
cgcgcgccat ggtgagcaag ggcgaggag                                    29

<210> SEQ ID NO 159
<211> LENGTH: 50
<212> TYPE: DNA
<213> ORGANISM: ARTIFICIAL SEQUENCE
<220> FEATURE:
<223> OTHER INFORMATION: Synthetic Polynucleotide

<400> SEQUENCE: 159
cgcgcggatc ccgaccagtt tcaggaagct tgtacagctc gtccatgccg             50

<210> SEQ ID NO 160
<211> LENGTH: 11
<212> TYPE: PRT
<213> ORGANISM: ARTIFICIAL SEQUENCE
<220> FEATURE:
<223> OTHER INFORMATION: Synthetic Polypeptide

<400> SEQUENCE: 160

Leu Pro Glu Thr Gly His His His His His His
1               5                   10

<210> SEQ ID NO 161
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 161

Leu Pro Arg Thr
1

<210> SEQ ID NO 162
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 162

Gly Gly Gly Gly Gly
1               5

<210> SEQ ID NO 163
<211> LENGTH: 11
<212> TYPE: PRT
<213> ORGANISM: ARTIFICIAL SEQUENCE
<220> FEATURE:
<223> OTHER INFORMATION: Synthetic Polypeptide

<400> SEQUENCE: 163

Leu Pro Glu Thr Gly His His His His His His

```
                              1               5                   10

<210> SEQ ID NO 164
<211> LENGTH: 10
<212> TYPE: PRT
<213> ORGANISM: ARTIFICIAL SEQUENCE
<220> FEATURE:
<223> OTHER INFORMATION: Synthetic Polypeptide

<400> SEQUENCE: 164

Gly Gly Gly Gly Ser Gly Gly Gly Gly Ser
 1               5                   10

<210> SEQ ID NO 165
<211> LENGTH: 16
<212> TYPE: PRT
<213> ORGANISM: ARTIFICIAL SEQUENCE
<220> FEATURE:
<223> OTHER INFORMATION: Synthetic Polypeptide

<400> SEQUENCE: 165

Gly Gly Gly Gly Gly Leu Pro Glu Thr Gly His His His His His His
 1               5                   10                  15

<210> SEQ ID NO 166
<211> LENGTH: 14
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (13)..(14)
<223> OTHER INFORMATION: Xaa can be any naturally occurring amino acid

<400> SEQUENCE: 166

Gly His His His His His His Leu Pro Ser Thr Gly Xaa Xaa
 1               5                   10

<210> SEQ ID NO 167
<211> LENGTH: 10
<212> TYPE: PRT
<213> ORGANISM: ARTIFICIAL SEQUENCE
<220> FEATURE:
<223> OTHER INFORMATION: Synthetic Polypeptide

<400> SEQUENCE: 167

Gly Gly Gly Gly Ser Gly Gly Gly Gly Ser
 1               5                   10

<210> SEQ ID NO 168
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 168

Leu Pro Ser Thr Gly
 1               5

<210> SEQ ID NO 169
<211> LENGTH: 4
<212> TYPE: PRT
<213> ORGANISM: ARTIFICIAL SEQUENCE
<220> FEATURE:
<223> OTHER INFORMATION: Synthetic Polypeptide
```

```
<400> SEQUENCE: 169

Leu Pro Ser Thr
1

<210> SEQ ID NO 170
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 170

Leu Pro Glu Thr Gly Gly
1               5

<210> SEQ ID NO 171
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 171

Gly Gly Gly Lys
1

<210> SEQ ID NO 172
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 172

Gly Gly Gly Lys
1

<210> SEQ ID NO 173
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 173

Leu Pro Glu Thr Ala Ala
1               5

<210> SEQ ID NO 174
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 174

His His His His His His
1               5

<210> SEQ ID NO 175
<211> LENGTH: 8
<212> TYPE: PRT
<213> ORGANISM: ARTIFICIAL SEQUENCE
<220> FEATURE:
<223> OTHER INFORMATION: Synthetic Polypeptide

<400> SEQUENCE: 175
```

```
Gly Gly His His His His His
1               5

<210> SEQ ID NO 176
<211> LENGTH: 7
<212> TYPE: PRT
<213> ORGANISM: ARTIFICIAL SEQUENCE
<220> FEATURE:
<223> OTHER INFORMATION: Synthetic Polypeptide

<400> SEQUENCE: 176

Gly His His His His His His
1               5

<210> SEQ ID NO 177
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 177

Gly Gly Gly Gly Gly
1               5

<210> SEQ ID NO 178
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 178

Ala Gly Gly Gly Gly
1               5

<210> SEQ ID NO 179
<211> LENGTH: 8
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 179

Leu Pro Glu Thr Gly Gly Gly Xaa
1               5

<210> SEQ ID NO 180
<211> LENGTH: 7
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (6)..(7)
<223> OTHER INFORMATION: Xaa can be any naturally occurring amino acid

<400> SEQUENCE: 180

Leu Pro Glu Thr Gly Xaa Xaa
1               5

<210> SEQ ID NO 181
```

```
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 181

Leu Pro Glu Thr Gly
1               5

<210> SEQ ID NO 182
<211> LENGTH: 7
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 182

Leu Pro Xaa Thr Gly Xaa Xaa
1               5

<210> SEQ ID NO 183
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 183

Leu Pro Glu Thr
1

<210> SEQ ID NO 184
<211> LENGTH: 9
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 184

Leu Pro Xaa Thr Gly Gly Gly Gly Gly
1               5

<210> SEQ ID NO 185
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 185

Ala Glu Lys Ala Ala
1               5

<210> SEQ ID NO 186
<211> LENGTH: 5
<212> TYPE: PRT
```

```
<213> ORGANISM: ARTIFICIAL SEQUENCE
<220> FEATURE:
<223> OTHER INFORMATION: Synthetic Polypeptide

<400> SEQUENCE: 186

Gly Gly Gly Gly Gly
1               5

<210> SEQ ID NO 187
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 187

Leu Pro Glu Thr Gly
1               5

<210> SEQ ID NO 188

<400> SEQUENCE: 188

000

<210> SEQ ID NO 189
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 189

Leu Pro Glu Thr
1

<210> SEQ ID NO 190
<211> LENGTH: 11
<212> TYPE: PRT
<213> ORGANISM: ARTIFICIAL SEQUENCE
<220> FEATURE:
<223> OTHER INFORMATION: Synthetic Polypeptide

<400> SEQUENCE: 190

Leu Pro Glu Thr Gly His His His His His His
1               5                   10

<210> SEQ ID NO 191

<400> SEQUENCE: 191

000

<210> SEQ ID NO 192
<211> LENGTH: 8
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 192

Gly Leu Pro Glu Thr Gly Xaa Xaa
1               5
```

```
<210> SEQ ID NO 193
<211> LENGTH: 14
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (13)..(14)
<223> OTHER INFORMATION: Xaa can be any naturally occurring amino acid

<400> SEQUENCE: 193

Gly His His His His His His Leu Pro Glu Thr Gly Xaa Xaa
1               5                   10

<210> SEQ ID NO 194
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 194

Leu Pro Xaa Thr Gly
1               5

<210> SEQ ID NO 195
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 195

Asn Pro Gln Thr Asn
1               5

<210> SEQ ID NO 196
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 196

Asn Pro Lys Thr Gly
1               5

<210> SEQ ID NO 197
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 197

Leu Ala Xaa Thr Gly
1               5

<210> SEQ ID NO 198
```

```
<211> LENGTH: 5
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 198

Leu Pro Xaa Thr Gly
1               5

<210> SEQ ID NO 199
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 199

Leu Pro Arg Thr Gly
1               5

<210> SEQ ID NO 200
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 200

Ala Gly Gly Gly Gly
1               5

<210> SEQ ID NO 201
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 201

Met Leu Val Pro Arg Gly
1               5

<210> SEQ ID NO 202
<211> LENGTH: 11
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 202

Leu Pro Xaa Thr Gly His His His His His
1               5                   10

<210> SEQ ID NO 203
<211> LENGTH: 6
<212> TYPE: PRT
<213> ORGANISM: ARTIFICIAL SEQUENCE
<220> FEATURE:
<223> OTHER INFORMATION: Synthetic Polypeptide
<220> FEATURE:
```

```
<221> NAME/KEY: misc_feature
<222> LOCATION: (3)..(3)
<223> OTHER INFORMATION: Xaa can be any naturally occurring amino acid

<400> SEQUENCE: 203

Leu Pro Xaa Thr Ala Ala
1               5

<210> SEQ ID NO 204
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 204

Leu Pro Arg Thr
1

<210> SEQ ID NO 205
<211> LENGTH: 11
<212> TYPE: PRT
<213> ORGANISM: ARTIFICIAL SEQUENCE
<220> FEATURE:
<223> OTHER INFORMATION: Synthetic Polypeptide

<400> SEQUENCE: 205

Leu Pro Glu Thr Gly His His His His His His
1               5                   10

<210> SEQ ID NO 206
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 206

Leu Pro Glu Thr Ala Ala
1               5

<210> SEQ ID NO 207
<211> LENGTH: 12
<212> TYPE: PRT
<213> ORGANISM: ARTIFICIAL SEQUENCE
<220> FEATURE:
<223> OTHER INFORMATION: Synthetic Polypeptide

<400> SEQUENCE: 207

Leu Pro Glu Thr Gly Gly His His His His His His
1               5                   10

<210> SEQ ID NO 208
<211> LENGTH: 4
<212> TYPE: PRT
<213> ORGANISM: ARTIFICIAL SEQUENCE
<220> FEATURE:
<223> OTHER INFORMATION: Synthetic Polypeptide

<400> SEQUENCE: 208

Leu Pro Glu Thr
1

<210> SEQ ID NO 209
<211> LENGTH: 8
<212> TYPE: PRT
<213> ORGANISM: ARTIFICIAL SEQUENCE
```

<220> FEATURE:
<223> OTHER INFORMATION: Synthetic Polypeptide

<400> SEQUENCE: 209

Leu Pro Glu Thr Gly Gly Gly Lys
1               5

<210> SEQ ID NO 210
<211> LENGTH: 173
<212> TYPE: PRT
<213> ORGANISM: ARTIFICIAL SEQUENCE
<220> FEATURE:
<223> OTHER INFORMATION: Synthetic Polypeptide

<400> SEQUENCE: 210

Phe Gly Phe Pro Gln Glu Glu Phe Gly Asn Gln Phe Gln Lys Ala Glu
1               5                   10                  15

Thr Ile Pro Val Leu His Glu Met Ile Gln Gln Ile Phe Asn Leu Phe
            20                  25                  30

Ser Thr Lys Asp Ser Ser Ala Ala Trp Asp Glu Thr Leu Leu Asp Lys
        35                  40                  45

Phe Tyr Thr Glu Leu Tyr Gln Gln Leu Asn Asp Leu Glu Ala Cys Val
    50                  55                  60

Ile Gln Gly Val Gly Val Thr Glu Thr Pro Leu Met Lys Glu Asp Ser
65                  70                  75                  80

Ile Leu Ala Val Arg Lys Tyr Phe Gln Arg Ile Thr Leu Tyr Leu Lys
                85                  90                  95

Glu Lys Lys Tyr Ser Pro Cys Ala Trp Glu Val Val Arg Ala Glu Ile
            100                 105                 110

Met Arg Ser Phe Ser Leu Ser Thr Asn Leu Gln Glu Ser Leu Arg Ser
        115                 120                 125

Lys Glu Gly Gly Leu Pro Glu Thr Gly Gly Cys Asp Leu Pro Gln Thr
    130                 135                 140

His Ser Leu Gly Ser Arg Arg Thr Leu Met Leu Leu Ala Gln Met Arg
145                 150                 155                 160

Arg Ile Ser Leu Phe Ser Cys Leu Lys Asp Arg His Asp
                165                 170

<210> SEQ ID NO 211
<211> LENGTH: 18
<212> TYPE: PRT
<213> ORGANISM: ARTIFICIAL SEQUENCE
<220> FEATURE:
<223> OTHER INFORMATION: Synthetic Polypeptide

<400> SEQUENCE: 211

Ser Lys Glu Gly Gly Leu Pro Glu Thr Gly Gly Cys Asp Leu Pro Gln
1               5                   10                  15

Thr His

<210> SEQ ID NO 212
<211> LENGTH: 23
<212> TYPE: PRT
<213> ORGANISM: ARTIFICIAL SEQUENCE
<220> FEATURE:
<223> OTHER INFORMATION: Synthetic Polypeptide

```
<400> SEQUENCE: 212

Ser Lys Glu Gly Gly Leu Pro Glu Thr Gly Gly Cys Asp Leu Pro Gln
1               5                   10                  15

Thr His Ser Leu Gly Ser Arg
            20

<210> SEQ ID NO 213
<211> LENGTH: 16
<212> TYPE: PRT
<213> ORGANISM: ARTIFICIAL SEQUENCE
<220> FEATURE:
<223> OTHER INFORMATION: Synthetic Polypeptide

<400> SEQUENCE: 213

Glu Gly Gly Leu Pro Glu Thr Gly Gly Cys Asp Leu Pro Gln Thr His
1               5                   10                  15

<210> SEQ ID NO 214
<211> LENGTH: 21
<212> TYPE: PRT
<213> ORGANISM: ARTIFICIAL SEQUENCE
<220> FEATURE:
<223> OTHER INFORMATION: Synthetic Polypeptide

<400> SEQUENCE: 214

Glu Gly Gly Leu Pro Glu Thr Gly Gly Cys Asp Leu Pro Gln Thr His
1               5                   10                  15

Ser Leu Gly Ser Arg
            20

<210> SEQ ID NO 215
<211> LENGTH: 6
<212> TYPE: PRT
<213> ORGANISM: ARTIFICIAL SEQUENCE
<220> FEATURE:
<223> OTHER INFORMATION: Synthetic Polypeptide

<400> SEQUENCE: 215

Leu Pro Glu Thr Ala Ala
1               5

<210> SEQ ID NO 216
<211> LENGTH: 6
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: Phosphorylated
<222> LOCATION: (5)..(5)

<400> SEQUENCE: 216

Leu Pro Glu Thr Gly Gly
1               5

<210> SEQ ID NO 217

<400> SEQUENCE: 217

000

<210> SEQ ID NO 218

<400> SEQUENCE: 218

000
```

```
<210> SEQ ID NO 219
<211> LENGTH: 7
<212> TYPE: PRT
<213> ORGANISM: ARTIFICIAL SEQUENCE
<220> FEATURE:
<223> OTHER INFORMATION: Synthetic Polypeptide
<220> FEATURE:
<221> NAME/KEY: misc_feature
<222> LOCATION: (6)..(7)
<223> OTHER INFORMATION: Xaa can be any naturally occurring amino acid

<400> SEQUENCE: 219

Leu Pro Glu Thr Gly Xaa Xaa
1               5

<210> SEQ ID NO 220
<211> LENGTH: 5
<212> TYPE: PRT
<213> ORGANISM: ARTIFICIAL SEQUENCE
<220> FEATURE:
<223> OTHER INFORMATION: Synthetic Polypeptide

<400> SEQUENCE: 220

Leu Pro Glu Thr Gly
1               5
```

METHODS FOR LIGATION AND USES THEREOF

CROSS-REFERENCE TO RELATED APPLICATION

The present application is a national stage filing under 35 U.S.C. §371 of international PCT application, PCT/US2010/000274, filed Feb. 1, 2010, which claims priority under 35 U.S.C. §119(e) to U.S. provisional application, U.S. Ser. No. 61/148,787, filed Jan. 30, 2009, both of which are incorporated herein by reference.

GOVERNMENT SUPPORT

The invention was supported in part by grants from the National Institutes of Health (R01-AI057182, P01-CA100707, R01-AI033456, R21-EB008875. The government has certain rights in the invention.

FIELD OF THE INVENTION

The present invention relates to compositions and methods for ligation and uses thereof. The invention provides novel reagents and methods for ligating an acyl donor compound with a nucleophilic acyl acceptor compound to form an amide bond using a transamidase. The invention also relates to novel products, e.g., novel polypeptides, that can be produced using transamidate-mediated ligation.

BACKGROUND OF THE INVENTION

Protein engineering is becoming a widely used tool in many areas of protein biochemistry. One engineering method is controlled protein ligation, and over the past ten years some progress has been made. For instance, synthetic-based chemistry allows the joining of synthetic peptides together through native chemical ligation and a 166 amino-acid polymer-modified erythropoiesis protein has been synthesized using this method. However, native chemical ligation relies on efficient preparation of synthetic peptide esters, which can be technically difficult to prepare for large polypeptides such as proteins. For example, the reaction sometimes is performed in an organic solvent to produce the requisite protein ester for ligation. Other ligation methods not requiring the production of protein esters generate protein thioesters. An intein-based protein ligation system was used to generate a protein by thiolysis of a corresponding protein-intein thioester fusion. A prerequisite for this intein-mediated ligation method is that the target protein is expressed as a correctly folded fusion with the intein, and that sufficient spacing between the target and intein is needed to allow formation of the intein-thioester. In many instances, the intein-fusion proteins can only be obtained from inclusion bodies when expressed in *Escherichia coli*, which often cannot be refolded. This difficulty significantly limits the application of intein-based protein ligation methods.

Purification of a tag-free recombinant protein often is challenging and often requires multiple chromatography steps. A tag can be linked to a recombinant protein, and after purification, the tag on the fusion may be cleaved from the target protein by treatment with an exogenously added site-specific protease. Additional chromatographic steps then are required to separate the target protein from the uncleaved fusion, the affinity tag, and the protease. For example, an N-terminal 6× His tag from a recombinant protein may be cleaved by an engineered 6× His-tagged aminoprotease, and a subtractive immobilized metal-ion affinity chromatography (IMAC) step can be used to recover the untagged target. Other methods may require two or more chromatography steps and even special treatment of the exogenous protease, such as biotinylation, to facilitate its removal.

Methods for the site-specific modification of proteins remain in high demand, and the transpeptidation reaction catalyzed by sortases has emerged as a general method for derivatizing proteins with various types of modifications. Target proteins are engineered to contain the sortase A recognition motif (LPXTG, SEQ ID NO: 45) near their C-termini. When incubated with synthetic peptides containing one or more N-terminal glycine residues and a recombinant sortase, these artificial sortase substrates undergo a transacylation reaction resulting in the exchange of residues C-terminal to the threonine residue with the synthetic oligoglycine peptide.

SUMMARY OF THE INVENTION

The present invention encompasses the recognition that existing methods of transamidase ligation suffer from competition effects and efficiency issues. The inventors sought to extend the practical applications of sortase-mediated ligation to include ligation/labeling at the polypeptide N-terminus using synthetic peptides containing the LPXTG (SEQ ID NO: 45) motif and protein substrates with N-terminal glycine residues. In the course of these efforts it was recognized that each successful transfer of an LPXT unit to a target protein releases a stoichiometric amount of a peptide fragment containing an N-terminal glycine. This by-product competes with the protein nucleophile for the same acyl enzyme intermediate, thereby limiting the efficiency of the ligation reaction. In certain aspects, the invention provides compositions and methods that facilitate N-terminal ligation using a transamidase, e.g., a sortase. According to one aspect, the present invention provides methods of ligation utilizing a modified transamidase recognition sequence. In some embodiments, a modified transamidase sequence comprises an ester group in place of a C-terminal amino acid residue.

According to one aspect, the present invention provides a method of ligation comprising the step of contacting an acyl donor compound of formula:

wherein the transamidase recognition sequence is any peptide motif recognized by a transamidase enzyme;

X is —O—, —NR—, or —S—;

R is hydrogen, substituted or unsubstituted aliphatic, or substituted or unsubstituted heteroaliphatic;

$A^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;

$R^1$ is acyl, substituted or unsubstituted aliphatic, substituted or unsubstituted heteroaliphatic, substituted or unsubstituted aryl, or substituted or unsubstituted heteroaryl; and with a nucleophilic compound of formula:

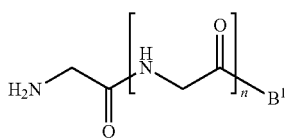

wherein

B¹ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and n is an integer from 0 to 100, inclusive;

in the presence of a transamidase enzyme under suitable conditions to form a compound of formula:

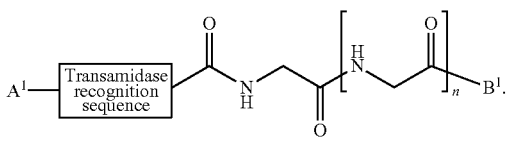

In some embodiments, the recognition sequence is LPXT, wherein X is the amino acid D, E, A, N, Q, K, or R.

In another aspect, the present invention provides a ligation method comprising the step of contacting an acyl donor compound of formula:

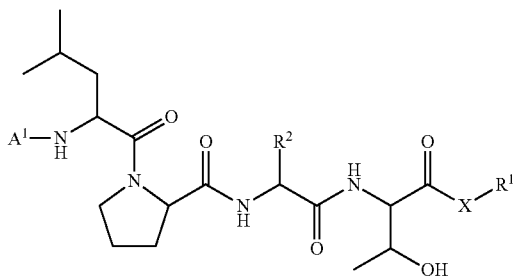

wherein

A¹, X, and R¹ are defined as described above; and

R² is a natural or unnatural amino acid side chain;

with a nucleophilic compound of formula:

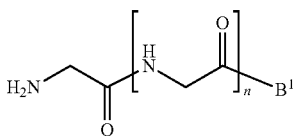

wherein

B¹ and n are are defined as described above;

in the presence of a transamidase enzyme under suitable conditions to form a compound of formula:

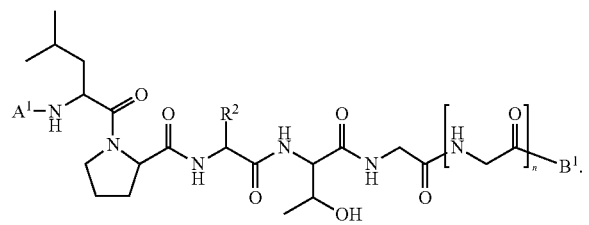

In some embodiments, X is —O—. In some embodiments, R¹ is $C_{1-6}$ aliphatic. In some embodiments, R¹ is methyl. In some embodiments, R² is a natural amino acid side chain. In some embodiments, R² is the side chain group of arginine. In some embodiments, R² is the side chain group of glutamic acid. In some embodiments, R² is the side chain group of lysine. In some embodiments, A¹ and B¹ are each selected from the group consisting of an antibody, an antibody chain, an antibody fragment, an antibody epitope, a recombinant protein, a peptide comprising one or more D-amino acids, a branched peptide, a therapeutic protein, an enzyme, a polypeptide subunit of a multisubunit protein, a transmembrane protein, a cell surface protein, a methylated peptide or protein, an acylated peptide or protein, a lipidated peptide or protein, a phosphorylated peptide or protein, and a glycosylated peptide or protein. In certain embodiments, n is 2. In certain embodiments, n is 4.

In some embodiments, the transamidase is a sortase. In certain embodiments, the sortase is sortase A. In certain embodiments, the sortase is sortase B.

According to one aspect, the present invention provides a compound of formula:

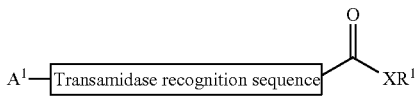

wherein the transamidase recognition sequence, A¹, X, and R¹ are as defined above and described herein. In certain embodiments, X is —O— and R¹ is methyl.

According to one aspect, the present invention provides a compound of formula:

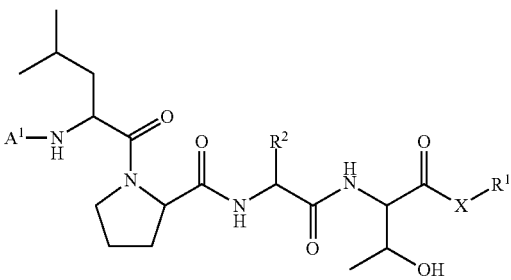

wherein A¹, X, R¹, and R² are as defined above and described herein. In certain embodiments, the compound is of formula:

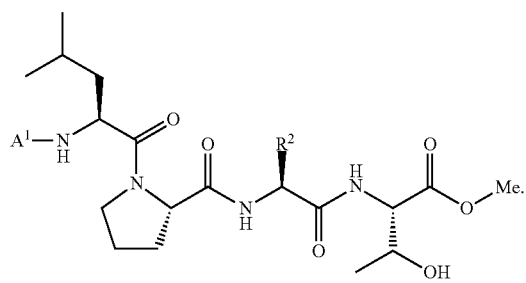

According to one aspect, the present invention provides kits comprising an acyl donor compound as described herein. In some embodiments, the kit further comprises a transamidase. In some embodiments, the kit further comprises a sortase. In some embodiments, the kit provides a nucleophilic acyl acceptor as described herein.

One aspect of the instant invention is improved methods for removing sortase from a reaction system in which sortase has been used to perform a transamidation reaction. See Example 1 for exemplary description. It will be appreciated that the methods though described in reference to particular materials, are generalizable to other materials.

Other aspects of the invention are methods and compositions related to use of multiple sortases, recognizing different motifs, for multiple labeling of polypeptides and other applications.

Other aspects of the invention provide masked transamidase recognition sequences and compounds containing them and methods of use thereof, e.g., for modifying polypeptides. In some aspects, the invention provides methods and compositions relating to use of transamidase-mediated, e.g., sortase-mediated, transpeptidation for the site-specific attachment of a moiety, e.g., a non-polypeptide polymer, e.g., polyethylene glycol or a derivative thereof, to a protein, e.g., a clinically useful protein, to enhance at least one property of the protein, such as extend the circulating half-life, while maintaining high biological activity, as well as covalently joining the N- and C-termini of the protein, e.g. to increase thermal stability. In some aspects, the inventive methods and compositions combine both of these properties by exploiting two distinct transamidase, e.g., sortase, enzymes and engineering a suitable compound (sometimes referred to herein as a "probe") that allows for site-specific modification (e.g., PEGylation) as well as allowing covalent closure in a second transamidase-mediated reaction. The invention provides a circularized version of a polypeptide, wherein the original C- and N-termini of the polypeptide are joined to each other via a linker peptide, wherein the linker peptide comprises a transamidase recognition sequence. In some embodiments of the invention, the polypeptide is a four-helix bundle polypeptide, e.g., a four-helix bundle cytokine. In some embodiments the polypeptide is a secreted polypeptide. In some embodiments the polypeptide binds to a cellular receptor. In some embodiments, the C-terminus, N-terminus, or both, of the polypeptide are not involved in receptor binding.

The entire contents of all references cited above and herein (including databases and sequences associated with accession numbers) are hereby incorporated by reference.

BRIEF DESCRIPTION OF THE DRAWING

FIG. 9. (a) Fluorescence gel scan showing robust labeling of CtxB polypeptide containing 3 or 5 (SEQ ID NO: 49) glycines. (b) ESI-MS showing labeling of CtxB polypeptide containing 5 glycines (SEQ ID NO: 49). AGGGG—SEQ ID NO: 178.

FIG. 38 shows a nucleotide sequence (SEQ ID NO: 1) encoding an IFN alpha2 variant and corresponding encoded protein (SEQ ID NO: 2). In blue and bold print at the N-terminus of SEQ ID NO: 2 is the initiating methioinine (which gets clipped off when the coding sequence is translated in bacteria), followed by the two glycines used by the transamidase for cyclization. These are not present in the delGG variant described herein. In black (normal text) is the interferon alpha sequence from the normal human interferon alpha 2 protein. This is followed by two glycines in green (underlined), and the SrtAstaph recognition sequence LPETGG (SEQ ID NO: 58) in red italics. Finally, the rest of the sequence (GSHHHHHH, SEQ ID NO: 59) in blue (immediately following the LPETGG, SEQ ID NO: 58) includes the 6His tag for purification. It should be noted that the IFN alpha sequence lacks the signal sequence for insertion into the ER and secretion that is found in the naturally occurring version prior to cleavage and secretion. This sequence is dispensable when a secreted eukaryotic, e.g., mammalian, polypeptide is produced in prokaryotes, e.g., in bacteria, or in an in vitro translation system. Sequences in SEQ ID NO: 1 are shown using the same notation as in SEQ ID NO: 2, i.e., blue and bold print denotes start codon (encoding methionine) followed by codons for two glycines; black (normal text) denotes IFN alpha2 coding sequence; followed by green (underlined) codons encoding two glycines; sequence encoding SrtAstaph recognition sequence is in red italics, followed by sequence in blue encoding GSHHHHHH (SEQ ID NO: 59).

FIG. 39B shows MS/MS identification of the junction peptide for the circular interferon alpha. Sequences, from top to bottom, correspond to SEQ ID NOs: 210-214.

DETAILED DESCRIPTION OF CERTAIN EMBODIMENTS

Figure 1A:
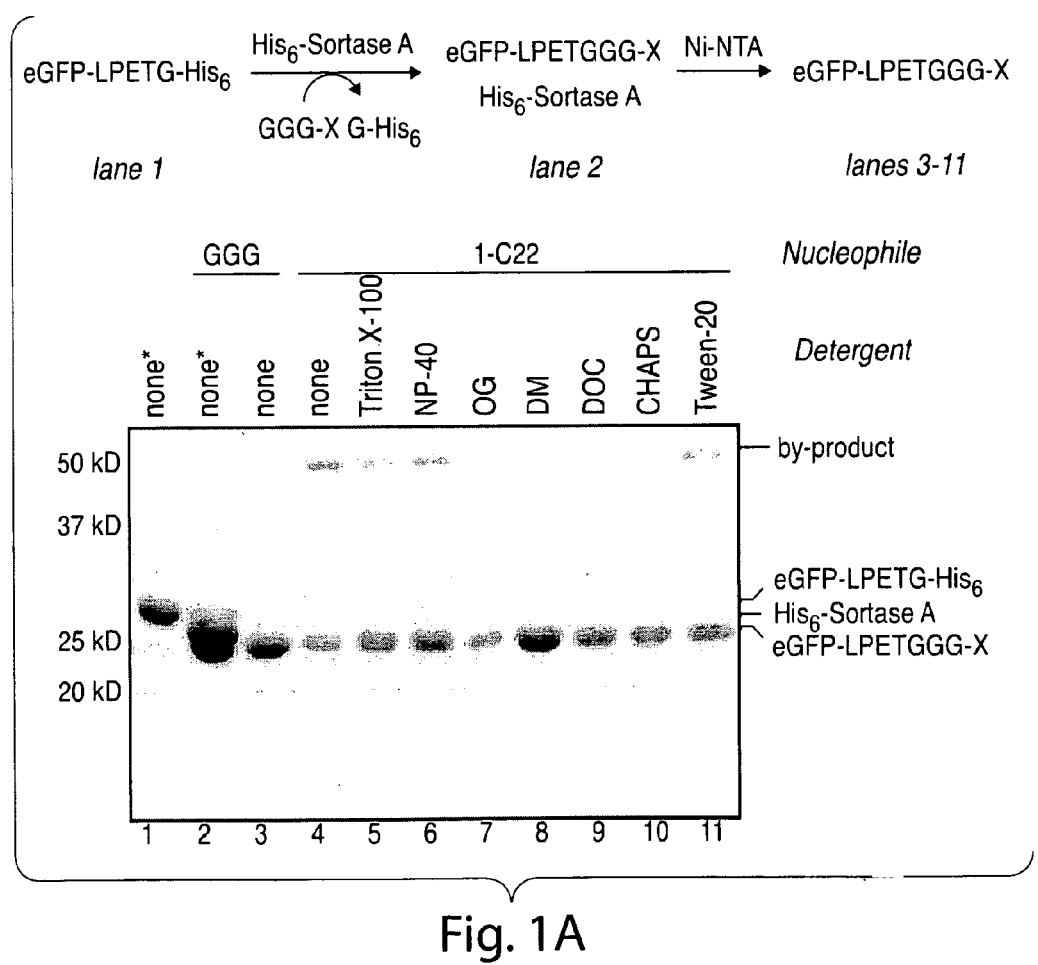
FIG. 1. (a) Optimization of a two-step protocol for lipid ligation followed by removal of the sortase enzyme. Conditions: 77 µM eGFP-LPETG-His$_6$ (SEQ ID NO: 46), 150 µM sortase A, 2 mM nucleophile, 1% (w/v) detergent, 50 mM Tris, pH 7.5, 150 mM NaCl, 10 mM CaCl2, 3 h at 37° C. After transpeptidation, Ni-NTA resin was added as a slurry in 1 M NaCl and 40 mM imidazole and incubated for 2 h at room temperature. Abbreviations: OG=n-octyl glucoside, DM=n-dodecyl maltoside, DOC=deoxycholate. The asterisks indicate samples not treated with Ni-NTA resin. (b) ESI-MS spectrum of eGFP-LPET-1-C22 (LPET—SEQ ID NO: 208) ligation product. His6—SEQ ID NO: 174; LPETGGG-X—SEQ ID NO: 179.

In simplest terms, the transpeptidation reaction results in the ligation of species containing a transamidase recognition sequence with those bearing one or more N-terminal glycine residues. In certain embodiments, the recognition sequence is an LPXTG (SEQ ID NO: 45) motif. However, a drawback of using such recognition sequences as acyl donors is that the transfer of an LPXT unit to a nucleophilic acyl acceptor releases a stoichiometric amount of a peptide fragment containing an N-terminal glycine. Such by-products compete with the desired acyl acceptor and hinder the progress of the ligation reaction. Moreover, hydrolytic cleavage of an LPXTG (SEQ ID NO: 45) peptide, although a relatively slow process, can exacerbate competition with the protein nucleophile as the reaction proceeds. Indeed, initial attempts to perform N-terminal protein labeling with peptides containing all five residues (LPXTG, SEQ ID NO: 45) yielded disappointing results as useful levels of ligation could only be obtained using concentrations >5 mM of the LPXTG (SEQ ID NO: 45)-containing peptide.

Applicants have found that the substitution of the C-terminal residue of the recognition sequence with a moiety exhibiting poor nucleophilicity once released from the transamidase provides for a more efficient ligation. Any moiety exhibiting such poor nucleophilicity can be used in accordance with the present invention. Exemplary embodiments are described herein.

The present invention provides methods for efficiently linking an acyl donor with a nucleophilic acyl acceptor. The development of these methods is significant as they are widely applicable to many acyl donors and a multitude of different acyl acceptors. In certain embodiments, the processes are useful for ligating proteins and/or peptides to one another, ligating synthetic peptides to recombinant proteins, linking a reporting molecule to a protein or peptide, joining a nucleic acid to a protein or peptide, conjugating a protein or peptide to a solid support or polymer, and linking a protein or peptide to a label. Such products and processes save cost and time associated with ligation product synthesis and are useful for conveniently linking an acyl donor to an acyl acceptor. In certain embodiments, the ligation products and purified products are useful in diagnostic procedures (e.g., an antibody that specifically binds to a cancer cell epitope is joined to a radioisotope and the conjugate is administered to a patient to detect the presence or absence of cancer cells). In certain embodiments, the ligation products and purified products are useful in therapeutic procedures (e.g., an antibody that specifically binds to a cancer cell epitope is joined to a toxin such as ricin A and the conjugate is administered to a patient to selectively treat the cancer). In certain embodiments, the ligation products and purified products are useful in research methods (e.g., a $NH_2$—$CH_2$-derivatized fluorophore and sortase are contacted with fixed cells that express a protein linked to a sortase recognition sequence and the location of the protein is detected by a fluorescence imaging technique).

Methods for ligation described herein are catalyzed by a transamidase. A transamidase is an enzyme that can form a peptide linkage (i.e., amide linkage) between an acyl donor compound and a nucleophilic acyl acceptor containing a $NH_2$—$CH_2$-moiety. Sortases are enzymes having transamidase activity and have been isolated from Gram-positive bacteria. They have, as part of their cell wall structure, peptidoglycan as well as polysaccharides and/or teichoic acids. Gram-positive bacteria include the following genera: *Actinomyces, Bacillus, Bifidobacterium, Cellulomonas, Clostridium, Corynebacterium, Micrococcus, Mycobacterium, Nocardia, Staphylococcus, Streptococcus* and *Streptomyces*.

In certain embodiments, the present invention provides a ligation method comprising the step of contacting an acyl donor compound of formula:

wherein
the transamidase recognition sequence is any peptide motif recognized by a transamidase enzyme;
X is —O—, —NR—, or —S—;
R is hydrogen, substituted or unsubstituted aliphatic, or substituted or unsubstituted heteroaliphatic;
$A^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;
$R^1$ is acyl, substituted or unsubstituted aliphatic, substituted or unsubstituted heteroaliphatic, substituted or unsubstituted aryl, or substituted or unsubstituted heteroaryl; and
with a nucleophilic compound of formula:

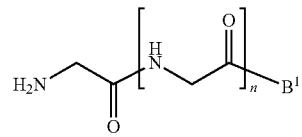

wherein
$B^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and
n is an integer from 0 to 100, inclusive;
in the presence of a transamidase enzyme under suitable conditions to form a compound of formula:

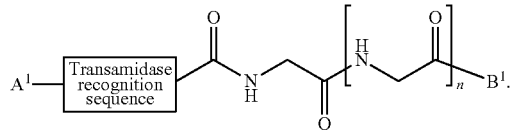

One of ordinary skill will appreciate that, in certain embodiments, the C-terminal amino acid of the transamidase recognition sequence is omitted. That is, an acyl group

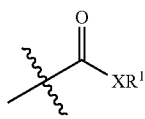

replaces the C-terminal amino acid of the transamidase recognition sequence. In some embodiments, the acyl group is

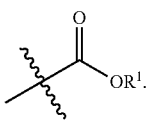

In some embodiments, the acyl group is

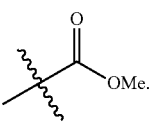 [SMILES: *C(=O)OC]

In some embodiments, the transamidase recognition sequence is LPXT, wherein X is a standard or non-standard amino acid. In some embodiments, X is selected from D, E, A, N, Q, K, or R. In some embodiments, the recognition sequence is selected from LPXT, LPXT, SPXT, LAXT, LSXT, NPXT, VPXT, IPXT, and YPXR. In some embodiments X is selected to match a naturally occurring transamidase recognition sequence. In some embodiments, the transamidase recognition sequence is selected from: LPKT (SEQ ID NO: 69), LPIT (SEQ ID NO: 70), LPDT (SEQ ID NO: 71), SPKT (SEQ ID NO: 72), LAET (SEQ ID NO: 73), LAAT (SEQ ID NO: 74), LAET (SEQ ID NO: 75), LAST (SEQ ID NO: 76), LAET (SEQ ID NO: 77), LPLT (SEQ ID NO: 78), LSRT (SEQ ID NO: 79), LPET (SEQ ID NO: 53), VPDT (SEQ ID NO: 80), IPQT (SEQ ID NO: 81), YPRR (SEQ ID NO: 82), LPMT (SEQ ID NO: 83), LPLT (SEQ ID NO: 84), LAFT (SEQ ID NO: 85), LPQT (SEQ ID NO: 86), NSKT (SEQ ID NO: 87), NPQT (SEQ ID NO: 88), NAKT (SEQ ID NO: 89), and NPQS (SEQ ID NO: 90). In some embodiments, e.g., in certain embodiments in which sortase A is used (see below), the transamidase recognition motif comprises the amino acid sequence $X_1PX_2X_3$, where $X_1$ is leucine, isolucine, valine or methionine; $X_2$ is any amino acid; $X_3$ is threonine, serine or alanine; P is proline and G is glycine. In specific embodiments, as noted above $X_1$, is leucine and $X_3$ is threonine. In certain embodiments, $X_2$ is aspartate, glutamate, alanine, glutamine, lysine or methionine. In certain embodiments, e.g., where sortase B is utilized, the recognition sequence often comprises the amino acid sequence $NPX_1TX_2$, where $X_1$ is glutamine or lysine; $X_2$ is asparagine or glycine; N is asparagine; P is proline and T is threonine. The invention encompasses the recognition that selection of X may be based at least in part in order to confer desired properties on the compound containing the recognition motif. In some embodiments, X is selected to modify a property of the compound that contains the recognition motif, such as to increase or decrease solubility in a particular solvent. In some embodiments, X is selected to be compatible with reaction conditions to be used in synthesizing a compound comprising the recognition motif, e.g., to be unreactive towards reactants used in the synthesis.

In some embodiments, X is —O—. In some embodiments, X is —NR—. In some embodiments, X is —NH—. In some embodiments, X is —S—.

In certain embodiments, $R^1$ is substituted aliphatic. In certain embodiments, $R^1$ is unsubstituted aliphatic. In some embodiments, $R^1$ is substituted $C_{1-12}$ aliphatic. In some embodiments, $R^1$ is unsubstituted $C_{1-12}$ aliphatic. In some embodiments, $R^1$ is substituted $C_{1-6}$ aliphatic. In some embodiments, $R^1$ is unsubstituted $C_{1-6}$ aliphatic. In some embodiments, $R^1$ is $C_{1-3}$ aliphatic. In some embodiments, $R^1$ is butyl. In some embodiments, $R^1$ is n-butyl. In some embodiments, $R^1$ is isobutyl. In some embodiments, $R^1$ is propyl. In some embodiments, $R^1$ is n-propyl. In some embodiments, $R^1$ is isopropyl. In some embodiments, $R^1$ is ethyl. In some embodiments, $R^1$ is methyl.

In certain embodiments, $R^1$ is substituted aryl. In certain embodiments, $R^1$ is unsubstituted aryl. In certain embodiments, $R^1$ is substituted phenyl. In certain embodiments, $R^1$ is unsubstituted phenyl.

It will be appreciated that a variety of functional groups, motifs, macromolecules, etc., can comprise part of the acyl donor as the $A^1$ moiety. In some embodiments, $A^1$ comprises a protein. In some embodiments, $A^1$ comprises a peptide. In some embodiments, $A^1$ comprises an element selected from the group consisting of an antibody, an antibody chain, an antibody fragment, an antibody epitope, a recombinant protein, a peptide comprising one or more D-amino acids, a branched peptide, a therapeutic protein, an enzyme, a polypeptide subunit of a multisubunit protein, a transmembrane protein, a cell surface protein, a methylated peptide or protein, an acylated peptide or protein, a lipidated peptide or protein, a phosphorylated peptide or protein, and a glycosylated peptide or protein. In some embodiments, $A^1$ is an amino acid. In some embodiments, $A^1$ comprises a protein. In some embodiments, $A^1$ comprises a peptide. In some embodiments, $A^1$ comprises an antibody. In some embodiments, $A^1$ comprises an antibody fragment. In some embodiments, $A^1$ comprises an antibody epitope. In some embodiments, $A^1$ comprises green fluorescent protein.

In some embodiments, $A^1$ comprises a lipid. In some embodiments, $A^1$ comprises a saturated hydrocarbon. In some embodiments, $A^1$ comprises a partially unsaturated hydrocarbon. In some embodiments, $A^1$ comprises a $C_{1-40}$ hydrocarbon chain. In some embodiments, $A^1$ comprises a $C_{1-30}$ hydrocarbon chain. In some embodiments, $A^1$ comprises a $C_{1-20}$ hydrocarbon chain. In some embodiments, $A^1$ comprises a $C_{1240}$ hydrocarbon chain.

In some embodiments, $A^1$ comprises a substituted or unsubstituted $C_{1-20}$ aliphatic group. In some embodiments, $A^1$ comprises an adamantyl group.

In certain embodiments, $A^1$ comprises a small molecule. In certain embodiments, $A^1$ comprises a bioactive small molecule. In certain embodiments, $A^1$ comprises a FDA-approved drug. In certain embodiments, $A^1$ comprises a cytotoxic agent. In certain embodiments, $A^1$ comprises a steroid. In certain embodiments, $A^1$ comprises a steroid analog.

In certain embodiments, $A^1$ comprises a label. In some embodiments, $A^1$ comprises a fluorescent label. In certain embodiments, $A^1$ comprises a radiolabel. In certain embodiments, $A^1$ comprises a chemiluminescent label. In certain embodiments, $A^1$ comprises a phosphorescent label.

In certain embodiments, $A^1$ comprises biotin. In certain embodiments, $A^1$ comprises streptavidin. In certain embodiments, $A^1$ comprises fluorescein.

One of ordinary skill in the art will appreciate that $A^1$ and $B^1$ groups of the present invention are interchangable. That is, a given group $A^1$ on an acyl donor could also be used as a group $B^1$ on a nucleophilic acyl acceptor, and vice versa. Thus, all embodiments and variants of $A^1$ as described herein are also contemplated as $B^1$ groups.

In certain embodiments, n is an integer from 0 to 50, inclusive. In certain embodiments, n is an integer from 0 to 20, inclusive. In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6.

In some embodiments, the present invention provides a ligation method comprising the step of contacting an acyl donor compound of formula:

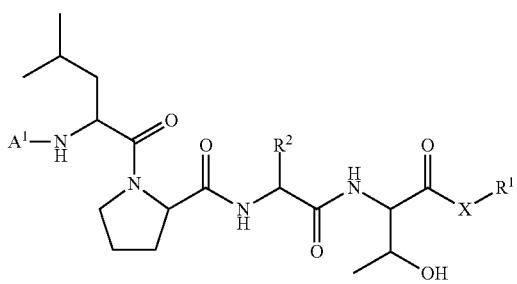

wherein each of $A^1$, X, R, and $R^1$ is as defined above; and $R^2$ is a natural or unnatural amino acid side chain;

with a nucleophilic compound of formula:

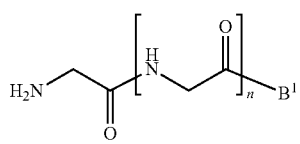

wherein $B^1$ and n are as defined above;

in the presence of a transamidase enzyme under suitable conditions to form a compound of formula:

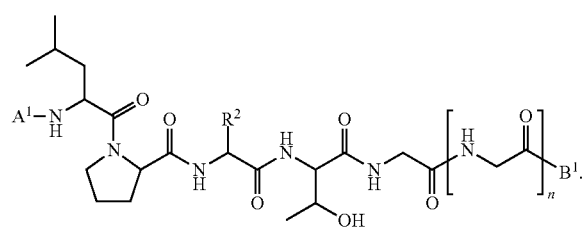

In some embodiments, $R^2$ is a natural amino acid side chain. In some embodiments, $R^2$ is the side chain group of aspartic acid, glutamic acid, alanine, asparagine, glutamine, lysine, or arginine. In some embodiments, $R^2$ is the side chain group of arginine. In some embodiments, $R^2$ is the side chain group of glutamic acid. In some embodiments, $R^2$ is the side chain group of lysine. In some embodiments, $R^2$ is the side chain group of aspartic acid. In some embodiments, $R^2$ is the side chain group of alanine. In some embodiments, $R^2$ is the side chain group of asparagine. In some embodiments, $R^2$ is the side chain group of glutamine.

In certain embodiments, $R^2$ is an unnatural amino acid side chain.

In some embodiments, the acyl donor compound is of formula:

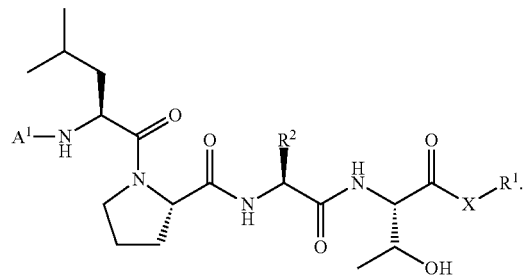

In some embodiments, the acyl donor compound is of formula:

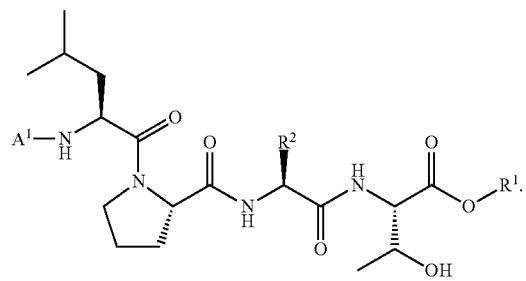

In some embodiments, the acyl donor compound is of formula:

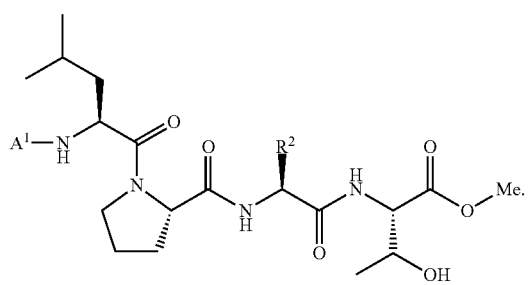

In some embodiments, the acyl donor compound is of formula:

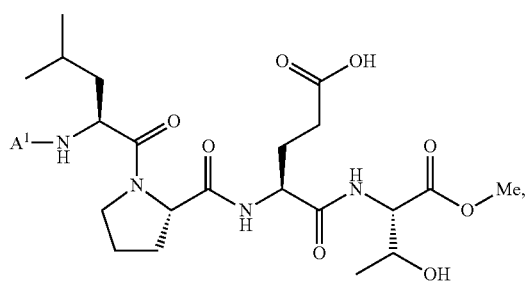

In some embodiments, the acyl donor compound is selected from:

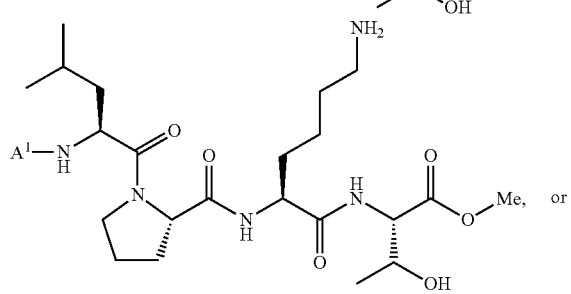

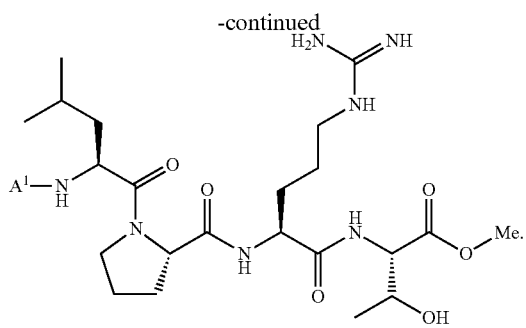

In certain embodiments, the transamidase is a sortase. Enzymes identified as "sortases" from Gram-positive bacteria cleave and translocate proteins to proteoglycan moieties in intact cell walls. Among the sortases that have been isolated from *Staphylococcus aureus*, are sortase A (SrtA) and sortase B (SrtB). Thus, in certain embodiments, a transamidase used in accordance with the present invention is a sortase A, e.g., from *S. aureus*. In certain embodiments, a transamidase is a sortase B, e.g., from *S. aureus*.

Sortases have been classified into 4 classes, designated A, B, C, and D, based on sequence alignment and phylogenetic analysis of 61 sortases from Gram positive bacterial genomes (Dramsi S, Trieu-Cuot P, Bierne H, Sorting sortases: a nomenclature proposal for the various sortases of Gram-positive bacteria. Res Microbiol. 156(3):289-97, 2005. These classes correspond to the following subfamilies, into which sortases have also been classified by Comfort and Clubb (Comfort D, Clubb R T. A comparative genome analysis identifies distinct sorting pathways in gram-positive bacteria. Infect Immun., 72(5):2710-22, 2004): Class A (Subfamily 1), Class B (Subfamily 2), Class C (Subfamily 3), Class D (Subfamilies 4 and 5). The aforementioned references disclose numerous sortases and recognition motifs. See also Pallen, M. J.; Lam, A. C.; Antonio, M.; Dunbar, K. *TRENDS in Microbiology*, 2001, 9(3), 97-101. Those skilled in the art will readily be able to assign a sortase to the correct class based on its sequence and/or other characteristics such as those described in Drami, et al., supra. The term "sortase A" is used herein to refer to a class A sortase, usually named SrtA in any particular bacterial species, e.g., SrtA from *S. aureus*. Likewise "sortase B" is used herein to refer to a class B sortase, usually named SrtB in any particular bacterial species, e.g., SrtB from *S. aureus*. The invention encompasses embodiments relating to a sortase A from any bacterial species or strain. The invention encompasses embodiments relating to a sortase B from any bacterial species or strain. The invention encompasses embodiments relating to a class C sortase from any bacterial species or strain. The invention encompasses embodiments relating to a class D sortase from any bacterial species or strain.

Amino acid sequences of Srt A and Srt B and the nucleotide sequences that encode them are disclosed in a number of references cited herein and which are incorporated herein by reference. The amino acid sequences of *S. aureus* SrtA and SrtB are homologous, sharing, for example, 22% sequence identity and 37% sequence similarity. The amino acid sequence of a sortase-transamidase from *Staphylococcus aureus* also has substantial homology with sequences of enzymes from other Gram-positive bacteria, and such transamidases can be utilized in the ligation processes described herein. For example, for SrtA there is about a 31% sequence identity (and about 44% sequence similarity) with best alignment over the entire sequenced region of the *S. pyogenes* open reading frame. There is about a 28% sequence identity with best alignment over the entire sequenced region of the *A. naeslundii* open reading frame. It will be appreciated that different bacterial strains may exhibit differences in sequence of a particular polypeptide, and the sequences herein are exemplary.

In certain embodiments a transamidase bearing 18% or more sequence identity, 20% or more sequence identity, or 30% or more sequence identity with the *S. pyogenes, A. naeslundii, S. mutans, E. faecalis* or *B. subtilis* open reading frame encoding a sortase can be screened, and enzymes having transamidase activity comparable to Srt A or Srt B from *S. aureas* can be utilized (e.g., comparable activity sometimes is 10% of Srt A or Srt B activity or more).

Thus in some embodiments of the invention the sortase is a sortase A (SrtA). SrtA recognizes the motif LPXTG (SEQ ID NO: 45), with common recognition motifs being, e.g., LPKTG (SEQ ID NO: 91), LPATG (SEQ ID NO: 92), LPNTG (SEQ ID NO: 93). In some embodiments LPETG (SEQ ID NO: 55) is used. However, motifs falling outside this consensus may also be recognized. For example, in some embodiments the motif comprises an 'A' rather than a 'T' at position 4, e.g., LPXAG (SEQ ID NO: 94), e.g., LPNAG (SEQ ID NO: A). In some embodiments the motif comprises an 'A' rather than a 'G' at position 5, e.g., LPXTA (SEQ ID NO: 95), e.g., LPNTA (SEQ ID NO: 96). In some embodiments the motif comprises a 'G' rather than 'P' at position 2, e.g., LGXTG (SEQ ID NO: 97), e.g., LGATG (SEQ ID NO: 98). In some embodiments the motif comprises an 'I' rather than 'L' at position 1, e.g., IPXTG (SEQ ID NO: 99), e.g., IPNTG (SEQ ID NO: 100) or IPETG (SEQ ID NO: 101).

It will be appreciated that the terms "recognition motif" and "recognition sequence", with respect to sequences recognized by a transamidase, are used interchangeably. The term "transamidase recognition sequence" is sometimes abbreviated "TRS" herein.

In some embodiments of the invention the sortase is a sortase B (SrtB), e.g., a sortase B of *S. aureus, B. anthracis,* or *L. monocytogenes*. Motifs recognized by sortases of the B class (SrtB) often fall within the consensus sequences NPXTX, e.g., NP[Q/K]-[T/s]-[N/G/s] (SEQ ID NO: 102), such as NPQTN (SEQ ID NO: 103) or NPKTG (SEQ ID NO: 104). For example, sortase B of *S. aureus* or *B. anthracis* cleaves the NPQTN (SEQ ID NO: 103) or NPKTG (SEQ ID NO: 104) motif of IsdC in the respective bacteria (see, e.g., Marraffini, L. and Schneewind, O., Journal of Bacteriology, 189(17), p. 6425-6436, 2007). Other recognition motifs found in putative substrates of class B sortases are NSKTA_ (SEQ ID NO: 105), NPQTG_(SEQ ID NO: 106), NAKTN_ (SEQ ID NO: 107), and NPQSS_(SEQ ID NO: 108). For example, SrtB from *L. monocytogenes* recognizes certain motifs lacking P at position 2 and/or lacking Q or K at position 3, such as NAKTN_(SEQ ID NO: 107) and NPQSS_ (SEQ ID NO: 108) (Mariscotti J F, Garcia-Del Portillo F, Pucciarelli M G. The *listeria monocytogenes* sortase-B recognizes varied amino acids at position two of the sorting motif. J Biol Chem. 2009 Jan. 7. [Epub ahead of print])

In some embodiments, the sortase is a class C sortase. Class C sortases may utilize LPXTG_(SEQ ID NO: 45) as a recognition motif.

In some embodiments, the sortase is a class D sortase. Sortases in this class are predicted to recognize motifs with a consensus sequence NA-[E/A/S/H]-TG_(SEQ ID NO: 109) (Comfort D, supra). Class D sortases have been found, e.g., in *Streptomyces* spp., *Corynebacterium* spp., *Tropheryma whipplei, Thermobifida fusca,* and *Bifidobacterium longhum*. LPXTA (SEQ ID NO: 110) or LAXTG (SEQ ID NO: 111) may serve as a recognition sequence for class D sortases, e.g., of subfamilies 4 and 5, respectively subfamily-4 and subfamily-5 enzymes process the motifs LPXTA (SEQ ID NO: 110) and LAXTG (SEQ ID NO: 111), respectively). For example, *B. anthracis* Sortase C, which is a class D sortase, has been shown to specifically cleave the LPNTA motif in *B. anthracis* BasI and BasH (Marrafini, supra).

See Barnett and Scott for description of a sortase from that recognizes QVPTGV (SEQ ID NO: 112) motif (Barnett, T C and Scott, J R, Differential Recognition of Surface Proteins in *Streptococcus pyogenes* by Two Sortase Gene Homologs. Journal of Bacteriology, Vol. 184, No. 8, p. 2181-2191, 2002).

The invention contemplates use of sortases found in any gram positive organism, such as those mentioned herein and/or in the references (including databases) cited herein. The invention also contemplates use of sortases found in gram negative bacteria, e.g., *Colwellia psychrerythraea, Microbulbifer degradans, Bradyrhizobium japonicum, Shewanella oneidensis*, and *Shewanella putrefaciens*. They recognize sequence motifs LP[Q/K]T[A/S]T (SEQ ID NO:). In keeping with the variation tolerated at position 3 in sortases from gram positive organisms, a sequence motif LPXT[A/S] (SEQ ID NO: 113), e.g., LPXTA (SEQ ID NO: 110) or LPSTS (SEQ ID NO: 114) may be used.

The invention contemplates use of sortase recognition motifs from any of the experimentally verified or putative sortase substrates listed at http://bamics3.cmbi.kun.nl/jos/sortase_substrates/help.html, the contents of which are incorporated herein by reference, and/or in any of the above-mentioned references. In some embodiments the sortase recognition motif is selected from: LPKTG (SEQ ID NO: 115), LPITG (SEQ ID NO: 116), LPDTA (SEQ ID NO: 117), SPKTG (SEQ ID NO: 118), LAETG (SEQ ID NO: 119), LAATG (SEQ ID NO: 120), LAHTG (SEQ ID NO: 121), LASTG (SEQ ID NO: 122), LAETG (SEQ ID NO: 123), LPLTG (SEQ ID NO: 124), LSRTG (SEQ ID NO: 125), LPETG (SEQ ID NO: 55), VPDTG (SEQ ID NO: 126), IPQTG (SEQ ID NO: 127), YPRRG (SEQ ID NO: 128), LPMTG (SEQ ID NO: 129), LPLTG (SEQ ID NO: 130), LAFTG (SEQ ID NO: 131), LPQTS (SEQ ID NO: 132), it being understood that in various embodiments of the invention the 5$^{th}$ residue is replaced, as described elsewhere herein. For example, the sequence used may be LPXT, LAXT, LPXA, LGXT, IPXT, NPXT, NPQS (SEQ ID NO: 133), LPST (SEQ ID NO: 134), NSKT (SEQ ID NO: 125), NPQT (SEQ ID NO: 136), NAKT (SEQ ID NO: 137), LPIT (SEQ ID NO: 138), LAET (SEQ ID NO: 139), or NPQS (SEQ ID NO: 133). The invention comprises embodiments in which 'X' in any sortase recognition motif disclosed herein or known in the art is any standard or non-standard amino acid. Each variation is disclosed. In some embodiments, X is selected from the 20 standard amino acids found most commonly in proteins found in living organisms. In some embodiments, e.g., where the recognition motif is LPXTG (SEQ ID NO: 45) or LPXT, X is D, E, A, N, Q, K, or R. In some embodiments, X in a particular recognition motif is selected from those amino acids that occur naturally at position 3 in a naturally occurring sortase substrate. For example, in some embodiments X is selected from K, E, N, Q, A in an LPXTG (SEQ ID NO: 45) or LPXT motif where the sortase is a sortase A. In some embodiments X is selected from K, S, E, L, A, N in an LPXTG (SEQ ID NO: 45) or LPXT motif and a class C sortase is used.

In some embodiments, a recognition sequence further comprises one or more additional amino acids, e.g., at the N or C terminus. For example, one or more amino acids (e.g., up to 5 amino acids) having the identity of amino acids found immediately N-terminal to, or C-terminal to, a 5 amino acid recognition sequence in a naturally occurring sortase substrate may be incorporated. Such additional amino acids may provide context that improves the recognition of the recognition motif.

The term "transamidase recognition sequence" may refer to a masked or unmasked transamidase recognition sequence. A unmasked transamidase recognition sequence can be recognized by a transamidase. An unmasked transamidase recognition sequence may have been previously masked, e.g., as described herein. In some embodiments, a "masked transamidase recognition sequence" is a sequence that is not recognized by a transamidase but that can be readily modified ("unmasked") such that the resulting sequence is recognized by a transamidase. For example, in some embodiments at least one amino acid of a masked transamidase recognition sequence has a side chain that comprises a moiety that inhibits, e.g., substantially prevents, recognition of the sequence by a transamidase of interest, wherein removal of the moiety allows the transamidase to recognize the sequence. Masking may, for example, reduce recognition by at least 80%, 90%, 95%, or more (e.g., to undetectable levels) in certain embodiments. By way of example, in certain embodiments a threonine residue in a transamidase recognition sequence such as LPXTG (SEQ ID NO: 45) is phosphorylated, thereby rendering it refractory to recognition and cleavage by SrtA. The masked recognition sequence can be unmasked by treatment with a phosphatase, thus allowing it to be used in a SrtA-catalyzed transamidation reaction. The invention provides novel masked transamidase recognition sequences, and compounds comprising them. In certain embodiments, the transamidase recognition sequence comprises the formula:

wherein

R$^2$ is the side chain of any natural or unnatural amino acid, optionally modified or substituted; and R$^B$ is hydrogen; phosphate; sulfate; an oxygen-protecting group; substituted or unsubstituted acyl; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic aryl; or branched or unbranched, substituted or unsubstituted, cyclic or acyclic heteroaryl.

In certain embodiments, the transamidase recognition sequence comprises the formula:

In certain embodiments, the transamidase recognition sequence is of the formula:

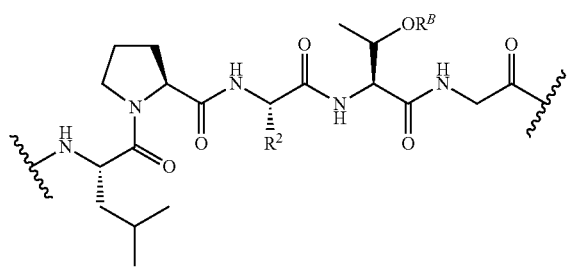

wherein $R^2$ is the side chain of any natural or unnatural amino acid, optionally modified or substituted; and $R^B$ is hydrogen; phosphate; sulfate; an oxygen-protecting group; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, the transamidase recognition sequence is of the formula:

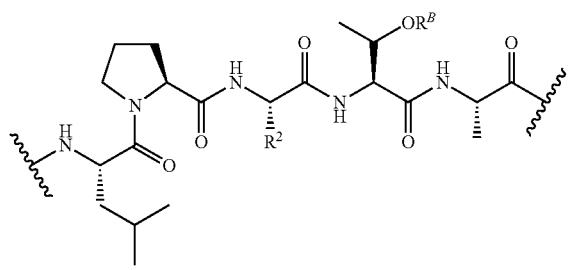

wherein $R^2$ is the side chain of any natural or unnatural amino acid, optionally modified or substituted; and $R^B$ is hydrogen; phosphate; sulfate; an oxygen-protecting group; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^2$ is the side chain of a natural amino acid. In certain embodiments, $R^2$ is the side chain group of aspartic acid, glutamic acid, alanine, asparagine, glutamine, lysine, or arginine. In certain embodiments, $R^2$ is the side chain group of arginine. In certain embodiments, $R^2$ is the side chain group of glutamic acid. In certain embodiments, $R^2$ is the side chain group of lysine. In certain embodiments, $R^2$ is the side chain group of aspartic acid. In certain embodiments, $R^2$ is the side chain group of alanine. In certain embodiments, $R^2$ is the side chain group of asparagine. In certain embodiments, $R^2$ is the side chain group of glutamine. In certain embodiments, the side chain of aspartic acid, glutamic acid, alanine, asparagine, glutamine, lysine, arginine, or other amino acid of $R^2$ is modified so as to mask the recognition sequence of the transamidase. For example, a lysine side chain may be acylated or the terminal amino group may be protected with a nitrogen-protecting group. An aspartic acid or glutamic acid may be esterified or amidated. A threonine, serine, or asparagine may be glycosylated. A threonine, serine, or tyrosine may be phosphorylated or sulfated.

An amino acid side chain may also be modified using a photocleavable moiety such as o-nitrobenzyl or dimethoxynitrobenzyl or derivatives thereof. In other embodiments, a chemical cleavage method is employed. For example, periodate cleavage can be used to cleave a vicinal diol. See, e.g., Rodenko B J, lass I major histocompatibility complexes loaded by a periodate trigger. J. Am Chem Soc.; 131(34): 12305-13, 2009.

A masked transamidase recognition sequence may be unmasked by a chemical or biological process that does not adversely affect other moieties of the protein or the protein itself. In certain embodiments, a phosphatase is used to remove a phosphate group masking a recognition sequence. In certain embodiments, a sulfatase is used to remove a sulfate group. In certain embodiments, an esterase or amidase is used to remove an acyl group. In certain embodiments, a glycosidase, e.g., an N-glycosidase, is used to remove a carbohydrate moiety. In certain embodiments, a photocleavable moiety is removed by exposing the protein or peptide to light. In some embodiments, mild alkaline hydrolysis is used to remove a masking moiety. In certain embodiments, a protecting group is removed using reagents and/or conditions typically used to remove the protecting group. See, e.g., Wuts et al., *Greene's Protective Groups in Organic Synthesis* (Wiley-Interscience; 4 edition; Oct. 30, 2006).

In certain embodiments, the unmasked transamidase recognition sequence is of the formula:

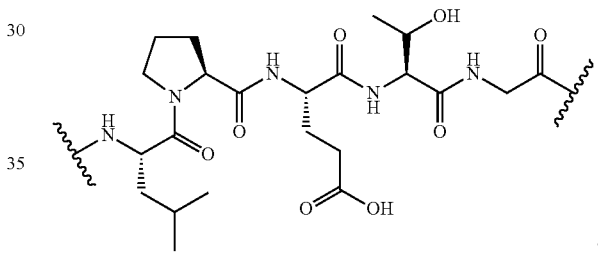

In certain embodiments, the masked transamidase recognition sequence is of the formula:

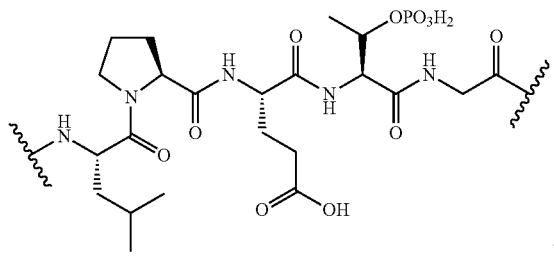

In certain embodiments, the unmasked transamidase recognition sequence is of the formula:

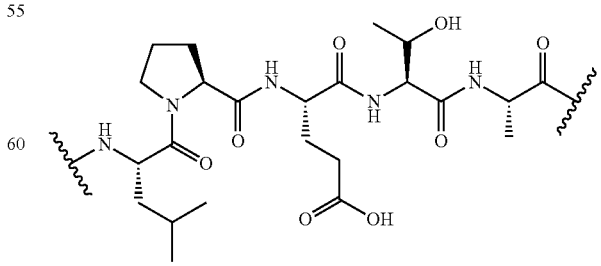

In certain embodiments, the masked transamidase recognition sequence is of the formula:

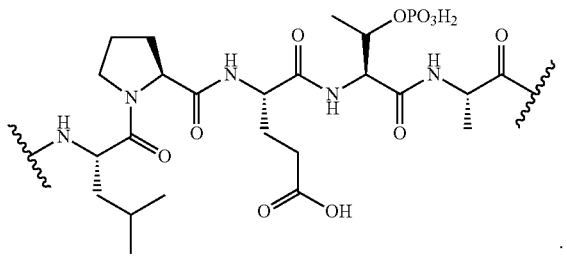

The invention provides compounds, sometimes referred to herein as "probes" that comprise a novel masked transamidase recognition sequence and are of use in a transamidase-mediated reaction. Optionally, the probe further comprises one or more additional amino acids either N- or C-terminal to the masked transamidase recognition sequence. Such additional amino acid(s) may be modified with, e.g., carbohydrates, lipids, phosphate groups, labels, tags, other polymers (for example, a non-polypeptide polymer such as polyethylene glycol), and acetyl groups. The invention further provides methods of ligation using an inventive probe. In some aspects, inventive methods comprise N-terminal and/or C-terminal modification of a polypeptide using an inventive probe. In some embodiments, both N- and C-termini are modified (dual modification). In some aspects, the invention provides methods of circularizing a polypeptide using an inventive probe. The invention further provides methods of joining two or more polypeptides using an inventive probe, thereby resulting in insertion of a non-genetically encoded peptide element between the two polypeptides. The non-genetically encoded peptide element in some embodiments comprises a modifying moiety, e.g., an acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a particle, a metal atom, a contrast agent, a catalyst, a non-polypeptide polymer (e.g., a polyethylene glycol), a recognition element, a small molecule, a lipid, or a label.

The invention provides methods of using inventive transamidase recognition sequences, and probes containing them, for a variety of purposes. In some embodiments, a probe comprising a masked transamidase recognition sequence is used for C-terminal labeling, which in some embodiments is followed by unmasking and cyclization (see, e.g., FIG. 43 and discussion below). In some embodiments, a probe comprising a masked transamidase recognition sequence is used for transamidase-mediated C-terminal labeling, followed by unmasking, followed by a second transamidase-mediated reaction. The second transamidase-mediated reaction may append a second polypeptide at the C-terminus of the oligopeptide probe. (See, e.g., FIG. 44, wherein the second transamidase-mediated reaction appends a GGG sequence to an IFNalpha variant that has undergone a first transamidase-mediated reaction.) Optionally, the first transamidase-mediated reaction installs a modifying group near the C-terminus, as shown in FIG. 33, wherein the modifying group is denoted as "Label". The first and second polypeptides are often each produced by translation of an RNA, e.g., recombinantly produced. The resulting product comprises two polypeptides joined by a non-genetically encoded element. Products produced using an inventive ligation method and/or probe are aspects of the invention.

Figure 43:
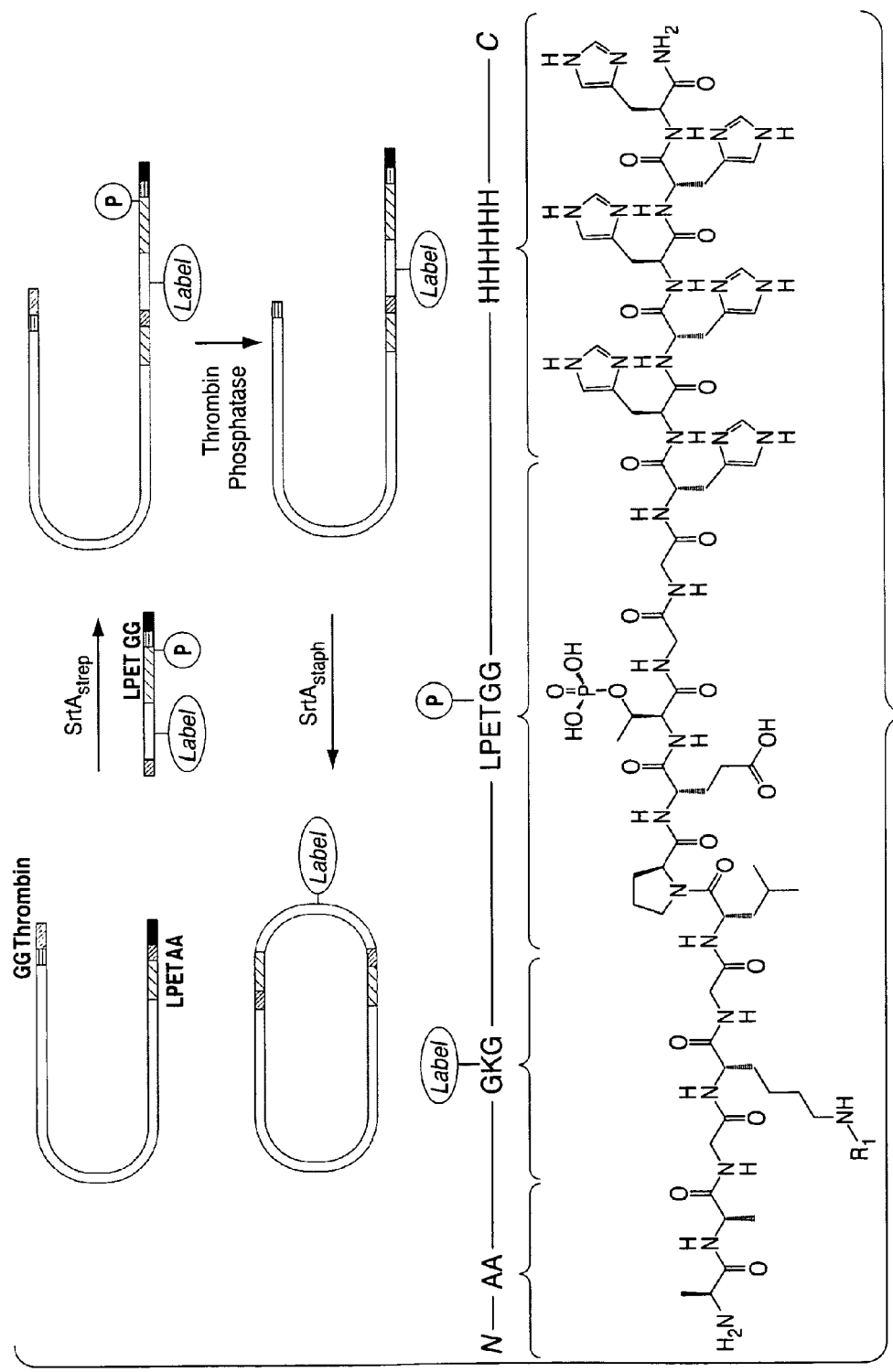
FIG. 43 shows a scheme for scheme for double transpeptidation using two sortases and a probe that contains a masked sortase recognition sequence (masking achieved by using phosphothreonine in the LPXTG (SEQ ID NO: 45) motif). LPETAA—SEQ ID O: 215; LPETGG—SEQ ID NO: 216; HHHHHH—SEQ ID NO: 216.
Figure 44:
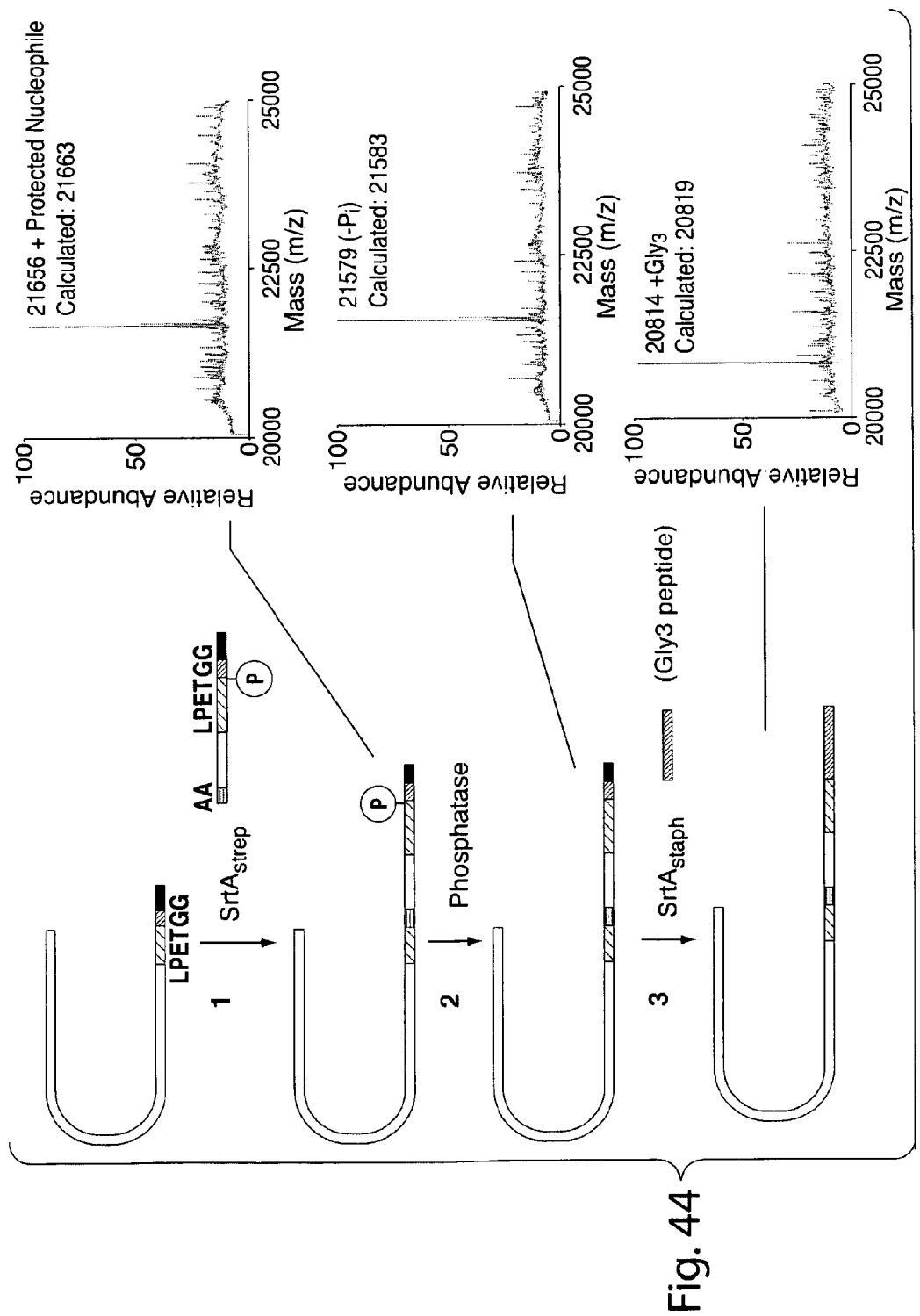
FIG. 44 shows mass spectrometry results showing sequential transpeptidation using a probe containing a masked sortase recognition sequence. Upper panel: IFNαL-PETAAGKGLPEtGG-His6 (SEQ ID NO: 66), LPETGG—SEQ ID NO: 216; Middle panel: IFNαLPETAAGKGLPETGG-His6 (SEQ ID NO: 67); IFNαLPETAAGKGLPETGGG (SEQ ID NO: 68).

For C-terminal labeling, e.g., as shown in FIG. 43 (upper reaction) or FIG. 44 (step 1), in certain embodiments the inventive method uses an oligopeptide with a nucleophilic amino N-terminus to attack the acyl enzyme and form an amide bond between the protein to be labeled and the oligopeptide. The oligopeptide may have any sequence of natural and/or unnatural amino acids and one or more of the amino acids may be modified or labeled in various embodiments. To give a few examples, the label may include a fluorescent tag, a phosphorescent tag, biotin, poly(histidine) tag, or a radioactive label. The oligopeptide may also be modified with carbohydrates, lipids, phosphate groups, labels, tags, other polymers (for example, a non-polypeptide polymer such as polyethylene glycol), and acetyl groups. Any biological or chemical modification of an amino acid or protein may be incorporated into the oligopeptide to be ligated using a transamidase. In certain embodiments, the oligopeptide includes a second transamidase recognition sequence or a masked transamidase recognition sequence. In certain embodiments, the oligopeptide is of the formula:

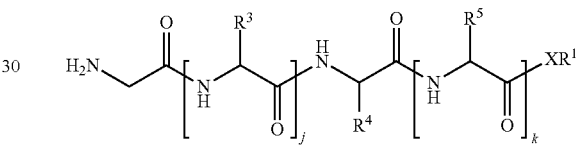

wherein j is an integer between 0 and 10, inclusive;

k is an integer between 0 and 10, inclusive;

X is —O—, —NR—, or —S—;

R is hydrogen; substituted or unsubstituted aliphatic; or substituted or unsubstituted heteroaliphatic;

$R^1$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl;

each occurrence of $R^3$ is independently the side chain of a natural or unnatural amino acid;

$R^4$ is the side chain of a natural or unnatural amino acid, optionally modified or substituted; substituted or unsubstituted acyl; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl; and each occurrence of $R^5$ is independently the side chain of a natural or unnatural amino acid.

In certain embodiments, the oligopeptide is of the formula:

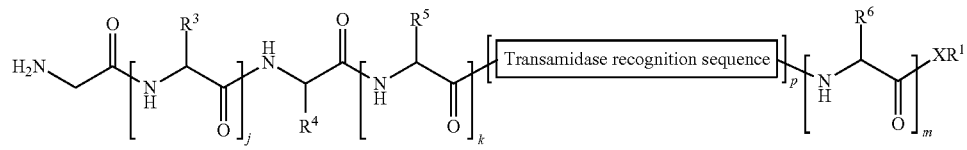

wherein transamidase recognition sequence is a sequence recognized by a transamidase;

j is an integer between 0 and 10, inclusive;

k is an integer between 0 and 10, inclusive;

m is an integer between 0 and 10, inclusive;

p is 1 or 2;

X is —O—, —NR—, or —S—;

R is hydrogen; substituted or unsubstituted aliphatic; or substituted or unsubstituted heteroaliphatic;

each occurrence of $R^1$ is independently hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl;

each occurrence of $R^3$ is independently the side chain of a natural or unnatural amino acid, optionally modified or substituted; substituted or unsubstituted acyl; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;

$R^4$ is the side chain of a natural or unnatural amino acid, optionally modified or substituted; substituted or unsubstituted acyl; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;

each occurrence of $R^5$ is independently the side chain of a natural or unnatural amino acid, optionally modified or substituted; substituted or unsubstituted acyl; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl; and each occurrence of $R^6$ is independently the side chain of a natural or unnatural amino acid.

In certain embodiments, the transamidase recognition sequence is LPXT, wherein X is a natural or unnatural amino acid. In certain embodiments, X is selected from D, E, A, N, Q, K, or R. In certain embodiments, the recognition sequence is selected from LPXT, LPXT, SPXT, LAXT, LSXT, NPXT, VPXT, IPXT, and YPXR. In certain embodiments, X is selected to match a naturally occurring transamidase recognition sequence. In certain embodiments, the transamidase recognition sequence is selected from: LPKT (SEQ ID NO: 69), LPIT (SEQ ID NO: 70), LPDT (SEQ ID NO: 71), SPKT (SEQ ID NO: 72), LAET (SEQ ID NO: 73), LAAT (SEQ ID NO: 74), LAET (SEQ ID NO: 75), LAST (SEQ ID NO: 76), LAET (SEQ ID NO: 77), LPLT (SEQ ID NO: 78), LSRT (SEQ ID NO: 79), LPET (SEQ ID NO: 53), VPDT (SEQ ID NO: 80), IPQT (SEQ ID NO: 81), YPRR (SEQ ID NO: 82), LPMT (SEQ ID NO: 83), LPLT (SEQ ID NO: 84), LAFT (SEQ ID NO: 85), LPQT (SEQ ID NO: 86), NSKT (SEQ ID NO: 87), NPQT (SEQ ID NO: 88), NAKT (SEQ ID NO: 89), and NPQS (SEQ ID NO: 90). In certain embodiments, e.g., in which sortase A is used, the transamidase recognition motif comprises the amino acid sequence $X_1PX_2X_3$, where $X_1$ is leucine, isolucine, valine or methionine; $X_2$ is any amino acid; $X_3$ is threonine, serine, or alanine; P is proline; and G is glycine. In specific embodiments, as noted above $X_1$ is leucine, and $X_3$ is threonine. In certain embodiments, $X_2$ is aspartate, glutamate, alanine, glutamine, lysine, or methionine. In certain embodiments, e.g., where sortase B is utilized, the recognition sequence often comprises the amino acid sequence $NPX_1TX_2$, where $X_1$ is glutamine or lysine; $X_2$ is asparagine or glycine; N is asparagine; P is proline and T is threonine. In certain embodiments, e.g., where sortase A from Staphylcoccus aureus ($SrtA_{staph}$) is utilized, the recognition sequence comprises the amino acid sequence $LPX_1TX_2$, where $X_1$ is selected from D, E, A, N, Q, K, or R; $X_2$ is alanine or glycine; L is leucine; P is proline and T is threonine. In certain embodiments, for recognition sequence of $SrtA_{staph}$ is $LPX_1TA$ (SEQ ID NO: 140). In other embodiments, for recognition sequence of $SrtA_{staph}$ is $LPX_1TG$ (SEQ ID NO: 141). The invention encompasses the recognition that selection of X may be based at least in part in order to confer desired properties on the compound containing the recognition motif. In some embodiments, X is selected to modify a property of the compound that contains the recognition motif, such as to increase or decrease solubility in a particular solvent. In some embodiments, X is selected to be compatible with reaction conditions to be used in synthesizing a compound comprising the recognition motif, e.g., to be unreactive towards reactants used in the synthesis.

In certain embodiments, j is 0. In certain embodiments, j is 1. In certain embodiments, j is 2. In certain embodiments, j is 3. In certain embodiments, j is 4. In certain embodiments, j is 5.

In certain embodiments, k is 0. In certain embodiments, k is 1. In certain embodiments, k is 2. In certain embodiments, k is 3. In certain embodiments, k is 4. In certain embodiments, k is 5.

In certain embodiments, m is 0. In certain embodiments, m is 1. In certain embodiments, m is 2. In certain embodiments, m is 3. In certain embodiments, m is 4. In certain embodiments, m is 5.

In certain embodiments, X is —O—. In certain embodiments, X is —NH—.

In certain embodiments, $R^1$ is substituted hydrogen. In certain embodiments, $R^1$ is substituted aliphatic. In certain embodiments, $R^1$ is unsubstituted aliphatic. In some embodiments, $R^1$ is substituted $C_{1-12}$ aliphatic. In some embodiments, $R^1$ is unsubstituted $C_{1-12}$ aliphatic. In some embodiments, $R^1$ is substituted $C_{1-6}$ aliphatic. In some embodiments, $R^1$ is unsubstituted $C_{1-6}$ aliphatic. In some embodiments, $R^1$ is $C_{1-3}$ aliphatic. In certain embodiments, $R^1$ is $C_{1-6}$ alkyl. In some embodiments, $R^1$ is butyl. In some embodiments, $R^1$ is n-butyl. In some embodiments, $R^1$ is isobutyl. In some embodiments, $R^1$ is propyl. In some embodiments, $R^1$ is n-propyl. In some embodiments, $R^1$ is isopropyl. In some embodiments, $R^1$ is ethyl. In some embodiments, $R^1$ is methyl. In certain embodiments, $R^1$ is substituted aryl. In certain embodiments, $R^1$ is unsubstituted aryl. In certain embodiments, $R^1$ is substituted phenyl. In certain embodiments, $R^1$ is unsubstituted phenyl.

In certain embodiments, —$XR^1$ is —$OCH_3$. In certain embodiments, —$XR^1$ is —OH. In certain embodiments, —$XR^1$ is —$NH_2$.

In certain embodiments, $R^3$ is the side chain of a natural amino acid. In certain embodiments, $R^3$ is hydrogen. In certain embodiments, $R^3$ is methyl.

In certain embodiments, $R^4$ is a modified side chain of a natural amino acid. In certain embodiments, $R^4$ is a modified side chain of serine, threonine, lysine, aspartate, glutamate, arginine, asparagine, glutamine, or tyrosine.

In certain embodiments, $R^4$ is of the formula:

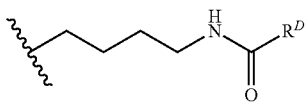

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

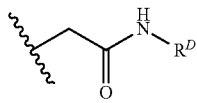

wherein $R^D$ is substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

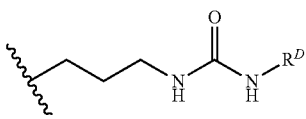

wherein $R^D$ is substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

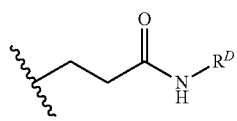

wherein $R^D$ is substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

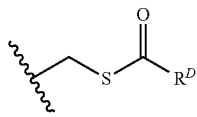

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

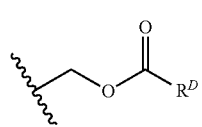

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

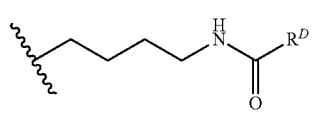

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

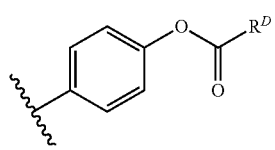

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^D$ is of the formula:

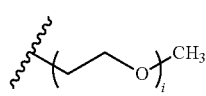

wherein i is an integer between 1 and 100, inclusive.

In certain embodiments, $R^5$ is the side chain of a natural amino acid. In certain embodiments, $R^5$ is hydrogen. In certain embodiments, $R^5$ is methyl.

In certain embodiments, $R^6$ is the side chain of a natural amino acid. In certain embodiments, $R^6$ is hydrogen. In certain embodiments, $R^6$ is methyl.

In certain embodiments, m is 0, and $-XR^1$ is $-OCH_3$. In certain embodiments, m is 1, $R^6$ is methyl, and $-XR^1$ is $-OH$. In certain embodiments, m is 1, $R^6$ is hydrogen, and $-XR^1$ is $-OH$.

In certain embodiments, the oligopeptide for c-terminal labeling is of the formula:

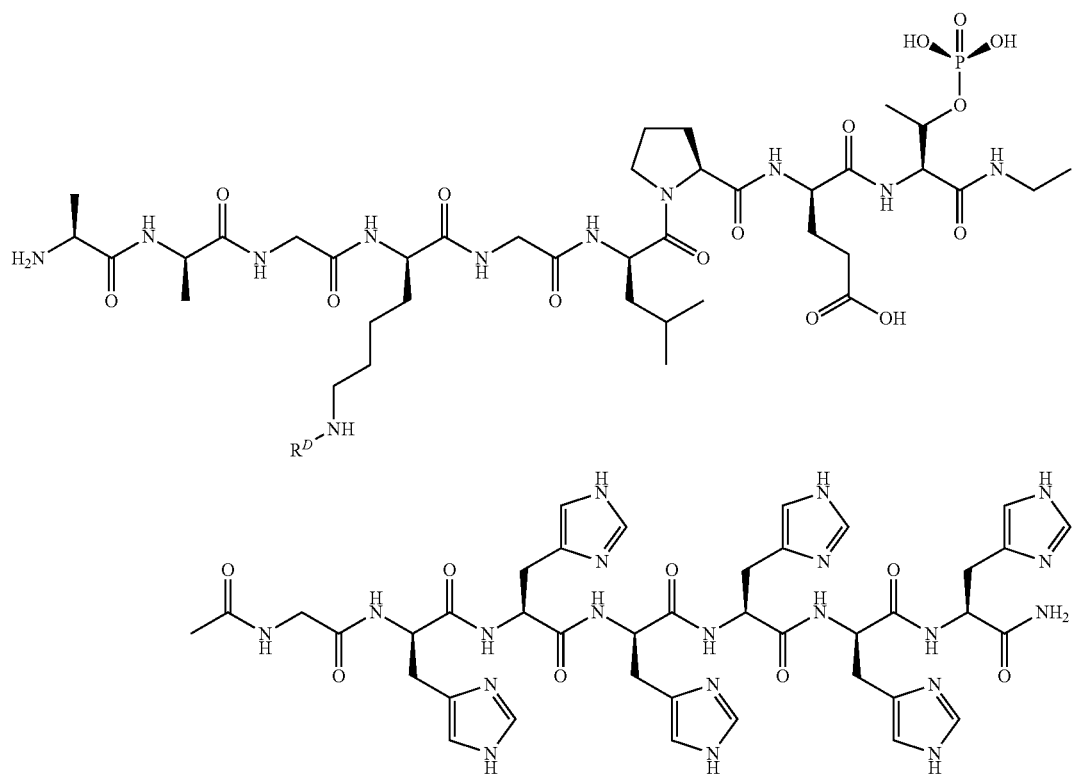

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl. In certain embodiments, $R^D$ is of the formula:

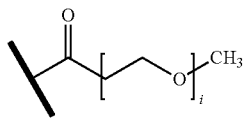

wherein i is an integer between 1 and 100, inclusive.
In certain embodiments, $R^D$ is of the formula:

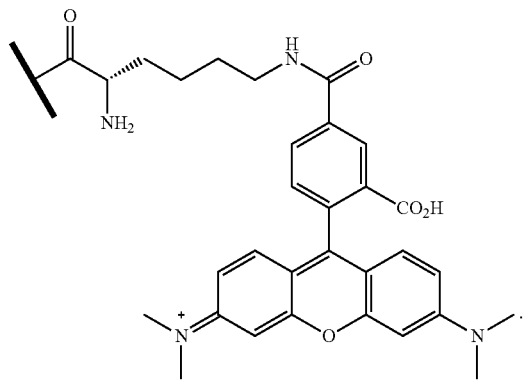

In certain embodiments, $R^D$ is of the formula:

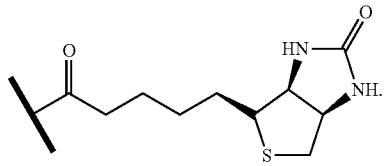

Figure 24:
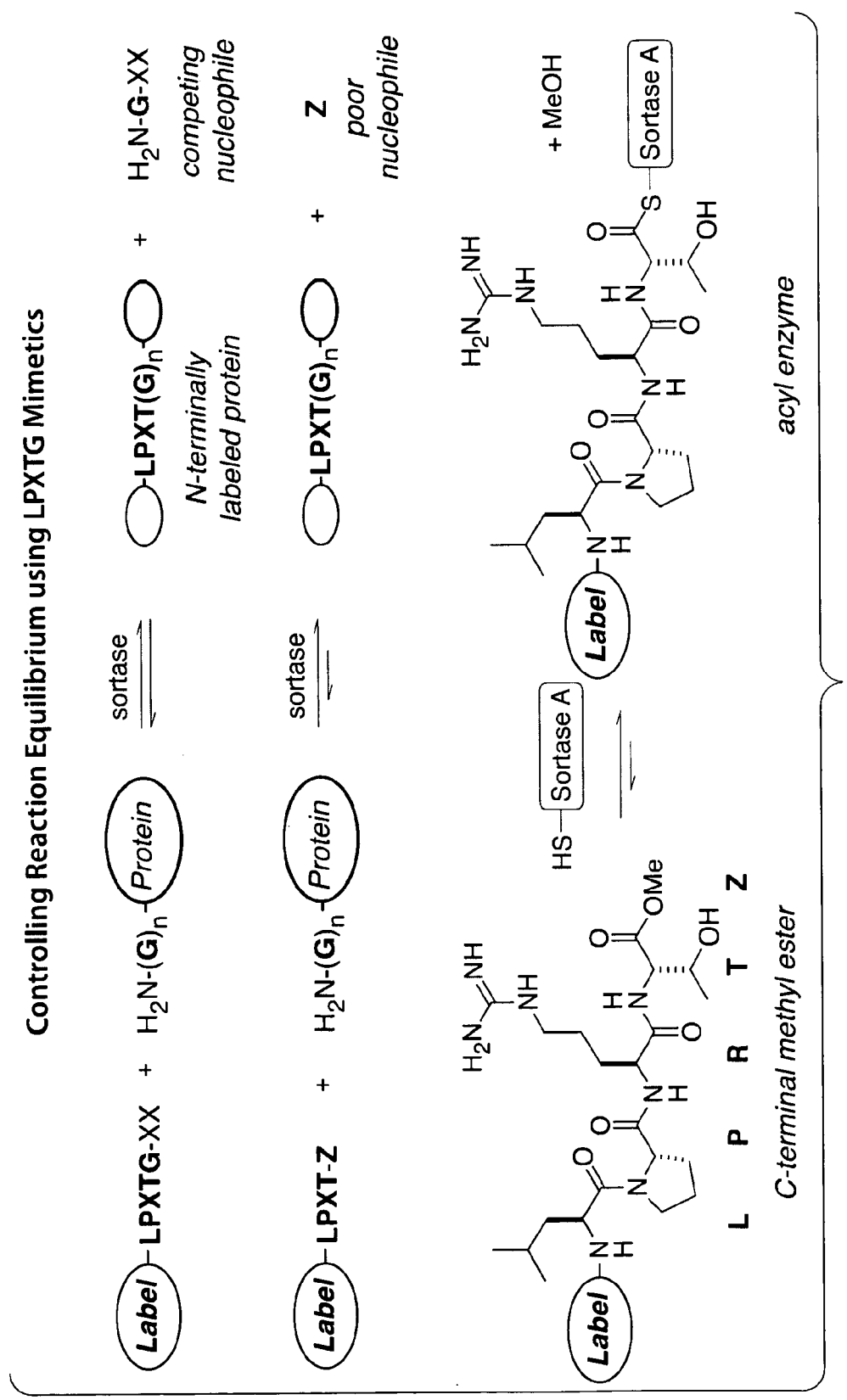
FIG. 24 schematically depicts control of reaction equilibrium using inventive LPXTG (SEQ ID NO: 45) mimetics. LPXTG-XX—SEQ ID NO: 182.
Figure 25:
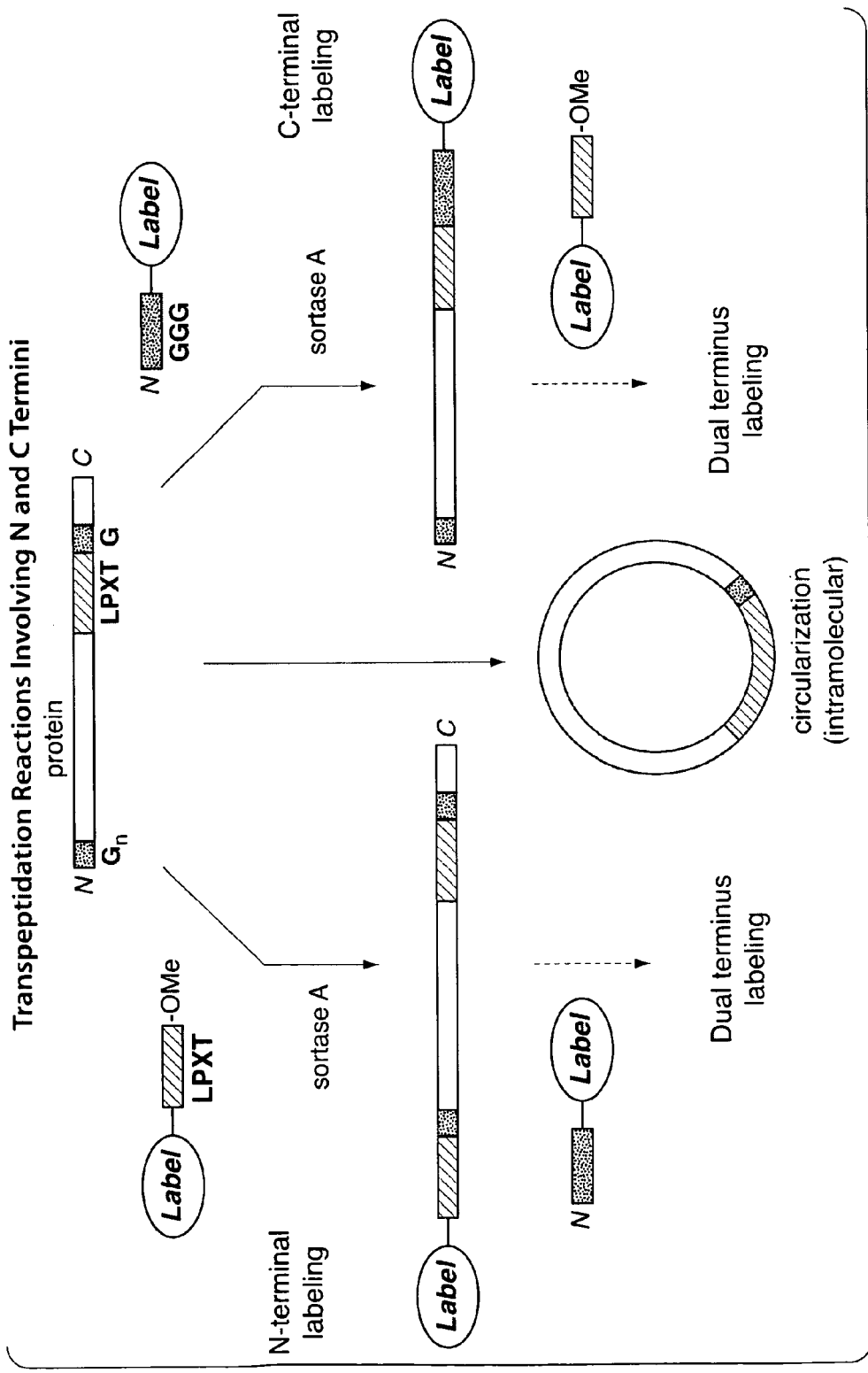
FIG. 25 schematically shows transpeptidation reactions involving N and C termini. LPXTG—SEQ ID NO: 45.

For N-terminal labeling, e.g., as shown in FIG. 24, inventive methods use an oligopeptide with a transamidase recognition sequence that forms an acyl enzyme. The oligopeptide may have any sequence of natural and/or unnatural amino acids and one or more of the amino acids may be modified or labeled in various embodiments. To give a few examples, the label may include a fluorescent tag, a phosphorescent tag, biotin, poly(histidine) tag, or a radioactive label. The oligopeptide may also be modified with carbohydrates, lipids, phosphate groups, labels, tags, other polymers (for example, a non-polypeptide polymer such as polyethylene glycol), and acetyl groups. Any biological or chemical modification of an amino acid or protein may be incorporated into the oligopeptide to be ligated using a transamidase. In certain embodiments, the oligopeptide includes a second transamidase recognition sequence or a masked transamidase recognition sequence. In certain embodiments, the oligopeptide is of the formula:

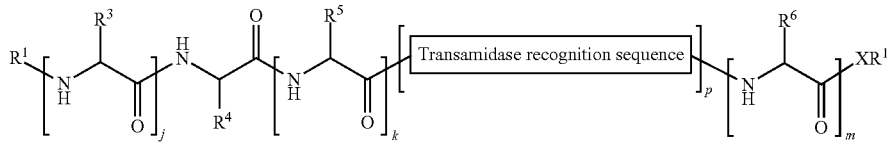

wherein
transamidase recognition sequence is a sequence recognized by a transamidase;
j is an integer between 0 and 10, inclusive;
k is an integer between 0 and 10, inclusive;
m is an integer between 0 and 10, inclusive;
p is 1 or 2;
X is —O—, —NR—, or —S—;
R is hydrogen; substituted or unsubstituted aliphatic; or substituted or unsubstituted heteroaliphatic;
each occurrence of $R^1$ is independently hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl;
each occurrence of $R^3$ is independently the side chain of a natural or unnatural amino acid, optionally modified or substituted; substituted or unsubstituted acyl; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
$R^4$ is the side chain of a natural or unnatural amino acid, optionally modified or substituted; substituted or unsubstituted acyl; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl;
each occurrence of $R^5$ is independently the side chain of a natural or unnatural amino acid, optionally modified or substituted; substituted or unsubstituted acyl; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl; and
each occurrence of $R^6$ is independently the side chain of a natural or unnatural amino acid, optionally modified or substituted; substituted or unsubstituted acyl; branched or unbranched, substituted or unsubstituted, cyclic or acyclic aliphatic; branched or unbranched, substituted or unsubstituted, cyclic or acyclic heteroaliphatic; substituted or unsubstituted aryl; or substituted or unsubstituted heteroaryl.

In certain embodiments, the transamidase recognition sequence is LPXT, wherein X is a natural or unnatural amino acid. In certain embodiments, X is selected from D, E, A, N, Q, K, or R. In certain embodiments, the recognition sequence is selected from LPXT, LPXT, SPXT, LAXT, LSXT, NPXT, VPXT, IPXT, and YPXR. In certain embodiments, X is selected to match a naturally occurring transamidase recognition sequence. In certain embodiments, the transamidase recognition sequence is selected from: LPKT (SEQ ID NO: 69), LPIT (SEQ ID NO: 70), LPDT (SEQ ID NO: 71), SPKT (SEQ ID NO: 72), LAET (SEQ ID NO: 73), LAAT (SEQ ID NO: 74), LAET (SEQ ID NO: 75), LAST (SEQ ID NO: 76), LAET (SEQ ID NO: 77), LPLT (SEQ ID NO: 78), LSRT (SEQ ID NO: 79), LPET (SEQ ID NO: 53), VPDT (SEQ ID NO: 80), IPQT (SEQ ID NO: 81), YPRR (SEQ ID NO: 82), LPMT (SEQ ID NO: 83), LPLT (SEQ ID NO: 84), LAFT (SEQ ID NO: 85), LPQT (SEQ ID NO: 86), NSKT (SEQ ID NO: 87), NPQT (SEQ ID NO: 88), NAKT (SEQ ID NO: 89), and NPQS (SEQ ID NO: 90). In certain embodiments, e.g., in which sortase A is used, the transamidase recognition motif comprises the amino acid sequence $X_1PX_2X_3$, where $X_1$ is leucine, isolucine, valine or methionine; $X_2$ is any amino acid; $X_3$ is threonine, serine, or alanine; P is proline; and G is glycine. In specific embodiments, as noted above $X_1$ is leucine, and $X_3$ is threonine. In certain embodiments, $X_2$ is aspartate, glutamate, alanine, glutamine, lysine, or methionine. In certain embodiments, e.g., where sortase B is utilized, the recognition sequence often comprises the amino acid sequence $NPX_1TX_2$, where $X_1$ is glutamine or lysine; $X_2$ is asparagine or glycine; N is asparagine; P is proline and T is threonine. In certain embodiments, e.g., where sortase A from *Streptococcus pyogenes* ($SrtA_{strep}$) is utilized, the recognition sequence comprises the amino acid sequence $LPX_1TX_2$, where $X_1$ is selected from D, E, A, N, Q, K, or R; $X_2$ is alanine or glycine; L is leucine; P is proline and T is threonine. In certain embodiments, a recognition sequence for $SrtA_{strep}$ is $LPX_1TG$ (SEQ ID NO: 141). In certain embodiments, a recognition sequence for $SrtA_{strep}$ is $LPX_1TA$ (SEQ ID NO: 140). In certain embodiments, a recognition sequence for $SrtA_{strep}$ is LPETA (SEQ ID NO: 142) or LPETG (SEQ ID NO: 55). In certain embodiments, e.g., where sortase A from *Staphylcoccus aureus* ($SrtA_{staph}$) is utilized, the recognition sequence comprises the amino acid sequence $LPX_1TG$ (SEQ ID NO: 141), where $X_1$ is selected from D, E, A, N, Q, K, or R; $X_2$ is glycine; L is leucine; P is proline and T is threonine. In certain embodiments, a recognition sequence for $SrtA_{staph}$ is LPETG (SEQ ID NO: 55). In certain embodiments, a recognition sequence for $SrtA_{strep}$ is $LPX_1TA$ (SEQ ID NO: 140). The invention encompasses the recognition that selection of X may be based at least in part in order to confer desired properties on the compound containing the recognition motif. In some embodiments, X is selected to modify a property of the compound that contains the recognition motif, such as to increase or decrease solubility in a particular solvent. In some embodiments, X is selected to be compatible with reaction conditions to be used in synthesizing a compound comprising the recognition motif, e.g., to be unreactive towards reactants used in the synthesis. In some embodiments, X, e.g., $X_1$, is selected such that the transamidase recognition sequence is masked.

In certain embodiments, j is 0. In certain embodiments, j is 1. In certain embodiments, j is 2. In certain embodiments, j is 3. In certain embodiments, j is 4. In certain embodiments, j is 5.

In certain embodiments, k is 0. In certain embodiments, k is 1. In certain embodiments, k is 2. In certain embodiments, k is 3. In certain embodiments, k is 4. In certain embodiments, k is 5.

In certain embodiments, m is 0. In certain embodiments, m is 1. In certain embodiments, m is 2. In certain embodiments, m is 3. In certain embodiments, m is 4. In certain embodiments, m is 5.

In certain embodiments, p is 1. In certain embodiments, p is 2.

In certain embodiments, X is —O—. In certain embodiments, X is —NH—.

In certain embodiments, $R^1$ is hydrogen. In certain embodiments, $R^1$ is substituted aliphatic. In certain embodiments, $R^1$ is unsubstituted aliphatic. In some embodiments, $R^1$ is substituted $C_{1-12}$ aliphatic. In some embodiments, $R^1$ is unsubstituted $C_{1-12}$ aliphatic. In some embodiments, $R^1$ is substituted $C_{1-6}$ aliphatic. In some embodiments, $R^1$ is unsubstituted $C_{1-6}$ aliphatic. In some embodiments, $R^1$ is $C_{1-3}$ aliphatic. In certain embodiments, $R^1$ is $C_{1-6}$ alkyl. In some embodiments, $R^1$ is butyl. In some embodiments, $R^1$ is n-butyl. In some embodiments, $R^1$ is isobutyl. In some embodiments, $R^1$ is propyl. In some embodiments, $R^1$ is n-propyl. In some embodiments, $R^1$ is isopropyl. In some embodiments, $R^1$ is ethyl. In some embodiments, $R^1$ is methyl. In certain embodiments, $R^1$ is substituted aryl. In certain embodiments, $R^1$ is unsubstituted aryl. In certain embodiments, $R^1$ is substituted phenyl. In certain embodiments, $R^1$ is unsubstituted phenyl.

In certain embodiments, —$XR^1$ is —$OCH_3$. In certain embodiments, —$XR^1$ is —OH. In certain embodiments, —$XR^1$ is —$NH_2$.

In certain embodiments, $R^3$ is the side chain of a natural amino acid. In certain embodiments, $R^3$ is hydrogen. In certain embodiments, $R^3$ is methyl.

In certain embodiments, $R^4$ is a modified side chain of a natural amino acid. In certain embodiments, $R^4$ is a modified side chain of serine, threonine, lysine, aspartate, glutamate, arginine, asparagine, glutamine, or tyrosine.

In certain embodiments, $R^4$ is of the formula:

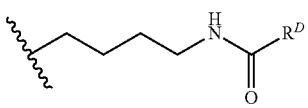

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

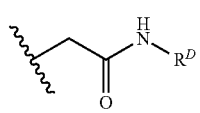

wherein $R^D$ is substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

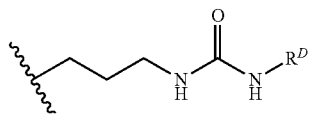

wherein $R^D$ is substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

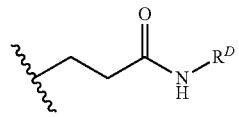

wherein $R^D$ is substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

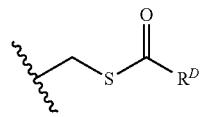

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

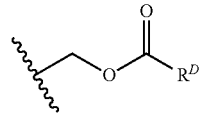

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

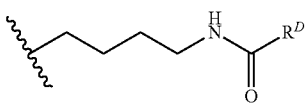

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^4$ is of the formula:

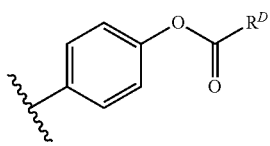

wherein $R^D$ is hydrogen; substituted or unsubstituted acyl; branched or unbranched, substituted or unsubstituted, cyclic or acyclic aliphatic, branched or unbranched, substituted or unsubstituted, cyclic or acyclic heteroaliphatic, branched or unbranched, substituted or unsubstituted, cyclic or acyclic aryl, or branched or unbranched, substituted or unsubstituted, cyclic or acyclic heteroaryl.

In certain embodiments, $R^D$ is of the formula:

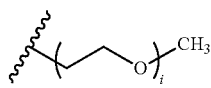

wherein i is an integer between 1 and 100, inclusive.

In certain embodiments, $R^5$ is the side chain of a natural amino acid. In certain embodiments, $R^5$ is hydrogen. In certain embodiments, $R^5$ is methyl.

In certain embodiments, $R^6$ is the side chain of a natural amino acid. In certain embodiments, $R^6$ is hydrogen. In certain embodiments, $R^6$ is methyl.

In certain embodiments, m is 0, and —$XR^1$ is —$OCH_3$. In certain embodiments, m is 1, $R^6$ is methyl, and —$XR^1$ is —OH. In certain embodiments, m is 1, $R^6$ is hydrogen, and —$XR^1$ is —OH.

In certain embodiments, the oligopeptide for c-terminal labeling is of the formula:

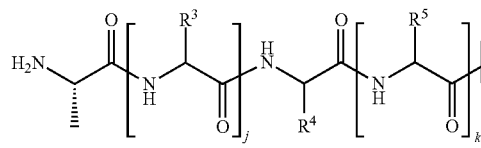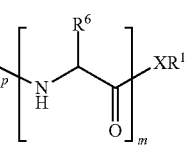

wherein j, k, p, m, X, $R^1$, $R^3$, $R^4$, $R^5$, and $R^6$ are as defined herein.

In some embodiments, a probe for use in N-terminal labeling comprises a modified transamidase sequence that comprises an ester group in place of a C-terminal amino acid residue. In some embodiments, a probe for use in n-terminal labeling comprises an amino acid residue at the C-terminus, e.g., G, GG, GGG, etc. In some embodiments, a nucleophile located at the N-terminus of a polypeptide to be labeled comprises at least 2 G residues, e.g., 2, 3, 4, 5, or more G residues.

Transamidase fragments having transamidation activity can be utilized in the methods described herein. Such fragments can be identified by producing transamidase fragments by known recombinant techniques or proteolytic techniques, for example, and determining the rate of protein or peptide ligation. The fragment sometimes consists of about 80% of the full-length transamidase amino acid sequence, and sometimes about 70%, about 60%, about 50%, about 40% or about 30% of the full-length transamidase amino acid sequence such as that of S. aureus Sortase A (GenBank Accession number AAD48437). In some embodiments, the fragment lacks an N-terminal portion of the full-length sequence, e.g., the fragment lacks the N-terminal portion extending to the end of the membrane anchor sequence. In some embodiments the fragment comprises the C-terminus of a full-length transamidase amino acid sequence. In some embodiments, a catalytic core region from a sortase is utilized, e.g., a region is from about position 60 to about position 206 of SrtA, e.g., S. aureus SrtA, or about from position 82 to about position 249 of SrtAstrep.

Transamidases from other organisms also can be utilized in the processes described herein. Such transamidases often are encoded by nucleotide sequences substantially identical or similar to the nucleotide sequences that encode Srt A and Srt B. A similar or substantially identical nucleotide sequence may include modifications to the native sequence, such as substitutions, deletions, or insertions of one or more nucleotides. Included are nucleotide sequences that sometimes are 55%, 60%, 65%, 70%, 75%, 80%, or 85% or more identical to a native nucleotide sequence, and often are 90% or 95% or more identical to the native nucleotide sequence (each identity percentage can include a 1%, 2%, 3% or 4% variance). One test for determining whether two nucleic acids are substantially identical is to determine the percentage of identical nucleotide sequences shared between the nucleic acids.

Calculations of sequence identity can be performed as follows. Sequences are aligned for optimal comparison purposes and gaps can be introduced in one or both of a first and a second nucleic acid sequence for optimal alignment. Also, non-homologous sequences can be disregarded for comparison purposes. The length of a reference sequence aligned for comparison purposes sometimes is 30% or more, 40% or more, 50% or more, often 60% or more, and more often 70%, 80%, 90%, 100% of the length of the reference sequence. The nucleotides at corresponding nucleotide positions then are compared among the two sequences. When a position in the first sequence is occupied by the same nucleotide as the corresponding position in the second sequence, the nucleotides are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two nucleotide sequences can be determined using the algorithm of Meyers & Miller, CABIOS 4: 11 17 (1989), which has been incorporated into the ALIGN program (version 2.0), using a PAM120 weight residue table, a gap length penalty of 12 and a gap penalty of 4. Percent identity between two nucleotide sequences can be determined using the GAP program in the GCG software package (available at www.gcg.com), using a NWSgapdna. CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frame shift gap penalty of 5.

Another manner for determining if two nucleic acids are substantially identical is to assess whether a polynucleotide homologous to one nucleic acid will hybridize to the other nucleic acid under stringent conditions. As use herein, the term "stringent conditions" refers to conditions for hybridization and washing. Stringent conditions are known to those skilled in the art and can be found in Ausubel et al. *Current Protocols in Molecular Biology* (John Wiley & Sons, Inc., New York, 1999). Aqueous and non-aqueous methods are described in that reference and either can be used. An example of stringent conditions is hybridization in 6× sodium chloride/sodium citrate (SSC) at about 45° C., followed by one or more washes in 0.2×SSC, 0.1% SDS at 50° C. Another example of stringent conditions are hybridization in 6× sodium chloride/sodium citrate (SSC) at about 45° C., followed by one or more washes in 0.2×SSC, 0.1% SDS at 55° C. A further example of stringent conditions is hybridization in 6× sodium chloride/sodium citrate (SSC) at about 45° C., followed by one or more washes in 0.2×SSC, 0.1% SDS at 60° C. Often, stringent conditions are hybridization in 6× sodium chloride/sodium citrate (SSC) at about 45° C., followed by one or more washes in 0.2×SSC, 0.1% SDS at 65° C. Also, stringency conditions include hybridization in 0.5M sodium phosphate, 7% SDS at 65° C., followed by one or more washes at 0.2×SSC, 1% SDS at 65° C.

A variant sequence can depart from a native amino acid sequence in different manners. Amino acid substitutions may be made on the basis of similarity in polarity, charge, solubility, hydrophobicity, hydrophilicity, helix-forming properties and/or amphipathic properties and the resulting variants are screened for antimicrobial activity. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. In certain embodiments, conservative substitutions may be made, according to Table A. Amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

TABLE A

| Aliphatic | Non-polar | G A P |
| | | I L V |
| | Polar-uncharged | C S T M |
| | | N Q |
| | Polar-charged | D E |
| | | K R |
| Aromatic | | H F W Y |

In certain embodiments homologous substitution may occur, which is a substitution or replacement of like amino acids, such as basic for basic, acidic for acidic, polar for polar amino acids, and hydrophobic for hydrophobic, for example. Non-homologous substitutions can be introduced to a native sequence, such as from one class of residue to another (e.g., a non-hydrophobic to a hydrophobic amino acid), or substituting a naturally occurring amino acid with an unnatural amino acids or non-classical amino acid replacements.

Srt A and Srt B nucleotide sequences may be used as "query sequences" to perform a search against public databases to identify related sequences. Such searches can be performed using the NBLAST and XBLAST programs (version 2.0) of Altschul, et al., J. Mol. Biol. 215: 403 410 (1990). BLAST nucleotide searches can be performed with the NBLAST program, score=100, wordlength=12 to obtain homologous nucleotide sequences. To obtain gapped alignments for comparison purposes, gapped BLAST can be utilized as described in Altschul, et al., Nucleic Acids Res. 25 (17): 3389-3402 (1997). When utilizing BLAST and Gapped BLAST programs, default parameters of the respective programs (e.g., XBLAST and NBLAST) can be used (see www.ncbi.nlm.nih.gov).

Different transamidases may specifically recognize different recognition sequences. In some embodiments, acyl donors utilized in the ligation processes described herein include or are modified with an appropriate sortase recognition motif. One or more appropriate sortase recognition sequences can be added to an acyl donor not having one by known synthetic and recombinant techniques. In certain embodiments, 2, 3, 4, 5, 6, 7, 8, 9, or 10 or more sortase or transamidase recognition sequences are incorporated in an acyl donor.

In certain embodiments where Srt A is utilized as a transamidase enzyme, the acyl donor comprises the amino acid sequence $X_1PX_2X_3G$, where $X_1$ is leucine, isolucine, valine or methionine; $X_2$ is any amino acid; $X_3$ is threonine, serine or alanine; P is proline and G is glycine. In some embodiments, $X_1$ is leucine and $X_3$ is threonine. In certain embodiments, $X_2$ is aspartate, glutamate, alanine, glutamine, lysine or methionine. In certain embodiments, the G is omitted and replaced with a acyl group as described herein. In some embodiments, the acyl donor comprises the sequence

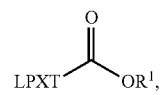

wherein X is any amino acid and $R^1$ is as described herein.

In certain embodiments where Srt B is utilized as a transamidase enzyme, the acyl donor comprises the amino acid sequence $NPX_1TX_2$, where $X_1$ is glutamine or lysine; $X_2$ is asparagine or glycine; N is asparagine; P is proline and T is threonine.

Transamidases utilized in the inventive ligation methods described herein sometimes are isolated and incorporated into a kit. Any convenient method known can be utilized to isolate the sortase or transamidase. In certain embodiments, the transamidase is produced with a N-terminal or C-terminal amino acid sequence that facilitates purification. For example, the transamidase sometimes is produced with a C-terminal or N-terminal polyhistidine sequence, often six histidines, which have affinity and bind to nickel-derivitized solid supports. In some embodiments, a transamidase used in accordance with the present invention further comprises an affinity tag. Examples of affinity tags include, e.g., His-tag (His6, SEQ ID NO: 174), FLAG, Streptag, HA tag, Myc tag, maltose binding protein, SNUT tag, NusA, T7, thioredoxin, GST, etc. (See, e.g., Arnau J, Lauritzen C, Petersen G E, Pedersen J., "Current strategies for the use of affinity tags and tag removal for the purification of recombinant proteins." Protein Expr Purif., 48(1):1-13, 2006).

In some embodiments, a kit includes a plasmid having a transamidase-encoding nucleotide sequence that the user uses to produce the sortase or transamidase in a cell culture or cell free translation system, and often, then purifies the sortase or transamidase according to instructions provided with the kit.

In the ligation methods described herein, the transamidase, acyl donor, and nucleophilic acyl acceptor are contacted with one another under suitable conditions to effect ligation of the acyl donor to the acyl acceptor. As used herein, the term "contacting" refers to placing the components of the process in close proximity to one another and allowing the molecules to collide by diffusion. Contacting these components with one another can be accomplished by adding them to one body of fluid and/or in one reaction vessel, for example. The components in the system may be mixed in a variety of manners, such as by oscillating a vessel, subjecting a vessel to a vortex generating apparatus, repeated mixing with a pipette or pipettes, or by passing fluid containing one assay component over a surface having another assay component immobilized thereon, for example. The components may be added in any order to the system.

The ligation may be performed in any convenient vessel (e.g., tubes such as microfuge tubes, flask, dish), microtiter plates (e.g., 96-well or 384-well plates), glass slides, silicon chips, filters, or any solid or semisolid support having surface (optionally coated) having molecules immobilized thereon and optionally oriented in an array (see, e.g., U.S. Pat. No. 6,261,776 and Fodor, Nature 364: 555-556 (1993)), and microfluidic devices (see, e.g., U.S. Pat. Nos. 6,440,722; 6,429,025; 6,379,974; and 6,316,781). The system can include attendant equipment such as signal detectors, robotic platforms, and pipette dispensers.

The reaction mixture often is cell free and often does not include bacterial cell wall components or intact bacterial cell walls. In some embodiments, the system includes one or more cells or cell wall components, often non-bacterial cells or non-Gram-positive bacterial cells. In such embodiments, one or more components often are expressed by one or more recombinant nucleotide sequences in a cell, which nucleotide sequences are integrated into the cell genome or non-integrated (e.g., in a plasmid). Cells in such systems often are maintained in vivo, sometimes ex vivo, and sometimes in vitro.

The reaction mixture is maintained at any convenient temperature at which the ligation reaction can be performed. In some embodiments, the ligation is performed at a temperature ranging from about 15° C. to about 50° C. In some embodiments, the ligation is performed at a temperature ranging from about 23° C. to about 37° C. In certain embodiments, the temperature is room temperature (e.g., about 25° C.). The temperature can be optimized by repetitively performing the same ligation procedure at different temperatures and determining ligation rates. Any convenient assay volume and component ratio is utilized. In certain embodiments, a component ratio of 1:1000 or greater transamidase enzyme to acyl donor is utilized, or a ratio of 1:1000 or greater transamidase enzyme to acyl acceptor is utilized. In specific embodiments, ratios of enzyme to acyl donor or enzyme to acyl acceptor is about 1:1, including 1:2 or greater, 1:3 or greater, 1:4 or greater, 1:5 or greater, 1:6 or greater, 1:7 or greater, 1:8 or greater, and 1:9 or greater.

In some embodiments, the acyl donor is present at a concentration ranging from about 10 $\mu$M to about 10 mM. In some embodiments, the acyl donor is present at a concentration ranging from about 100 $\mu$M to about 1 mM. In some embodiments, the acyl donor is present at a concentration ranging from about 100 $\mu$M to about 5 mM. In some embodiments, the acyl donor is present at a concentration ranging from about 200 $\mu$M to about 1 mM. In some embodiments, the acyl donor is present at a concentration ranging from about 200 $\mu$M to about 800 $\mu$M. In some embodiments, the acyl donor is present at a concentration ranging from about 400 $\mu$M to about 600 $\mu$M.

In certain embodiments, the nucleophilic acyl acceptor is present at a concentration ranging from about 1 $\mu$M to about 500 $\mu$M. In certain embodiments, the nucleophilic acyl acceptor is present at a concentration ranging from about 15 $\mu$M to about 150 $\mu$M. In certain embodiments, the nucleophilic acyl acceptor is present at a concentration ranging from about 25 $\mu$M to about 100 $\mu$M. In certain embodiments, the nucleophilic acyl acceptor is present at a concentration ranging from about 40 $\mu$M to about 60 $\mu$M.

In certain embodiments, the transamidase is present at a concentration ranging from about 1 $\mu$M to about 500 $\mu$M. In certain embodiments, the transamidase is present at a concentration ranging from about 15 $\mu$M to about 150 $\mu$M. In certain embodiments, the transamidase is present at a concentration ranging from about 25 $\mu$M to about 100 $\mu$M. In certain embodiments, the transamidase is present at a concentration ranging from about 40 $\mu$M to about 60 $\mu$M.

In certain embodiments, the ligation method is performed in a reaction mixture comprising an aqueous environment. Water with an appropriate buffer and/or salt content often may be utilized. An alcohol or organic solvent may be included in certain embodiments. The amount of an organic solvent often does not appreciably esterify a protein or peptide in the ligation process (e.g., esterified protein or peptide often increase only by 5% or less upon addition of an alcohol or organic solvent). Alcohol and/or organic solvent contents sometimes are 20% or less, 15% or less, 10% or less or 5% or less, and in embodiments where a greater amount of an alcohol or organic solvent is utilized, 30% or less, 40% or less, 50% or less, 60% or less, 70% or less, or 80% or less alcohol or organic solvent is present. In certain embodiments, the system includes only an alcohol or an organic solvent, with only limited amounts of water if it is present.

In some embodiments, suitable ligation conditions comprise a buffer. One of ordinary skill in the art will be familiar with a variety of buffers that could be used in accordance with the present invention. In some embodiments, the buffer solution comprises calcium ions. In certain embodiments, the buffer solution does not contain substances that precipitate calcium ions. In some embodiments, the buffer solution does not include phosphate ions. In some embodiments, the buffer solution does not contain chelating agents.

In some embodiments, suitable ligation conditions comprise pH in the range of 6 to 8.5. In some embodiments, suitable ligation conditions comprise pH in the range of 6 to 8. In some embodiments, suitable ligation conditions comprise pH in the range of 6 to 7.5. In some embodiments, suitable ligation conditions comprise pH in the range of 6.5 to 8.5. In some embodiments, suitable ligation conditions comprise pH in the range of 7 to 8.5. In some embodiments, suitable ligation conditions comprise pH in the range of 7.5 to 8.5. In some embodiments, suitable ligation conditions comprise pH in the range of 7.0 to 8.5. In some embodiments, suitable ligation conditions comprise pH in the range of 7.3 to 7.8.

One or more components for ligation or a ligation product may be immobilized to a solid support. The attachment between an assay component and the solid support may be covalent or non-covalent (e.g., U.S. Pat. No. 6,022,688 for non-covalent attachments). The solid support may be one or more surfaces of the system, such as one or more surfaces in each well of a microtiter plate, a surface of a glass slide or silicon wafer, Biacore chip, a surface of a particle, e.g., a bead (e.g., Lam, Nature 354: 82-84 (1991)) that is optionally linked to another solid support, or a channel in a microfluidic device, for example. Types of solid supports, linker molecules for covalent and non-covalent attachments to solid supports, and methods for immobilizing nucleic acids and other molecules to solid supports are known (e.g., U.S. Pat. Nos. 6,261,776; 5,900,481; 6,133,436; and 6,022, 688; and WIPO publication WO 01/18234). Any material may be used, e.g., plastic (e.g., polystyrene), metal, glass, cellulose, gels (e.g., formed at least in part from organic polymers such as PDMS), etc. In some embodiments the solid support is semi-solid and/or gel-like, deformable, flexible, or the like.

Any protein or peptide may be utilized as an acyl donor or nucleophilic acyl acceptor in the ligation process described herein. The protein or peptide often is isolated when utilized in a cell-free system. The protein or peptide sometimes is a subregion of a protein, such as in the N-terminus, C-terminus, extracellular region, intracellular region, transmembrane region, active site (e.g., nucleotide binding region or a substrate binding region), a domain (e.g., an SH2 or SH3 domain) or a post-translationally modified region (e.g., phosphorylated, glycosylated or ubiquinated region), for example. Peptides often are 50 amino acids or fewer in length (e.g., 45, 40, 35, 30, 25, 20, or 15 amino acids or fewer in length) and proteins sometimes are 100 or fewer amino acids in length, or 200, 300, 400, 500, 600, 700, or 900 or fewer amino acids in length. The protein or peptide sometimes includes the modification moiety or a portion thereof (e.g., the glycosyl group or a portion thereof). In certain embodiments, the protein is a signal transduction factor, cell proliferation factor, apoptosis factor, angiogenesis factor, or cell interaction factor. Examples of cell interaction factors include but are not limited to cadherins (e.g., cadherins E, N, BR, P, R, and M; desmocollins; desmogleins; and protocadherins); connexins; integrins; proteoglycans; immunoglobulins (e.g., ALCAM, NCAM-1 (CD56), CD44, intercellular adhesion molecules (e.g., ICAM-1 and ICAM-2), LFA-1, LFA-2, LFA-3, LECAM-1, VLA-4, ELAM and N-<BR>CAM); selectins (e.g., L-selectin (CD62L), E-selectin (CD62e), and P-selectin (CD62P)); agrin; CD34; and a cell surface protein that is cyclically internalized or internalized in response to ligand binding.

Examples of signal transduction factors include but are not limited to protein kinases (e.g., mitogen activated protein (MAP) kinase and protein kinases that directly or indirectly phosphorylate it, Janus kinase (JAK1), cyclin dependent kinases, epidermal growth factor (EGF) receptor, platelet-derived growth factor (PDGF) receptor, fibroblast-derived growth factor receptor (FGF), insulin receptor and insulin-like growth factor (IGF) receptor); protein phosphatases (e.g., PTP1B, PP2A and PP2C); GDP/GTP binding proteins (e.g., Ras, Raf, ARF, Ran and Rho); GTPase activating proteins (GAFs); guanine nucleotide exchange factors (GEFs); proteases (e.g., caspase 3, 8 and 9), ubiquitin ligases (e.g., MDM2, an E3 ubiquitin ligase), acetylation and methylation proteins (e.g., p300/CBP, a histone acetyl transferase) and tumor suppressors (e.g., p53, which is activated by factors such as oxygen tension, oncogene signaling, DNA damage and metabolite depletion). The protein sometimes is a nucleic acid-associated protein (e.g., histone, transcription factor, activator, repressor, co-regulator, polymerase or origin recognition (ORC) protein), which directly binds to a nucleic acid or binds to another protein bound to a nucleic acid. The protein sometimes is useful as a detectable label, such as a green or blue fluorescent protein. In some embodiments a protein is a therapeutically useful protein. Certain proteins of interest are described further in the section entitled "Polypeptides" below.

In certain embodiments, the acyl donor comprises an antibody or antibody chain (heavy or light chain) or a portion thereof comprising an immunoglobulin domain (e.g., constant domain or variable domain). In some embodiments, antibodies are IgG, IgM, IgA, or IgE. The antibody may be of any class, subclass, or isotype in various embodiments of the invention. In some embodiments the antibody is of a class or isotype that is secreted. See, e.g., Murphy, K., et al., Janeway's Immunobiology, Garland Science; 7th edition (Nov. 27, 2007). In some embodiments, antibodies are polyclonal or monoclonal, and may be chimeric, humanized or bispecific. Polyclonal and monoclonal antibodies that bind specific antigens are commercially available, and methods for generating such antibodies are known. In general, polyclonal antibodies are produced by injecting an isolated antigen into a suitable animal (e.g., a goat or rabbit); collecting blood and/or other tissues from the animal containing antibodies specific for the antigen and purifying the antibody. Methods for generating monoclonal antibodies, in general, include injecting an animal with an isolated antigen (e.g., often a mouse or a rat); isolating splenocytes from the animal; fusing the splenocytes with myeloma cells to form hybridomas; isolating the hybridomas and selecting hybridomas that produce monoclonal antibodies which specifically bind the antigen (e.g., Kohler & Milstein, Nature 256: 495 497 (1975) and StGroth & Scheidegger, J Immunol Methods 5: 1 21 (1980)). Examples of monoclonal antibodies are anti MDM 2 antibodies, anti-p53 antibodies (pAB421, DO 1, and an antibody that binds phosphoryl-ser15), anti-dsDNA antibodies and anti-BrdU antibodies, described hereafter.

Methods for generating chimeric and humanized antibodies also are known (see, e.g., U.S. Pat. No. 5,530,101 (Queen, et al.), U.S. Pat. No. 5,707,622 (Fung, et al.) and U.S. Pat. Nos. 5,994,524 and 6,245,894 (Matsushima, et al.)), which generally involve transplanting an antibody variable region from one species (e.g., mouse) into an antibody constant domain of another species (e.g., human). Antigen-binding regions of antibodies (e.g., Fab regions) include a light chain and a heavy chain, and the variable region is composed of regions from the light chain and the heavy chain.

Given that the variable region of an antibody is formed from six complementarity-determining regions (CDRs) in the heavy and light chain variable regions, one or more CDRs from one antibody can be substituted (e.g., grafted) with a CDR of another antibody to generate chimeric antibodies. Also, humanized antibodies are generated by introducing amino acid substitutions that render the resulting antibody less immunogenic when administered to humans.

In some embodiments, the acyl donor comprises an antibody fragment, such as a Fab, Fab', F(ab)'2, Dab, Fv or single-chain Fv (ScFv) fragment, and recombinant methods for generating antibody fragments are known (e.g., U.S. Pat. Nos. 6,099,842 and 5,990,296 and PCT/GB00/04317). In general, single-chain antibody fragments are constructed by joining a heavy chain variable region with a light chain variable region by a polypeptide linker (e.g., the linker is attached at the C-terminus or N-terminus of each chain), and such fragments often exhibit specificities and affinities for an antigen similar to the original monoclonal antibodies. Bifunctional antibodies sometimes are constructed by engineering two different binding specificities into a single antibody chain and sometimes are constructed by joining two Fab' regions together, where each Fab' region is from a different antibody (e.g., U.S. Pat. No. 6,342,221). Antibody fragments often comprise engineered regions such as CDR-grafted or humanized fragments. In certain embodiments the binding partner is an intact immunoglobulin, and in other embodiments the binding partner is a Fab monomer or a Fab dimer.

Acyl donors comprising proteins and peptides may chemically synthesized using known techniques (e.g., Creighton, 1983 Proteins. New York, N. Y.: W. H. Freeman and Company; and Hunkapiller et al., (1984) Nature July 12-18; 310 (5973): 105-11). For example, a peptide can be synthesized by a peptide synthesizer. If desired, non-classical amino acids or chemical amino acid analogs can be introduced as a substitution or addition into the fragment sequence. Non-classical amino acids include but are not limited to D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoroamino acids, designer amino acids such as b-methyl amino acids, Ca-methyl amino acids, Na-methyl amino acids, and amino acid analogs in general. Each amino acid in the peptide often is L (levorotary) and sometimes is D (dextrorotary). Proteins often are produced by known recombinant methods, or sometimes are purified from natural sources.

Native protein and peptide sequences sometimes are modified. For example, conservative amino acid modifications may be introduced at one or more positions in the amino acid sequences of target polypeptides. A "conservative amino acid substitution" is one in which the amino acid is replaced by another amino acid having a similar structure and/or chemical function. Families of amino acid residues having similar structures and functions are well known. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Also, essential and non-essential amino acids may be replaced. A "non-essential" amino acid is one that can be altered without abolishing or substantially altering the biological function of a target polypeptide, whereas altering an "essential" amino acid abolishes or substantially alters the biological function of a target polypeptide. Amino acids that are conserved among target polypeptides typically are essential amino acids.

Proteins or peptides of an acyl donor may exist as chimeric or fusion polypeptides. As used herein, a "chimeric polypeptide" or "fusion polypeptide" includes a protein or peptide linked to a different polypeptide. The different polypeptide can be fused to the N-terminus or C-terminus of the target polypeptide. Fusion polypeptides can include a moiety having high affinity for a ligand. For example, the fusion polypeptide can be a GST-target fusion polypeptide in which the protein or peptide sequences are fused to the C-terminus of the GST sequences, or a polyhistidine-target fusion polypeptide in which the protein or peptide is fused at the N- or C-terminus to a string of histidine residues (e.g., sometimes three to six histidines). Such fusion polypeptides can facilitate purification of recombinant protein or peptide. Expression vectors are commercially available that already encode a fusion moiety, and a nucleotide sequence encoding the peptide or polypeptide can be cloned into an expression vector such that the fusion moiety is linked in-frame to the target polypeptide. Further, the fusion polypeptide can be a protein or peptide containing a heterologous signal sequence at its N-terminus. In certain host cells (e.g., mammalian host cells), expression, secretion, cellular internalization, and cellular localization of a target polypeptide can be increased through use of a heterologous signal sequence. Fusion polypeptides sometimes include all or a part of a serum polypeptide (e.g., an IgG constant region or human serum albumin).

Suitable systems for producing polypeptides in prokaryotic and eukaryotic systems are well known in the art and are of use in the invention. One of skill in the art will select an appropriate system (e.g., appropriate cell type and appropriate vector for inserting a nucleic acid encoding the protein). In some embodiments, a host cell is transformed to contain a vector that encodes a polypeptide whereby the polypeptide is produced in the cell.

A host cell can be prokaryotic or eukaryotic cell, e.g., bacterial, fungal, plant, or animal (e.g., insect or mammalian). Exemplary host cells include bacterial cells (e.g., Gram-negative bacteria such as *E. coli* or Gram-positive bacteria such as *B. subtilis* or *Lactococcus lactis*), insect cells (e.g., Sf9), mammalian cells (e.g., CHO cells, COS cells, SP2/0 and NS/0 myeloma cells, human embryonic kidney (e.g., HEK 293) cells, baby hamster kidney (BHK) cell, human B cells, seed plant cells, and Ascomycete cells (e.g., *Neurospora*, *Aspergillus* and yeast cells; e.g., yeast of the genera *Saccharomyces*, *Pichia*, *Hansenula*, *Schizosaccharomyces*, *Kluyveromyces*, *Yarrowia*, and *Candida*). Exemplary yeast species include *S. cerevisiae*, *Hansenula polymorpha*, *Kluyveromyces lactis*, *Pichia pastoris*, *Schizosaccharomyces pombe*, and *Yarrowia lipolytica*.

For a glycosylated protein, a cell type capable of performing such glycosylation can be selected. For production in eukaryotic cells, e.g., mammalian cells, yeast cells, insect cells (e.g., baculovirus-based), plant cells, or transgenic non-human animals or plants, a suitable signal sequence may be included at the N-terminus. In such instances, the nucleophilic residue(s), e.g., G or GG, and optional masking residues (e.g., a sequence comprising a protease cleavage site), are located C-terminal to the signal sequence, so that they are located at the N-terminus of the mature, secreted polypeptide. In some embodiments, a secretion signal sequence whose cleavage generates an N-terminal nucleophilic residue (e.g., an A or G) is used if a polypeptide is produced in eukaryotic, e.g., mammalian, cells. For example, cleavage of the H-2kb secretion sequence generates an N-terminal glycine. The protein sequence of the H-2kb secretion signal sequence is MVPCTLLLLLAAALAPTQTRA-GG (SEQ ID NO: 3). It gets cleaved at the dash to leave the GG at the N-terminus). An exemplary nucleotide sequence encoding this sequence is: atggtaccgt gcacgctgct cctgctgttg g cggccgccc tggctccgac tcagacccgc gcg (SEQ ID NO: 4). In some embodiments, a secretion signal sequence is selected such that, when cleaved, it leaves a masked nucleophilic residue near the N-terminus.

In certain embodiments, the acyl donor or acyl acceptor is modified by a process or with a moiety not typically incorporated into a protein during translation. In specific embodiments, the acyl donor or acyl acceptor comprises one or more moieties selected from an alkyl moiety (e.g., methyl moiety), an alkanoyl moiety (e.g., an acetyl group (e.g., an acetylated histone)), an alkanoic acid or alkanoate moiety (e.g., a fatty acid), a glyceryl moiety (e.g., a lipid), a phosphoryl moiety, a glycosyl moiety (e.g., N-linked or O-linked carbohydrate chains) or an ubiquitin moiety. Further, any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; and the like. The N-terminal and/or C-terminal ends may be processed (e.g., the N-terminal methionine may not be present due to prokaryotic expression of the protein or peptide) and chemical moieties may be attached to the amino acid backbone. Proteins and peptides sometimes are modified with a detectable label, such as an enzymatic, fluorescent, isotopic or affinity label to allow for detection and isolation of the polypeptide.

When no transamidase or sortase recognition sequence is present in a acyl donor or acyl acceptor to be ligated, the acyl donor or acyl acceptor is modified to include an appropriate recognition sequence. When a recognition sequence is present in a native protein or peptide amino acid sequence, the recognition sequence often is removed unless it is located near the N-terminus or C-terminus. A recognition sequence can be removed in a native amino acid sequence by synthesizing it without the recognition sequence or by modifying some and/or all amino acids in the nucleotide sequence encoding the amino acid recognition sequence by known recombinant techniques. In some embodiments, when a recognition sequence and non-native sequence useful for purification are introduced to the native protein or peptide amino acid sequence, the recognition sequence is incorporated closer such that the non-native sequence useful for purification is cleaved from the acyl donor during ligation. In such embodiments, the transamidase also is modified with the non-native sequence and the ligated product is purified away from the reactants when contacted with a solid support that binds the non-native sequence. In embodiments where the acyl donor is modified with a detectable label or homing sequence for a detectable label, such sequences often are incorporated closer to the N-terminus than the recognition sequence so they are not cleaved from the protein or peptide in the ligation process.

In certain embodiments, the present invention provides an acyl donor compound of formula:

wherein the transamidase recognition sequence, X, $R^1$, and $A^1$ are as defined above.

In certain embodiments, the present invention provides an acyl donor compound of formula:

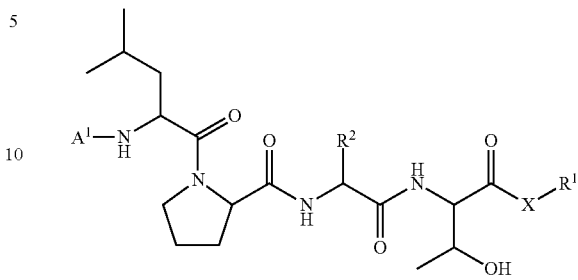

wherein X, $R^1$, $R^2$, and $A^1$ are as defined above.

It will be appreciated that any acyl donor compound described herein for use in methods of ligation is similarly provided by the present invention.

As described above, the transamidase catalyzes formation of an amide linkage between a $NH_2$—$CH_2$-moiety, which is joined to and/or is in the acyl acceptor, and an acyl moiety in the acyl donor. Suitable $NH_2$—$CH_2$-moieties are known and can be determined by performing the linkage processes described herein in a routine manner. Where an acyl acceptor does not include a suitable $NH_2$—$CH_2$-moiety, one or more $NH_2$—$CH_2$-moieties are joined to the molecule. Methods for joining one or more $NH_2$—$CH_2$-moieties to a molecule of interest are known and can be developed using techniques known in the art. In some embodiments, $NH_2$—$CH_2$-moieties utilized in the methods described herein are present as one or more glycine amino acids in attached to a $B^1$ group. In certain embodiments, between one and seven glycines are present in or are incorporated into/onto a $B^1$ group, and in specific embodiments, a $B^1$ group is derivitized with three glycines.

The nucleophilic acyl acceptor can be any molecule that leads to a useful ligated conjugate. In certain embodiments, the nucleophilic acyl acceptor comprises a protein or peptide. In some embodiments, the nucleophilic acyl acceptor comprises an antibody epitope, an antibody, a recombinant protein, a synthetic peptide or polypeptide, a peptide comprising one or more D-amino acids, a peptide comprising all D-amino acids, a peptide comprising one or more unnatural or non-classical amino acids (e.g., ornithine), a peptide mimetic, or a branched peptide. In some embodiments, the nucleophilic acyl acceptor comprises a peptide that confers enhanced cell penetrance to the acyl donor (e.g., a greater amount of the acyl donor compound conjugated to the acyl acceptor is translocated across a cell membrane in a certain time frame as compared to the acyl donor not conjugated to the acyl acceptor), which is referred to herein as a "protein transduction domain (PTD)" peptide or "transduction peptide." Any PTD can be conjugated to a protein or peptide using the methods described herein. PTD peptides are known, and include amino acid subsequences from HIV-tat (e.g., U.S. Pat. No. 6,316,003), sequences from a phage display library (e.g., U.S. 20030104622) and sequences rich in amino acids having positively charged side chains (e.g., guanidino-, amidino- and amino-containing side chains; e.g., U.S. Pat. No. 6,593,292). The PTD peptide sometimes is branched. The appended peptides promote cellular uptake and in some cases, cell-type specificity. Organelle-specific PTDs have also been generated, providing a means to target specific subcellular sites. See, e.g., Stewart K M, Horton K L, Kelley S O. Cell-penetrating peptides as delivery vehicles for biology and medicine. Org Biomol Chem. 6(13):2242-55, 2008. Also of interest are moieties that enhance stability of a second moiety such as a polypeptide, when conjugated thereto. For example, such moieties may increase the half-life of a compound in vivo. Examples include non-polypeptide polymers such as polyethylene glycol and derivatives thereof. In some embodiments a polymer is biocompatible. In some embodiments a polymer is biodegradable.

In some embodiments, the nucleophilic acyl acceptor comprises a detectable moiety. Any known and convenient detectable moiety can be utilized. In certain embodiments, avidin, streptavidin, a fluorescent molecule, or a radioisotope is linked to the acyl donor. In some embodiments, biotin or another vitamin, such as thiamine or folate, is linked to the acyl donor. Examples of detectable moieties include various enzymes, prosthetic groups, fluorescent materials, luminescent materials, bioluminescent materials, and radioisotopes. Examples of suitable enzymes include horseradish peroxidase, alkaline phosphatase, p-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioisotopes include $^{125}I$, $^{131}I$, $^{35}S$ or $^{3}H$. The radioisotope sometimes is selected based upon its appropriate use in a nuclear medicinal procedure, such as Be-7, Mg-28, Co-57, Zn-65, Cu-67, Ge-68, Sr-82, Rb-83, Tc-95m, Tc-96, Pd-103, Cd-109, and Xe-127, to name but a few.

Conjugates between an acyl donor and a detectable label are useful in diagnostic procedures. Diagnostic procedures include, for example, nuclear medicinal procedures for locating diseased locations of a subject, and procedures for detecting specific components or pathogens in a biological sample from a subject. The conjugates also are useful as research tools. For example, the conjugates are useful in flow cytometry techniques and for detecting a cellular location of a specific protein or peptide in a cell. Thus, in certain embodiments, a $NH_2$—$CH_2$-derivitized fluorophore and a transamidase are contacted with cells that express a protein linked to a sortase recognition sequence. The transamidase, often a sortase, joins the fluorophore to the protein and allows detection of the cell, protein in the cell, or protein on the cell surface. In certain embodiments, the transamidase is expressed by a nucleotide sequence that encodes it in the cell (e.g., the nucleotide sequence sometimes is in a plasmid), and in other embodiments useful for detecting a protein on a cell surface or in a fixed cell, exogenous transamidase protein, often isolated protein, is contacted with the cell.

The location of a protein in a cell sometimes is detected by a fluorescence imaging technique in cells fixed to a solid support. Imaging techniques include, for example, using a standard light microscope or a confocal microscope (e.g., U.S. Pat. Nos. 5,283,433 and 5,296,703 (Tsien)). Appropriate light microscopes are commercially available and are useful for probing cells in two dimensions (i.e., the height of a cell often is not resolved), and confocal microscopy is useful for probing cells in three-dimensions. Many microscopy techniques are useful for determining the location of a protein in a cell (e.g., in the nucleus, cytoplasm, plasma cell membrane, nucleolus, mitochondria, vacuoles, endoplasmic reticulum or Golgi apparatus). Some microscopic techniques are useful for determining the location of molecular antigens in groups of cells, tissue samples, and organs. Cellular locations often are visualized by counter-staining for subcellular organelles.

In some embodiments, cells expressing the protein are subjected to a known flow cytometry procedure, such as flow microfluorimetry (FMF) and fluorescence activated cell sorting (FACS); U.S. Pat. No. 6,090,919 (Cormack, et al.); U.S. Pat. No. 6,461,813 (Lorens); and U.S. Pat. No. 6,455,263 (Payan)). For use in these procedures, the protein often is expressed on the cell surface.

In certain embodiments, the nucleophilic acyl acceptor comprises a polymer or a small molecule. Polymers can be useful for enhancing protein or peptide solubility, stability and circulating time, and/or for decreasing immunogenicity when the protein or peptide is administered to a subject. In some embodiments, the polymer is a water soluble polymer such as polyethylene glycol, ethylene glycol/propylene glycol copolymers, carboxymethylcellulose, dextran, polyvinyl alcohol and the like, for example. The acyl donor may include one, two, three or more attached polymer moieties after ligation. The polymer may be of any molecular weight, and may be branched or unbranched. For polyethylene glycol, the molecular weight often is between about 1 kDa and about 100 kDa (the term "about" indicating that in preparations of polyethylene glycol, some molecules will weigh more, some less, than the stated molecular weight). Other sizes may be used, depending on a desired therapeutic profile (e.g., the duration of sustained release desired, the effects if any on biological activity, the ease in handling, the degree or lack of antigenicity and other known effects of the polyethylene glycol to a therapeutic protein or analog).

Any small molecule derivatized with or having a $NH_2$—$CH_2$-moiety can be linked to an acyl donor having a transamidase recognition site. In certain embodiments, the small molecule is known to be bioactive. Such small molecules can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive (see, e.g., Zuckermann et al., J. Med. Chem. 37: 2678-85 (1994)); spatially addressable parallel solid phase or solution phase libraries; synthetic library methods requiring deconvolution; "one-bead one-compound" library methods; and synthetic library methods using affinity chromatography selection. Biological library and peptoid library approaches are typically limited to peptide libraries, while the other approaches are applicable to peptide, non-peptide oligomer or small molecule libraries of compounds (Lam, Anticancer Drug Des. 12: 145, (1997)). Examples of methods for synthesizing molecular libraries are described, for example, in DeWitt et al., Proc. Natl. Acad. Sci. U.S.A. 90: 6909 (1993); Erb et al., Proc. Natl. Acad. Sci. USA 91: 11422 (1994); Zuckermann et al., J. Med. Chem. 37: 2678 (1994); Cho et al., Science 261: 1303 (1993); Carrell et al., Angew. Chem. Int. Ed. Engl. 33: 2059 (1994); Carell et al., Angew. Chem. Int. Ed. Engl. 33: 2061 (1994); and in Gallop et al., J. Med. Chem. 37: 1233 (1994). Libraries of compounds may be presented in solution (e.g., Houghten, Biotechniques 13: 412-421 (1992)), or on beads (Lam, Nature 354: 82-84 (1991)), chips (Fodor, Nature 364: 555-556 (1993)), bacteria or spores (Ladner, U.S. Pat. No. 5,223,409), plasmids (Cull et al., Proc. Natl. Acad. Sci. USA 89: 1865-1869 (1992)). Small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. In certain embodiments, the small molecule folate, spermine or puromycin is a component of an acyl donor. In other embodiments, the small molecule is a modification moiety described above, such as a phosphoryl moiety, ubiquitin moiety or a glycosyl moiety, for example.

In some embodiments, the acyl acceptor comprises is a nucleic acid, such as a deoxyribonucleic acid, a ribonucleic acid, nucleic acid derivatives, and a modified nucleic acid. The nucleic acid may comprise or consist of DNA nucleotide sequences (e.g., genomic DNA (gDNA) and complementary DNA (cDNA)) or RNA nucleotide sequences (e.g., mRNA, tRNA, and rRNA). The nucleic acid sometimes is about 8 to about 50 nucleotides in length, about 8 to about 35 nucleotides in length, and sometimes from about 10 to about 25 nucleotides in length. Nucleic acids often are 40 or fewer nucleotides in length, and sometimes are 35 or fewer, 30 or fewer, 25 or fewer, 20 or fewer, and 15 or fewer nucleotides in length. Synthetic oligonucleotides can be synthesized using standard methods and equipment, such as by using an ABI3900 High Throughput DNA Synthesizer, which is available from Applied Biosystems (Foster City, Calif.).

A nucleic acid sometimes is an analog or derivative nucleic acid, which can include backbone/linkage modifications (e.g., peptide nucleic acid (PNA) or phosphothioate linkages) and/or nucleobase modifications. Examples of such modifications are set forth in U.S. Pat. No. 6,455,308 (Freier et al.); in U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929, 226; 5,977,296; 6,140,482; and in WIPO publications WO 00/56746 and WO 01/14398. Methods for synthesizing oligonucleotides comprising such analogs or derivatives are disclosed, for example, in the patent publications cited above, and in U.S. Pat. Nos. 6,455,308; 5,614,622; 5,739,314; 5,955,599; 5,962,674; 6,117,992; and in WO 00/75372. Nucleic acids may be modified by chemical linkages, moieties, or conjugates that enhance activity, cellular distribution, or cellular uptake of nucleic acid, and examples of modifications in modified nucleic acids are in U.S. Pat. No. 6,455,308 (Freier), U.S. Pat. No. 6,455,307 (McKay et al.), U.S. Pat. No. 6,451,602 (Popoff et al.), and U.S. Pat. No. 6,451,538 (Cowsert).

In some embodiments, the acyl acceptor comprises a toxin. Any toxin may be selected, and often is selected for high cytotoxic activity. Proteins or peptides ligated to a toxin often are useful as therapeutics. For example, a protein or peptide antibody or receptor that specifically binds to a cancer cell when linked to a toxin such as ricin is useful for treating cancer in subjects. In certain embodiments, the toxin is selected from the group consisting of abrin, ricin A, *pseudomonas* exotoxin and diphtheria toxin.

In some embodiments, the acyl acceptor comprises a solid support. The solid support often is derivitized with multiple $NH_2$—$CH_2$-moieties, such as triglycine moieties. The solid support may be any described herein. In certain embodiments, the solid support is a glass slide, a glass bead, an agarose bead, a magnetic bead, a silicon wafer or a resin. In specific embodiments, a resin such as EAH Sepharose is derivitized with triglycine moieties using a FMOC/EDC derivitization procedure. In certain embodiments the solid support is a particle, e.g., a microparticle (e.g. a particle having an average diameter or smallest cross-sectional length greater than about 1 micron) or nanoparticle (average diameter or smallest cross-sectional length equal to or less than about 1 micron), liposome, etc.

In some embodiments, the acyl acceptor comprises a phage that expresses a $NH_2$—$CH_2$-moiety on the surface. In some embodiments, the phage expresses a protein or peptide comprising one or more N-terminal glycines, sometimes three or five glycines at the N-terminus, and the phage expressing such a protein is contacted with a protein or peptide containing a transamidase recognition motif and a transamidase, thereby producing a phage/protein or phage/peptide conjugate. In some embodiments, a protein or peptide expressed at the phage surface comprises the transamidase recognition motif, and the phage is contacted with an acyl acceptor comprising a $NH_2$—$CH_2$-moiety and a transamidase, thereby producing a conjugate between the phage and the acyl acceptor. Methods for displaying a wide variety of peptides or proteins at the surface of a phage are known. The protein or peptide often is expressed as a fusion with a bacteriophage coat protein (Scott & Smith, Science 249: 386-390 (1990); Devlin, Science 249: 404-406 (1990); Cwirla et al., Proc. Natl. Acad. Sci. 87: 6378-6382 (1990); Felici, J. Mol. Biol. 222: 301-310 (1991)). Methods also are available for linking the test polypeptide to the N-terminus or the C-terminus of the phage coat protein. The original phage display system was disclosed, for example, in U.S. Pat. Nos. 5,096,815 and 5,198, 346. This system used the filamentous phage M13, which required that the cloned protein be generated in *E. coli* and required translocation of the cloned protein across the *E. coli* inner membrane. Lytic bacteriophage vectors, such as lambda, T4 and T7 are more practical since they are independent of *E. coli* secretion. T7 is commercially available and described in U.S. Pat. Nos. 5,223,409; 5,403,484; 5,571,698; and 5,766,905. A protein or peptide comprising a $NH_2$—$CH_2$-moiety or a transamidase recognition sequence can be expressed on the surface of any other phage or virus, including but not limited to, murine leukemia virus (MLV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV), human immunodeficiency virus (HIV), simian immunodeficiency virus (SW), visna/maedi virus (VMV), caprine arthritis-encephalitis virus (CAEV), equine infectious anemia virus (EIAV), feline immunodeficiency virus (FIV), bovine immunodeficiency virus (BIV), a hepatitis virus (e.g., hepatitis B or C), rhinovirus, herpes-zoster virus (VZV), herpes simplex virus (e.g., HSV-1 or HSV-2), cytomegalovirus (CMV), vaccinia virus, influenza virus, encephalitis virus, hantavirus, arbovirus, West Nile virus, human papilloma virus (HPV), Epstein-Barr virus, and respiratory syncytial virus.

In some embodiments, the acyl donor or acyl acceptor comprises a cleavable moiety, e.g., $A_1$ or $B_1$ comprises a cleavable moiety. In some embodiments the acyl donor or acyl acceptor comprises a cleavage site for a protease (e.g., a polypeptide sequence that is recognized by a protease and cleaved). In such embodiments, a cleavage reagent, e.g., a protease, may be used to cleave the product of a transamidation reaction. The cleavable moiety may be positioned at any desired location, e.g., between a sortase recognition sequence and a moiety of interest such as a tag, label, etc. A number of proteases that cleave polypeptides at particular sequences are known in the art. Examples of sequences having peptidase activity are known (e.g., cysteine-type endopeptidases, aspartic-type endopeptidases, elastases, metalloendopeptidases, mitochondrial inner membrane peptidases, serine-type endopeptidases, threonine endopeptidases, thrombin and other proteases involved in the coagulation and/or clotting cascade or other biological cascades. In some embodiments the cleavable moiety is photocleavable. In some embodiments the cleavage site is located at a position 1, 2, 3, 4, 5, 6, 7, 8, 9 or 10 amino acids away from an end of the recognition sequence, and sometimes at a position 15 or fewer, 20 or fewer, 50 or fewer or 100 or fewer amino acids away from the an end of the recognition sequence or, in some embodiments, from an N- or C-terminal end of a polypeptide comprising a recognition sequence or that acts as a nuclephile in a method described herein. In some embodiments, the acyl donor or acyl acceptor comprises a linker sequence, also referred to as a "spacer". A linker sequencemay be, e.g., 1, 2, 3, 4, 5, 6, 7, 8, 9, 10, 11, 12, 13, 14, 15, 16, 17, 18, 19, 20, 25 or fewer, 30 or fewer, 40 or fewer, 50 or fewer, 60 or fewer, 70 or fewer, 80 or fewer, 90 or fewer or 100 or fewer amino acids in length. The linker may be positioned at any desired location, e.g., between a sortase recognition sequence and a moiety of interest such as a tag, label, etc.

The invention provides kits comprising one or more acyl donor compounds as described above. In certain embodiments, a kit comprises a compound of formula:

wherein the transamidase recognition sequence, X, $R^1$, and $A^1$ are as defined above. In certain embodiments, a kit comprises a compound of formula:

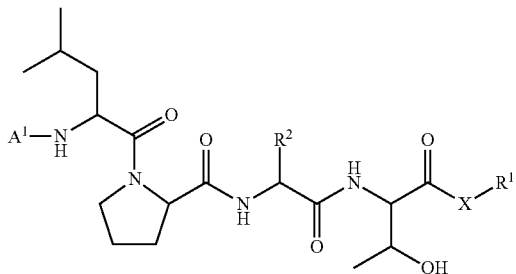

wherein X, $R^1$, $R^2$, and $A^1$ are as defined above. In some embodiments, a kit comprises a compound comprising a masked transamidase recognition sequence, e.g., any of the inventive probes described herein. In some embodiments, the kit further comprises a transamidase. In some embodiments, the kit further comprises a sortase. In some embodiments, the kit further comprises sortase A, e.g., SrtA$_{staph}$, SrtA$_{strep}$, or both. In certain embodiments a kit comprises an enzyme or other reagent for unmasking a masked transamidase recognition sequence. In certain embodiments, the kit further comprises instructions for ligation with a nucleophilic compound.

In some embodiments, a kit provides a nucleophilic compound of formula:

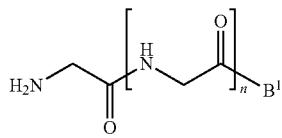

wherein $B^1$ and n are as defined above.

Other techniques, ligands, antibodies, and enzymes are known in the art and may be used in accordance with the present invention, including those described by Hornbeck, P., Curr Protoc Immunol., *Enzyme-Linked Immunosorbent Assays*, 2001 May; Chapter 2, Unit 2.1; Ausubel et al. *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989); *Antibodies: A Laboratory Manual*, E. Harlow and D. Lane, ed., Cold Spring Harbor Laboratory (Cold Spring Harbor, N.Y., 1988), each of which is herein incorporated by reference.

Transamidase-Mediated Protein Circularization

The invention encompasses the recognition that transamidases can be used to circularize polypeptides with high efficiency. In one aspect, the invention provides a method of circularizing a polypeptide comprising contacting the polypeptide with a transamidase, e.g., sortase, wherein the polypeptide comprises one or more nucleophilic residue(s) at its N-terminus and a transamidase recognition sequence (e.g., LPXTG (SEQ ID NO: 45)) at or near its C-terminus, under suitable conditions such that circularization occurs. The nucleophilic residue at the N-terminus is one that can be used by the transamidase and the transamidase recognition sequence is one that can be recognized by the transamidase. For example, if the transamidase is *S. aureus* SrtA, the N-terminus can comprise one or more G residues (e.g., 1, 2, 3, 4, 5, etc.), and the transamidase recognition sequence can comprise LPXTG (SEQ ID NO: 45). The resulting circular polypeptide comprises a transamidase recognition sequence positioned between the original C- and N-termini of the polypeptide. Remarkably, it has been discovered that circularization can proceed with high efficiency, thus making the transamidase-mediated circularization reaction a feasible means of producing circular proteins with yield and purity compatible with the needs of large-scale and/or commercially feasible production. In certain embodiments of the invention at least 30%, 40%, 50%, 60%, 70%, 80%, 90%, or more of the starting polypeptide is converted to circular form.

In certain embodiments, the invention provides a circular variant of a polypeptide of interest, wherein the original N- and C-terminal amino acids of the polypeptide of interest are joined together via a linker oligopeptide that comprises or consists of a transamidase recognition sequence. For example, in some embodiments the circular polypeptide comprises the sequence

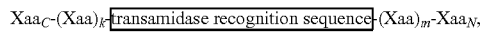

where "Xaa$_C$" and "Xaa$_N$" represent the amino acids present at the C- and N-termini of the original linear polypeptide, "Xaa" is any amino acid (wherein each Xaa may be a natural or unnatural amino acid and optionally comprises a modified or substituted side chain in certain embodiments, e.g., as defined elsewhere herein), and k and m are independently integers between 0 and 15. In some embodiments, k and m are each independently between 0 and 5 (e.g., 0, 1, or 2), or between 0 and 10. In some embodiments, k+m is between 0 and 5, between 0 and 10, or between 0 and 20. In some embodiments the transamidase recognition sequence is LPXTG (SEQ ID NO: 45), e.g., LPETG (SEQ ID NO: 55). In some embodiments the circular polypeptide comprises Xaa$_C$-LPXTG-Xaa$_N$ (SEQ ID NO: 143); Xaa$_C$-LPXTGG-Xaa$_N$ (SEQ ID NO: 144); Xaa$_C$-GLPXTGG-Xaa$_N$ (SEQ ID NO: 145); Xaa$_C$-GGLPXTGG-Xaa$_N$ (SEQ ID NO: 146). In some embodiments X is E.

The invention provides means for purifying a circularized polypeptide away from a starting linear polypeptide. In one aspect, the method comprises (i) providing a polypeptide of interest that comprises one or more nucleophilic residue(s) at its N-terminus and a sequence comprising a transamidase recognition sequence (e.g., LPXTG (SEQ ID NO: 45)) and a peptide that serves as an affinity tag at or near its C-terminus; and (ii) contacting the polypeptide of interest with a transamidase under conditions suitable for transamidation reaction to occur. For example, the sequence at or near the C-terminus of the polypeptide of interest can comprise His6 (SEQ ID NO: 174), e.g., LPXTGG-His6 (SEQ ID NO: 147). The transamidase in some embodiments also comprisesa tag, which may be the same or different from the tag present in the polypeptide of interest. In accordance with the inventive method, transamidase-mediated circularization removes a portion of the C-terminal sequence comprising the tag. The reaction mixture can then be contacted with a moiety that binds to the tag(s). The circular polypeptide will not be bound and can be conveniently separated from the starting linear polypeptide and/or transamidase. For example, the reaction mixture can be contacted with a resin that binds to the tag (e.g., by passing the material through a column containing the resin). The circular polypeptide does not bind to the resin, flows through the column, and can thus be easily purified.

The invention provides purified preparations of a circularized polypeptide as described above, wherein the circularized polypeptide is at least 50%, 60%, 70%, 80%, 90%, 95%, 96%, 97%, 98%, 99%, or more of the polypeptide material in the preparation by dry weight. In some embodiments, the circularized polypeptide is at least 50%, 60%, 70%, 80%, 90%, 95%, 96%, 97%, 98%, 99%, or more of the material in the preparation by dry weight (optionally excluding counterions that may be present). In some embodiments, a polypeptide preparation comprises at least 10 mg, at least 100 mg, or at least 1 g of polypeptide by dry weight.

In some embodiments, a circularized polypeptide of the invention displays at least one enhanced property relative to a non-circular form. In some embodiments, the polypeptide displays increased stability, e.g., increased resistance to exoprotease(s), increased thermal stability, increased circulating time in vivo, increased biological half-life, less propensity to aggregate, and/or increased rate of refolding.

Dual Modification Using Different Sortases

The invention provides methods for modifying a polypeptide at both the N- and C-termini. In some embodiments, the inventive methods make use of two transamidases, e.g., sortases, that recognize distinct transamidase recognition sequences. In some embodiments a first transamidase is able to recognize a first TRS but is not able to significantly recognize a second TRS, while the second transamidase is able to recognize the second TRS but is not able to significantly recognize the first TRS. In such embodiments the transamidase reactions can be carried out sequentially (in either order) or simultaneously in various embodiments. In some embodiments the inventive methods make use of two transamidases, e.g., sortases, wherein the first transamidase is able to recognize a first TRS but is not able to recognize a second TRS, and the second transmidase is able to recognize both the first TRS and a second TRS. For example, *Streptococcus pyogenes* Sortase A (SrtAstrep) will accept di-alanine based nucleophiles. This sortase will efficiently cleave LPXTA (SEQ ID NO: 148) between theronine and alanine and install modified alanine-based nucleophiles. SrtAstrep will also recognize and cleave LPXTG (SEQ ID NO: 45) motifs, albeit with reduced efficiency. SrtAstaph will not significantly cleave LPXTA (SEQ ID NO: 148) motifs or accept alanine based nucleophiles. In one embodiment, a polypeptide is contacted with SrtAstrep and an alanine-containing nucleophile comprising the desired modifying moiety. The polypeptide comprises a TRS that can recognized by SrtA strep at or near its C-terminus and one or more amino acids capable of serving as a nucleophile for a SrtAstaph-mediated reaction at or near its N-terminus (e.g., (G)n, where n is between 1 and 10, e.g., between 1 and 5). This leads to the formation of an LPXTA (SEQ ID NO: 148) sequence at the site of ligation, a motif refractory to cleavage by SrtA$_{staph}$. This allows SrtA$_{staph}$ to act on the N terminus without affecting the C-terminal modification installed with SrtA$_{strep}$. In certain embodiments the nucleophilic amino acid(s) are masked, so that they are not recognized by SrtA$_{strep}$. For example, a sequence that can be cleaved by a protease can be positioned so that cleavage exposes the nucleophilic amino acid(s). In the absence of such cleavage, the nucleophilic residue cannot participate in a sortase-mediated reaction. A sequence that contains two amino acids in suitable context for cleavage by a protease is referred to as a "protease recognition site" herein. The protease recognition sequence serves to mask the nucleophilic amino acid. Additional amino acids may be present N-terminal of the protease recognition site. In some embodiments, the protease recognition site is a thrombin recognition site. In some embodiments the thrombin recognition site comprises the sequence LVPRG (SEQ ID NO: 149), LVPRGG (SEQ ID NO: 150) or LVPRGS (SEQ ID NO: 151), wherein thrombin cleaves between R and G. In another embodiment, PreScission Protease, a genetically engineered fusion protein consisting of human rhinovirus 3C protease and GST, is used. LEVLFQ/GP (SEQ ID NO: 152) is the standard recognition site. Alternative sites can be cleaved. LE-P4-LFQ/GP (SEQ ID NO: 153, where $P_4$=Val Ala or Thr) can be used. Other proteases that cleave between a first amino acid and a second amino acid, wherein the second amino acid can serve as a nucleophile for a transamidase, can be used. One of skill in the art will be able to select an appropriate protease to cleave C-terminal to a nucleophilic amino acid of interest. The protease and/or cleavage conditions can be selected such that minimal or no undesired cleavage within the polypeptide occurs. The cleaving conditions and agent (e.g., protease) may be selected consistent with maintaining stability of the engineered protein except with respect to the desired cleavage. After cleavage, the protease may be removed or the protein isolated from the reaction mixture in which cleavage was performed. The protease can comprise a tag for convenient removal after cleavage. In some embodiments the protease is immobilized, e.g., on a solid or semi-solid support, e.g., particles. Following a transamidase-mediated ligation at the C-terminus, the polypeptide is contacted with the protease to expose the N-terminal nucleophilic amino acid. The polypeptide is contacted with a second transamidase and an appropriate probe for N-terminal modification. An exemplary strategy for dual-terminus labeling is outlined in FIGS. 33b and 34. The invention also encompasses use of chemical agents for cleavage to expose a nucleophilic amino acid. Polypeptides comprising a masked nucleophilic amino acid usable by a transamidase and appropriate cleavable masking sequence (often positioned near the N-terminus of the polypeptide) and a transamidase recognition sequence at or near the C-terminus are an aspect of the invention and have a variety of uses.

Site-Specific Modification and Circularization of Polypeptides

The invention provides methods for both circularizing and site-specifically modifying a polypeptide. In some embodiments, modification is performed using an oligonucleotide probe comprising a TRS, which in some embodiments is a masked TRS. The TRS comprises a side chain comprising a modifying moiety of interest. FIG. 43 shows a schematic diagram of an inventive approach according to this aspect of the invention. A polypeptide is equipped with a nucleophilic residue at or near the N-terminus and a first TRS at or near its C-terminus. The nucleophilic residue may be masked, e.g., with a protease recognition sequence that, when cleaved, exposes a nucleophilic residue. The polypeptide is contacted with a transamidase and an inventive oligonucleotide probe comprising a second TRS (which is masked in some embodiments and/or is different in sequence to the first TRS in some embodiments) and an amino acid having a modifying moiety (e.g., a label) attached thereto. The transamidase appends the oligonucleotide probe at the C-terminus of the polypeptide. In embodiments in which the second TRS (in the probe) is a masked TRS, the polypeptide is contacted with an agent or condition (phosphatase, light, etc.) that unmasks the TRS. In embodiments in which the nucleophilic residue at the N terminus is masked, the polypeptide is also contacted with an agent that unmasks it (e.g., a protease). The polypeptide is contacted with a second transamidase, which catalyzes a second transamidase reaction, which circularizes the polypeptide. The sequence of the polypeptide between the original N- and C-terminal amino acids can be unchanged relative to the original sequence. The N- and C-termini of the polypeptide are joined in the circularized version by a short linker peptide that comprises at least one TRS. In some embodiments the linker peptide comprises two TRSs. It should be noted that the probe depicted in FIG. 43 is exemplary. In some embodiments, the G residues in the GKG sequence are omitted, or other amino acids are used. In some embodiments, a probe comprises two or more lysine residues (or other residues having a readily modifiable side chain), wherein at least two moieties are attached to the side chains. In some embodiments, the probe comprises two or more different modifying moieties, which are optionally attached to different amino acids.

In some embodiments, a polypeptide circularized using an inventive probe comprises the following sequence: ---lpetAAGKGLPETgg---- (SEQ ID NO: 154) wherein lpet (SEQ ID NO: 53) in lower case is from the C-terminus of the polypeptide. The AAGKGLPET (SEQ ID NO: 155) is from the probe. The gg in lower case is from the N-terminus of the polypeptide. It will be understood that the lpet and gg are often not present in an original naturally occurring polypeptide but are present in a modified polypeptide for purposes of serving as a TRS and nucleophile, respectively, in transamidase-mediated reactions. Thus, in certain embodiments a circularized polypeptide comprises the sequence $(Xaa)_C$--- TRS1-SP-TRS2---$(Xaa)_N$, wherein TRS1 is a first TRS, TRS2 is a second TRS, SP is a spacer peptide comprising sequences from the probe (e.g., GKG), and each --- represents one or more optionally present amino acid residues. In some embodiments, a circularized version of an original (e.g., naturally occurring) polypeptide comprises the sequence (Xaa)$_C$lpetAAGKGLPETgg(Xaa)$_N$ (SEQ ID NO: 156), wherein $(Xaa)_C$ is from the C-terminus of the original polypeptide, and $(Xaa)_N$ is from the N-terminus of the original polypeptide. A moiety, e.g., a PEG, is attached to the lysine side chain in some embodiments. In some embodiments, one or more of the G residues in the probe (and thus the circularized polypeptide) is omitted.

Joining Two or More Polypeptides or Polypeptide Domains

Figure 45:
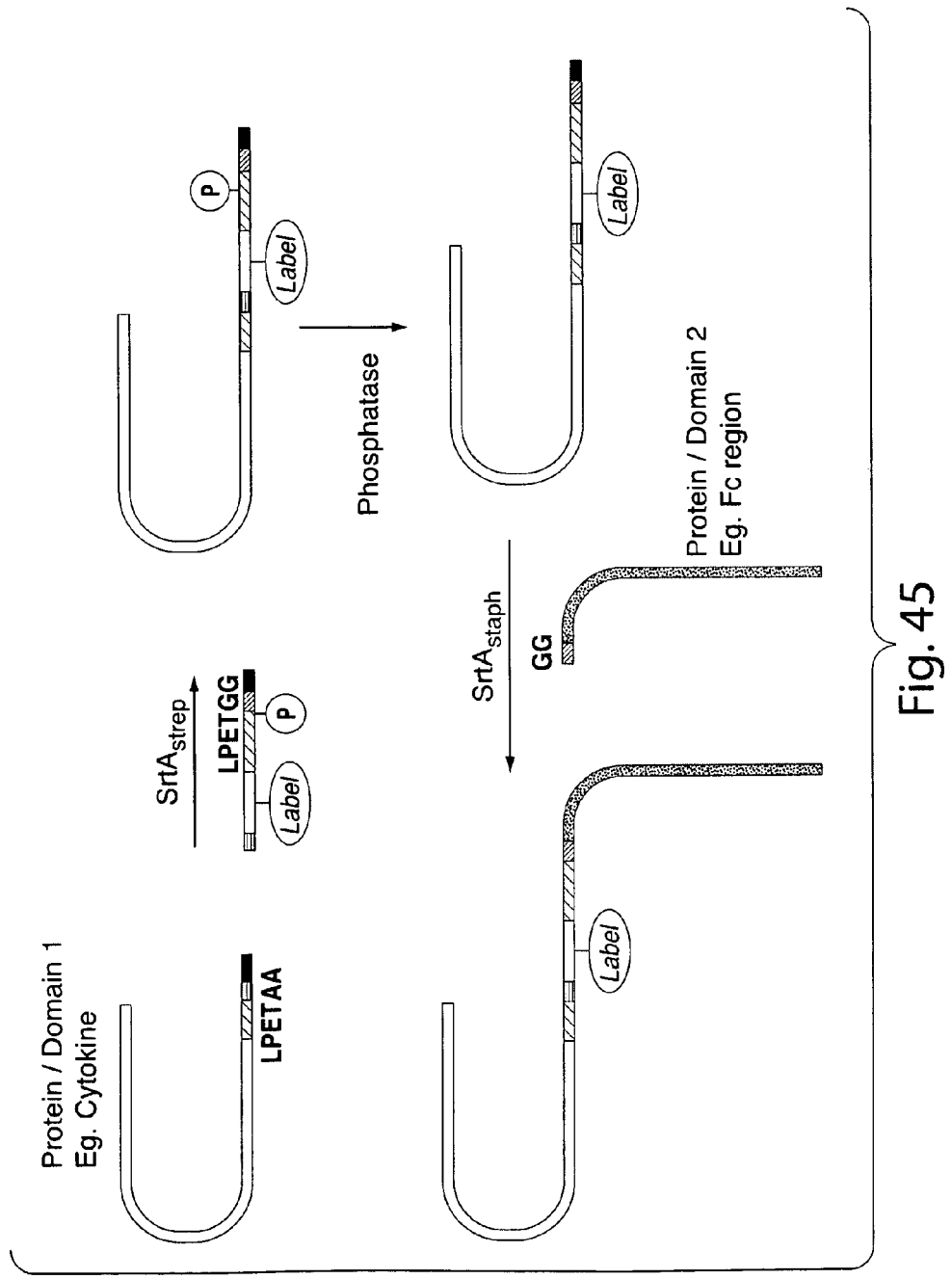
FIG. 45 shows a scheme for ligating a first protein or protein domain to a second protein or protein domain using two sortase-mediated reactions. LPETAA—SEQ ID NO: 215; LPETGG—SEQ ID NO: 216.

The invention provides methods of covalently linking two or more polypeptides using an inventive olignucleotide probe, which in some embodiments comprises a TRS, e.g., a masked TRS. FIG. 45 is a schematic diagram showing certain embodiments of the inventive approach. In some embodiments, the probe comprises a moiety of interest such as PEG, a detectable label, etc. In some embodiments, at least one of the polypeptides comprises a targeting or delivery domain. A delivery domain facilitates delivery of a compound, e.g., a polypeptide, to a site of interest, e.g., a site in the body. A targeting domain (which can function as a delivery domain in some embodiments) specifically binds to a molecule of interest, such as a receptor. For example, a targeting domain can be an an antibody, antibody chain, antibody fragment, e.g., a single-chain antibody or an antigen-binding portion thereof. In some embodiments, one of the polypeptides comprises an Fc domain of an antibody, e.g., an IgG1 antibody. In some embodiments an Fc domain is dimeric. Without limitation, an Fc domain can confer one or more desired properties. For example, an Fc domain can prolong the half-life of a polypeptide. An Fc domain can function as a targeting/delivery domain. For example, the neonatal constant region fragment (Fc) receptor (FcRn), which is responsible for IgG transport across the intestinal epithelium in newborn rodents, is expressed in epithelial cells in adult humans and non-human primates, and FcRn-mediated transport is functional in the lung of non-human primates. This transport system can be used to deliver a polypeptide of interest when it is conjugated to the Fc domain of IgG1. See, e.g., Bitonti A J, et al., "Pulmonary delivery of an erythropoietin Fc fusion protein in non-human primates through an immunoglobulin transport pathway. Proc Natl Acad Sci USA 101(26):9763-8, 2004. See also U.S. Pat. Pub. No. 2007/0178112. In some embodiments, one of the polypeptides comprises albumin, e.g., human serum albumin. In some embodiments, a targeting or delivery domain comprises a ligand for a receptor, wherein the receptor is expressed at the surface of a target cell.

Selected Moieties of Interest

Without limiting the invention in any way, in some embodiments of interest, a moiety comprises a biocompatible polymer, e.g., a polyalkylene glycol, e.g., a polyethylene glycol (PEG), a polypropylene glycol, or a derivative thereof. In some aspects, the invention offers a number of advantages relative to various other available methods for modifying a polypeptide with a polymer, e.g., other PEGyation methods. PEG is discussed herein for exemplary purposes. Without limitation, the inventive methods permit installation of a single PEG chain (or a small number of chains, e.g., 2, 3, 4) at a defined location and avoid PEGylation of residues within the native polypeptide sequence, which could reduce activity, e.g., potency. Inventive methods provide means to modify a polypeptide at a defined position without introducing a cysteine residue into the polypeptide or appending a cysteine residue thereto. In some embodiments, PEG with an average molecular weight of about 5 kD is used. In some embodiments a PEG with an average molecular weight of 10 kD is used. In some embodiments, PEG with an average molecular weight of about 15 kD, 20 kD, 25 kD, 30 kD, 40 kD, 45 kD, 50 kD, 55 kD, or more is used. In some embodiments, a linear PEG is used. In some embodiments a branched PEG, forked PEG, or comb structure PEG is used. In some embodiments, a polypeptide PEGylated using an inventive method displays increased circulating time without causing a significant reduction in potency. In contrast, standard, random PEGylation approaches often result in considerable reduction in potency. See, e.g., Jevgevar, S, et al., PEGylation of Therapeutic Proteins, Biotechnol. J. 5, 113-128, 2010, and references therein, for discussion of certain PEGylated pharmaceuticals, PEG reagents, etc.

Selected Polypeptides of Interest

Without limiting the invention in any way, this section discusses certain polypeptides of interest. Certain aspects of the present invention relate to the recognition that certain polypeptides are particularly amenable to the circularization approaches described herein. In certain embodiments, a polypeptide to be circularized is one whose N- and C-terminus are located within close proximity to each other in the native structure. For example, in certain embodiments the termini are located no more than 15 Angstroms (Å) apart. In certain embodiments the termini are located no more than 20 Å apart. In certain embodiments the termini are located no more than 25 Å apart. In certain embodiments, where the termini are located more than, e.g., about 15A apart in the native structure, the polypeptide is modified to extend either the N- or C-terminus, or both, with a flexible spacer peptide so that the termini can be in closer proximity to each other. In certain embodiments, a polypeptide to be circularized and, optionally, labeled as described herein (e.g., PEGylated) is characterized in that its N- and C-termini are positioned such that they are not required for the activity of the polypeptide and/or for interaction of the polypeptide with a biological target of the polypeptide. For example, if the polypeptide is one that naturally interacts with a receptor, the N- and C-termini are positioned such that they are not required for such interaction, e.g., they are positioned away from the receptor binding domain. In some embodiments the polypeptide of interest comprises or consists of a polypeptide that is at least 80%, or at least 90%, e.g., at least 95%, 86%, 97%, 98%, 99%, 99.5%, or 100% identical to a naturally occurring polypeptide. In some embodiments, the polypeptide has no more than 1, 2, 3, 4, 5, 6, 7, 8, 9, or 10 amino acid differences relative to a naturally occurring sequence. In some embodiments the naturally occurring polypeptide is a mammalian polypeptide, e.g., of human origin. In some embodiments the naturally occurring polypeptide is a cytokine, e.g., a type I cytokine. In some embodiments of particular interest, the polypeptide of interest is a four-helix bundle protein, e.g., a four-helix bundle cytokine. Exemplary four-helix bundle cytokines include, e.g., certain interferons (e.g., a type I interefereon, e.g., IFN-α), interleukins (e.g., IL-2, IL-3, IL-4, IL-5, IL-6, IL-7, IL-12), and colony stimulating factors (e.g., G-CSF, GM-CSF, M-CSF). The IFN can be, e.g., interferon alpha 2a or interferon alpha 2b. See, e.g., Mott HR and Campbell ID. "Four-helix bundle growth factors and their receptors: protein-protein interactions." Curr Opin Struct Biol. 1995 February; 5(1):114-21; Chaiken I M, Williams W V. "Identifying structure-function relationships in four-helix bundle cytokines: towards de novo mimetics design." Trends Biotechnol. 1996 October; 14(10):369-75; Klaus W, et al., "The three-dimensional high resolution structure of human interferon alpha-2a determined by heteronuclear NMR spectroscopy in solution". J Mol Biol., 274(4):661-75, 1997, for further discussion of certain of these cytokines.

In some embodiments, the cytokine has a similar structure to one or more of the afore-mentioned cytokines. For example, the cytokine can be an IL-6 class cytokine such as leukemia inhibitory factor (LIF) or oncostatin M. In some embodiments, the cytokine is one that in nature binds to a receptor that comprises a GP130 signal transducing subunit. Other four-helix bundle proteins of interest include growth hormone (GH), prolactin (PRL), and placental lactogen. In some embodiments, the polypeptide of interest is an erythropoiesis stimulating agent, e.g., erythropoietin (EPO), which is also a four-helix bundle cytokine. In some embodiments, an erythropoiesis stimulating agent is an EPO variant, e.g., darbepoetin alfa, also termed novel erythropoiesis stimulating protein (NESP), which is engineered to contain five N-linked carbohydrate chains (two more than recombinant HuEPO). In some embodiments, the polypeptide comprises five helices. For example, the polypeptide can be an interferon beta, e.g., interferon beta-1a or interferon beta-1b, which (as will be appreciated) is often classified as a four-helix bundle cytokine.

In some embodiments, a polypeptide of interest is IL-9, IL-10, IL-11, IL-13, or IL-15. In some embodiments. See, e.g., Hunter, C A, Nature Reviews Immunology 5, 521-531, 2005, for discussion of certain cytokines. See also Paul, W E (ed.), Fundamental Immunology, Lippincott Williams & Wilkins; 6th ed., 2008.

In some embodiments, a polypeptide is one that is approved by the US Food & Drug Administration (or an equivalent regulatory authority such as the European Medicines Evaluation Agency) for use in treating a disease or disorder in humans. Such polypeptide may or may not be one for which a PEGylated version has been tested in clinical trials and/or has been approved for marketing.

In some embodiments, a polypeptide of interest is a neurotrophic factor, i.e., a factor that promotes survival, development and/or function of neural lineage cells (which term as used herein includes neural progenitor cells, neurons, and glial cells, e.g., astrocytes, oligodendrocytes, microglia). For example, the factor could promote neurite outgrowth. In some embodiments, the polypeptide is ciliary neurotrophic factor (CNTF; a four-helix bundle protein) or an analog thereof such as Axokine, which is a modified version of human Ciliary neurotrophic factor with a 15 amino acid truncation of the C terminus and two amino acid substitutions, which is three to five times more potent than CNTF in in vitro and in vivo assays and has improved stability properties.

In some embodiments, the polypeptide of interest is one that forms homodimers or heterodimers, (or homo- or heterooligomers comprising more than two subunits, such as tetramers). In certain embodiments the homodimer, heterodimer, or oligomer structure is such that a terminus of a first subunit is in close proximity to a terminus of a second subunit. For example, an N-terminus of a first subunit is in close proximity to a C-terminus of a second subunit. In certain embodiments the homodimer, heterodimer, or oligomer structure is such that a terminus of a first subunit and a terminus of a second subunit are not involved in interaction with a receptor, so that the termini can be joined via a non-genetically encoded peptide element without significantly affecting biological activity. An inventive ligation method is used to join termini of two subunits of a homodimer, heterodimer, or oligomer via a non-genetically encoded peptide element, which optionally comprises a moiety attached to a side chain thereof, thereby producing a dimer (or oligomer) in which at least two subunits are covalently joined. For example, the neurotrophins nerve growth factor (NGF); brain-derived neurotrophic factor (BDNF); neurotrophin 3 (NT3); and neurotrophin 4 (NT4) are dimeric molecules which share approximately 50% sequence identity and exist in dimeric forms. See, e.g., Robinson R C, et al., "Structure of the brain-derived neurotrophic factor/neurotrophin 3 heterodimer.", Biochemistry. 34(13):4139-46, 1995; Robinson R C, et al., "The structures of the neurotrophin 4 homodimer and the brain-derived neurotrophic factor/neurotrophin 4 heterodimer reveal a common Trk-binding site." Protein Sci. 8(12):2589-97, 1999, and references therein. In some embodiments, the dimeric polypeptide is a cytokine, e.g., an interleukin. Other polypeptides of interest are enzymes, e.g., enzymes that are important in metabolism or other physiological processes. As known in the art, deficiencies of enzymes or other proteins can lead to a variety of disease. Such diseases include diseases associated with defects in carbohydrate metabolism, amino acid metabolism, organic acid metabolism, porphyrin metabolism, purine or pyrimidine metabolism, lysosomal storage disorders, blood clotting, etc. Examples include Fabry disease, Gaucher disease, Pompe disease, adenosine deaminase deficiency, asparaginase deficiency, *porphyria*, hemophilia, and hereditary angioedema. In some embodiments, a polypeptide is a clotting or coagulation factor, (e.g., factor VII, VIIa, VIII or IX). In other embodiments a polypeptide is an enzyme that plays a role in carbohydrate metabolism, amino acid metabolism, organic acid metabolism, porphyrin metabolism, purine or pyrimidine metabolism, and/or lysosomal storage, wherein exogenous administration of the enzyme at least in part alleviates the disease.

In some embodiments, a polypeptide comprises a receptor or receptor fragment (e.g., extracellular domain). In some embodiments a receptor is a TNFα receptor.

In certain embodiments, a polypeptide comprises urate oxidase.

One of skill in the art will be aware of the sequences of polypeptides. Without limitation, sequences of certain polypeptides of interest are found in, e.g., U.S. Ser. Nos. 10/773,530; 11/531,531; U.S. Ser. Nos. 11/707,014; 11/429,276; 11/365,008. In some embodiments, a polypeptide of interest is listed in Table B. The invention encompasses application of the inventive techniques to any of the polypeptides described. The invention provides modified versions of any of these polypeptides, wherein a modified version comprises (i) one or more nucleophilic residues such as glycine at the N-terminus (e.g., between 1 and 10 residues) and, optionally, a cleavage recognition sequence, e.g., a protease cleavage recognition sequence that masks the nucleophilic residue(s); (ii) a TRS at or near the C-terminus; (iii) both (i) and (ii). Such modified polypeptides are useful, e.g., as substrates for transamidase-mediated ligation as described herein.

One of skill in the art will be aware that certain polypeptides, e.g., secreted eukaryotic (e.g., mammalian) polypeptides, often undergo intracellular processing (e.g., cleavage of a secretion signal prior to secretion and/or removal of other portion(s) that are not required for biological activity), to generate a mature form. Such mature, biologically active version, is used in certain embodiments of the invention.

TABLE B

| Protein Sequences | |
|---|---|
| Tissue plasminogen activator (1rtf) | Chain A: TTCCGLRQY (SEQ ID NO: 5) <br> Chain B: <br> IKGGLFADIASHPWQAAIFAKHHRRGGERFLCGGILISSCWILSAA <br> HCFQQQQQEEEEERRRRRFFFFFPPPPPPHHLTVILGRTYRVVPGE <br> EEQKFEVEKYIVHKEFDDDTYDNDIALLQLKSSSSSDDDDDSSSSS <br> SSSSSRRRRRCAQESSVVRTVCLPPADLQLPDWTECELSGYGKHE <br> ALSPFYSERLKEAHVRLYPSSRCTTTSSSQQQHLLNRTVTDNMLC <br> AGDTTTRRRSSSNNNLHDACQGDSGGPLVCLNDGRMTLVGIISW <br> GLGCGGQQKDVPGVYTKVTNYLDWIRDNMRP (SEQ ID NO: 41) |
| Factor IX | Chain A: <br> VVGGEDAKPGQFPWQVVLNGKVDAFCGGSIVNEKWIVTAAHCV <br> EETTGVKITVVAGEHNIEETEHTEQKRNVIRIIPHHNYNNNAAAA <br> AAINKYNHDIALLELDEPLVLNSYVTPICIADKEYTTTNNNIIIFLK <br> FGSGYVSGWGRVFHKGRSALVLQYLRVPLVDRATCLRSTKFTIY <br> NNMFCAGGFFHEGGGRRDSCQGDSGGPHVTEVEGTSFLTGIISW <br> GEECAAMMKGKYGIYTKVSRYVNWIKEKTKLT (SEQ ID NO: 6) <br> Chain B: <br> MTCNIKNGRCEQFCKNSADNKVVCSCTEGYRLAENQKSCEPAVP <br> FPCGRVSVSQTSK (SEQ ID NO: 7) |
| glucocerebrosidase | EFARPCIPKSFGYSSVVCVCNATYCDSFDPPALGTFSRYESTRSGR <br> RMELSMGPIQANHTGTGLLLTLQPEQKFQKVKGFGGAMTDAAA <br> LNILALSPPAQNLLLKSYFSEEGIGYNIIRVPMASCDFSIRTYTYAD <br> TPDDFQLHNFSLPEEDTKLKIPLIHRALQLAQRPVSLLASPWTSPT <br> WLKTNGAVNGKGSLKGQPGDIYHQTWARYFVKFLDAYAEHKL <br> QFWAVTAENEPSAGLLSGYPFQCLGFTPEHQRDFIARDLGPTLAN <br> STHHNVRLLMLDDQRLLLPHWAKVVLTDPEAAKYVHGIAVHW <br> YLDFLAPAKATLGETHRLFPNTMLFASEACVGSKFWEQSVRLGS <br> WDRGMQYSHSIITNLLYHVVGWTDWNLALNPEGGPNWVRNFV <br> DSPIIVDITKDTFYKQPMFYHLGHFSKFIPEGSQRVGLVASQKNDL <br> DAVALMHPDGSAVVVVLNRSSKDVPLTIKDPAVGFLETISPGYSI <br> HTYLWHRQ (SEQ ID NO: 8) |
| alpha galactosidase A | LDNGLARTPTMGWLHWERFMCNLDCQEEPDSCISEKLFMEMAE <br> LMVSEGWKDAGYEYLCIDDCWMAPQRDSEGRLQADPQRFPHGI <br> RQLANYVHSKGLKLGIYADVGNKTCAGFPGSFGYYDIDAQTFAD <br> WGVDLLKFDGCYCDSLENLADGYKHMSLALNRTGRSIVYSCEW <br> PLYMWPFQKPNYTEIRQYCNHWRNFADIDDSWKSIKSILDWTSF <br> NQERIVDVAGPGGWNDPDMLVIGNFGLSWNQQVTQMALWAIM <br> AAPLFMSNDLRHISPQAKALLQDKDVIAINQDPLGKQGYQLRQG <br> DNFEVWERPLSGLAWAVAMINRQEIGGPRSYTIAVASLGKGVAC <br> NPACFITQLLPVKRKLGFYEWTSRLRSHINPTGTVLLQLENTM <br> (SEQ ID NO: 9) |

TABLE B-continued

| Protein Sequences | |
|---|---|
| arylsulfatase-A (iduronidase, α-L-) | RPPNIVLIFADDLGYGDLGCYGHPSSTTPNLDQLAAGGLRFTDFY VPVSLPSRAALLTGRLPVRMGMYPGVLVPSSRGGLPLEEVTVAE VLAARGYLTGMAGKWHLGVGPEGAFLPPHQGFHRFLGIPYSHD QGPCQNLTCFPPATPCDGGCDQGLVPIPLLANLSVEAQPPWLPGL EARYMAFAHDLMADAQRQDRPFFLYYASHHTHYPQFSGQSFAE RSGRGPFGDSLMELDAAVGTLMTAIGDLGLLEETLVIFTADNGPE TMRMSRGGCSGLLRCGKGTTYEGGVREPALAFWPGHIAPGVTHE LASSLDLLPTLAALAGAPLPNVTLDGFDLSPLLLGTGKSPRQSLFF YPSYPDEVRGVFAVRTGKYKAHFFTQGSAHSDTTADPACHASSS LTAHEPPLLYDLSKDPGENYNLLGATPEVLQALKQLQLLKAQLD AAVTFGPSQVARGEDPALQICCHPGCTPRPACCHCP (SEQ ID NO: 10) |
| arylsulfatase B (N-acetylgalactos- amine-4-sulfatase) (1fsu) | SRPPHLVFLLADDLGWNDVGFHGSRIRTPHLDALAAGGVLLDNY YTQPLTPSRSQLLTGRYQIRTGLQHQIIWPCQPSCVPLDEKLLPQL LKEAGYTTHMVGKWHLGMYRKECLPTRRGFDTYFGYLLGSEDY YSHERCTLIDALNVTRCALDFRDGEEVATGYKNMYSTNIFTKRAI ALITNHPPEKPLFLYLALQSVHEPLQVPEEYLKPYDFIQDKNRHH YAGMVSLMDEAVGNVTAALKSSGLWNNTVFIFSTDNGGQTLAG GNNWPLRGRKWSLWEGGVRGVGFVASPLLKQKGVKNRELIHIS DWLPTLVKLARGHTNGTKPLDGFDVWKTISEGSPSPRIELLHNID PNFVDSSPCSAFNTSVHAAIRHGNWKLLTGYPGCGYWFPPPSQY NVSEIPSSDPPTKTLWLFDIDRDPEERHDLSREYPHIVTKLLSRLQF YHKHSVPVYFPAQDPRCDPKATGVWGPWM (SEQ ID NO: 11) |
| beta-hexosaminidase A (2gjx) | LWPWPQNFQTSDQRYVLYPNNFQFQYDVSSAAQPGCSVLDEAF QRYRDLLFGTLEKNVLVVSVVTPGCNQLPTLESVENYTLTINDDQ CLLLSETVWGALRGLETFSQLVWKSAEGTFFINKTEIEDFPRFPHR GLLLDTSRHYLPLSSILDTLDVMAYNKLNVFHWHLVDDPSFPYES FTFPELMRKGSYNPVTHIYTAQDVKEVIEYARLRGIRVLAEFDTP GHTLSWGPGIPGLLTPCYSGSEPSGTFGPVNPSLNNTYEFMSTFFL EVSSVFPDFYLHLGGDEVDFTCWKSNPEIQDFMRKKGFGEDFKQ LESFYIQTLLDIVSSYGKGYVVWQEVFDNKVKIQPDTIIQVWREDI PVNYMKELELVTKAGFRALLSAPWYLNRISYGPDWKDFYVVEPL AFEGTPEQKALVIGGEACMWGEYVDNTNLVPRLWPRAGAVAER LWSNKLTSDLTFAYERLSHFRCELLRRGVQAQPLNVGFCEQEFEQ (SEQ ID NO: 12) |
| Hexosaminidase A and B (2gjx) | CHAIN A: LWPWPQNFQTSDQRYVLYPNNFQFQYDVSSAAQPGCSVLDEAF QRYRDLLFGTLEKNVLVVSVVTPGCNQLPTLESVENYTLTINDDQ CLLLSETVWGALRGLETFSQLVWKSAEGTFFINKTEIEDFPRFPHR GLLLDTSRHYLPLSSILDTLDVMAYNKLNVFHWHLVDDPSFPYES FTFPELMRKGSYNPVTHIYTAQDVKEVIEYARLRGIRVLAEFDTP GHTLSWGPGIPGLLTPCYSGSEPSGTFGPVNPSLNNTYEFMSTFFL EVSSVFPDFYLHLGGDEVDFTCWKSNPEIQDFMRKKGFGEDFKQ LESFYIQTLLDIVSSYGKGYVVWQEVFDNKVKIQPDTIIQVWREDI PVNYMKELELVTKAGFRALLSAPWYLNRISYGPDWKDFYVVEPL AFEGTPEQKALVIGGEACMWGEYVDNTNLVPRLWPRAGAVAER LWSNKLTSDLTFAYERLSHFRCELLRRGVQAQPLNVGFCEQEFEQ (SEQ ID NO: 13) Chain B: PALWPLPLSVKMTPNLLHLAPENFYISHSPNSTAGPSCTLLEEAFR RYHGYIFGTQVQQLLVSITLQSECDAFPNISSDESYTLLVKEPVAV LKANRVWGALRGLETESQLVYQDSYGTFTINESTIIDSPRFSHRGI LIDTSRHYLPVKIILKTLDAMAFNKFNVLHWHIVDDQSFPYQSITF PELSNKGSYSLSHVYTPNDVRMVIEYARLRGIRVLPEFDTPGHTLS WGKGQKDLLTPCYSDSFGPINPTLNTTYSFLTTFFKEISEVFPDQFI HLGGDEVEFKCWESNPKIQDFMRQKGFGTDFKKLESFYIQKVLDI IATINKGSIVWQEVFDDKAKLAPGTIVEVWKDSAYPEELSRVTAS GFPVILSAPWYLDLISYGQDWRKYYKVEPLDFGGTQKQKQLFIG GEACLWGEYVDATNLTPRLWPRASAVGERLWSSKDVRDMDDA YDRLTRHRCRMVERGIAAQPLYAGYCN (SEQ ID NO: 14) Chain C: PALWPLPLSVKMTPNLLHLAPENFYISHSPNSTAGPSCTLLEEAFR RYHGYIFGTQVQQLLVSITLQSECDAFPNISSDESYTLLVKEPVAV LKANRVWGALRGLETESQLVYQDSYGTFTINESTIIDSPRFSHRGI LIDTSRHYLPVKIILKTLDAMAFNKFNVLHWHIVDDQSFPYQSITF PELSNKGSYSLSHVYTPNDVRMVIEYARLRGIRVLPEFDTPGHTLS WGKGQKDLLTPCYSLDSFGPINPTLNTTYSFLTTFFKEISEVFPDQ FIHLGGDEVEFKCWESNPKIQDFMRQKGFGTDFKKLESFYIQKVL DIIATINKGSIVWQEVFDDKAKLAPGTIVEVWKDSAYPEELSRVT ASGFPVILSAPWYLDLISYGQDWRKYYKVEPLDFGGTQKQKQLFI GGEACLWGEYVDATNLTPRLWPRASAVGERLWSSKDVRDMDD AYDRLTRHRCRMVERGIAAQPLYAGYCN (SEQ ID NO: 15) |

TABLE B-continued

| | Protein Sequences |
|---|---|
| | Chain D:<br>LWPWPQNFQTSDQRYVLYPNNFQFQYDVSSAAQPGCSVLDEAF<br>QRYRDLLFGTLEKNVLVVSVVTPGCNQLPTLESVENYTLTINDDQ<br>CLLLSETVWGALRGLETESQLVWKSAEGTFFINKTEIEDFPRFPHR<br>GLLLDTSRHYLPLSSILDTLDVMAYNKLNVFHWHLVDDPSFPYES<br>FTEPELMRKGSYNPVTHIYTAQDVICEVIEYARLRGIRVLAEFDTP<br>GHTLSWGPGIPGLLTPCYSGSEPSGTFGPVNPSLNNTYEFMSTFFL<br>EVSSVFPDFYLHLGGDEVDFTCWKSNPEIQDFMRKKGFGEDFKQ<br>LESFYIQTLLDIVSSYGKGYVVWQEVFDNKVKIQPDTIIQVWREDI<br>PVNYMKELELVTICAGFRALLSAPWYLNRISYGPDWKDFYVVEPL<br>AFEGTPEQKALVIGGEACMWGEYVDNTNLVPRLWPRAGAVAER<br>LWSNKLTSDLTFAYERLSHFRCELLRRGVQAQPLNVGFCEQEFEQ<br>(SEQ ID NO: 16) |
| phenylalanine hydroxylase<br>(PAH)(1j8u) | VPWFPRTIQELDRFANQILSYGAELDADHPGFKDPVYRARRKQFA<br>DIAYNYRHGQPIPRVEYMEEEKKTWGTVEKTLKSLYKTHACYEY<br>NHIFPLLEKYCGFHEDNIPQLEDVSQFLQTCTGFRLRPVAGLLSSR<br>DFLGGLAFRVFHCTQYIRHGSKPMYTPEPDICHELLGHVPLFSDRS<br>FAQFSQEIGLASLGAPDEYIEKLATIYWFTVEFGLCKQGDSIKAYG<br>AGLLSSFGELQYCLSEKPKLLPLELEKTAIQNYTVTEFQPLYYVAE<br>SFNDAKEKVRNFAATIPRPFSVRYDPYTQRIEVL (SEQ ID NO: 17) |
| Cathepsin A | APDQDEIQRLPGLAKQPSFRQYSGYLKSSGSKHLHYWFVESQKD<br>PENSPVVLWLNGGPGCSSLDGLLTEHGPFLVQPDGVTLEYNPYS<br>WNLIANVLYLESPAGVGFSYSDDKFYATNDTEVAQSNFEALQDF<br>FRLFPEYKNNKLFLTGESYAGIYIPTLAVLVMQDPSMNLQGLAVG<br>NGLSSYEQNDNSLVYFAYYHGLLGNRLWSSLQTHCCSQNKCNF<br>YDNKDLECVTNLQEVARIVGNSGLNIYNLYAPCAGGVPSHFRYE<br>KDTVVVQDLGNIFTRLPLKRMWHQALLRSGDKVRMDPPCTNTT<br>AASTYLNNPYVRKALNIPEQLPQWDMCNFLVNLQYRRLYRSMN<br>SQYLKLLSSQKYQILLYNGDVDMACNFMGDEWFVDSLNQKMEV<br>QRRPWLVKYGDSGEQIAGFVKEFSHIAFLTIKGAGHMVPTDKPLA<br>AFTMFSRFLNKQPY (SEQ ID NO: 18) |
| G-CSF | LPQSFLLKCLEQVRKIQGDGAALQEKLCATYKLCHPEELVLLGHS<br>LGIPWAPLLAGCLSQLHSGLFLYQGLLQALEGISPELGPTLDTLQL<br>DVADFATTIWQQMEELGMMPAFASAFQRRAGGVLVASHLQSFL<br>EVSYRVLRHLA (SEQ ID NO: 19) |
| GM-CSF | EHVNAIQEARRLLNLSRDTAAEMNETVEVISEMFDLQEPTCLQTR<br>LELYKQGLRGSLTKLKGPLTMMASHYKQHCPPTPETSCATQIITF<br>ESFKENLKDFLLVIP (SEQ ID NO: 20) |
| Interferon alfa-2 | CDLPQTHSLGSRRTLMLLAQMRKISLFSCLKDRHDFGFPQEEFGN<br>QFQKAETIPVLHEMIQQIFNLFSTKDSSAAWDETLLDKFYTELYQ<br>QLNDLEACVIQGVGVTETPLMKEDSILAVRKYFQRITLYLKEKKY<br>SPCAWEVVRAEIMRSFSLSTNLQESLRSKE (SEQ ID NO: 21) |
| Interferon beta-1 | MSYNLLGELQRSSNFQCQKLLWQLNGRLEYCLKDRMNFDIPEEI<br>KQLQQFQICEDAALTIYEMLQNIFAIFRQDSSSTGWNETIVENLLA<br>NVYHQINHLKTVLEEKLEKEDFTRGKLMSSLHLKRYYGRILHYL<br>KAKEYSHCAWTIVRVEILRNFYFINRLTGYLRN (SEQ ID NO: 22) |
| Interferon gamma-1b | MQDPYVKEAENLKKYFNAGHSDVADNGTLFLGILKNWKEESDR<br>KIMQSQIVSFYFKLFKNFKDDQSIQKSVETIKEDMNVKFENSNKK<br>KRDDFEKLTNYSVTDLNVQRKAIDELIQVMAELGANVSGEFVKE<br>AENLKKYFNDNGTLFLGILKNWKEESDRKIMQSQIVSFYFKLFKN<br>FKDDQSIQKSVETIKEDMNVKFFNSNKKKRDDFEKLTNYSVTDL<br>NVQRKAIHELIQVMAELSPAA (SEQ ID NO: 23) |
| IL-2 (1M47) | STKKTQLQLEHLLLDLQMILNGINNYKNPKLTRMLTFKFYMPKK<br>ATELKHLQCLEEELKPLEEVLNLAQNFHLRPRDLISNINVIVLELK<br>GFMCEYADETATIVEFLNRWITFCQSIISTLT (SEQ ID NO: 24) |
| IL-1 (2nvh) | APVRSLNCTLRDSQQKSLVMSGPYELICALHLQGQDMEQQVVFS<br>MSFVQGEESNDKIPVALGLKEKNLYLSCVLKDDKPTLQLESVDP<br>KNYPKKKMEKRFVFNKIEINNICLEFESAQFPNWYISTSQAENMPV<br>FLGGTKGGQDITDFTMQFVS (SEQ ID NO: 25) |
| TNF-alpha (4tsv) | DKPVAHVVANPQAEGQLQWSNRRANALLANGVELRDNQLVVPI<br>EGLFLIYSQVLFKGQGCPSTHVLLTHTISRIAVSYQTKVNLLSAIKS<br>PCQRETPEGAEAKPWYEPIYLGGVFQLEKGDRLSAEINRPDYLDF<br>AESGQVYFGIIAL (SEQ ID NO: 26) |
| TNF-beta (lymphotoxin) (1tnr) | KPAAHLIGDPSKQNSLLWRANTDRAFLQDGFSLSNNSLLVPTSGI<br>YFVYSQVVFSGKAYSPKATSSPLYLAHEVQLFSSQYPFHVPLLSS<br>QKMVYPGLQEPWLHSMYHGAAFQLTQGDQLSTHTDGIPHLVLSP<br>STVFFGAFAL (SEQ ID NO: 27) |

TABLE B-continued

| Protein Sequences | |
|---|---|
| Erythropoietin | APPRLICDSRVLERYLLEAKEAEKITTGCAEHCSLNEKITVPDTKV NFYAWKRMEVGQQAVEVWQGLALLSEAVLRGQALLVKSSQPW EPLQLHVDKAVSGLRSLTTLLRALGAQKEAISNSDAASAAPLRTI TADTFRKLFRVYSNFLRGKLKLYTGEACRTGDR (SEQ ID NO: 28) |
| Insulin | Chain A: GIVEQCCTSICSLYQLENYCN (SEQ ID NO: 29)<br>Chain B: FVNQHLCGSHLVEALYLVCGERGFFYTPK (SEQ ID NO: 30) |
| Growth hormone (GH) (Somatotropin) (1huw) | FPTIPLSRLADNAWLRADRLNQLAFDTYQEFEEAYIPKEQIHSFW WNPQTSLCPSESIPTPSNKEETQQKSNLELLRISLLLIQSWLEPVQF LRSVFANSLVYGASDSNVYDLLKDLEEGIQTLMGRLEALLKNYG LLYCFNKDMSKVSTYLRTVQCRSVEGSCGF (SEQ ID NO: 31) |
| Follicle-stimulating hormone (FSH) | CHHRICHCSNRVFLCQESKVTEIPSDLPRNAIELRFVLTKLRVIQK GAFSGFGDLEKIEISQNDVLEVIEADVFSNLPKLHEIRIEKANNLLY INPEAFQNLPNLQYLLISNTGIKHLPDVHKIHSLQKVLLDIQDNINI HTIERNSFVGLSFESVILWLNKNGIQEIHNCAFNGTQLDELNLSDN NNLEELPNDVFHGASGPVILDISRTRIHSLPSYGLENLKKLRARST YNLKKLPTLE (SEQ ID NO: 32) |
| Leptin (1ax8) | IQKVQDDTKTLIKTIVTRINDILDFIPGLHPILTLSKMDQTLAVYQQ ILTSMPSRNVIQISNDLENLRDLLHVLAFSKSCHLPEASGLETLDSL GGVLEASGYSTEVVALSRLQGSLQDMLWQLDLSPGC (SEQ ID NO: 33) |
| Insulin-like growth factor (or somatomedin) (1wqj) | PETLCGAELVDALQFVCGDRGFYFNKPTGYGSSSRRAPQTGIVDE CCFRSCDLRRLEMYCAP (SEQ ID NO: 34) |
| Adiponectin (1c28) | Chain A:<br>MYRSAFSVGLETRVTVPNVPIRFTKIFYNQQNHYDGSTGKFYCNI PGLYYFSYHITVYMKDVKVSLFKKDKAVLFTYDQYQENVDQAS GSVLLHLEVGDQVWLQVYYADNVNDSTFTGFLLYHDT (SEQ ID NO: 35)<br>Chain B:<br>MYRSAFSVGLPNVPIRFTKIFYNQQNHYDGSTGKFYCNIPGLYYF SYHITVYMKDVKVSLFKKDKVLFTYDQYQEKVDQASGSVLLHL EVGDQVWLQVYDSTFTGFLLYHD (SEQ ID NO: 36)<br>Chain C:<br>MYRSAFSVGLETRVTVPIRFTKIFYNQQNHYDGSTGKFYCNIPGL YYFSYHITVDVKVSLFKKDKAVLFTQASGSVLLHLEVGDQVWLQ NDSTFTGFLLYHD (SEQ ID NO: 37) |
| Factor VIII (aka antihemophilic factor) (2r7e) | Chain A:<br>ATRRYYLGAVELSWDYMQSDLGELPVDAREPPRVPKSFPENTSV VYKKTLFVEFTDHLFNIAKPRPPWMGLLGPTIQAEVYDTVVITLK NMASHPVSLHAVGVSYWKASEGAEYDDQTSQREKEDDKVFPGG SHTYVWQVLKENGPMASDPLCLTYSYLSHVDLVKDLNSGLIGAL LVCREGSLAKEKTQTLHKFILLFAVFDEGKSWHSETKNAASARA WPKMHTVNGYVNRSLPGLIGCHRKSVYWHVIGMGTTPEVHSIFL EGHTFLVRNHRQASLEISPITFLTAQTLLMDLGQFLLFCHISSHQH DGMEAYVKVDSCPEEPQFDDDNSPSFIQIRSVAKKHPKTWVHYIA AEEEDWDYAPLVLAPDDRSYKSQYLNNGPQRIGRKYKKVRFMA YTDETFKTREAIQHESGILGPLLYGEVGDTLLIIFKNQASRPYNIYP HGITDVRPLYSRRLPKGVKHLKDFPILPGEIFKYKWTVTVEDGPT KSDPRCLTRYYSSFVNMERDLASGLIGPLLICYKESVDQRGNQIM SDKRNVILFSVFDENRSWYLTENIQRFLPNPAGVQLEDPEFQASNI MHSINGYVFDSLQLSVCLHEVAYWYILSIGAQTDFLSVFFSGYTF KHKMVYEDTLTLFPFSGETVFMSMENPGLWILGCHNSDFRNRGM TALLKVSSCDKNTGDYYEDSYED (SEQ ID NO: 38)<br>Chain B:<br>RSFQKKTRHYFIAAVERLWDYGMSSSPHVLRNRAQSGSVPQFKK VVFQEFTDGSFTQPLYRGELNEHLGLLGPYIRAEVEDNIMVTFRN QASRPYSFYSSLISYEEDQRQGAEPRKNFVKPNETKTYFWKVQH HMAPTKDEFDCKAWAYSSDVDLEKDVHSGLIGPLLVCHTNTLNP AHGRQVTVQEFALFFTIFDETKSWYFTENMERNCRAPCNIQMED PTFKENYRFHAINGYIMDTLPGLVMAQDQRIRWYLLSMGSNENI HSIHFSGHVETVRICKEEYKMALYNLYPGVFETVEMLPSKAGIWR VECLIGEHLHAGMSTLFLVYSNKCQTPLGMASGHIRDFQITASGQ YGQWAPKLARLHYSGSINAWSTKEPFSWIKVDLLAPMIIHGIKTQ GARQKFSSLYISQFIIMYSLDKKWQTYRGNSTGTLMVFFGNVDS SGIKHNIFNPPIIARYIRLHPTHYSIRSTLRMELMGCDLNSCSMPLG MESKAISDAQITASSYFTNMFATWSPSKARLHLQGRSNAWRPQV NNPKEWLQVDFQKTMKVTGVTTQGVKSLLTSMYVKEFLISSSQD GHQWTLFFQNGKVKVFQGNQDSFTPVVNSLDPPLLTRYLRIHPQS WVHQIALRMEVLGCEAQDLY (SEQ ID NO: 39) |

TABLE B-continued

Protein Sequences

Human serum albumin (1ao6)
Chain A:
SEVAHRFKDLGEENFKALVLIAFAQYLQQCPFEDHVKLVNEVTEF
AKTCVADESAENCDKSLHTLFGDKLCTVATLRETYGEMADCCA
KQEPERNECFLQHKDDNPNLPRLVRPEVDVMCTAFHDNEETFLK
KYLYEIARRHPYFYAPELLFFAKRYKAAFTECCQAADKAACLLP
KLDELRDEGICASSAKQRLKCASLQKFGERAFICAWAVARLSQRFP
KAEFAEVSKLVTDLTKVHTECCHGDLLECADDRADLAKYICENQ
DSISSKLKECCEKPLLEKSHCIAEVENDEMPADLPSLAADFVESKD
VCKNYAEAKDVFLGMFLYEYARRHPDYSVVLLLRLAKTYETTLE
KCCAAADPHECYAKVFDEFKPLVEEPQNLIKQNCELFEQLGEYKF
QNALLVRYTKKVPQVSTPTLVEVSRNLGKVGSKCCKHPEAKRMP
CAEDYLSVVLNQLCVLHEKTPVSDRVTKCCTESLVNRRPCFSALE
VDETYVPKEFNAETFTFHADICTLSEICERQIKKQTALVELVKHKP
KATKEQLKAVMDDFAAFVEKCCKADDKETCFAEEGKKLVAASQ
AA (SEQ ID NO: 40)
Chain B:
SEVAHRFKDLGEENFKALVLIAFAQYLQQCPFEDHVKLVNEVTEF
AKTCVADESAENCDKSLHTLFGDKLCTVATLRETYGEMADCCA
KQEPERNECFLQHKDDNPNLPRLVRPEVDVMCTAFHDNEETFLK
KYLYEIARRHPYFYAPELLFFAKRYKAAFTECCQAADKAACLLP
KLDELRDEGKASSAKQRLKCASLQICFGERAFKAWAVARLSQRFP
KAEFAEVSKLVTDLTKVHTECCHGDLLECADDRADLAKYICENQ
DSISSKLKECCEKPLLEKSHCIAEVENDEMPADLPSLAADFVESKD
VCKNYAEAKDVFLGMFLYEYARRHPDYSVVLLLRLAKTYETTLE
KCCAAADPHECYAKVFDEFKPLVEEPQNLIKQNCELFEQLGEYKF
QNALLVRYTKKVPQVSTPTLVEVSRNLGKVGSKCCKHPEAKRMP
CAEDYLSVVLNQLCVLHEKTPVSDRVTKCCTESLVNRRPCFSALE
VDETYVPKEFNAETFTFHADICTLSEKERQIICKQTALVELVKHKP
KATKEQLKAVMDDFAAFVEKCCKADDKETCFAEEGKKLVAASQ
AA (SEQ ID NO: 42)

Hemoglobin (1bz0)
Chain A:
VLSPADKTNVKAAWGKVGAHAGEYGAEALERMFLSFPTTKTYF
PHFDLSHGSAQVKGHGKKVADALTNAVAHVDDMPNALSALSDL
HAHKLRVDPVNFKLLSHCLLVTLAAHLPAEFTPAVHASLDKFLA
SVSTVLTSKYR (SEQ ID NO: 43)
Chain B:
VHLTPEEKSAVTALWGKVNVDEVGGEALGRLLVVYPWTQRFFE
SFGDLSTPDAVMGNPKVKAHGKKVLGAFSDGLAHLDNLKGTFA
TLSELHCDKLHVDPENFRLLGNVLVCVLAHHFGKEFTPPVQAAY
QKVVAGVANALAHKYH (SEQ ID NO: 44)

It will be appreciated that considerable structure/function information is available regarding many of the afore-mentioned polypeptides, as well as sequences from different mammalian species, that can be used to design variants of the naturally occurring sequence that retain significant biological activity (e.g., at least 25%, 75%, 90% or more of the activity of the naturally occurring polypeptide). For example, crystal structures or NMR structures of a number of these polypeptides, in some instances in a complex with the corresponding receptor, are available. In addition, it will be understood that, if the naturally occurring N- and C-termini are not located in close proximity to each other in the native structure, a naturally occurring sequence can be extended at the N- and/or C-termini, e.g., with a flexible peptide spacer so that the termini can come into close proximity.

Pharmaceutical Compositions

The invention provides pharmaceutical compositions comprising any of the polypeptides described herein, i.e., a polypeptide that has been modified using an inventive ligation composition or method. In some embodiments the polypeptide is circular. In some embodiments the polypeptide is PEGylated in a site-specific manne. In some embodiments the polypeptide is circular and PEGylated, e.g., the polypeptide is circularized via a linker peptide that comprises a PEG moiety attached to at least one side chain.

A pharmaceutical composition may comprise a variety of pharmaceutically acceptable carriers. Pharmaceutically acceptable carriers are well known in the art and include, for example, aqueous solutions such as water, 5% dextrose, or physiologically buffered saline or other solvents or vehicles such as glycols, glycerol, oils such as olive oil, or injectable organic esters that are suitable for administration to a human or non-human subject. See, e.g., Remington: The Science and Practice of Pharmacy, 21$^{st}$ edition; Lippincott Williams & Wilkins, 2005. In some embodiments, a pharmaceutically acceptable carrier or composition is sterile. A pharmaceutical composition can comprise, in addition to the active agent, physiologically acceptable compounds that act, for example, as bulking agents, fillers, solubilizers, stabilizers, osmotic agents, uptake enhancers, etc. Physiologically acceptable compounds include, for example, carbohydrates, such as glucose, sucrose, lactose; dextrans; polyols such as mannitol; antioxidants, such as ascorbic acid or glutathione; preservatives; chelating agents; buffers; or other stabilizers or excipients. The choice of a pharmaceutically acceptable carrier(s) and/or physiologically acceptable compound(s) can depend for example, on the nature of the active agent, e.g., solubility, compatibility (meaning that the substances can be present together in the composition without interacting in a manner that would substantially reduce the pharmaceutical efficacy of the pharmaceutical composition under ordinary use situations) and/or route of administration of the composition. The pharmaceutical composition could be in the form of a liquid, gel, lotion, tablet, capsule, ointment, cream, transdermal patch, etc. A pharmaceutical composition can be administered to a subject by various routes including, for example, parenteral administration. Exemplary routes of administration include intravenous administration; respiratory administration (e.g., by inhalation), intramuscular administration, nasal administration, intraperitoneal administration, oral administration, subcutaneous administration and topical administration. For oral administration, the compounds can be formulated with pharmaceutically acceptable carriers as tablets, pills, dragees, capsules, liquids, gels, syrups, slurries, suspensions, etc. In some embodiments a compound may be administered directly to a target tissue. Direct administration could be accomplished, e.g., by injection or by implanting a sustained release implant within the tissue. Of course a sustained release implant could be implanted at any suitable site. In some embodiments, a sustained release implant may be particularly suitable for prophylactic treatment of subjects at risk of developing a recurrent cancer. In some embodiments, a sustained release implant delivers therapeutic levels of the active agent for at least 30 days, e.g., at least 60 days, e.g., up to 3 months, 6 months, or more. One skilled in the art would select an effective dose and administration regimen taking into consideration factors such as the patient's weight and general health, the particular condition being treated, etc. Exemplary doses may be selected using in vitro studies, tested in animal models, and/or in human clinical trials as standard in the art.

In some embodiments, the pharmaceutical composition is delivered by means of a microparticle or nanoparticle or a liposome or other delivery vehicle or matrix. A number of biocompatible synthetic or naturally occurring polymeric materials are known in the art to be of use for drug delivery purposes. Examples include polylactide-co-glycolide, polycaprolactone, polyanhydride, cellulose derivatives, and copolymers or blends thereof. Liposomes, for example, which consist of phospholipids or other lipids, are nontoxic, physiologically acceptable and metabolizable carriers that are relatively simple to make and administer.

A compound, e.g., a polypeptide of the invention (e.g., a polypeptide produced at least in part using an inventive ligation method) may be delivered in an effective amount, by which is meant an amount sufficient to achieve a biological response of interest, e.g., reducing one or more symptoms or manifestations of a disease or condition. The exact amount required will vary from subject to subject, depending on factors such as the species, age, weight, sex, and general condition of the subject, the severity of the disease or disorder, the particular compound and its activity, its mode of administration, concurrent therapies, and the like. In some embodiments, a compound, e.g., a polypeptide, is formulated in unit dosage unit form for ease of administration and uniformity of dosage, which term as used herein refers to a physically discrete unit of agent appropriate for the patient to be treated. It will be understood, however, that the total daily dosage will be decided by the attending physician within the scope of sound medical judgment. In some embodiments, e.g., when administering a PEGylated polypeptide, information available regarding a suitable dose of the unPEGylated version, optionally in conjunction with in vitro activity data, can be used as a guideline in selecting an appropriate dose for preclinical testing and/or for clinical use.

The pharmaceutical compositions can be used to treat a wide variety of different diseases and disorders. In some embodiments, a pharmaceutical composition is used, e.g., to treat any disease or condition for which the unmodified polypeptide is of use. Thus the invention provides methods of treatment comprising administering an inventive polypeptide to a subject in need thereof. The subject is typically a mammalian subject, e.g., a human. In some embodiments the subject is a non-human animal that serves as a model for a disease or disorder that affects humans. The animal model may be used, e.g., in preclinical studies, e.g., to assess efficacy and/or determine a suitable dose.

In some embodiments, an inventive polypeptide is administered prophylactically, e.g., to a subject who does not exhibit signs or symptoms of the disease or disorder (but may be at increased risk of developing the disorder or is expected to develop the disease or disorder). In some embodiments an inventive polypeptide is administered to a subject who has developed one or more signs or symptoms of the disease or sorder, e.g., the subject has been diagnose as having the disease or disorder. Optionally, the method comprises diagnosing the subject as having a disease or disorder for which the polypeptide is an appropriate treatment. For example, interferons have a variety of uses, e.g., in the treatment of autoimmune diseases (e.g., multiple sclerosis) and infectious diseases (e.g., viral infections such as those caused by viruses belonging to the Flaviviridae family, e.g., HBV, HCV; bacterial infections, fungal infections, parasites). Exemplary viruses include, but are not limited to, viruses of the Flaviviridae family, such as, for example, Hepatitis C Virus, Yellow Fever Virus, West Nile Virus, Japanese Encephalitis Virus, Dengue Virus, and Bovine Viral Diarrhea Virus; viruses of the Hepadnaviridae family, such as, for example, Hepatitis B Virus; viruses of the Picornaviridae family, such as, for example, Encephalomyocarditis Virus, Human Rhinovirus, and Hepatitis A Virus; viruses of the Retroviridae family, such as, for example, Human Immunodeficiency Virus, Simian Immunodeficiency Virus, Human T-Lymphotropic Virus, and Rous Sarcoma Virus; viruses of the Coronaviridae family, such as, for example, SARS coronavirus; viruses of the Rhabdoviridae family, such as, for example, Rabies Virus and Vesicular Stomatitis Virus, viruses of the Paramyxoviridae family, such as, for example, Respiratory Syncytial Virus and Parainfluenza Virus, viruses of the Papillomaviridae family, such as, for example, Human Papillomavirus, and viruses of the Herpesviridae family, such as, for example, Herpes Simplex Virus.

Interferon therapy is used (often in combination with chemotherapy and radiation) as a treatment for many cancers, which term is used herein to encompass solid tumors (carcinomas, sarcomas), and leukemias. In some embodiments the tumor is an adenocarcinoma. In some embodiments the tumor is a sarcoma. In some embodiments the tumor affects an organ or organ system selected from breast, lymph node, prostate, kidney, bladder, lung, liver, gastrointestinal tract, colon, testis, stomach, pancreas, thyroid, skin, ovary, uterus, cervix, skin, nerve, bone, and nervous system (e.g., brain). In some embodiments, an interferon is used for treating a hematological malignancy, e.g., a leukemia or a lymphoma, e.g., hairy cell leukemia, chronic myeloid leukemia, nodular lymphoma, cutaneous T-cell lymphoma. In some embodiments an IFN, e.g., IFN-α2b, is used to treat a melanoma.

Erythropoiesis stimulating agents such as EPO are of use to treat anemia, which may result from a variety of causes. For example, the anemia may be an anemia of chronic disease, anemia associated with medications (e.g., cancer chemotherapy), radiation, renal disease (e.g., diabetes), infectious diseases, or blood loss. Colony stimulating factors such as G-CSF, GM-CSF, and/or M-CSF may be used to treat leukopenia, e.g., neutropenia and/or lymphopenia, which may result, e.g., from medications (e.g., cancer chemotherapy), radiation, infectious disease, or blood loss.

Neurotrophic factor polypeptides may be used, e.g., to treat neurodegenerative diseases (e.g., amyotrophic lateral sclerosis, Huntington disease, Alzheimer disease, Parkinson disease), central or peripheral nervous system injury.

Growth hormone may be used, e.g., to treat children's growth disorders and adult growth hormone deficiency.

Interleukins are of use to modulate the immune response for a wide variety of purposes, e.g., to stimulate an immune response against an infectious agent or cancer. In some embodiments, an interleukin stimulates immune system cells and/or increases the intensity and/or duration of innate and/or adaptive immune responses. As known in the art, certain interleukins help to limit the intensity and/or duration of innate and/or adaptive immune responses. Administration of such interleukins may be of use in treatment of autoimmune diseases, sepsis, or other conditions in which an aberrant or overactivated immune response can be deleterious.

Autoimmune disorders include type I diabetes (e.g., juvenile onset diabetes), multiple sclerosis, *scleroderma*, ankylosing spondylitis, sarcoid, pemphigus vulgaris, myasthenia gravis, systemic lupus erythemotasus, rheumatoid arthritis, juvenile arthritis, Behcet's syndrome, Reiter's disease, Berger's disease, dermatomyositis, Wegener's granulomatosis, autoimmune myocarditis, anti-glomerular basement membrane disease (including Goodpasture's syndrome), dilated cardiomyopathy, thyroiditis (e.g., Hashimoto's thyroiditis, Graves' disease), and Guillane-Barre syndrome, Diseases caused by gram-positive or gram-negative bacteria, mycobacteria, fungi such as *Candida* or *Aspergillus*, helminths, etc., are of interest in certain embodiments. Exemplary bacteria and fungi include those falling within the following groups Actinomycetales (e.g., *Corynebacterium, Mycobacterium, Norcardia*), Aspergillosis, Bacillaceae (e.g., *Anthrax, Clostridium*), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (*Klebsiella, Salmonella, Serratia, Yersinia*), Erysipelothrix, *Helicobacter, Legionella, Leptospires Listeria*, Mycoplasmatales, Neisseriaceae (e.g., *Acinetobacter, Menigococci*), Pasteurellacea (e.g., *Actinobacillus, Heamophilus, Pasteurella*), *Pseudomonas*, Rickettsiaceae, Chlamydiaceae, *Treponema*, and Staphylococci.

In some embodiments a modified, e.g., PEGylated and/or circularized polypeptide exhibits increase efficacy relative to an unmodified form and/or requires a lower dose or less frequent administration (greater dosing interval) to achieve equivalent efficacy and/or exhibits reduced toxicity (reduced side effects, greater tolerability, greater safety) and/or can be administered by a more convenient or preferable route of administration.

Use of Transamidases for Reporting on Cell-Cell Interactions

Figure 46:
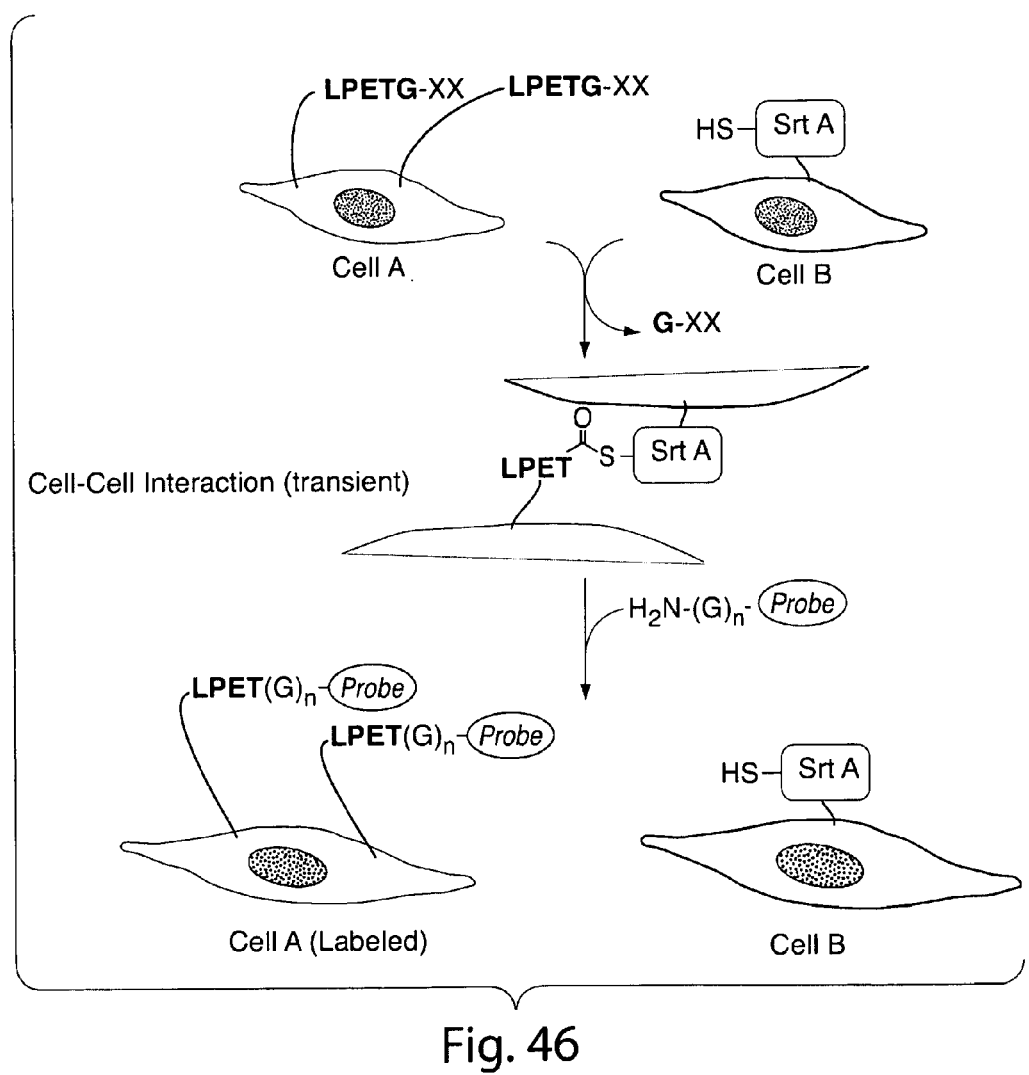
FIG. 46 shows a scheme for using transamidase-mediated reaction for detecting cell-cell interactions. LPETG-XX—SEQ ID NO: 219; LPETG—SEQ ID NO: 220.

There is a dearth of tools that report on cell-cell interactions. Currently available split-GFP reporters only detect long-lasting interactions (GFP Reconstitution Across Synaptic Partners (GRASP) defines cell contacts and synapses in living nervous systems. Feinberg E H, Vanhoven M K, Bendesky A, Wang G, Fetter R D, Shen K, Bargmann C I. Neuron. 2008 Feb. 7; 57(3):353-63.). We have previously shown that type II membrane proteins bearing the requisite sortase cleavage site at their C-terminus and expressed at the living cell surface are susceptible to sortase-mediated labeling when incubated with a soluble recombinant sortase and a suitable probe (Popp et al. Nature Chemical Biology, 2007). In one aspect, the invention provides tools and methods for reporting on (detecting, optionally quantifying) transient cell-cell interactions, where one cell bearing a sortase substrate comes into close proximity to another cell bearing a membrane anchored version of a transamidase, e.g., a SrtA, e.g., either SrtA$_{strep}$ or SrtA$_{staph}$. This would allow for acyl-enzyme formation between the sortase and substrate on opposite cells and when incubated with a functionalized probe (either based on an AA nucleophile or a GG nucleophile for SrtA$_{strep}$ and SrtA$_{staph}$, respectively) will ultimately result in labeling of the cell bearing the sortase substrate. In this way a long-lived, e.g., indelible, mark for a possibly transient cell-cell interaction is imparted on the cell bearing the sortase substrate, given that the interaction is long-lived enough for the transacylation reaction to occur (FIG. 46). In its natural context, sortases are embedded in the bacterial membrane through a transmembrane anchor at the N-terminus. We can thus express sortase at the mammalian cell surface by fusing the catalytic domain of sortase to a mammalian type II membrane protein bearing a signal-anchor sequence for ER insertion. This would result in insertion into the plasma membrane and exposure of the sortase catalytic domain to the extracellular space. In some embodiments, the label comprises a detectable moiety and/or a tag that can be used for isolating the cells. This approach can be applied in vitro (in cell culture) or in vivo. Potential applications include, e.g., examining interactions of immune system cells (e.g., lymphocytes, macrophages) with other immune or non-immune system cells, examining cell-cell interactions in the nervous system or during development, cell migration, etc. This approach can be used to report on cell interactions with noncellular materials as well, by attaching a sortase substrate thereto.

Immunoglobulins and Transgenic Non-Human Animals

The invention provides a transgenic, non-human animal comprising cells whose genome comprises a DNA segment comprising a portion that encodes a polypeptide of interest and a portion that encodes a sortase recognition motif. "Transgenic animal" is used consistently with usage in the art and refers to a non-human animal having a non-endogenous (i.e., heterologous) nucleic acid sequence (transgene) stably integrated into its DNA (i.e., in the genomic sequence of most or all of its cells, in many embodiments including somatic cells and cells of the germ line) or, in some embodiments, present as an extrachromosomal element in at least some of its cells. In some embodiments a transgenic animal is a "knock-out" animal, in which a gene has been inactivated, e.g., by at least partially deleting the gene or insertion of a heterologous sequence. It will be understood that the term "transgenic" applies both to the original genetically modified animal and to its descendants.

In certain embodiments the animal is of a type in which genetic modification, e.g., generating transgenic organisms, has been performed and in which methods for performing genetic modification, e.g., generating transgenic organisms, without undue experimentation are known in the art. In some embodiments of the invention, the transgenic non-human animal is a mammal. In some embodiments of the invention, the mammal is ovine, porcine, or bovine. In some embodiments of the invention, the transgenic non-human mammal is a rodent, e.g., a mouse or rat. In some embodiments, the transgenic non-human animal is an avian, e.g., a chicken. The invention further provides offspring of the transgenic animal, wherein the offspring are obtained by crossing the transgenic animal with an animal having a phenotype or genetic modification of interest.

The invention further provides a cell derived from the transgenic animal. The cell may be of any cell type. In some embodiments the cell is an immune system cell (e.g., a B or T lineage cell, neutrophil or neutrophil precursor), etc. "Derived from" refers to cells that are obtained from an animal and descendants of such cells. The cells may be subjected to genetic modification or other manipulation. In some embodiments the cells are immortalized.

Transgenic animals of the invention have a number of applications. They may be sources of sortase substrates and/or of cells that express sortase substrates comprising a sortase recognition motif. An application of particular interest is the production of antibodies or antibody chains that comprise a sortase recognition motif. Such antibodies may be conveniently labeled or attached to a solid support, e.g., an array, e.g., a glass slide. The animal may be immunized or otherwise contacted with (e.g., exposed to), an antigen of interest (e.g., an allergen, an infectious agent or an extract, portion, or product thereof such as a polypeptide, etc.), may be genetically predisposed to develop an autoimmune disease or immunodeficiency, may be infected with a pathogenic or non-pathogenic infectious agent, etc. Immune system cells, e.g., B-lineage cells, may be obtained from the animal. Hybridomas may be generated from the B-lineage cells. The invention provides collections ('panels') of antibodies and hybridomas. See, e.g., U.S. Ser. No. 10/324,114 (US Pub. No. 20030224490) for information regarding production of monoclonal antibodies, hybridomas, and various other methods that may be employed in the present invention.

In some embodiments, the transgenic non-human animal, e.g., transgenic mouse, is an animal in which at least one endogenous immunoglobulin locus has been at least in part replaced by a human immunoglobulin gene locus. In some embodiments, the transgenic animal is fully reconstituted with human immunoglobulin loci, and, optionally, the endogenous immunoglobulin loci are functionally inactivated, e.g., through targeted deletion, insertion, etc., making it possible to generate fully human antibodies in such animals. Such transgenic mice have been generated by introducing yeast artificial chromosomes (YACs) containing human heavy-chain and κ and λ light-chain immunoglobulin genes, into mice whose endogenous heavy-chain and κ loci were functionally inactivated by targeted deletion. See, e.g., Jakobovits, A., et al., "From XenoMouse technology to panitumumab, the first fully human antibody product from transgenic mice." Nature Biotechnology 25, 1134-1143 (2007), and references therein for further details. It will be appreciated that a variety of other approaches could have been used to generate such mice or mice having similar properties.

The invention also contemplates transgenic plants having genetic modifications as described herein for animals (e.g., such plants may have at least part of an immunoglobulin gene inserted into their genome). It will be understood that appropriate modifications may be made to achieve expression in plants.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term acyl as used herein refers to a moiety that includes a carbonyl group or a group having the general formula —C(=O)R, where R is alkyl, alkenyl, alkynyl, aryl, carbocyclic, heterocyclic, or aromatic heterocyclic. An example of an acyl group is acetyl.

The term aliphatic, as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The term alkyl as used herein refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-12 carbon atoms. In another embodiment, the alkyl group employed contains 1-8 carbon atoms. In still other embodiments, the alkyl group contains 1-6 carbon atoms. In yet another embodiment, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents.

In general, the terms aryl and heteroaryl, as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, aryl refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term heteroaryl, as used herein, refers to a cyclic aromatic radical having from five to ten ring atoms of which one ring atom is selected from the group consisting of S, O, and N; zero, one, or two ring atoms are additional heteroatoms independently selected from the group consisting of S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term carboxylic acid as used herein refers to a group of formula —CO$_2$H.

The terms halo and halogen as used herein refer to an atom selected from the group consisting of fluorine, chlorine, bromine, and iodine.

The term heteroaliphatic, as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term heterocyclic, as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from the group consisting of oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from the group consisting of O, S, and N (wherein the nitrogen and sulfur heteroatoms may be optionally oxidized), including, but not limited to, a bi- or tri-cyclic group, comprising fused six-membered rings having between one and three heteroatoms independently selected from the group consisting of the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term aromatic heterocyclic, as used herein, refers to a cyclic aromatic radical having from five to ten ring atoms of which one ring atom is selected from the group consisting of sulfur, oxygen, and nitrogen; zero, one, or two ring atoms are additional heteroatoms independently selected from the group consisting of sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl) piperazine, 4-(2,4-dimethoxyphenyl) piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl) piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3, 4-tetrahydroisoquinoline, 1,2,3,4-tetrahydroquinoline, azacyclooctane, decahydroquinoline, piperazine, piperidine, pyrrolidine, thiomorpholine, and triazole.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The term arylalkyl refers to alkyl groups in which a hydrogen atom has been replaced with an aryl group. Such groups include, without limitation, benzyl, cinnamyl, and dihyrocinnamyl.

The term heteroatom means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term unsaturated, as used herein, means that a moiety has one or more units of unsaturation.

As used herein, the term partially unsaturated refers to a ring moiety that includes at least one double or triple bond. The term "partially unsaturated" is intended to encompass rings having multiple sites of unsaturation, but is not intended to include aryl or heteroaryl moieties, as herein defined.

Additionally, unless otherwise stated, structures depicted herein are also meant to include compounds that differ only in the presence of one or more isotopically enriched positions of the compound. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably nontoxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

"Polypeptide", "peptide", or "protein": According to the present invention, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Carbohydrate": The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

"Polysaccharide", "carbohydrate" or "oligosaccharide": The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least two sugars. The polymer may include natural sugars (e.g., glucose, fructose, galactose, mannose, arabinose, ribose, and xylose) and/or modified sugars (e.g., 2'-fluororibose, 2'-deoxyribose, and hexose). "Sugar alcohols" include glycerol (glycertil, propane-1,2,3-triol), erythritol, threitol, ribitol (adonitol), arabinitol, xylitol, allitol, altritol, galactitol, glucitol (sorbitol), mannitol, or iditol.

As used herein, the phrase "natural amino acid side-chain" refers to the side-chain group of any of the 20 amino acids naturally occurring in proteins. Such natural amino acids include the nonpolar, or hydrophobic amino acids, glycine, alanine, valine, leucine, isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the phrase "unnatural amino acid side-chain" refers to the side-chain group of amino acids not included in the list of 20 amino acids naturally occurring in proteins, as described above. Such amino acids include the D-isomer of any of the 20 naturally occurring amino acids. Unnatural amino acids also include homoserine, ornithine, norleucine, and thyroxine. Other unnatural amino acids side-chains are well known to one of ordinary skill in the art and include unnatural aliphatic side chains. Other unnatural amino acids include modified amino acids, including those that are N-alkylated, cyclized, phosphorylated, acetylated, amidated, azidylated, labelled, and the like. In some embodiments, an unnatural amino acid is a D-isomer. In some embodiments, an unnatural amino acid is a L-isomer.

"Small molecule": As used herein, the term "small molecule" is used to refer to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, heterocyclic rings, etc.). In some embodiments, small molecules are monomeric and have a molecular weight of less than about 1500 g/mol. In certain embodiments, the molecular weight of the small molecule is less than about 1000 g/mol or less than about 500 g/mol. Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention.

"Polynucleotide" is used herein consistently with usage in the art and is used interchangeably with "nucleic acid" or "oligonucleotide", with "oligonucleotide" typically being used to refer to short (e.g, 50 residues or less) polynucleotides. The polynucleotide may include natural nucleosides found in RNA and/or DNA, nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), and/or nucleosides comprising chemically or biologically modified bases, (e.g., methylated bases) and/or modified sugars (e.g., 2'-fluororibose, ribose, 2'-deoxyribose, arabinose, and hexose). Polynucleotides containing modified backbones (relative to those found in RNA or DNA) or non-naturally occurring internucleoside linkages can also be used in the present invention. A polynucleotide may be single-stranded or double-stranded. It should be noted that where the present invention discloses a single-stranded polynucleotide, the perfect complement of the polynucleotide, and a double-stranded polynucleotide comprising both the single-stranded polynucleotide and its perfect complement, are also disclosed. Polynucleotide sequences are listed in a 5' to 3' direction unless otherwise indicated.

As used herein, the term "tag" refers to a moiety appended to another entity that imparts a characteristic or property otherwise not present in the un-tagged entity. In some embodiments, the tag is an affinity tag, an epitope tag, a fluorescent tag, etc. Examples of fluorescent tags include GFP and other fluorescent proteins mentioned above. Affinity tags can facilitate the purification or solubilization of fusion proteins. Examples of affinity tags include maltose binding protein (MBP), glutathione-S-transferase (GST), thioredoxin, polyhistidine (also known as hexa histidine, 6×His, and by the trademarked name HIS-TAG®), etc. Examples of epitope tags, which facilitate recognition by antibodies, include c-myc, FLAG (FLAG octapeptides), HA (hemagglutinin), etc.

As used herein, the term "catalyst" refers to a substance the presence of which increases the rate and/or extent of a chemical reaction, while not being consumed or undergoing a permanent chemical change itself.

The terms "label" and "labeling moiety" entity refer to agents that can be visualized, for example following binding to another entity. The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionuclides, fluorophores, chemiluminescent agents, microparticles, enzymes, colorimetric labels, magnetic labels, haptens, Molecular Beacons, aptamer beacons, and the like.

As used herein and in the claims, the singular forms "a", "an", and "the" include the plural reference unless the context clearly indicates otherwise. Thus, for example, a reference to "a compound" includes a plurality of such compounds.

It will be understood that wherein the claims or description use the word "is" (e.g., as in "$A^1$ is xxx" or "recognition motif is xxx"), the invention encompasses embodiments where $A^1$ (or recognition motif) "comprises xxx" and embodiments in which $A^1$ (or recognition motif) "consists of xxx".

As used herein, the term "isolated" often refers to having a specific activity of at least tenfold greater than the sortase-transamidase activity present in a crude extract, lysate, or other state from which proteins have not been removed and also in substantial isolation from proteins found in association with sortase-transamidase in the cell. An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the term "substantially free" refers to preparing a target polypeptide having less than about 30%, 20%, 10% and sometimes 5% (by dry weight), of non-target polypeptide (also referred to herein as a "contaminating protein"), or of chemical precursors or non-target chemicals. When the target polypeptide or a biologically active portion thereof is recombinantly produced, it also often is substantially free of culture medium, where culture medium represents less than about 20%, sometimes less than about 10%, and often less than about 5% of the volume of the polypeptide preparation. In certain embodiments, isolated or purified target polypeptide preparations are 0.01 milligrams or more. In certain embodiments, isolated or purified target polypeptide preparations are 0.1 milligrams or more. In certain embodiments, isolated or purified target polypeptide preparations are 1.0 milligrams or more and 10 milligrams or more in dry weight.

Those skilled in the art will recognize, or be able to ascertain using no more than routine experimentation, many equivalents to the specific embodiments of the invention described herein. The scope of the present invention is not intended to be limited to the description or examples herein. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

The invention encompasses all variations, combinations, and permutations in which one or more limitations, elements, clauses, descriptive terms, etc., from one or more of the claims or from the description (including specific details in the experimental section) is introduced into another claim dependent on the same base claim (or, as relevant, any claim) unless otherwise indicated or unless it would be evident to one of ordinary skill in the art that a contradiction or inconsistency would arise. Where lists or sets of elements are disclosed herein it is to be understood that each subgroup of the elements and each individual element are also disclosed. In general, where the invention, or aspects of the invention, is/are referred to as comprising particular elements, features, etc., certain embodiments of the invention or aspects of the invention consist, or consist essentially of, such elements, features, etc. It should also be understood that any embodiment of the invention can be explicitly excluded from the claims. For example, in some embodiments, a polypepide is not GFP or a derivative thereof.

Where the description or claims recite a method, the invention encompasses inventive compositions used in performing the method, and products produced using the method. Where the description or claims recite a composition, the invention encompasses methods of using the composition and methods of making the composition.

Where ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a list of numerical values is stated herein (whether or not prefaced by "at least"), the invention includes embodiments that relate analogously to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value).

EXEMPLIFICATION

Example 1

Lipid Modification Using Sortase

Overview

Protein-lipid conjugates and methods for their construction are valuable tools for studying the role of post-translational lipid modification in controlling protein function and localization. Lipid attachment also provides a means for manipulating the properties of peptides and proteins that normally do not possess these types of modifications. Highlighting the utility of synthetic lipoproteins, Bertozzi and co-workers recently reported the synthesis of GFP-containing GPI-anchor mimetics as a means for probing the role of individual sugar residues in this complex membrane anchor (1, 2). Numerous reports have also shown that the addition of lipids and fatty acids can endow proteins and peptides with cell-penetrating capabilities (3-7), modulate immunogenicity (8, 9), and provide anchors for incorporation into liposomes (10, 11).

With respect to full-size protein substrates, the attachment of lipids in site-specific fashion remains a significant bioconjugation challenge. Only a relatively limited set of chemical and chemoenzymatic strategies are available for this purpose. These include the use of enzymes such as myristoyl (12, 13) and prenyl (14-16) transferases, wherein the user is limited to the natural substrates of these enzymes or closely related analogues. In the case of chemical labeling, a common strategy is cysteine derivatization through alkylation (17, 18) or disulfide formation (19, 20), an approach that requires site-directed mutagenesis to ensure that protein substrates contain only a single reactive cysteine residue. Among the available strategies for lipid attachment, expressed protein ligation (EPL) (1, 2, 21-25) has proven to be the most versatile. For example, this method has been used to prepare GFP bearing a range of lipid modifications (1, 2, 24) and to generate lipidated Ras (25) and Rab (22) proteins. However, EPL mandates the expression of protein substrates as fusions with large intein domains, a necessity that can reduce protein expression yields and may require careful selection of the intein domain to prevent premature intein cleavage and a corresponding drop in the yield of ligation products (26-29).

With the goal of complementing existing strategies for lipoprotein synthesis, we have developed a general method for the site-specific installation of lipids and fatty acids using sortase-catalyzed transpeptidation (Scheme 1). As mentioned above, sortase A from *Staphylococcus aureus* recognizes a five amino acid sequence (LPXTG (SEQ ID NO: 45)) near the C-terminus of its natural protein targets (39-41). The active site cysteine of sortase cleaves between the threonine and glycine residues of the recognition site to produce a thioester intermediate which is then attacked by the amino terminus of an oligoglycine nucleophile, resulting in the formation of a new amide bond. The method is extremely versatile, stemming from the remarkable tolerance of the enzyme for substituents C-terminal to the oligoglycine unit. Synthetic nucleophiles, containing 1-5 glycine residues, have been decorated with a range of substituents including fluorophores (33, 34) photoaffinity probes (34), peptide nucleic acids (36), polymers (35), solid supports (32, 35, 42) or other polypeptides (33, 38) allowing the site-specific ligation of these moieties to peptide and protein substrates. Here we describe the synthesis of lipid-modified oligoglycine nucleophiles compatible with the sortase-mediated transpeptidation reaction and demonstrate their high-yielding ligation to a protein substrate. Lipoproteins prepared using this procedure were shown to strongly associate with mammalian cells in a lipid tail-dependent fashion and were found to localize to the plasma membrane and endosomes.

Materials and Instrumentation

Chemicals.

Unless otherwise noted, all chemicals were obtained from commercial sources and used without further purification. Rink amide resin (100-200 mesh, 0.7 mmol/g) was obtained from Advanced Chemtech. Fmoc-Gly-OH, Fmoc-Lys(Mtt)-OH, and Fmoc-Trp(Boc)-OH were obtained from EMD Biosciences/Novabiochem. Triglycine peptide was purchased from Sigma (G1377). Water used in biological procedures or as a reaction solvent was purified using a MilliQ purification system (Millipore). DriSolv anhydrous $CH_2Cl_2$ and DriSolv anhydrous MeCN were purchased from EMD Chemicals. Redistilled, anhydrous N,N'-diisopropylethylamine (DIPEA) was obtained from Sigma-Aldrich.

NMR.

$^1H$ and $^{13}C$ spectra were measured with a Bruker AVANCE-400 (400 MHz) spectrometer at the MIT Department of Chemistry Instrumentation Facility. H NMR chemical shifts are reported as δ in units of parts per million (ppm) relative to chloroform-d (δ 7.24, singlet). Multiplicities are reported as follows: s (singlet), d (doublet), or m (multiplet). Coupling constants are reported as a J value in Hertz (Hz). The number of protons (n) for a given resonance is indicated as nH, and is based on spectral integration values. $^{13}C$ NMR chemical shifts are reported as δ in units of parts per million (ppm) relative to chloroform-d (δ 77.23, triplet).

Mass Spectrometry.

Electrospray Ionization (ESI) mass spectra were obtained at the MIT Department of Chemistry Instrumentation Facility. Matrix assisted laser desorption-ionization time-of-flight mass spectrometry (MALDI-TOF MS) was performed on a MALDI micro MX™ system (Micromass® MS Technologies, USA). Samples were co-crystallized using a sinapinic acid solution (10 mg/mL in 70:30 MeCN:$H_2O$ with 0.1% TFA). LC-ESI-MS analysis was performed using a Micromass LCT mass spectrometer (Micromass® MS Technologies, USA) and a Paradigm MG4 HPLC system equipped with a HTC PAL autosampler (Michrom BioResources, USA) and a Waters Symmetry 5 µm C8 column (2.1×50 mm, MeCN:$H_2O$ (0.1% formic acid) gradient mobile phase, 150 µL/min).

HPLC/FPLC.

HPLC purifications were achieved using an Agilent 1100 Series HPLC system equipped with a Waters Delta Pak 5 µm, 100 Å C4 column (3.9×150 mm, MeCN:$H_2O$ gradient mobile phase containing 0.1% trifluoroacetic acid, 1 mL/min), a Waters Delta Pak 15 µm, 100 Å C18 column (7.8×300 mm, 2-propanol:$H_2O$ gradient mobile phase, 2 mL/min), or a Waters Cosmosil 5PE column (8×250 mm, 2propanol:$H_2O$ gradient mobile phase, 1 mL/min) as indicated below. Size exclusion chromatography was performed on a Pharmacia AKTA Purifier system equipped with a HiLoad 16/60 Superdex 75 column (Amersham).

UV-Vis Spectrocopy.

UV-Vis spectroscopy was performed on a Nanodrop ND-1000 spectrophotometer (Thermo Scientific, USA).

Flow Cytometry.

Flow cytometry was performed on a LSR-II system (BD Biosciences).

Spinning Disc Confocal Microscopy.

Fluorescence microscopy was performed on a Nikon spinning disc confocal microscope with MetaMorph 7 software. Multidimensional acquisition was used to collect images in the 488, 647, and phase contrast channels from the same focal plane.

Design, Synthesis, and Characterization of Lipid-Modified Triglycine Nucleophiles Most nucleophiles compatible with sortase-mediated transpeptidation that have been identified to date have the simple structural requirement of a stretch of glycine residues with a free amino terminus. While successful transpeptidation has been reported with nucleophiles containing anywhere from one to five glycines, maximum reaction rates are obtained when two or more glycines are present.(32, 38). It should be noted that primary alkylamines have been shown to participate in the transpeptidation reaction, (31, 35) though in general these appeared to be less efficient than oligoglycine derivatives. With these considerations in mind, we synthesized a panel of lipid-modified triglycine nucleophiles using solid-phase synthesis (Scheme 2).

Figure 11A:
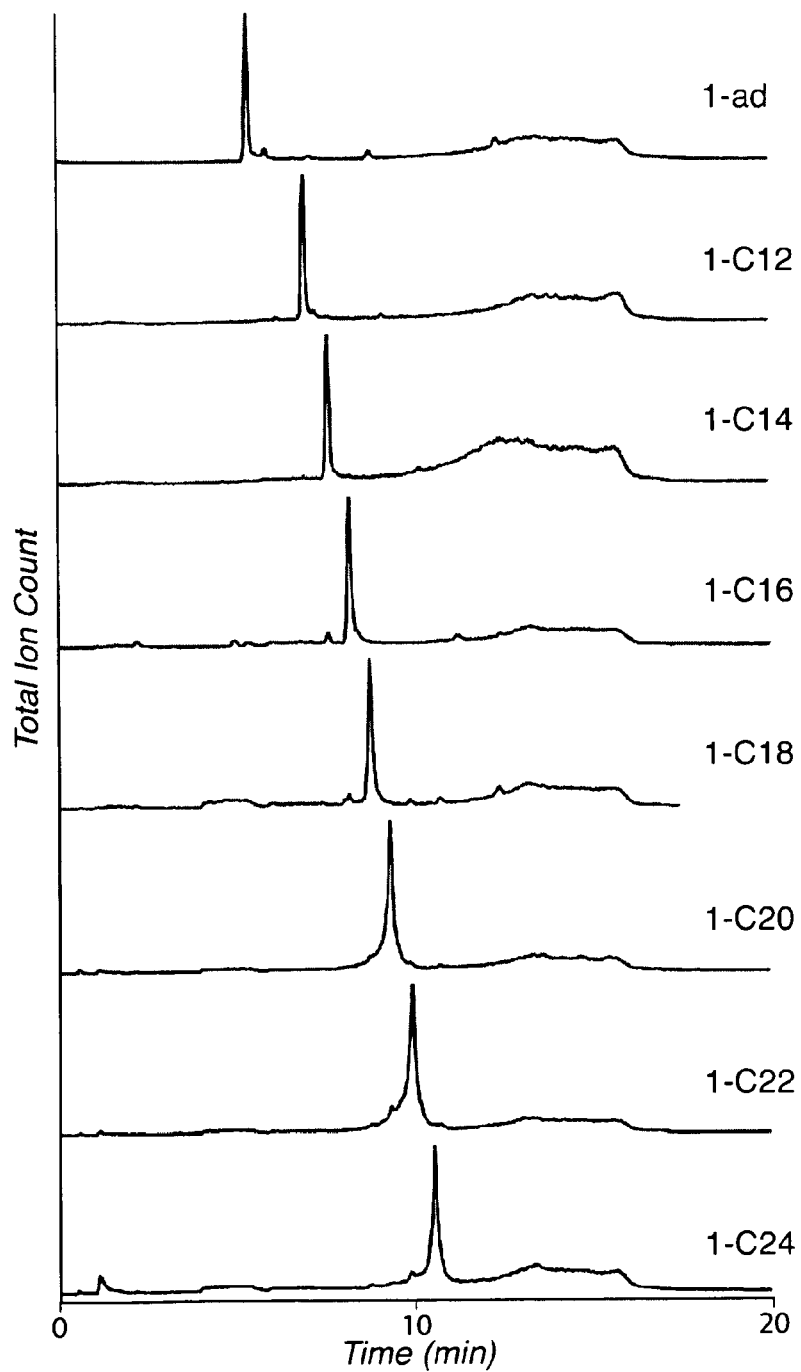
FIG. 11. Characterization of lipidated triglycine nucleophiles. (a) LC-ESI-MS total ion current chromatogram for lipidated triglycine nucleophiles. (b) RP-HPLC chromatogram (280 nm) for purified 2-chol. (c) ESI-MS data for lipidated triglycine nucleophiles.
Figures 11B, 11C:
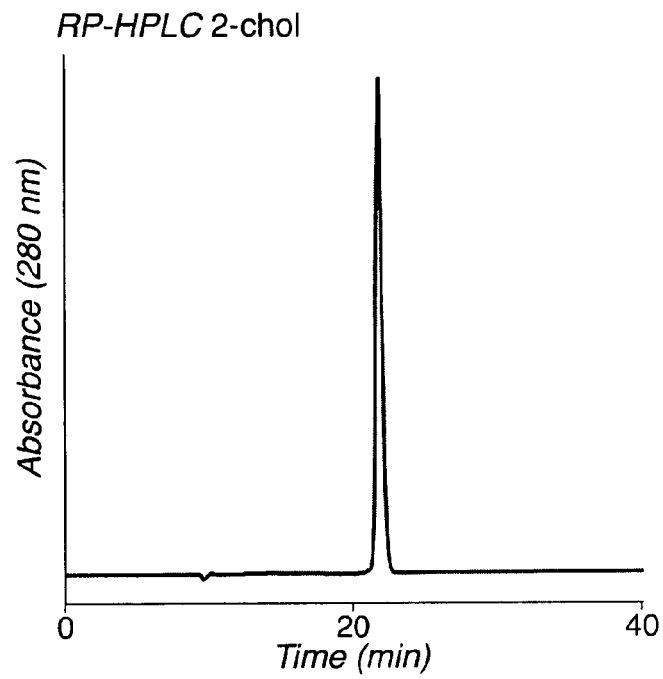

Resin-bound precursor 1 was prepared on Rink amide resin using standard Fmoc chemistry. An orthogonally protected lysine residue was incorporated to allow selective liberation and subsequent acylation of the ε-amino group. Following removal of the 4-methyltrityl (Mtt) group, the lysine side chain was acylated with a range of hydrophobic carboxylic acids, including naturally occurring post-translational modifications such as myristic (1-C14) and palmitic (1-C16) acid, as well as modifications not found in eukaryotic cells (1-ad). The couplings of C18, C20, C22, and C24 acids were performed at 50° C. to maintain the solubility of all the reaction components. Following Fmoc deprotection and resin cleavage, the identity of nucleophiles derived from 1 was confirmed by LC-ESI-MS (FIG. 11, and see below). All peptides were obtained with good purity and did not require extensive purification prior to transpeptidation.

In addition to purely aliphatic substituents, we also prepared a cholesterol-modified triglycine nucleophile (2-chol, Scheme 2). Peptide 2 was prepared on Rink amide resin and then cleaved from the solid support, leaving the N-terminal Fmoc group intact. A tryptophan residue was included in this peptide as a UV-active chromophore to aid in purification by HPLC. Peptide 2 was then reacted with cholesterol NHS-carbonate 3, followed by the addition of piperidine to remove the Fmoc group. The crude material was then purified by RP-HPLC to yield 2-chol in 22% yield.

Further details regarding synthesis and characterization of the lipidated triglycine nucleophiles are as follows:

Resin-Bound Intermediate 1.

A glass solid-phase reaction vessel containing a fritted glass filter and a Teflon stopcock was loaded with Rink amide resin (1.0 g, 0.70 mmol). The resin was first washed/swollen extensively with N-methyl-2-pyrrolidone (NMP) by gentle agitation with a wrist action shaker. The Fmoc protecting group was then removed by treatment with ~30 mL of 80:20 NMP/piperidine for 20 min at RT. The resin was washed with ~30 mL of NMP (3×, 3-5 min per wash). Amino acid building blocks were then coupled as follows: Fmoc-protected amino acid (1.75 mmol, 2.5 equivalents relative to initial resin loading), benzotriazole-1-yl-oxy-tris-pyrrolidino-phosphonium hexafluorophosphate (PyBOP) (911 mg, 1.75 mmol), N-hydroxybenzotriazole (HOBt) (236 mg, 1.75 mmol), and N,N'-diisopropylethylamine (DIPEA) (914 µL, 5.25 mmol) were dissolved in NMP to a final volume of 8.75 mL (200 mM final concentration of amino acid building block). This solution was mixed until all reagents had dissolved, and then added to the deprotected Rink amide resin. Couplings were incubated for 16-48 h at RT. The resin was then washed with ~30 mL of NMP (3×, 3-5 min per wash). The extent of coupling was assessed by Kaiser test. In the event that the coupling was incomplete, the above procedure was repeated. Fmoc removal was then achieved by exposing the resin to ~30 mL of 80:20 NMP/piperidine for 20 min at RT, followed by additional washing with ~30 mL of NMP (3×, 3-5 min per wash). Cycles of amino acid coupling and Fmoc deprotection were then repeated to complete the synthesis of 1. The resin was then washed with ~30 mL of $CH_2Cl_2$ (5×, 3-5 min per wash) and dried.

1-ad, 1-C12, and 1-C14 (General Procedure).

A 3.0 mL fritted polypropylene syringe equipped with a capped hypodermic needle was loaded with dry resin 1 (50 mg). The resin was washed with 2.5 mL of $CH_2Cl_2$ (3×, 3-5 min per wash). Next, the 4methyltrityl (Mtt) protecting group was removed by treatment with 2.5 mL of 94:5:1 $CH_2Cl_2$/TIPS/TFA at RT (5×, 5 min each) followed by washing with 2.5 mL of NMP (3×, 3-5 min per wash). The resin was then treated with a solution of the appropriate carboxylic acid ($R_1$—COOH, 0.12 mmol), PyBOP (65 mg, 0.12 mmol), HOBt (16 mg, 0.12 mmol), and DIPEA (65 µL, 0.38 mmol) in 1.0 mL of NMP. The reaction was incubated at RT for 21 h followed by washing with 2.5 mL of NMP (3×, 3-5 min per wash). Fmoc removal was achieved by treatment with 2.5 mL of 80:20 NMP/piperidine for 20 min at RT followed by washing with 2.5 mL of NMP (3×, 3-5 min per wash) and 2.5 mL of $CH_2Cl_2$ (3×, 3-5 min per wash). The peptide was cleaved from the resin with 2.5 mL of 95:3:2 TFA/TIPS/$H_2O$ (4×, ~30 min each) and the combined cleavage solutions were concentrated in vacuo. 1-ad was then precipitated from ether and dried under vacuum. Crude 1-C12 and crude 1-C14 were washed with hexanes (1 mL, 2×) and then dried under vacuum. The identity of all peptides was confirmed by LC-ESI-MS analysis (FIG. 11). Peptides were used without further purification and the yield was not determined.

1-C16.

A 3.0 mL fritted polypropylene syringe equipped with a capped hypodermic needle was loaded with dry resin 1 (200 mg). The resin was washed with 2.5 mL of $CH_2Cl_2$ (3×, 3-5 min per wash). Next, the 4-methyltrityl (Mtt) protecting group was removed by treatment with 2.5 mL of 94:5:1 $CH_2Cl_2$/TIPS/TFA at RT (5×, 5 min each). The resin was then washed with 2.5 mL of NMP (3×, 3-5 min per wash). The resin was then treated with a solution of palmitic acid (103 mg, 0.40 mmol), PyBOP (208 mg, 0.40 mmol), HOBt (54 mg, 0.4 mmol), and DIPEA (207 µL, 1.2 mmol) in 1.6 mL of NMP. The reaction was incubated at RT overnight. The resin was then washed with 2.5 mL of NMP (3×, 3-5 min per wash). Fmoc removal was achieved by treatment with 2.5 mL of 80:20 NMP/piperidine for 20 min at RT followed by washing with 2.5 mL of NMP (3×, 3-5 min per wash) and 2.5 mL of $CH_2Cl_2$ (3×, 3-5 min per wash). The peptide was cleaved from the resin with 2.5 mL of 95:3:2 TFA/TIPS/$H_2O$ (4×, ~30 min each) and the combined cleavage solutions were dried under vacuum. The identity of 1-C16 was confirmed by LC-ESI-MS analysis (FIG. 11). This material was used without further purification and yield was not determined.

1-C18, 1-C20, 1-C22, and 1-C24 (General Procedure).

A 3.0 mL fritted polypropylene syringe equipped with a capped hypodermic needle was loaded with dry resin 1 (50 mg). The resin was washed with 2.5 mL of $CH_2Cl_2$ (3×, 3-5 min per wash). Next, the 4-methyltrityl (Mtt) protecting group was removed by treatment with 2.5 mL of 94:5:1 $CH_2Cl_2$/TIPS/TFA at RT (5×, 5 min each) followed by washing with 2.5 mL of NMP (3×, 3-5 min per wash). The resin was then carefully transferred to a 1.5 mL microcentrifuge tube. The resin was treated with a solution of the appropriate carboxylic acid (R2-COOH, 0.12 mmol), PyBOP (65 mg, 0.12 mmol), HOBt (16 mg, 0.12 mmol), and DIPEA (65 µL, 0.38 mmol) in 1.0 mL of NMP. The reaction was incubated at 50° C. for 5 h. The reaction was then centrifuged, and 0.5 mL of the supernatant was discarded. An additional 0.5 mL of NMP was then added followed again by centrifugation and removal of 0.5 mL of the supernatant. This process was repeated two additional times. The resin slurry was carefully transferred to a 3.0 mL fritted polypropylene syringe equipped with a capped hypodermic needle and washed with 2.5 mL of NMP (3×, 3-5 min per wash). Fmoc removal was achieved by treatment with 2.5 mL of 80:20 NMP/piperidine for 20 min at RT followed by washing with 2.5 mL of NMP (3×, 3-5 min per wash) and 2.5 mL of $CH_2Cl_2$ (3×, 3-5 min per wash). The peptide was cleaved from the resin with 2.5 mL of 95:3:2 TFA/TIPS/$H_2O$ (3×, ~30 min each) and the combined cleavage solutions were concentrated in vacuo. 1-C18, 1-C20, 1-C22, and 1-C24 were precipitated from cold ether and dried under vacuum. The identity of all peptides was confirmed by LC-ESIMS analysis (FIG. 11). Peptides were used without further purification and yield was not determined.

Cholesterol NHS-Carbonate (3).

An oven dried round bottom flask equipped with an argon inlet was charged with cholesterol (500 mg, 1.29 mmol) and N,N'-disuccinimidyl carbonate (DSC) (665 mg, 2.59 mmol) in 15 mL of 1:1:1 $CH_2Cl_2$/MeCN/DIPEA (all anhydrous). The reaction was stirred at RT for 24 h. The reaction mixture was then partitioned between brine and $CH_2Cl_2$. The aqueous layer was extracted two additional times with $CH_2Cl_2$. The combined organic layers were then dried over $MgSO_4$, filtered, and concentrated. The remaining residue was then purified by flash chromatography (95:5 $CH_2Cl_2$/EtOAc) to yield 3 as a white solid (274 mg, 40%). $^1$H NMR (400 MHz, $CDCl_3$): δ, 5.39 (d, 1H, J=4.4 Hz), 4.57 (m, 1H), 2.81 (s, 4H), 2.46 (m, 2H), 2.05-0.80 (m, 26H), 1.00 (s, 3H), 0.89 (d, 3H, J=6.4 Hz), 0.84 (d, 3H, J=6.4 Hz), 0.83 (d, 3H, J=6.8 Hz), 0.65 (s, 3H). $^{13}$C NMR (100 MHz, $CDCl_3$): δ, 169.0, 151.0, 138.7, 123.9, 82.4, 56.8, 56.3, 50.1, 42.5, 39.9, 39.7, 37.8, 36.9, 36.7, 36.4, 36.0, 32.1, 32.0, 28.4, 28.2, 27.6, 25.7, 24.5, 24.0, 23.0, 22.8, 21.2, 19.4, 18.9, 12.0. HRMS (ESI+) calculated for $C_{32}H_{49}NO_5Na$ ([M+Na]$^+$) 550.3503. found 550.3383.

Fmoc-Gly-Gly-Gly-Trp-Lys-CONH$_2$ (2).

Intermediate 2 was synthesized on Rink amide resin following the procedure described above for the preparation of 1. Peptide 2 was cleaved from the resin with 95:3:2 TFA/TIPS/H$_2$O (3×, ~30 min each). The combined cleavage solutions were concentrated and 2 was precipitated from ether and dried. The identity of 2 was confirmed by LC-ESI-MS. Yield not determined. LRMS (ESI+) calculated for C$_{38}$H$_{45}$N$_8$O$_7$ ([M+H]$^+$) 725.3. found 725.4.

2-chol.

To a 1.5 mL microcentrifuge tube was added 3 (10.5 mg dissolved in 50 µL of CHCl$_3$, 19.9 µmol), 2 (7.2 mg dissolved in 50 µL of NMP, 9.9 µmol), and anhydrous DIPEA (5.00 µL, 28.7 µmol). After overnight incubation at RT, piperidine (25 µL) was added and the reaction was incubated for an additional 2 h at RT. The reaction was then diluted with 0.5 mL of 2-propanol and fractionated by RP-HPLC [semi-preparative C18 column, 2-propanol:H$_2$O gradient mobile phase, 2 mL/min, 50% 2-propanol→90% 2-propanol (0-20 min)]. Fractions containing 2-chol were pooled, concentrated, and further purified by RP-HPLC [semi-preparative PE column, 2-propanol:H$_2$O gradient mobile phase, 1 mL/min, 50% 2-propanol→90% 2-propanol (0-20 min)] to yield 2-chol (2 mg, 22%). The identity of 2-chol was confirmed by LC-ESI-MS (FIG. 11).

Sortase-Mediated Ligation of Triglycine Nucleophiles to a Protein Substrate

With a series of lipidated nucleophiles in hand, we proceeded to explore their coupling to a protein substrate using sortase. A model protein consisting of eGFP equipped with a C-terminal LPETG (SEQ ID NO: 55) sequence followed by a His$_6$ (SEQ ID NO: 174) affinity handle was expressed and purified from *Escherichia coli*. Recombinant sortase A containing an N-terminal His$_6$ (SEQ ID NO: 174) tag was produced as described (40). At the outset of these studies, we decided to incorporate a procedure for removing the sortase enzyme after the reaction, similar to a purification scheme proposed by Parthasarathy et al. (35) but with important improvements. The configuration of His$_6$ (SEQ ID NO: 174) tags on both sortase and the eGFP substrate provided a simple means for doing so, where Ni-NTA resin was added following transpeptidation to retrieve the sortase enzyme as well as any unreacted eGFP-LPETG-His$_6$ (SEQ ID NO: 157). In this scenario, the transpeptidation product should no longer be His$_6$ (SEQ ID NO: 174)-tagged because residues C-terminal to the LPETG (SEQ ID NO: 55) motif are lost in the course of transpeptidation, and thus this material will not be bound by Ni-NTA.

eGFP-LPETG-His$_6$ (SEQ ID NO: 157) cloning and expression were performed as follows: The gene encoding eGFP was PCR amplified from the commercially available pEGFP-N1 plasmid (Clontech) using forward primer 5'-CGCGCGCCATGGTGAGCAAGGGCGAGGAG-3' (SEQ ID NO: 158) and reverse primer 5' CGCGCGGATCCGACCAGTTTCAGGAAGCTTGTA-CAGCTCGTCCATGCCG-3' (SEQ ID NO: 159). The PCR product was digested with NcoI and BamHI and ligated into pET28a+ (Novagen). This plasmid was then transformed into *E. coli* BL-21. In a typical experiment, cells were grown in two 2 L batches of sterile LB containing kanamycin (30 µg/mL) to an optical density of ~0.6-0.9 at 600 nm. Cells were induced with IPTG (1 mM) for 3 h at 37° C. Cells were harvested by centrifugation and the pellet was stored overnight at −20° C. The pellet was thawed and resuspended in 60 mL of 10 mM Tris pH 8.0, 100 mM phosphate, 300 mM NaCl, and 20 mM imidazole containing a protease inhibitor cocktail (complete mini tablet, EDTA-free, Roche) and treated with 240 µL of DNAse I (10 mg/mL in PBS), 480 µL of lysozyme (50 mg/mL in PBS), and 60 µL of MgCl$_2$ (1 M in PBS). The lysis reaction was incubated for 1 h at 4° C. The cells were then sonicated and centrifuged to remove insoluble material. The pellet was then treated with an additional 20 mL of 10 mM Tris pH 8.0, 100 mM phosphate, 300 mM NaCl, and 20 mM imidazole, briefly sonicated, and centrifuged. The combined supernatants were applied to a Ni-NTA column consisting of 7.5 mL of commercial Ni-NTA slurry (Qiagen) equilibrated with 10 mM Tris pH 8.0, 100 mM phosphate, 300 mM NaCl, and 20 mM imidazole. The column was washed with three 45 mL portion of 10 mM Tris pH 8.0, 100 mM phosphate, 300 mM NaCl, and 20 mM imidazole. eGFP-LPETG-His$_6$ (SEQ ID NO: 157) was eluted with ~10 mL of 10 mM Tris pH 8.0, 100 mM phosphate, 300 mM NaCl, and 300 mM imidazole. This material was concentrated and further purified by size exclusion chromatography on a HiLoad 16/60 Superdex 75 column (Amersham), eluting with 20 mM Tris pH 8.0, 150 mM NaCl at a flow rate of 1 mL/min. Fractions containing eGFP-LPETG-His$_6$ (SEQ ID NO: 157) were pooled, concentrated, and stored at −80° C.

Immediately prior to sortase-catalyzed transpeptidation, the eGFP-LPETG-His$_6$ (SEQ ID NO: 157) stock was thawed and again purified by affinity chromatography over commercial Ni-NTA resin. After binding eGFP-LPETG-His$_6$ (SEQ ID NO: 157) to the resin, the column was washed with three portions of 20 mM Tris pH 8.0, 150 mM NaCl, and 20 mM imidazole. The protein was eluted with 20 mM Tris pH 8.0, 150 mM NaCl, and 300 mM imidazole. This material was buffer exchanged into 20 mM Tris pH 8.0, 150 mM NaCl using a NAP™ 5 Sephadex™ column (GE Healthcare) and concentrated. The concentration was estimated by UV-Vis spectroscopy using the absorbance of eGFP at 488 nm (extinction coefficient 55,900 M$^{-1}$ cm$^{-1}$) (43).

As shown in FIG. 1a, exposing eGFP-LPETG-His$_6$ (SEQ ID NO: 157) to 150 µM sortase and 2 mM triglycine (GGG) in Tris buffer (pH 7.5) containing 10 mM CaCl$_2$ resulted in the appearance of a lower molecular weight species just below the band corresponding to sortase (lane 2). Excess sortase was used to drive the reaction to completion in a reasonable time frame. Near-quantitative conversion of the input eGFP-LPETG-His$_6$ (SEQ ID NO: 157) protein (lane 1) was observed over the course of a 3 h incubation at 37° C. A slurry of Ni-NTA resin containing 1 M NaCl and 40 mM imidazole was then added, and the mixture was incubated for 2 h. In further detail, removal of His$_6$ (SEQ ID NO: 174)-tagged proteins following transpeptidation was achieved with Ni-NTA resin treated in the following way: 500 µL of commercial Ni-NTA resin (Qiagen) was treated with 1 mL of 40 mM Tris pH 8.0, 1 M NaCl, and 40 mM imidazole. The mixture was then centrifuged and the supernatant was removed. This process was repeated two additional times. The resin was then suspended to a final volume of 500 µL with 40 mM Tris pH 8.0, 1 M NaCl, and 40 mM imidazole. This slurry was used to treat samples depicted in FIG. 1a lanes 3-11 and FIG. 2b lanes 3-13. For control experiments (FIG. 2b, lanes 1-2), the above procedure was performed on a separate batch of commercial Ni-NTA resin using 40 mM Tris pH 8.0, 1 M NaCl, and 600 mM imidazole to block binding of His$_6$ (SEQ ID NO: 174)-tagged proteins.

The addition of imidazole and NaCl at the specified concentrations contributed importantly to preventing nonspecific binding of the transpeptidation products. After filtration to remove Ni-NTA, the filtrate was analyzed by SDS-PAGE. A single polypeptide was observed with no evidence for the presence of residual sortase (lane 3). Characterization by ESI-MS confirmed that the protein observed in lane 3 was indeed the desired ligation product (FIG. 12, see below). Also, judging from the intensity of the band in lane 3 as compared to the corresponding eGFP bands in lanes 1 and 2, we were confident that very little material was lost over the course of the two-step transpeptidation/sortase-depletion protocol.

Initial attempts to ligate one of the lipid-modified nucleophiles (1-C22) using the conditions described above yielded only small amounts of the putative transpeptidation product as well as an unidentified higher molecular weight species (FIG. 1a, lane 4). The high molecular weight byproduct may correspond to the acyl enzyme intermediate formed between sortase A and the eGFP substrate. This assignment implies that the affinity of the His6 (SEQ ID NO: 174) tag on the N-terminus of sortase is impaired in the acyl enzyme intermediate because this species is not removed during depletion of His6 (SEQ ID NO: 174)-tagged proteins using Ni-NTA resin. Further characterization of this byproduct was not performed.

Figure 1B:
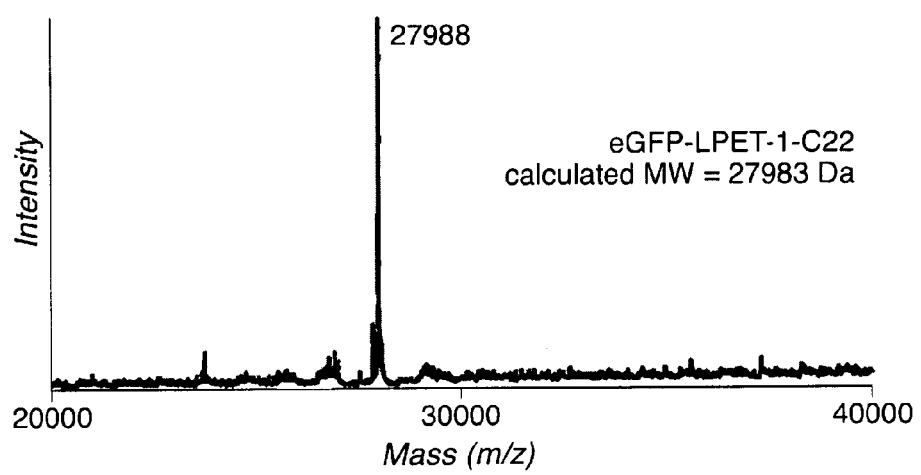

Not surprisingly, the solubility of 1-C22 in aqueous buffer was extremely poor, and we suspected that this may limit the amount of nucleophile available in solution. To improve solubility, we examined the effect of adding mild detergents to the reaction mixture. As shown in FIG. 1a (lane 8), the addition of 1% (w/v) n-dodecyl maltoside afforded a significant increase in the level of transpeptidation product relative to that of the other detergents tested. This material was further characterized by ESI-MS and found to consist exclusively of the desired lipid-modified eGFP derivative (FIG. 1b).

Figure 2A:
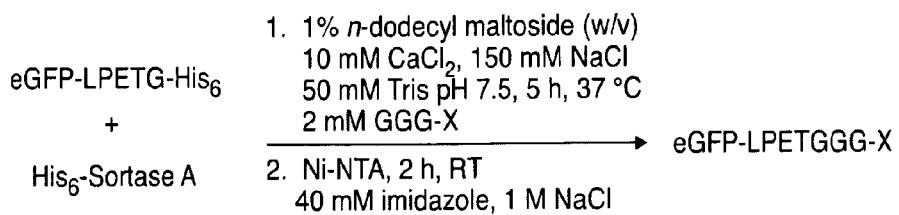
FIG. 2. Lipid attachment through sortase-catalyzed transpeptidation: (a) optimized procedure for lipid coupling followed by removal of His6 (SEQ ID NO: 174)-tagged proteins with Ni-NTA resin, (b) SDS-PAGE analysis of lipid-modified eGFP following transpeptidation and depletion of His6 (SEQ ID NO: 174)-tagged proteins ("Input"=eGFP-LPETG-His$_6$ (SEQ ID NO: 46) in the absence of sortase and nucleophile; the asterisks indicate samples incubated with Ni-NTA resin and 300 mM imidazole to block binding of His$_6$ (SEQ ID NO: 174)-tagged proteins). LPETGGG-X—SEQ ID NO: 179.
Figure 2B:
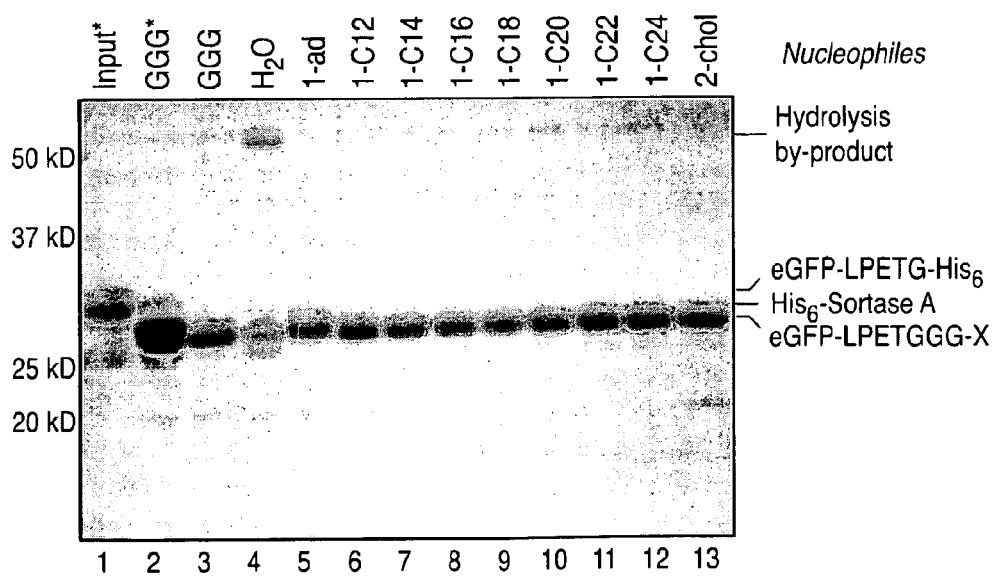
Figure 12A:
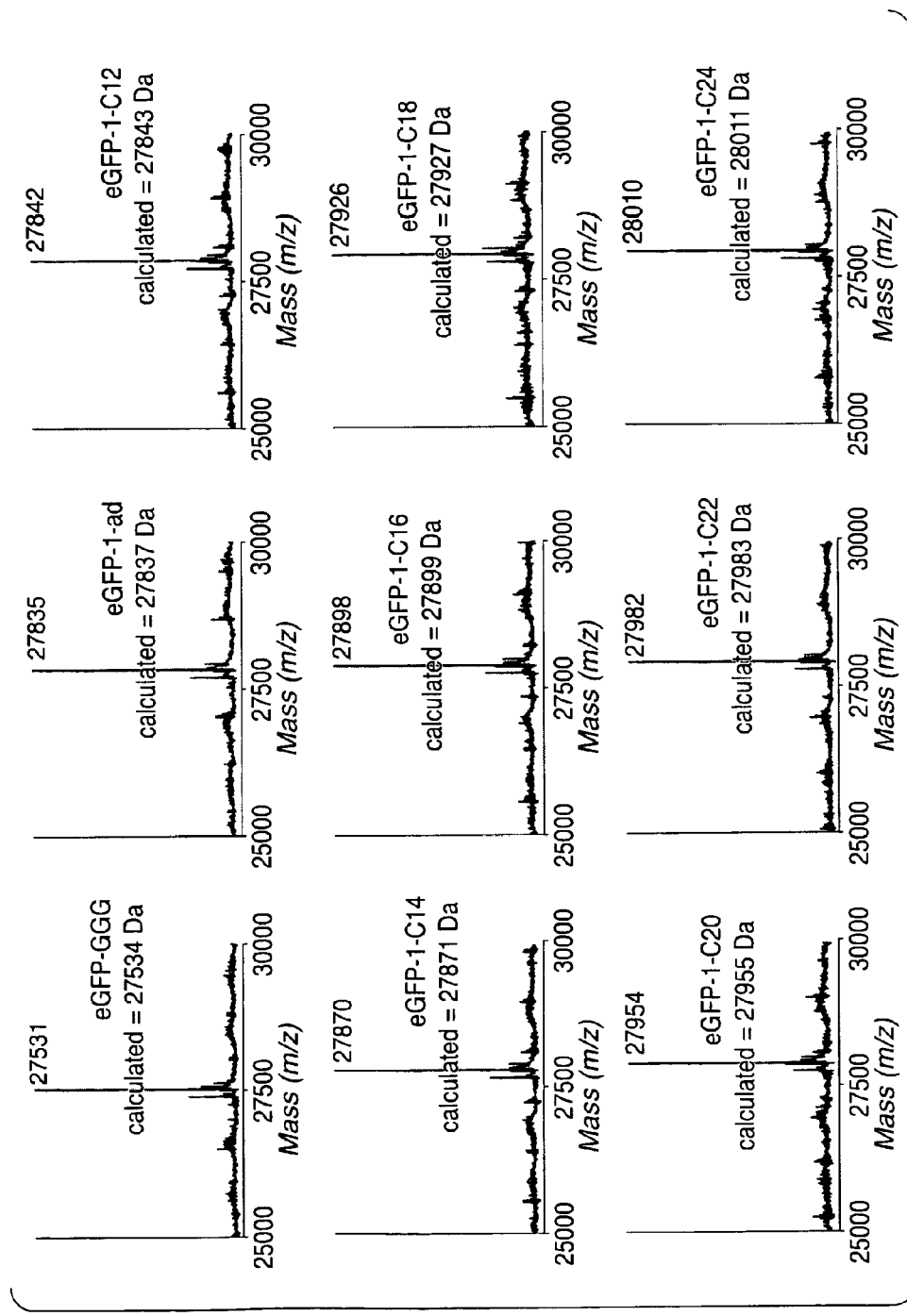
FIG. 12. (a) Reconstructed ESI-MS spectra for modified eGFP. (b) MALDI-TOF MS spectrum of eGFP-2-chol.
Figure 12B:
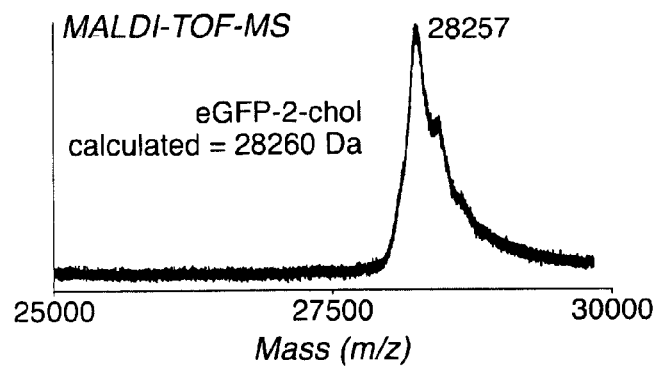
Figure 13:
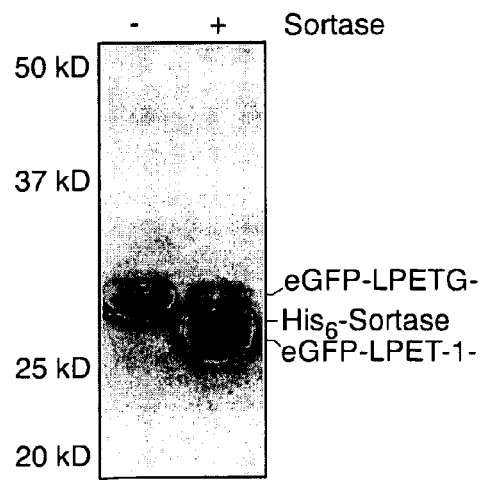
FIG. 13. Negative control experiment demonstrating that the formation of the eGFP-LPETG-1-C22 (SEQ ID NO: 55) transpeptidation product requires sortase. Conditions: 77 µM eGFP-LPETG-His6 (SEQ ID NO: 46), 150 µM sortase A, 2 mM nucleophile, 1% (w/v) n-dodecyl maltoside, 50 mM Tris pH 7.5, 150 mM NaCl, 10 mM CaCl$_2$, 5 h at 37° C. Samples analyzed by SDS PAGE. His6—SEQ ID NO: 174; LPET—SEQ ID NO: 183.
Figure 2:
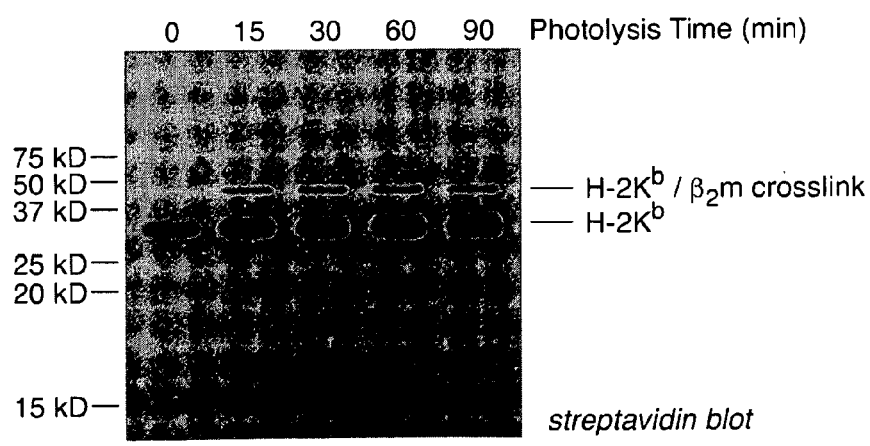
Figure 22:
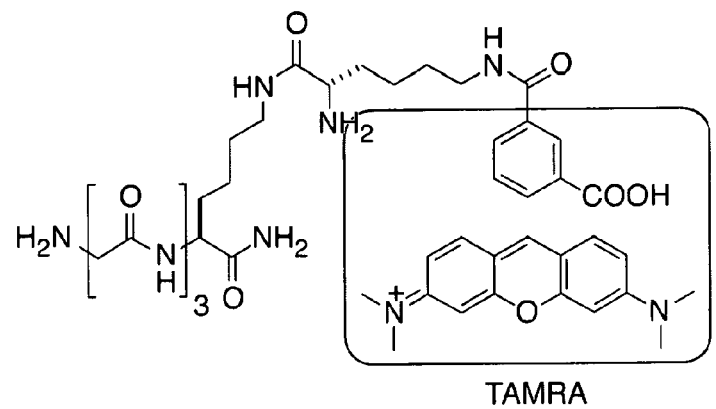
Figure 3:
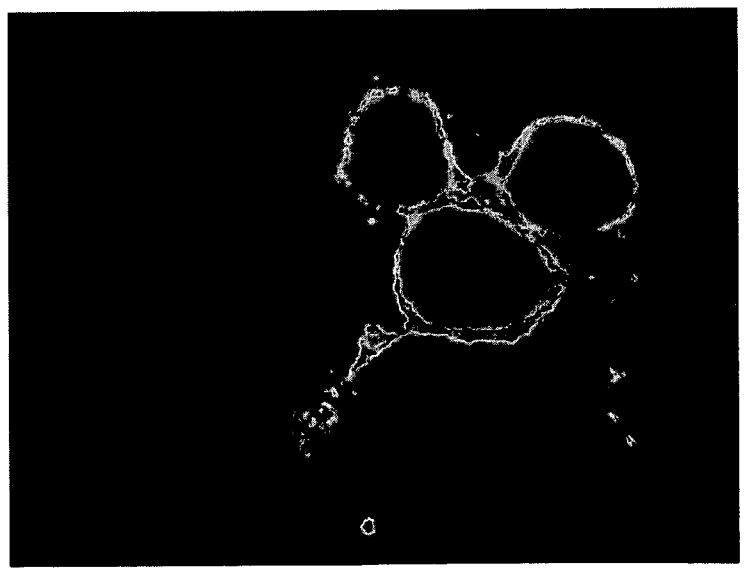
Figure 23:
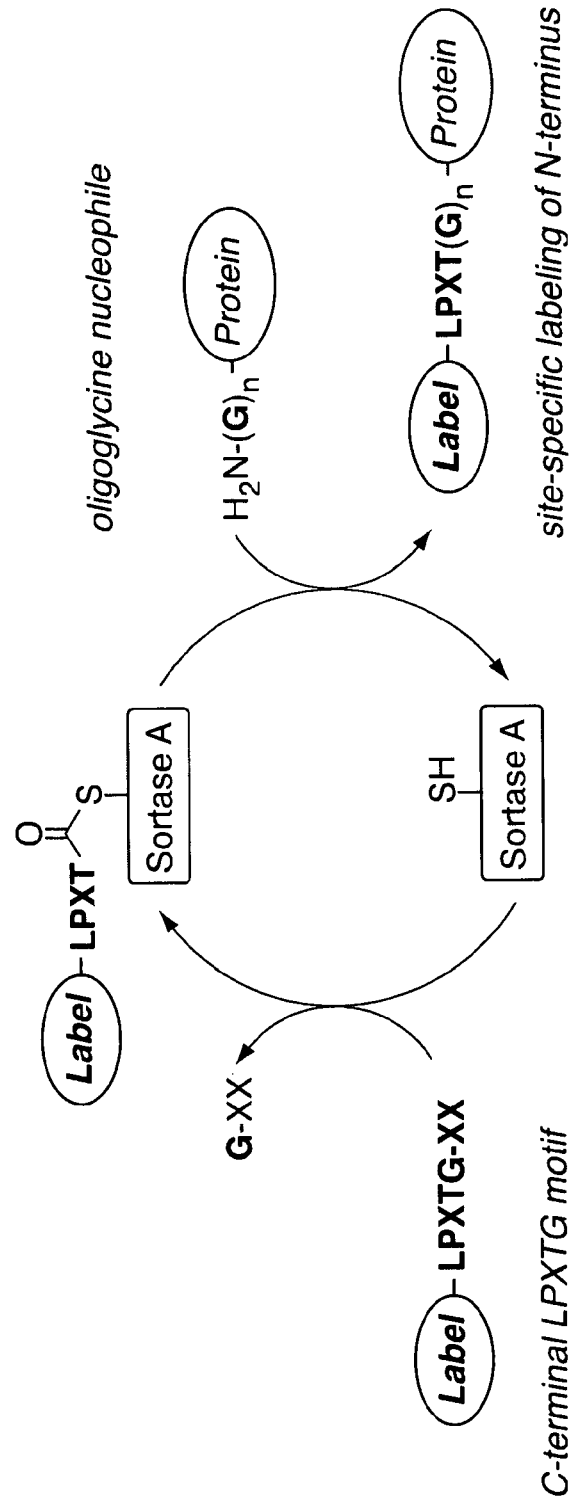
FIG. 23 shows a schematic overview of N-terminal labeling using sortase. LPXTG-XX—SEQ ID NO: 182; LPXTG—SEQ ID NO: 45.

Using 1% (w/v) n-dodecyl maltoside to maintain nucleophile solubility, we were able to successfully ligate the entire panel of lipid-modified triglycine nucleophiles to our eGFP model substrate (FIG. 2). In all cases, a single major protein that migrated at a lower apparent molecular weight than unreacted eGFP-LPETG-His$_6$ (SEQ ID NO: 157) (lane 1) was observed in the filtrate of reactions using lipidated nucleophiles (lanes 5-13). As expected, these samples also showed complete removal of the sortase enzyme. Coupling reactions using only triglycine (lanes 2 and 3) served as positive controls for transpeptidation. A reaction lacking an oligoglycine nucleophile resulted in slow hydrolysis of the acyl enzyme intermediate and the formation of a higher molecular weight byproduct (43) (lane 4). As an additional negative control, we confirmed that the formation of transpeptidation products was dependent on the presence of sortase (FIG. 13). The identity of all eGFP conjugates was ultimately established by mass spectrometry (Table 1 and FIG. 12).

TABLE 1

Mass Spectral Characterization and Yield (%) of eGFP-Lipid Conjugates

| eGFP conjugate | calcd mass (Da) | obsd mass (Da) | yield (%) |
|---|---|---|---|
| eGFP-GGG | 27534 | 27531 | 93 |
| eGFP-1-ad | 27837 | 27835 | 87 |
| eGFP-1-C12 | 27843 | 27842 | 87 |
| eGFP-1-C14 | 27871 | 27870 | 72 |
| eGFP-1-C16 | 27899 | 27898 | 64 |
| eGFP-1-C18 | 27927 | 27926 | 57 |
| eGFP-1-C20 | 27955 | 27954 | 66 |
| eGFP-1-C22 | 27983 | 27982 | 83 |
| eGFP-1-C24 | 28011 | 28010 | 84 |
| eGFP-2-chol | 28260 | 28257 | 87 |

The eGFP chromophore provided a convenient method for quantifying the yield of the eGFP conjugates. By comparing the absorbance at 488 nm of the conjugates relative to the input eGFP-LPETG-His$_6$ (SEQ ID NO: 157) protein, we estimated that the lipid-modified protein conjugates were all obtained in excellent (~60-90%) yield (Table 1 and FIG. 14). A reproducible drop in reaction yield for nucleophiles containing fatty acids of intermediate length (1-C16, 1-C18, 1-C20) was observed. Whether this reflects a drop in the efficiency of the actual transpeptidation reaction or limited solubility of the resulting lipoprotein conjugates, which could contribute to losses during the sortase depletion step, is presently unclear. It should be noted, however, that the purity of these eGFP conjugates, as determined by both SDS-PAGE (FIG. 2) and ESI-MS (FIG. 12), was not compromised.

Further details regarding lipid modification of GFP-LPETG-His$_6$ (SEQ ID NO: 157), removal of His$_6$ (SEQ ID NO: 174)-tagged proteins, acetone precipitation of eGFP conjugates and characterization by ESI-MS, and MALDI-TOF MS Characterization of eGFP-2-chol., and estimation of % yield of eGFP conjugates are as follows:

Lipid modification of GFP-LPETG-His$_6$ (SEQ ID NO: 160) and removal of His$_6$ (SEQ ID NO: 174)-tagged proteins (General Procedure).

Lipidated triglycine nucleophile (0.5 µL of a 100 mM solution in DMSO) was combined with 2.5 µL of 10× sortase reaction buffer (500 mM Tris pH 7.5, 100 mM CaCl2, 1.5 M NaCl) and 1.25 µL of 20% (w/v) n-dodecyl maltoside. This mixture was repeatedly heated in a 90° C. heat block and incubated in a sonicating water bath to disperse and solubilize the lipidated nucleophile. After cooling to room temperature, eGFP-LPETG-His$_6$ (SEQ ID NO: 157) (12.4 µL of a 110 µM solution in 20 mM Tris pH 8.0, 150 mM NaCl) and sortase A (8.35 µL of a 448 µM solution in 50 mM Tris pH 8.0, 150 mM NaCl, 10% glycerol (v/v)) were added. The reaction mixtures were incubated at 37° C. for 5 h in the dark and then treated with 50 µL of the appropriate Ni-NTA slurry described above and incubated for an additional 2 h at room temperature. The mixtures were then filtered (Spin-X Centrifugal Tube Filters 0.22 µm, Corning) to yield solutions containing lipid-modified eGFP. Samples were analyzed by SDS-PAGE with visualization by Coomassie blue staining.

Acetone Precipitation of eGFP conjugates and Characterization by ESI-MS.

20 µL of lipid-modified eGFP solution was treated with 1 mL of acetone and centrifuged at maximum speed for 3 minutes. The supernatant was removed and the pellet was washed with 1 mL of acetone. The sample was again centrifuged and the pellet was dissolved in 100 µL of 0.1% formic acid. Samples were then analyzed by LC-ESI-MS (FIG. 12a).

MALDI-TOF MS Characterization of eGFP-2-chol.

eGFP-2-chol was desalted by RP-HPLC [C4 column, MeCN:H$_2$O gradient mobile phase with 0.1% TFA, 1 mL/min, 5% MeCN→50% MeCN (0-15 min), 50% MeCN→80% MeCN (15-18 min)]. The fraction containing eGFP-2-chol was analyzed by MALDI-TOF-MS (FIG. 12b).

Estimation of % Yield of eGFP Conjugates.

Figures 14A, 14B:
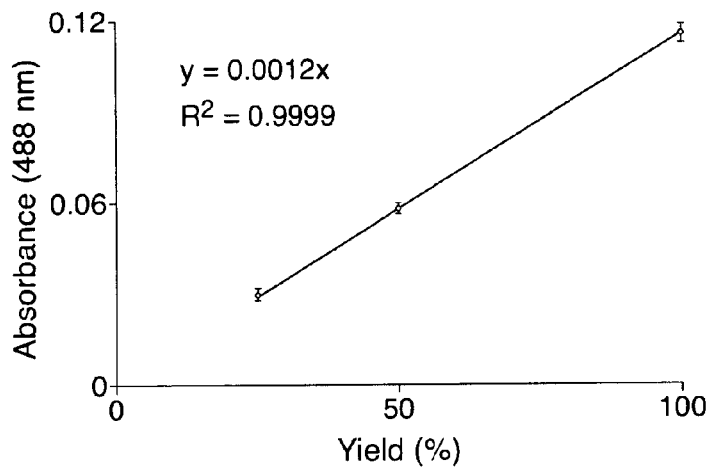
FIG. 14.(*a*) Standard curve for estimating the yield of lipid-modified eGFP. (*b*) Absorbance of lipid-modified eGFP and estimated yield.

The yield of lipid modified eGFP was estimated using the absorbance of eGFP at 488 nm. As a standard, a sample of unmodified eGFP-LPETG-His$_6$ (SEQ ID NO: 157) was incubated in the absence of sortase A and lipidated nucleophile (FIG. 2b, lane 1) and treated with Ni-NTA resin containing excess imidazole to prevent protein binding. After filtration to remove Ni-NTA, the absorbance of this sample at 488 nm was measured and assumed to represent 100% recovery. Serial dilutions of this sample were measured in triplicate and used to construct a standard curve (FIG. 14).

Interaction of Lipid-Modified eGFP with Mammalian Cells

Figure 3:
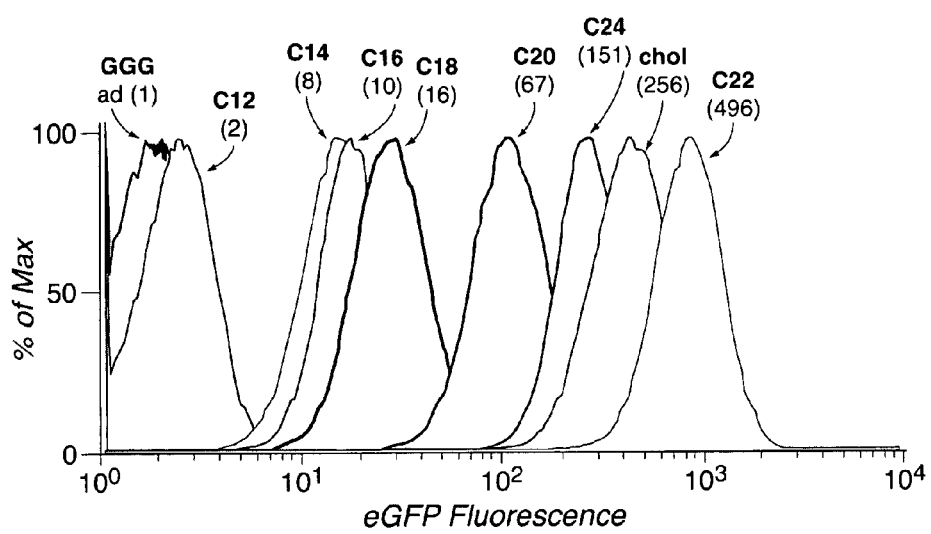
FIG. 3. Association of lipid-modified eGFP with HeLa cells. Cells were incubated with lipid-modified eGFP (2.5 µg/mL) for 1 h in serum-free medium and then analyzed by flow cytometry. Numbers in parentheses represent the fold enhancement in mean cellular fluorescence relative to that of eGFP-GGG. Histograms for eGFP-GGG (black) and eGFP-1-ad (gray) are overlapping.
Figure 4A:
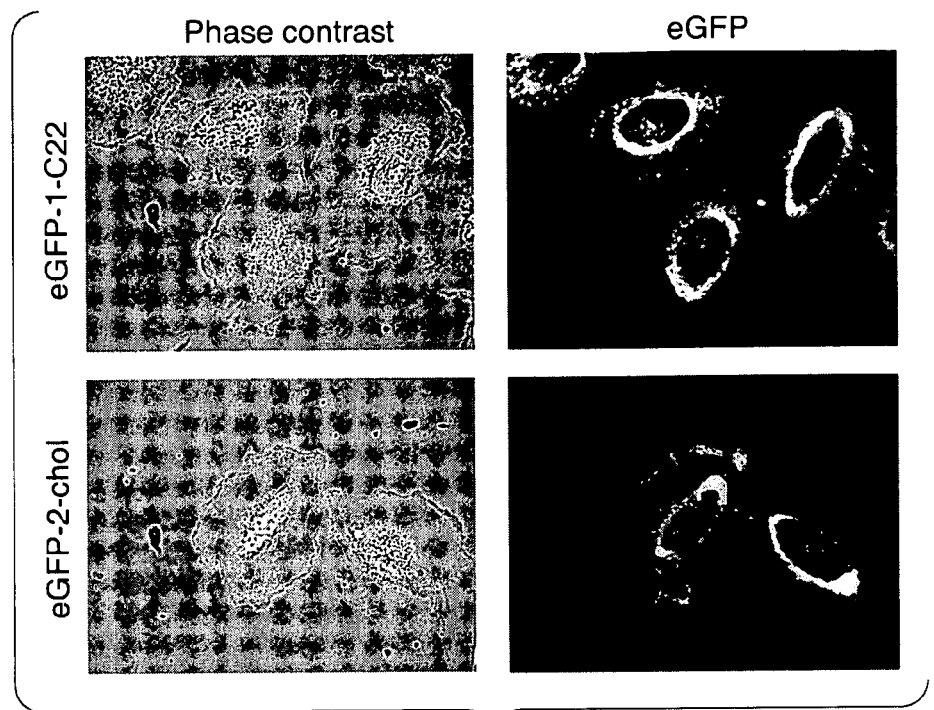
FIG. 4. Subcellular distribution of eGFP-1-C22 and eGFP-2-chol in U373 and HeLa cells. Cells were incubated with lipid-modified eGFP (2.5 µg/mL) at 37° C. in serum-free medium and then imaged live using spinning disk confocal microscopy. Key: (a) U373 cells, 1 h of incubation, (b) U373 cells, 5 h of incubation, (c) HeLa cells, 1.25 h of incubation, (d) HeLa cells, 5 h of incubation.
Figure 4B:
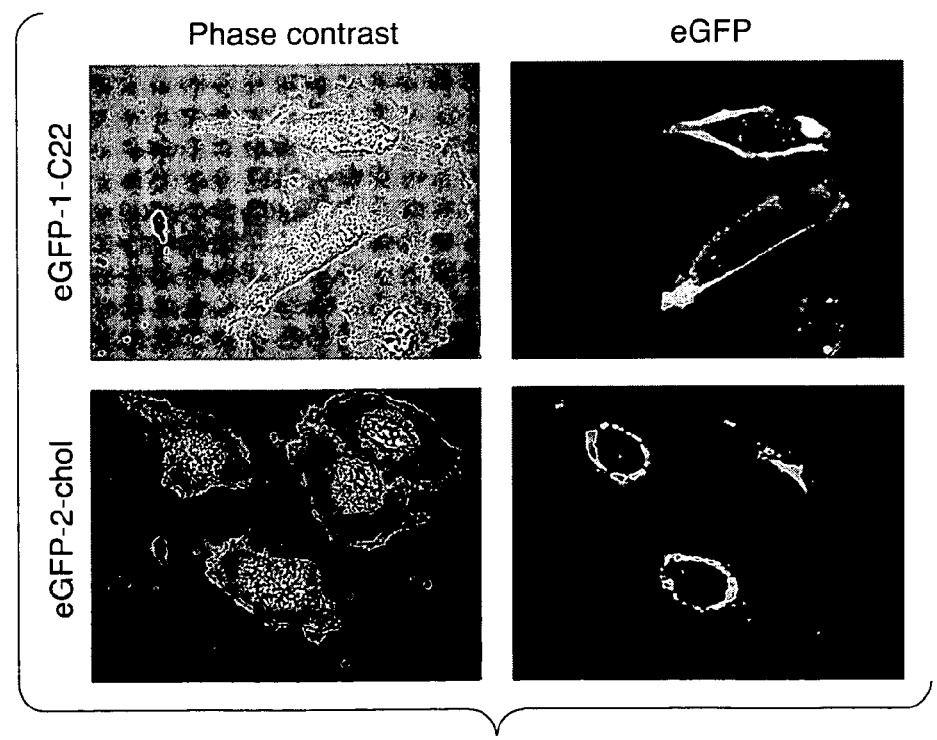
Figure 4C:
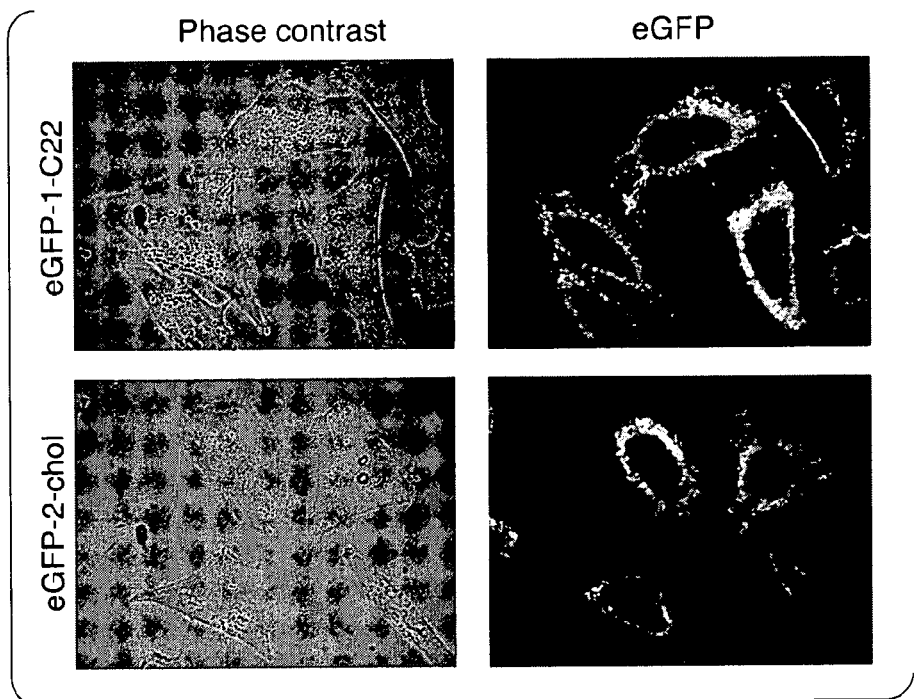
Figure 4D:
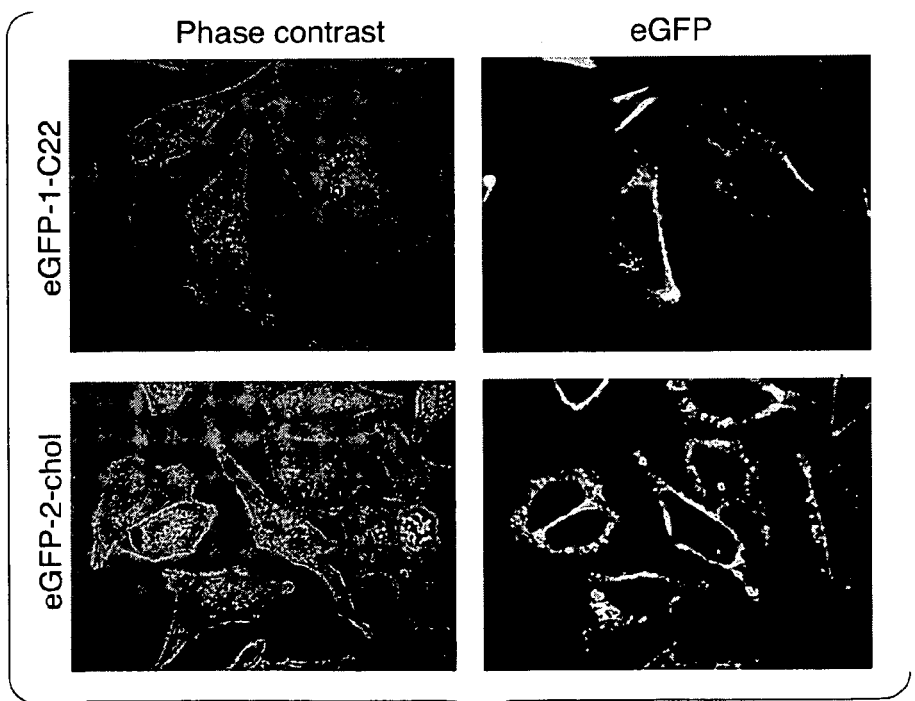
Figure 15:
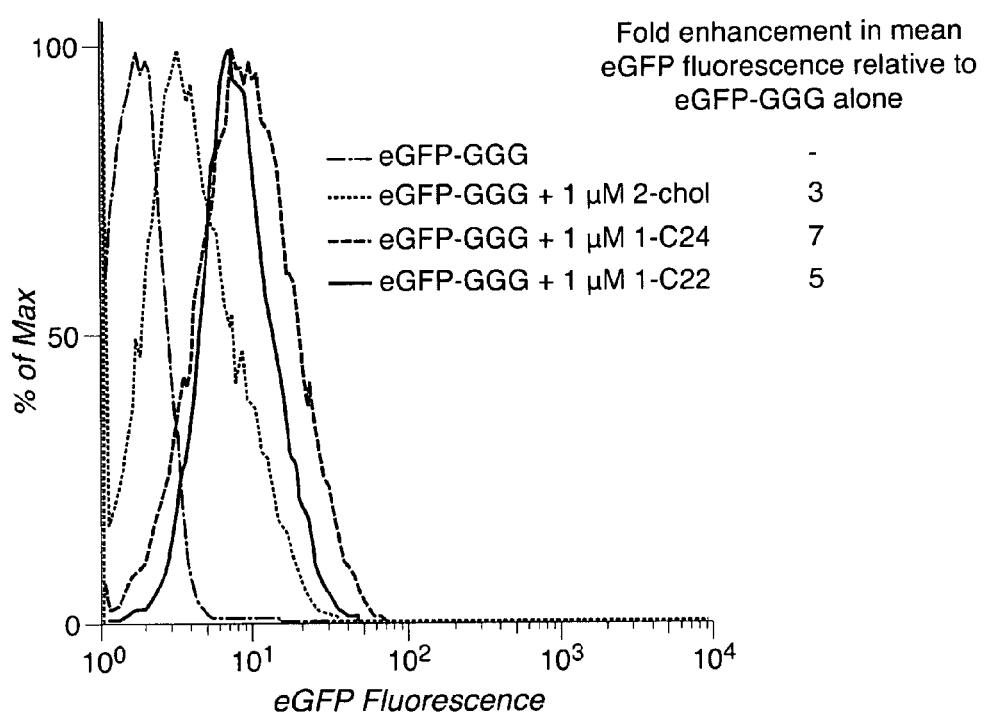
FIG. 15. Control experiment demonstrating minor increases in cellular fluorescence as a result of incubation with eGFP-GGG in combination with free lipidated triglycine nucleophiles.

The presence of a hydrophobic tail on eGFP should render it capable of spontaneous association with biological membranes (1, 2, 24, 44). As an initial investigation into the effect of the identity of the lipid tail on the ability of these lipoproteins to associate with cells, we incubated HeLa cells with lipid-modified eGFP (2.5 μg/mL) in serum-free medium for 1 h at 37° C. After washing, the cells were analyzed by flow cytometry (FIG. 3). In general, we observed a steady increase in cellular fluorescence with increasing length of the lipid tail. In the case of eGFP-1-C22, we recorded a 500-fold enhancement in mean cellular fluorescence relative to that of eGFP-GGG. Interestingly, eGFP-1-C24 consistently yielded lower association than eGFP-1-C22. For all samples cell viability was >94% as determined by exclusion of propidium iodide, indicative of a lack of cytotoxicity of the lipidated eGFP derivatives. Also, because the eGFP preparations contained low levels of free lipidated nucleophile (~1 μM in culture medium), we verified that this contaminant did not contribute to the observed increase in cellular fluorescence. eGFP-GGG in combination with 1 μM 1-C22, 1-C24, or 2-chol produced only modest increases in fluorescence, <5% of the magnitude observed for the corresponding covalently modified eGFP conjugates (FIG. 15). In this control experiment, cells were seeded into 6-well polystyrene cell culture plates at a density of ~100,000 cells per well and incubated overnight. The media was then removed and replaced with 2 mL of serum-free DME containing 2.5 μg/mL eGFP-GGG and 1 μM lipidated triglycine nucleophile (1-C22, 1-C24, or 2-chol). Cells were incubated for 1 h at 37° C. Next, the cells were washed three times with ~4 mL of cold PBS containing 1% FBS. The cells were lifted from the culture plate by treatment with 1 mL of 1 mM EDTA in PBS and pelleted at 250×g for 5 min. The cells were then resuspended in 200 μL of PBS containing 1% FBS and propidium iodide (0.5 μM) and analyzed by flow cytometry (FIG. 15).

Figure 5:
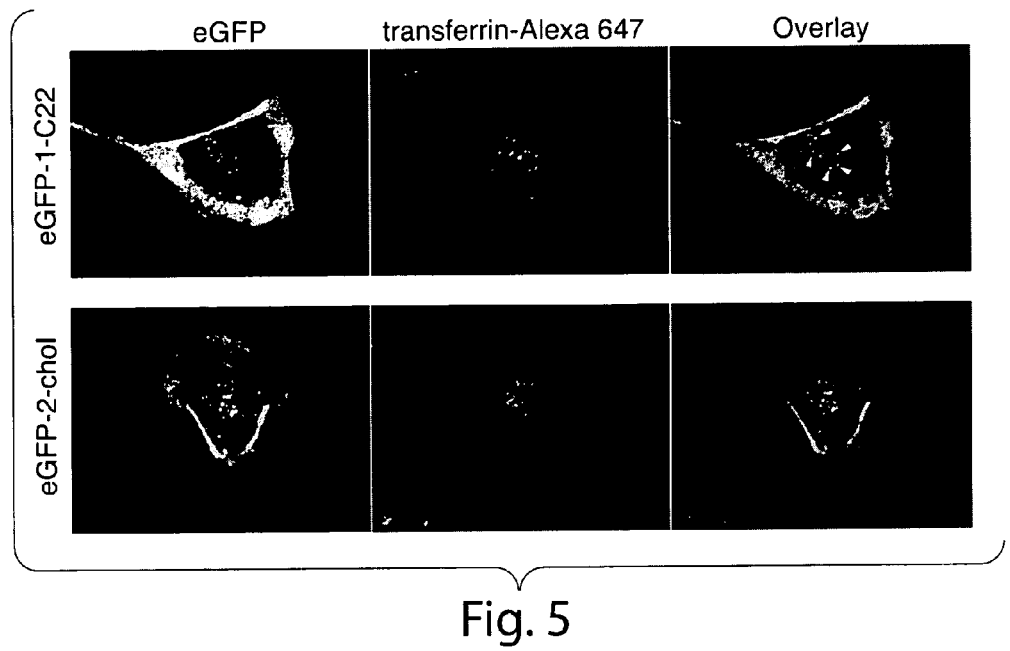
FIG. 5. eGFP-1-C22 is able to access early endosomal compartments as determined by partial colocalization with transferrin-Alexa 647. U373 cells were incubated with eGFP-1-C22 (2.5 µg/mL) for 5 h in serum-free medium followed by the addition of transferrin-Alexa 647 (100 µg/mL) during the final 15 min. White arrows indicate vesicles with positive staining for both eGFP-1-C22 and transferrin-Alexa 647. Significant colocalization between eGFP-2-chol and transferrin-Alexa 647 was not observed.
Figure 6:
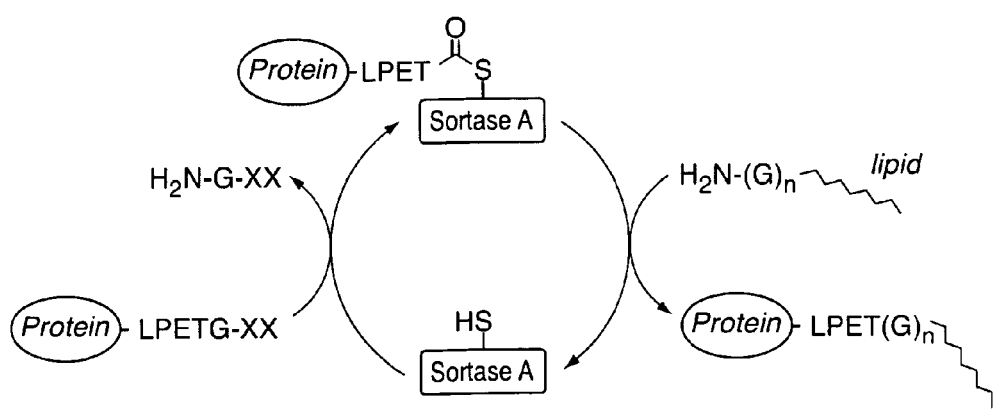
FIG. 6. Scheme 1. Site-Specific Lipid Attachment through Sortase-Mediated Transpeptidation. LPETG-XX—SEQ ID NO: 180; LPETG—SEQ ID NO: 181.
Figure 7:
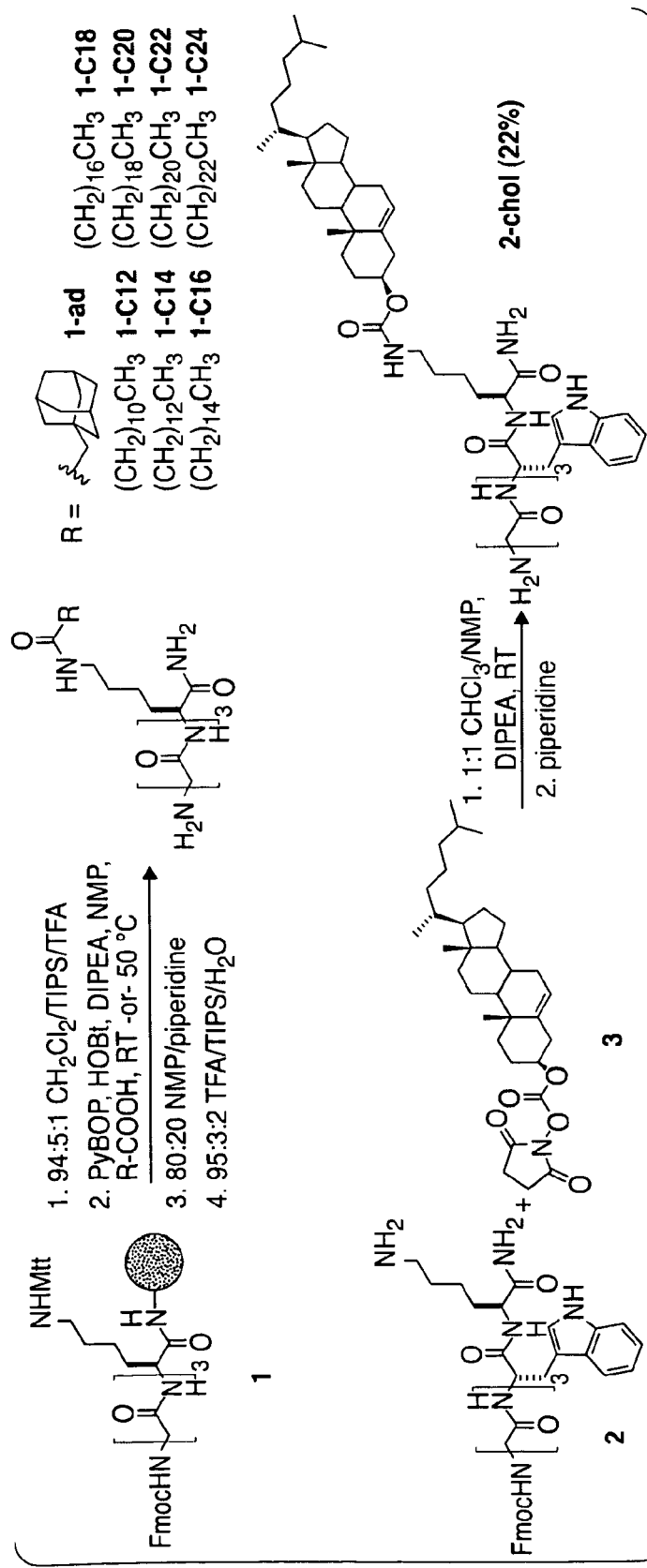
FIG. 7. Scheme 2. Synthesis of Lipid-Modified Triglycine Nucleophiles.

A preliminary evaluation of the subcellular localization of eGFP-1-C22 and eGFP-2-chol was performed using spinning disk confocal microscopy. HeLa cells and U373 cells were incubated with 2.5 μg/mL lipoprotein in serum-free medium, followed by washing and live cell imaging. For both cell types we observed staining of the cell surface as well as the appearance of internal fluorescent structures (FIG. 4). For all cells, filamentous membrane extensions, presumably filopodia, were evident in the fluorescent micrographs, indicating the presence of the eGFP lipoproteins on the plasma membrane. In U373 cells, distinct vesicular structures were observed at early (1 h) and later (5 h) time points, with a more pronounced presence of vesicles observed for eGFP-1-C22 than for eGFP-2-chol. In general, less internalization was observed for HeLa cells, though punctate internal staining could be observed with eGFP-1-C22 after a 5 h incubation in these cells. In the case of U373, we were also able to verify that eGFP-1-C22 had access to early/recycling endosomal compartments as determined by partial colocalization with transferrin (FIG. 5) (6, 45). Colocalization between eGFP-2-chol and transferrin was not observed (FIG. 5) for this cell line. Taken together, these results demonstrate that synthetic lipoproteins prepared using sortase-mediated transpeptidation can interact strongly with the plasma membrane and access endosomal compartments. The range of staining observed for our eGFP conjugates suggests that interactions with cells could be fine-tuned, and studies are under way to characterize the differences in the behavior of protein conjugates bearing different lipid anchors, specifically looking for differences in subcellular distribution and routes of endocytosis.

Further details regarding materials and methods used in the experiments described in this section are as follows:

1000× Stock Solutions of Lipid-Modified eGFP.

Solutions of lipid-modified eGFP obtained by transpeptidation and depletion of $His_6$ (SEQ ID NO: 174)-tagged proteins were used without further purification for cell membrane association studies. Prior to addition to cells, the concentration of eGFP in each sample was measured by UV-Vis (488 nm), and all solutions were adjusted to a final eGFP concentration of 2.5 mg/mL. Dilutions were made with a mock reaction mixture lacking eGFP, sortase A, and lipidated triglycine nucleophile to ensure that all samples contained the same amount of residual components (n-dodecyl maltoside, imidazole, $CaCl_2$, etc.) from the sortase labeling procedure.

Cell Culture and Membrane Association of Lipid-Modified eGFP.

HeLa cells were maintained in DME media supplemented with 10% fetal bovine serum (FBS), penicillin (50 units/mL), and streptomycin sulfate (50 μg/mL). Cells were incubated in a 5% $CO_2$ humidified incubator at 37° C. One day prior to treatment with lipid-modified eGFP, cells were seeded into 6-well polystyrene cell culture plates at a density of ~100,000 cells per well and incubated overnight. The media was then removed and replaced with 2 mL of serum-free DME containing 2.5 μg/mL modified eGFP (lipid modified proteins were delivered as 1000× stock solutions, see above). Cells were then incubated for 1 h at 37° C. Next, the cells were washed three times with ~4 mL of cold PBS containing 1% FBS. The cells were lifted from the culture plate by treatment with 1 mL of 1 mM EDTA in PBS and pelleted at 250×g for 5 min. The cells were then resuspended in 200 μL of PBS containing 1% FBS and propidium iodide (0.5 μM) and analyzed by flow cytometry.

Spinning Disc Confocal Microscopy.

HeLa and U373 cells were maintained in DME media supplemented with 10% fetal bovine serum (FBS), penicillin (50 units/mL), and streptomycin sulfate (50 μg/mL). Cells were incubated in a 5% CO2 humidified incubator at 37° C. One day prior to treatment with lipid-modified eGFP, cells were seeded into Lab-Tek™ II chambered coverglass slides (Nalge Nunc International) and allowed to adhere overnight. The media was then removed and replaced with 200 μL of serum-free DME containing 2.5 μg/mL modified eGFP (lipid modified proteins were delivered as 1000× stock solutions, see above). Cells were then incubated for 1-5 h at 37° C. Next, the cells were washed three times with ~0.5 mL of cold PBS containing 1% FBS. Cells were then covered with 200 μL of PBS containing 1% FBS and imaged. For transferrin colocalization, U373 were incubated with 200 μL of serum-free DME containing 2.5 μg/mL modified eGFP for 5 h at 37° C. Transferrin-Alexa 647 (Invitrogen, 100 μg/mL final concentration) was added during the final 15 minutes of this incubation. Cells were then washed as described above and imaged.

Discussion of Example 1

In summary, we have developed a general strategy using sortase-mediated transpeptidation as a means to install hydrophobic lipid modifications onto protein substrates in site-specific fashion. The ease of use of this method stands out as a significant asset. Protein substrates require, e.g., only a five amino acid extension (such as LPETG (SEQ ID NO: 55)) to serve as sortase substrates, a modest insertion that is not expected to impede the function of most proteins and should also have minimal impact on the expression yield of these polypeptides. Recombinant proteins containing the LPETG (SEQ ID NO: 55) motif are also stable and unreactive until activated by the sortase enzyme. This affords a distinct advantage over the expressed protein ligation approach where premature cleavage of intein fusion proteins has been documented, leading to a reduction in the yield of final ligation products. The requisite lipid-modified nucleophiles compatible with sortase-mediated transpeptidation also have a very straightforward structural requirement of a short stretch of glycine residues and are prepared by standard solid-phase synthesis. Therefore, both natural and non-natural hydrophobic modifications can be easily incorporated using this system.

While the requirement for the sortase enzyme itself could be perceived as a disadvantage of the transpeptidation strategy, it should be noted that we routinely express batches with yields of >50 mg/L, and stock solutions of the enzyme can be stored for several months with no apparent degradation in enzymatic activity. Moreover, in this work we provided a convenient method for removing sortase following transpeptidation. The ready availability of sortase and ease of removal following transpeptidation are important features as the enzyme is relatively inefficient and excess sortase is typically employed in the art to drive the labeling reactions to high levels of conversion in a reasonable period of time.

In this initial work, we used eGFP as our model protein substrate due to its natural fluorescence and verified that eGFP proteins lipidated through sortase-mediated transpeptidation strongly associate with mammalian cells. We envision further applications of this chemical modification strategy to include anchorage of proteins to cellular membranes that do not normally occur on the cell surface to create artificial cell surface receptors. Additionally, because the transpeptidation strategy is able to attach extremely hydrophobic modifications, it could provide a new method for interfacing proteins with materials that possess poor water solubility, such as carbon nanotubes.

References

1. Paulick, M. G., Forstner, M. B., Groves, J. T., and Bertozzi, C. R. *Proc. Natl. Acad. Sci. U.S.A.* 2007, 104, 20332-20337.
2. Paulick, M. G., Wise, A. R., Forstner, M. B., Groves, J. T., and Bertozzi, C. R. *J. Am. Chem. Soc.* 2007, 129, 11543-11550.
3. Martin, S. E., and Peterson, B. R. *Bioconjugate Chem.* 2003, 14, 67-74.
4. Boonyarattanakalin, S., Athavankar, S., Sun, Q., and Peterson, B. R. *J. Am. Chem. Soc.* 2006, 128, 4917-4917.
5. Covic, L., Gresser, A. L., Talavera, J., Swift, S., and Kuliopulos, A. *Proc. Natl. Acad. Sci. U.S.A.* 2002, 99, 643-648.
6. Sun, Q., Cai, S., and Peterson, B. R. *J. Am. Chem. Soc.* 2008, 130-10064-10065.
7. Nelson, A. R., Borland, L., Allbritton, N. L., and Sims, C. E. *Biochemistry* 2007, 46, 14771-14781.
8. Moyle, P. M., and Toth, I. *Curr. Med. Chem.* 2008, 15, 506-516.
9. BenMohamed, L., Wechsler, S. L., and Nesburn, A. B. *Lancet Infect. Dis.* 2002, 2, 425-431.
10. Reulen, S. W., Brusselaars, W. W., Langereis, S., Mulder, W. J., Breurken, M., and Merkx, M. *Bioconjugate Chem.* 2007, 18, 590-596.
11. Torchilin, V. P. *Nat. Rev. Drug Discovery* 2005, 4, 145-160.
12. Ha, V. L., Thomas, G. M., Stauffer, S., and Randazzo, P. A. *Methods Enzymol.* 2005, 404, 164-174.
13. Heal, W. P., Wickramasinghe, S. R., Bowyer, P. W., Holder, A. A., Smith, D. F., Leatherbarrow, R. J., and Tate, E. W. *Chem. Commun.* 2008, 480-482.
14. Kalinin, A., Thoma, N. H., Iakovenko, A., Heinemann, I., Rostkova, E., Constantinescu, A. T., and Alexandrov, K. *Protein Expression Purif.* 2001, 22, 84-91.
15. Gauchet, C., Labadie, G. R., and Poulter, C. D. *J. Am. Chem. Soc.* 2006, 128, 9274-9275.
16. Duckworth, B. P., Zhang, Z. Y., Hosokawa, A., and Distefano, M. D. *Chem Bio Chem* 2007, 8, 98-105.
17. Breydo, L., Sun, Y., Makarava, N., Lee, C. I., Novitskaia, V., Bocharova, O., Kao, J. P., and Baskakov, I. V. *Biochemistry* 2007, 46, 852-861.
18. Bader, B., Kuhn, K., Owen, D. J., Waldmann, H., Wittinghofer, A., and Kuhlmann, J. *Nature* 2000, 403, 223-226.
19. Eberl, H., Tittmann, P., and Glockshuber, R. *J. Biol. Chem.* 2004, 279, 25058-25065.
20. Hicks, M. R., Gill, A. C., Bath, I. K., Rullay, A. K., Sylvester, I. D., Crout, D. H., and Pinheiro, T. J. *FEBS J.* 2006, 273, 1285-1299.
21. Muir, T. W. *Annu. Rev. Biochem.* 2003, 72, 249-289.
22. Alexandrov, K., Heinemann, I., Durek, T., Sidorovitch, V., Goody, R. S., and Waldmann, H. *J. Am. Chem. Soc.* 2002 124 5648-5649.
23. Pellois, J. P., and Muir, T. W. *Angew. Chem., Int. Ed.* 2005, 44, 5713-5717.
24. Grogan, M. J., Kaizuka, Y., Conrad, R. M., Groves, J. T., and Bertozzi, C. R. *J. Am. Chem. Soc.* 2005, 127, 14383-14387.
25. Gottlieb, D., Grunwald, C., Nowak, C., Kuhlmann, J., and Waldmann, H. *Chem. Commun.* 2006, 260-262.
26. Luka, Z., and Wagner, C. *Protein Expression Purif.* 2003, 28, 280-286.
27. Zhao, W., Zhang, Y., Cui, C., Li, Q., and Wang, J. *Protein Sci.* 2008, 17, 736-747.
28. Cui, C., Zhao, W., Chen, J., Wang, J., and Li, Q. *Protein Expression Purif.* 2006, 50, 74-81.
29. Tan, L. P., Lue, R. Y., Chen, G. Y., and Yao, S. Q. *Bioorg. Med. Chem. Lett.* 2004, 14, 6067 6070.
30. Pritz, S., Kraetke, O., Klose, A., Klose, J., Rothemund, S., Fechner, K., Bienert, M., and Beyermann, M. *Angew. Chem., Int. Ed.* 2008, 47, 3642-3645.
31. Samantaray, S., Marathe, U., Dasgupta, S., Nandicoori, V. K., and Roy, R. P. *J. Am. Chem. Soc.* 2008, 130, 2132-2133.
32. Chan, L., Cross, H. F., She, J. K., Cavalli, G., Martins, H. F. P., and Neylon, C. *PLoS ONE* 2007, 2, e1164.
33. Tanaka, T., Yamamoto, T., Tsukiji, S., and Nagamune, T. *Chem Bio Chem* 2008, 9, 802-807.
34. Popp, M. W., Antos, J. M., Grotenbreg, G. M., Spooner, E., and Ploegh, H. L. *Nat. Chem. Biol.* 2007, 3, 707-708.
35. Parthasarathy, R., Subramanian, S., and Boder, E. T. *Bioconjugate Chem.* 2007, 18, 469-476.
36. Pritz, S., Wolf, Y., Kraetke, O., Klose, J., Bienert, M., and Beyermann, M. *J. Org. Chem.* 2007, 72, 3909-3912.
37. Mao, H. *Protein Expression Purif.* 2004, 37, 253-263.
38. Mao, H., Hart, S. A., Schink, A., and Pollok, B. A. *J. Am. Chem. Soc.* 2004, 126, 2670-2671.
39. Kruger, R. G., Otvos, B., Frankel, B. A., Bentley, M., Dostal, P., and McCafferty, D. G. *Biochemistry* 2004, 43, 1541-1551.
40. Ton-That, H., Liu, G., Mazmanian, S. K., Faull, K. F., and Schneewind, O. *Proc. Natl. Acad. Sci. U.S.A.* 1999, 96, 12424-12429.
41. Ton-That, H., Mazmanian, S. K., Faull, K. F., and Schneewind, O. *J. Biol. Chem.* 2000, 275, 9876-9881.
42. Clow, F., Fraser, J. D., and Proft, T. *Biotechnol. Lett.* 2008, 30, 1603-1607.
43. Tsien, R. Y. Annual Review of Biochemistry 1998, 67, 509-544.

44. Zacharias, D. A., Violin, J. D., Newton, A. C., and Tsien, R. Y. *Science* 2002, 296, 913-916.
45. Sheff, D., Pelletier, L., O'Connell, C. B., Warren, G., and Mellman, I. *J. Cell Biol.* 2002, 156, 797-804.

Please note that methods and references described in Exampes herein are applicable to other Eexamples and aspects of the invention.

Example 2

Modification of N-Terminal Glycine Residues Using Structural Mimetics of the Sortase a Recognition Sequence The transpeptidation reaction catalyzed by sortase A has emerged as a general method for derivatizing proteins with a variety of modifications. Yet, in its present incarnation, it appears that the practical application of this approach has been limited to the protein C-terminus. Target proteins are engineered to contain the sortase A recognition motif (LPXTG (SEQ ID NO: 45)) near their C-termini. When incubated with synthetic peptides containing one or more N-terminal glycine residues and recombinant sortase A, these artificial sortase substrates undergo a transacylation reaction resulting in the exchange of residues C-terminal to the threonine residue with the synthetic oligoglycine peptide. The use of excess oligoglycine drives this equilibrium process, and in most cases quantitative protein labeling can be achieved.

Figure 8A:
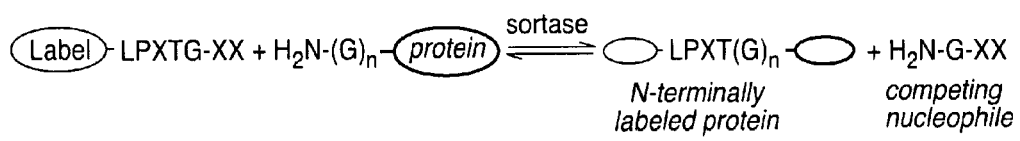
FIG. 8. Schematic representation of N-terminal labeling method using protein substrates with N-terminal glycine residues and ligating them to synthetic peptides containing the LPXTG (SEQ ID NO: 45) motif or structural analogs of this sequence element. LPETG-XX—SEQ ID NO: 182.
Figure 8B:
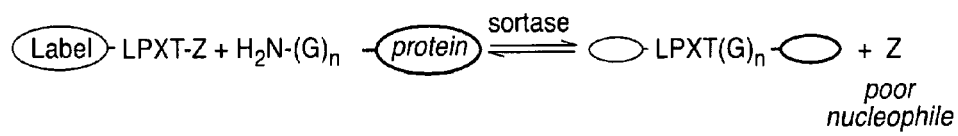
Figure 8C:
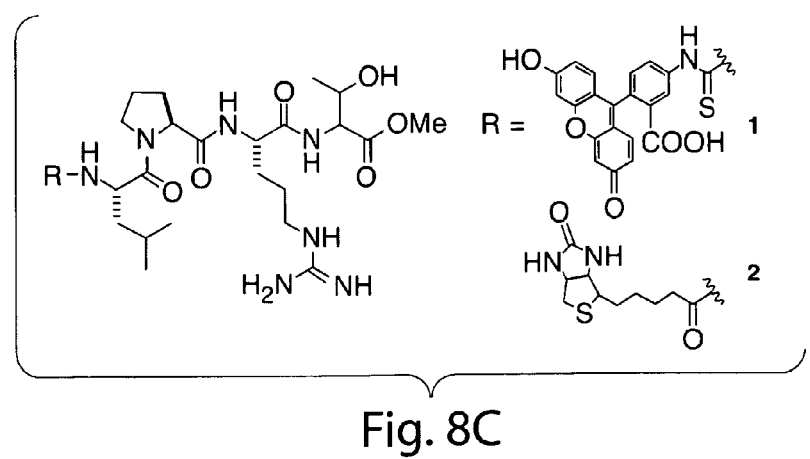

In simple terms, the transpeptidation reaction results in the ligation of species containing an LPXTG (SEQ ID NO: 45) motif with those bearing one or more N-terminal glycine residues. We therefore became interested in whether a similar method for N-terminal labeling could be achieved by preparing protein substrates with N-terminal glycine residues and ligating them to synthetic peptides containing the LPXTG (SEQ ID NO: 45) motif or structural analogs of this recognition element (FIG. 8). We herein describe the successful development of a general strategy for site-specific labeling of proteins with one or more N-terminal glycine residues. This technique allows for the installation of modifications suitable for a range of proteomic and biological applications.

Figure 16A:
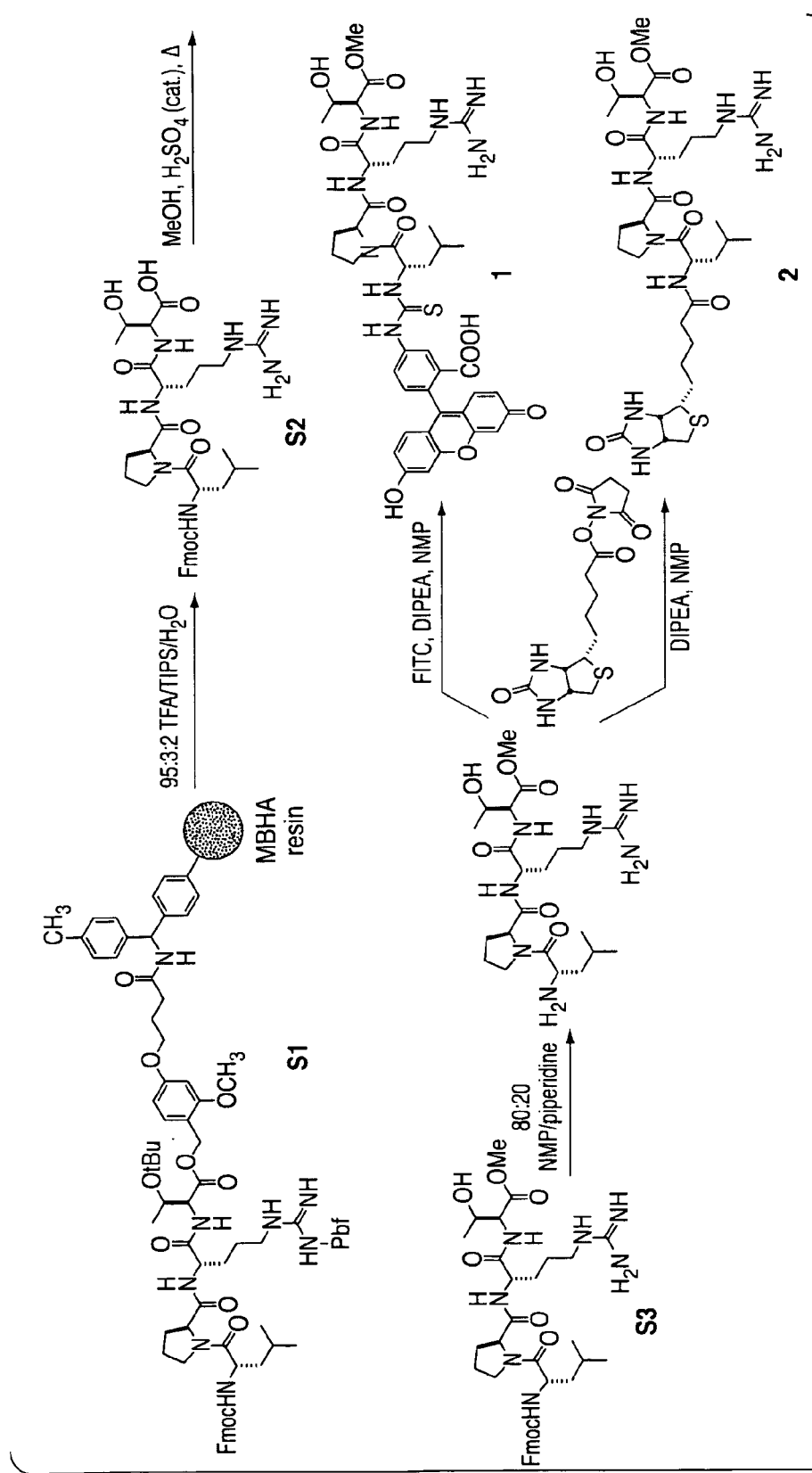
FIG. 16. (a) Preparation of compounds 1 and 2 (FITC-LPRT-OMe (SEQ ID NO: 47) and biotin-LPRT-OMe (SEQ ID NO: 48)); (b) Purification of compound 1 (SEQ ID NO: 47). (c) Purification of compound 2 (SEQ ID NO: 48).
Figure 16B:
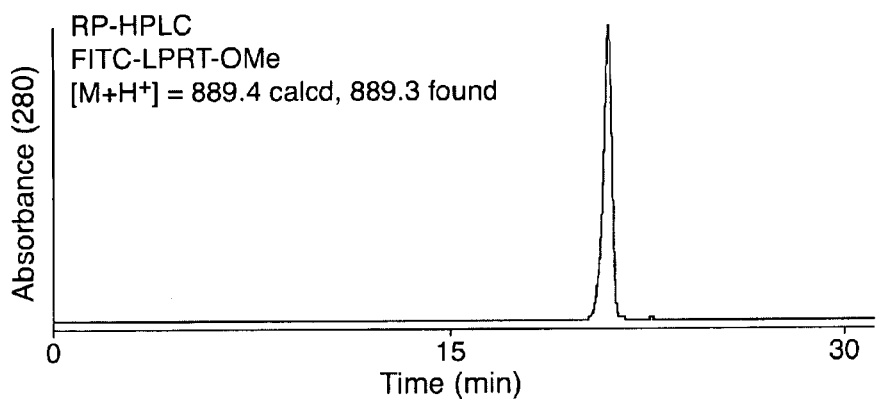
Figure 16C:
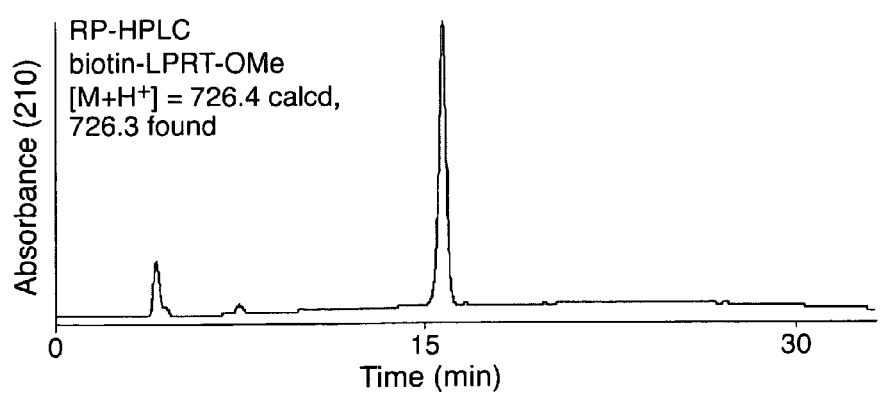
Figure 17A:
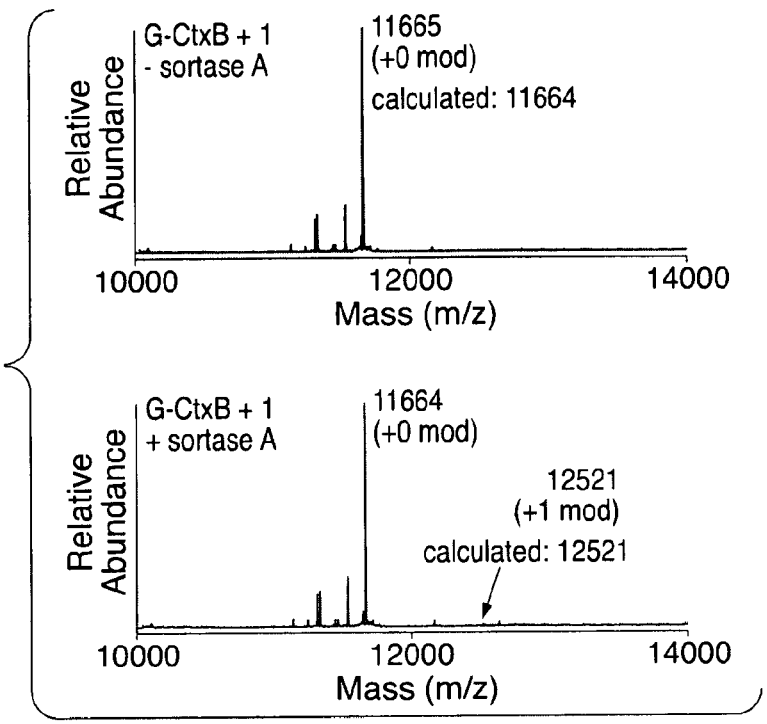
FIG. 17. ESI-MS showing quantitative labeling of CtxB constructs containing 3 or 5 (SEQ ID NO: 49) glycine residues. AGGGG—SEQ ID NO: 178.
Figure 17B:
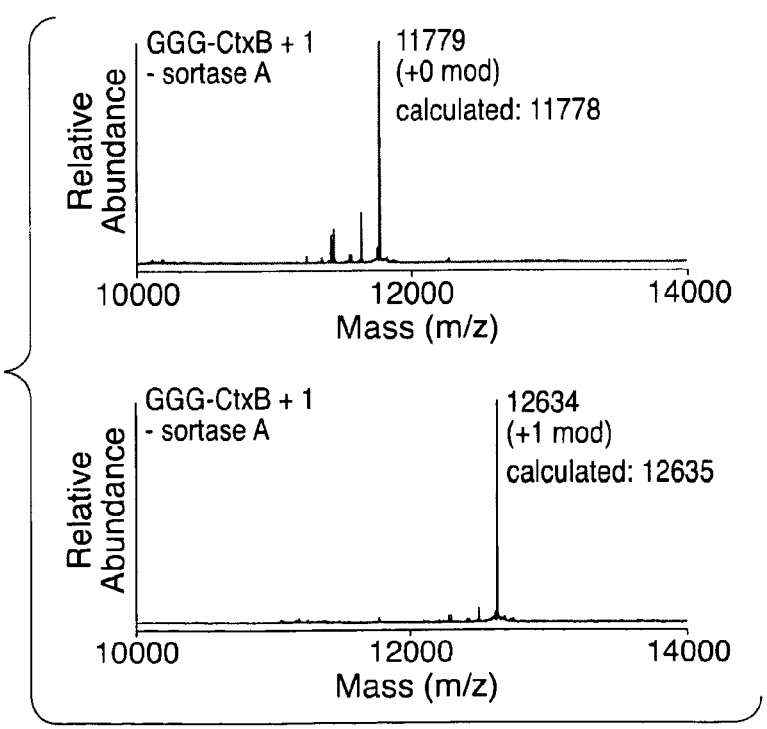
Figure 17C:
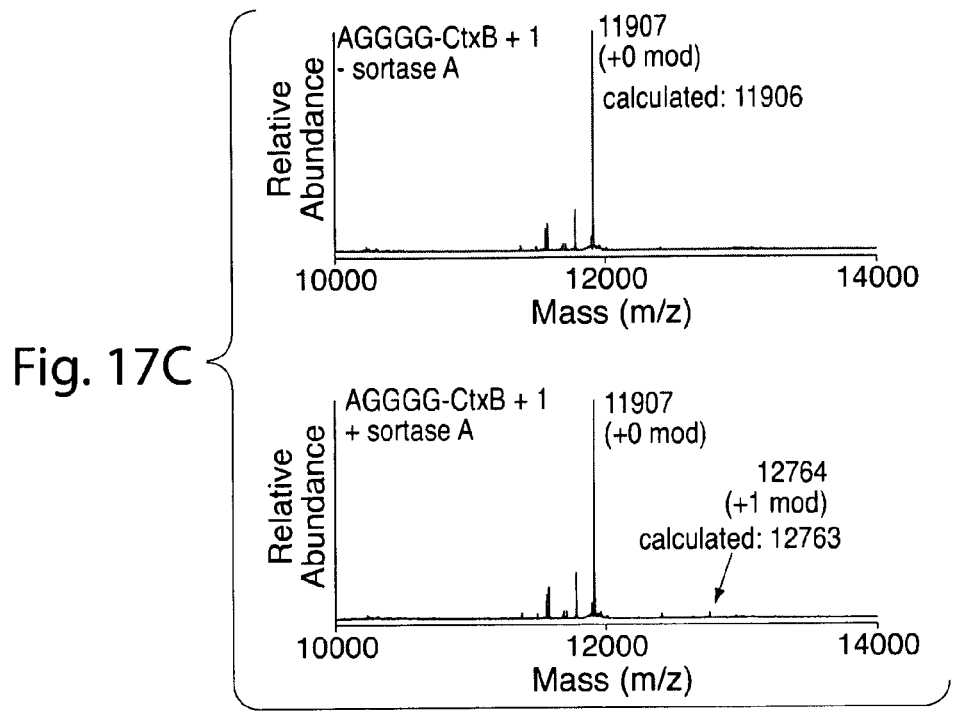
Figure 17D:
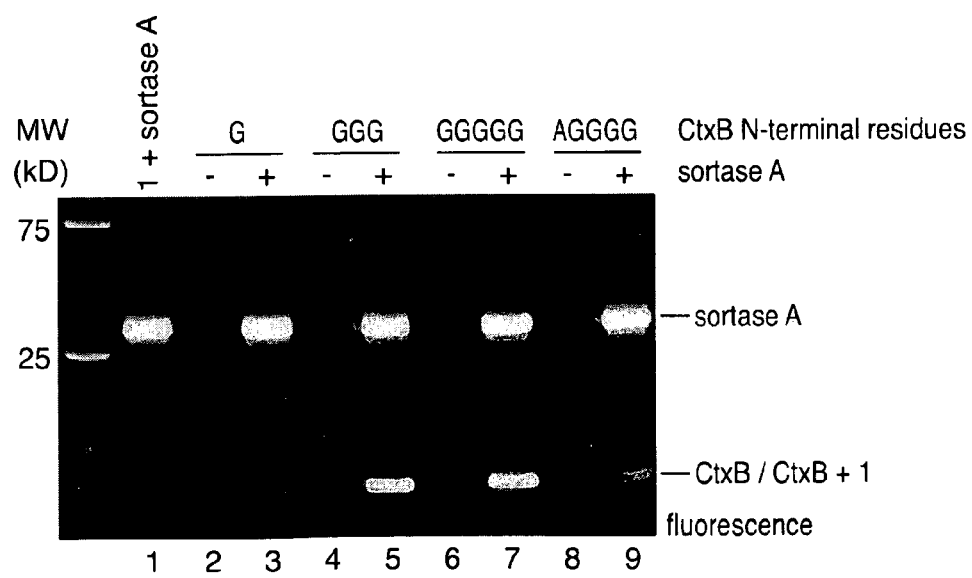

As noted above, synthetic peptides containing the LPXTG (SEQ ID NO: 45) motif have been shown to function as substrates for sortase A, generating the acyl enzyme intermediate necessary for transpeptidation. However, at the outset of our studies we were concerned that peptides containing the entire LPXTG (SEQ ID NO: 45) sequence could create a potential complication for N-terminal protein labeling. As outlined in FIG. 8a, each successful transfer of an LPXT unit to the target protein would release a stoichiometric amount of a peptide fragment containing an N-terminal glycine. This by-product would compete with the protein nucleophile for the same acyl enzyme intermediate, thereby limiting the efficiency of the labeling reaction. Moreover, hydrolytic cleavage of an LPXTG (SEQ ID NO: 45) peptide, although a relatively slow process, would exacerbate competition with the protein nucleophile as the reaction proceeded. Indeed, preliminary attempts in our laboratory to perform N-terminal protein labeling with peptides containing all five residues (LPXTG (SEQ ID NO: 45)) yielded disappointing results and useful levels of protein modification could only be obtained using high concentrations (>5 mM) of the LPXTG (SEQ ID NO: 45)-containing peptide (data not shown). We reasoned that a simple solution to this problem could be to substitute the glycine in the LPXTG (SEQ ID NO: 45) motif with a moiety that would exhibit poor nucleophilicity once released by sortase (FIG. 8b). With this design principle in mind, we synthesized fluorescein (1) and biotin (2) derivatives of an LPRT (SEQ ID NO: 161) peptide where the glycine residue was replaced by a simple methyl ester. Compounds 1 and 2 were prepared through a combination of solid-phase and solution-phase transformations and purified to homogeneity by reversed phase-HPLC (see FIG. 16). Arginine was placed in the X position to enhance water solubility and because a side chain that would be unreactive toward reagents used to modify the N-terminus of the LPRT (SEQ ID NO: 161) peptide.

Figure 18:
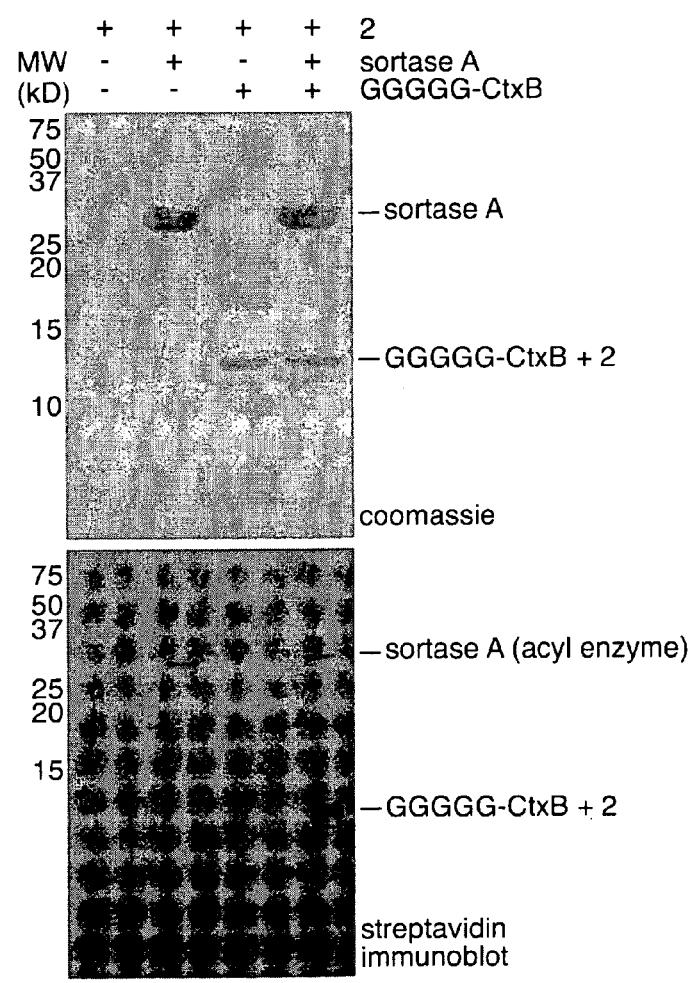
FIG. 18. Streptavidin immunoblot showing labeling of biotinylated derivative GGGGG-CtxB (SEQ ID NO: 49) with biotinylated LPRT (SEQ ID NO: 50) derivative. AGGGG—SEQ ID NO: 178.
Figure 19:
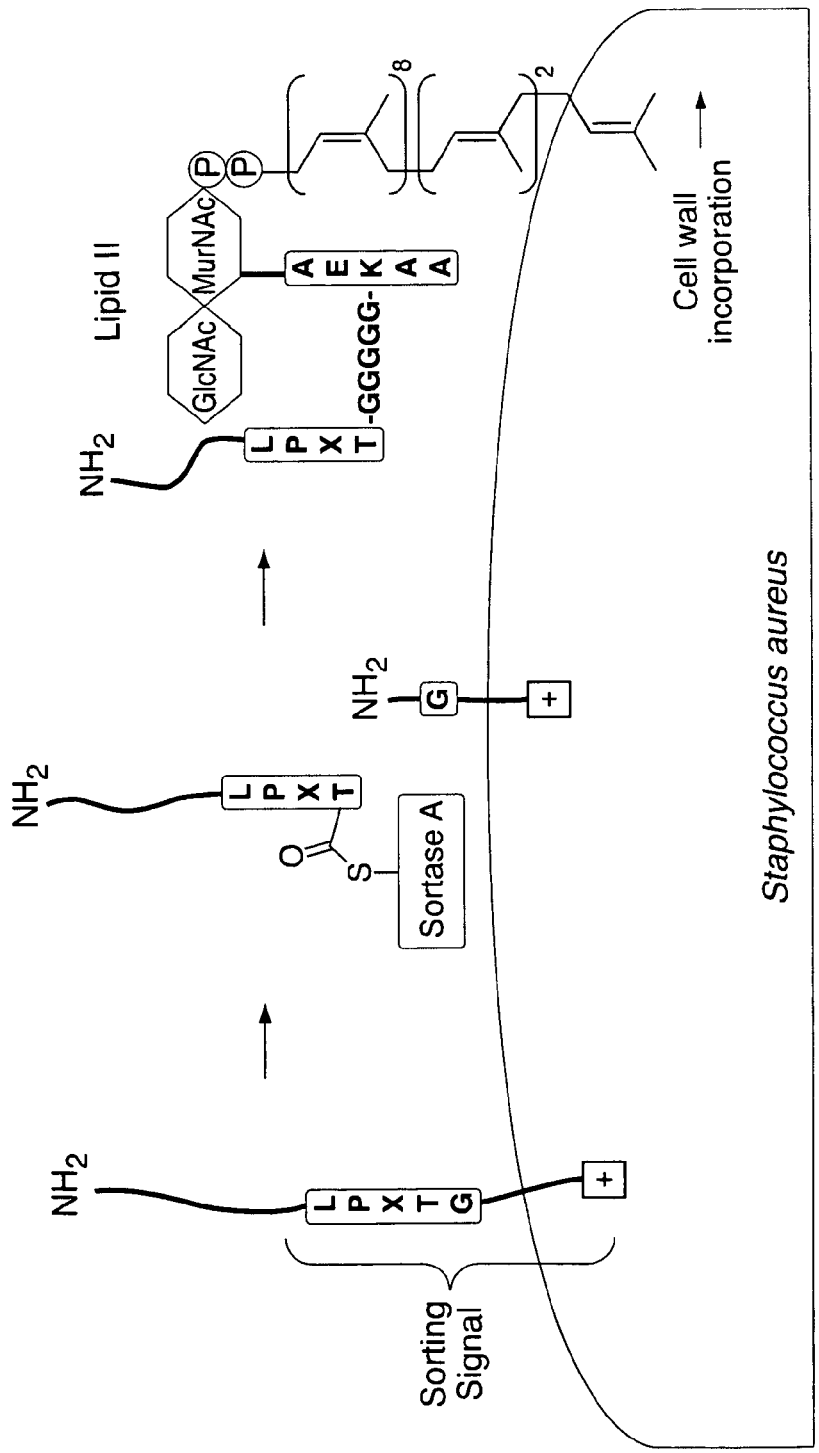
FIGS. 19-22 present an overview of biological function of sortase in bacterial cell wall anchoring and examples of C-terminal labeling using sortase. LPXTG—SEQ ID NO: 45; LPXTGGGGG—SEQ ID NO: 184; AEKAA—SEQ ID NO: 185; LPXTG-XX—SEQ ID NO: 182; GGGGG—SEQ ID NO: 186; LPETG—SEQ ID NO: 187; LPET—SEQ ID NO: 189; LPETG-His6—SEQ ID NO: 190.
Figure 20:
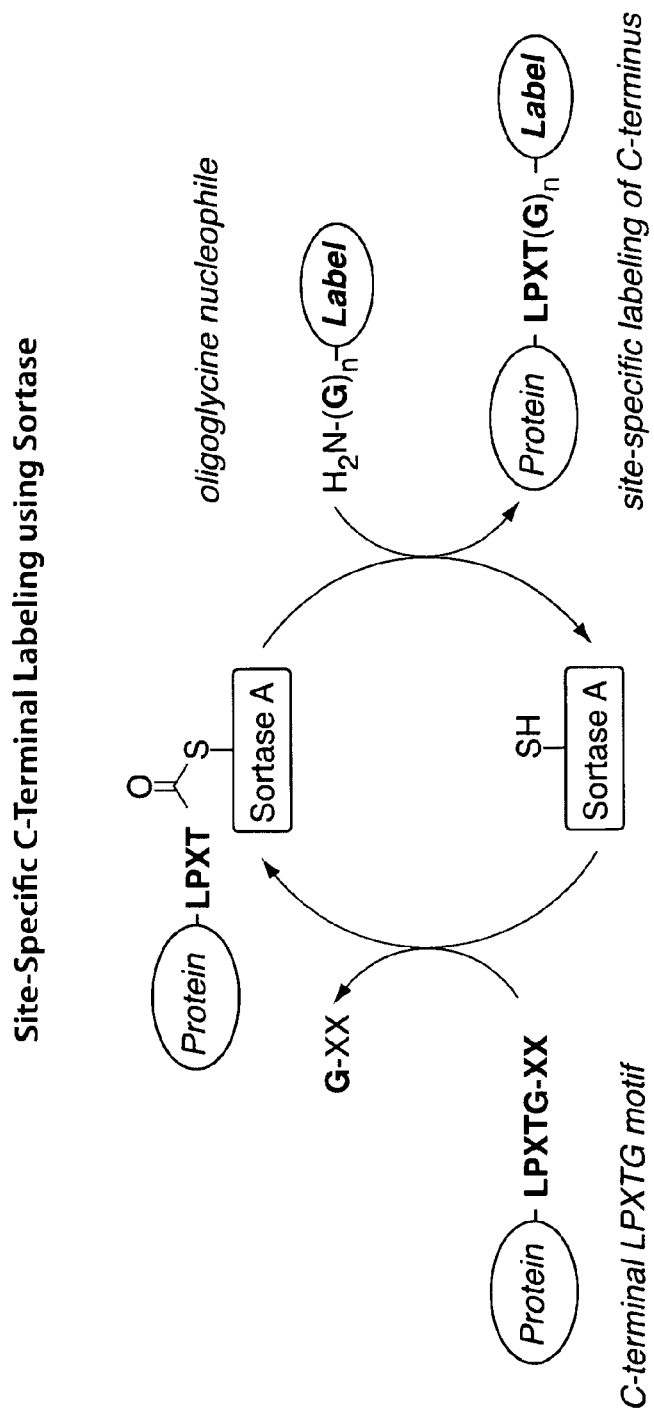
Figure 21:
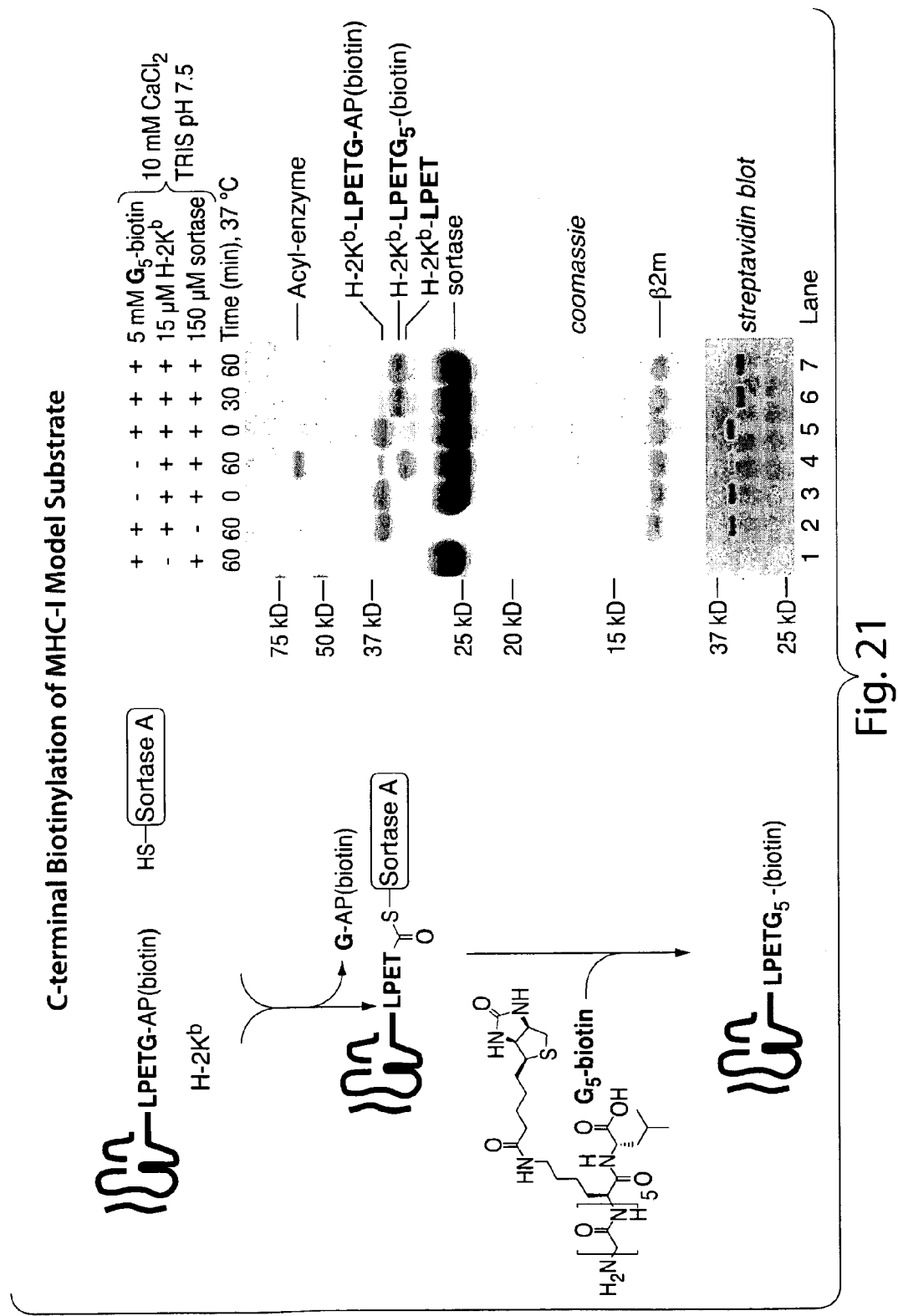
Figure 22:
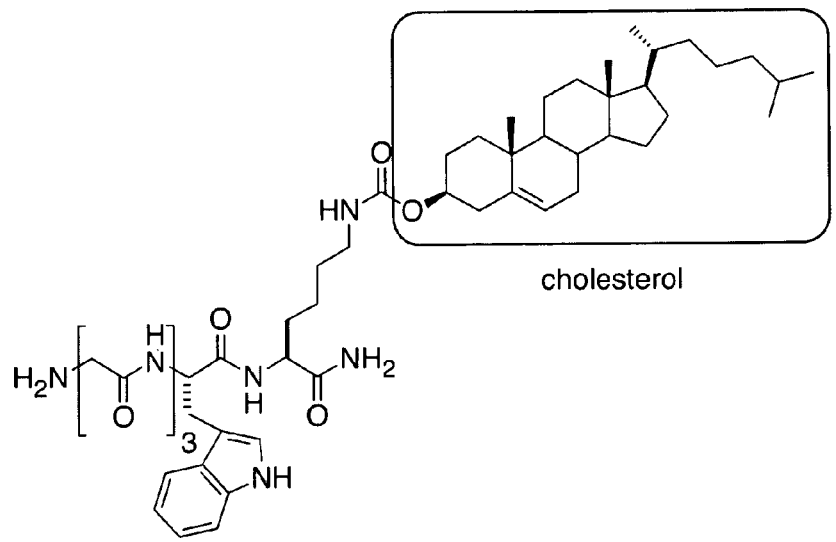
Figure 1:
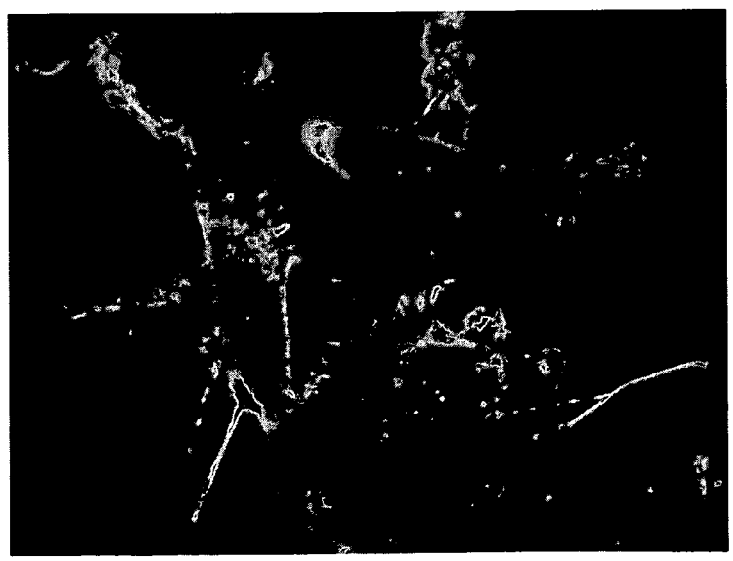
Figure 22:
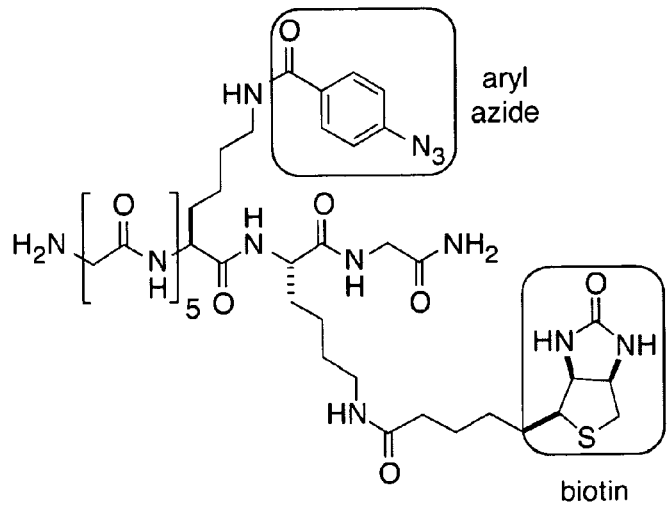

With 1 and 2 in hand we expressed a series of model protein substrates containing N-terminal glycine residues. It should be noted that recombinant protein bearing N-terminal glycine residues have been shown to function as nucleophiles for sortase-mediated transpeptidation, though only in the context of ligation to other proteins bearing the LPXTG (SEQ ID NO: 45) motif. For our studies, three variants of the cholera toxin B-subunit (CtxB) were prepared containing 1, 3, or 5 N-terminal glycine residues. To investigate selectivity for glycine, a final construct containing an N-terminal alanine residue was also prepared. Following some brief optimization, we were able to arrive at conditions that yielded quantitative labeling of constructs containing 3 or 5 glycines using 500 µM 1 with only trace labeling of the alanine-containing control. As shown in FIG. 9a, a fluorescence gel scan revealed robust labeling of CtxB if 3 or 5 glycines were present. No background labeling was observed in the absence of sortase A. For CtxB constructs containing 3 or 5 glycines residues, quantitative labeling was evident after 2 h at 37° C. as determined by ESI-MS (FIG. 9b, and FIG. 17). Similar labeling experiments with biotinylated derivative 2 GGGGG-CtxB (SEQ ID NO: 162) yielded identical results and the resulting conjugates could be detected by streptavidin immunoblot (FIG. 18) and conjugates were characterized using ESI-MS. Conditions used for experiment shown in FIG. 18 were: 33 µM $G_5$-CtxB (SEQ ID NO: 162), 50 mM SrtAstaph, 500 µM 2, 50 mM Tris pH 7.5, 150 mM NaCl, 10 mM CaCl2, 2 h at 37 degrees C. In all cases, residual labeling of the sortase enzyme itself could be detected. This was expected because the transpeptidation reaction proceeds through a covalent acyl enzyme intermediate.

Figure 10:
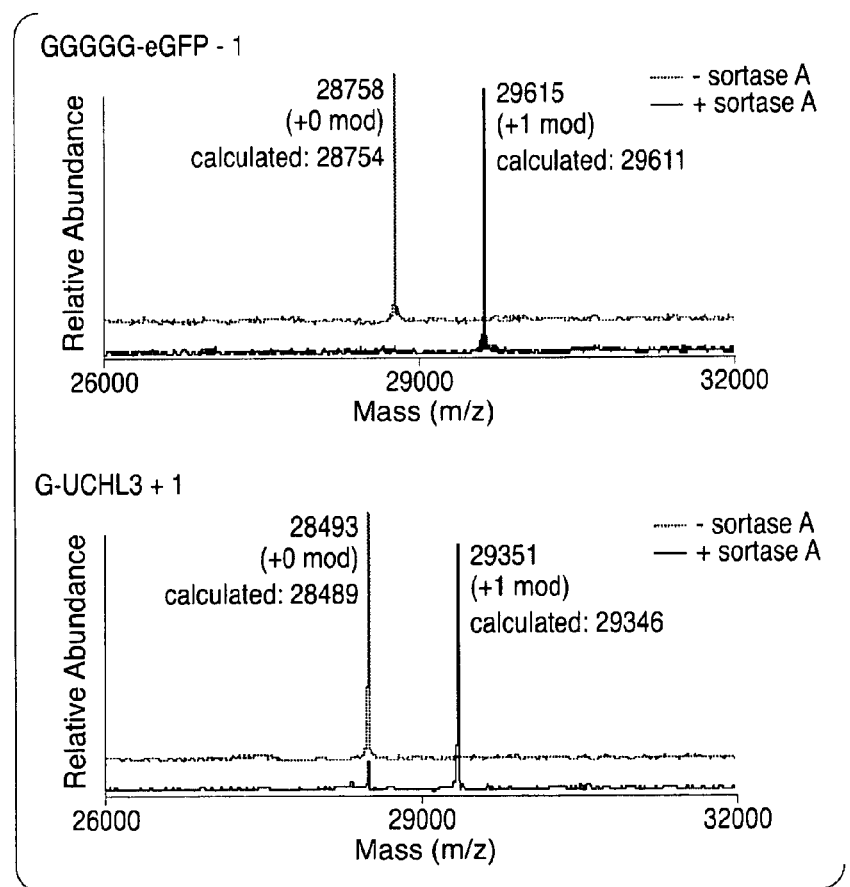
FIG. 10. ESI-MS showing labeling of eGFP and UCH-L3 polypeptides bearing 5 (SEQ ID NO: 49) or 1 glycine, respectively.

N-terminal transpeptidation was easily extended to two additional protein substrates (FIG. 10). eGFP bearing five glycines and the ubiquitin specific hydrolase UCH-L3 containing a single glycine were labeled efficiently as determined by ESI-MS. It should be noted that the utility of this labeling method for recombinant proteins expressed in *E. coli* is facilitated by natural processing of newly synthesized polypeptides by endogenous methionine aminopeptidase. When the initiator N-formylmethionine (N-fmet) is followed by small residues such as glycine, the removal of N-fmet is quantitative. Therefore, preparation of substrates for N-terminal transpeptidation requires only basic cloning techniques, and in most cases would only require a single residue substitution.

Example 3

Highly Efficient Sortase-Catalyzed Protein Circularization

This Example demonstrates that sortase-catalyzed transpeptidation can be used for efficient synthesis of circular and oligomeric proteins. This method has general applicability, as illustrated by successful intramolecular reactions with three structurally unrelated proteins. In addition to circularization of individual protein units, the multiprotein complex AAA-ATPase p97/VCP/CDC48, with six identical subunits containing the LPXTG (SEQ ID NO: 45) motif and an N-terminal glycine, was found to preferentially react in daisy chain fashion to yield linear protein fusions. For supplemental figures, additional methods, and references, please see, Amos, J M, et al, "A straight path to circular proteins" J Biol. Chem.; 284(23):16028-36, 2009.

Synthesis of Triglycine Tetramethylrhodamine Peptide. The structure of GGG-TMR[5] and a detailed synthetic protocol are provided in the supplemental material and supplemental FIG. S7.

Materials and Methods
Cloning and Protein Expression

Full amino acid sequences for all proteins used in this study are given in supplemental FIG. S8.

Recombinant sortase A (residues 26-206) containing an N-terminal hexahistidine tag was produced in *Escherichia coli* as described previously (8). Purified sortase A was stored in 10% glycerol, 50 mM Tris, pH 8.0, 150 NaCl at −80° C. until further use.

G-Cre-LPETG-His$_6$ (SEQ ID NO: 163) was cloned into the pTriEx-1.1 Neo expression vector (Novagen) using standard molecular biology techniques. The construct contains two point mutations (M117V and E340Q) and a flexible spacer (GGGGSGGGGS (SEQ ID NO: 164)) inserted before the LPETG (SEQ ID NO: 55) sortase recognition site. G-Cre-LPETG-His$_6$ (SEQ ID NO: 163) was expressed and purified using procedures similar to those reported previously for HTNCre (24). G-Cre-LPETG-His$_6$ (SEQ ID NO: 163) was first transformed into Tuner (DE3) pLacI cells (Novagen), and a starter culture was grown in sterile LB media supplemented with 1% (w/v) glucose, chloramphenicol (34 µg/ml), and ampicillin (100 µg/ml). This culture was used to inoculate a large scale culture of sterile LB containing chloramphenicol (34 µg/ml) and ampicillin (100 µg/ml). G-Cre-LPETG-His$_6$ (SEQ ID NO: 163) was expressed after a 3-h induction with isopropyl 1-thio-β-D-galactopyranoside (0.5 mM) at 37° C. Cells were resuspended in 10 Tris, 100 mM phosphate, 300 mM NaCl, and 20 mM imidazole, pH 8.0. The suspension was adjusted to 50 µg/ml DNase I, 460 µg/ml lysozyme, and 1 mM MgCl$_2$ and incubated at 4° C. for 1.5 h. The suspension was then sonicated and centrifuged. The clarified lysate was then treated with Ni-NTA-agarose (Qiagen) for 1 h at 4° C. The resin was washed with 12 column volumes of 10 mM Tris, 100 mM phosphate, 300 mM NaCl, and 20 mM imidazole, pH 8.0, followed by 4 column volumes of 10 mM Tris, 100 mM phosphate, 300 mM NaCl, and 30 mM imidazole, pH 8.0. The protein was then eluted with 10 mM Tris, 100 phosphate, 300 mM NaCl, and 300 mM imidazole, pH 8.0. The purified protein was then dialyzed first against 20 mM Tris, pH 7.5, 500 mM NaCl followed by 50% glycerol, 20 mM Tris, pH 7.5, 500 mM NaCl. G-Cre-LPETG-His$_6$ (SEQ ID NO: 163) was then passed through a 0.22-µm filter to remove minor precipitation and stored at 4° C.

G$_5$-eGFP-LPETG-His$_6$ (SEQ ID NO: 165) was prepared from a previously reported eGFP construct lacking the five N-terminal glycine residues using a QuickChange® II site-directed mutagenesis kit (Stratagene) and produced in *E. coli* using reported procedures (11). Purified G$_5$-eGFP-LPETG-His$_6$ (SEQ ID NO: 165) was buffer exchanged into 20 mM Tris, pH 8.0, 150 mM NaCl and stored at 4° C. UCHL3 with the sortase recognition sequence (LPETG (SEQ ID NO: 55)) substituted for amino acids 159-163 was cloned and produced in *E. coli* as described previously (25).

Human p97 (806 amino acids) was PCR-amplified and cloned via the NdeI and HindIII restriction sites into a pET28a+ expression vector (Novagen) to yield the G-His$_6$-p97 (SEQ ID NO: 176) construct. G-His$_6$-p97-LPSTG-xx (SEQ ID NO: 166) was generated by introducing two point mutations (G782L and Q785T) and a stop codon at position 791 using QuickChange® mutagenesis (Stratagene). Recombinant p97 was expressed at 30° C. in *E. coli* after induction for 3 h with 0.5 mM isopropyl 1-thio-β-D-galactopyranoside. Cells were resuspended in buffer A (50 Tris, pH 8.0, 300 mM NaCl, 5% glycerol, 20 mM imidazole, and 7.1 mM β-mercaptoethanol), adjusted to 15 µg/ml lysozyme and 10 µg/ml DNase I, and lysed by two passes through a French pressure cell at 1200 p.s.i. After centrifugation for 30 min at 40,000×g, the supernatant was bound to nickel-Sepharose resin (GE Healthcare). After washing the resin with 20 column volumes of buffer A, p97 was eluted with buffer A containing 250 mM imidazole. Hexameric rings of p97 were further purified on a Superdex 200 HR 16/60 column (GE Healthcare) using 25 mM Tris, pH 8.0, 150 mM KCl, 2.5 mM MgCl$_2$, 5% glycerol as the mobile phase. The purified protein was snap-frozen and stored at −80° C.

Circularization and Intermolecular Transpeptidation

Transpeptidation reactions were performed by combining the necessary proteins/reagents at the specified concentrations in the presence of sortase reaction buffer (50 mM Tris, pH 7.5, 150 mM NaCl, 10 mM CaCl$_2$) and incubating at 37° C. for the times indicated. Diglycine and triglycine (GGG) peptides were purchased from Sigma. Reactions were halted by the addition of reducing Laemmli sample buffer and analyzed by SDS-PAGE. Gels were visualized by staining with Coomassie Blue. Fluorescence was visualized on a Typhoon 9200 Imager (GE Healthcare). Crude reactions were also diluted into either 0.1% formic acid or water for ESI-MS analysis. ESI-MS was performed on a Micromass LCT mass spectrometer (Micromass® MS Technologies) and a Paradigm MG4 HPLC system equipped with an HTC PAL autosampler (Michrom BioResources) and a Waters symmetry 5-µm C8 column (2.1×50 mm, MeCN:H$_2$O (0.1% formic acid) gradient mobile phase, 150 µl/min).

Purification and Refolding of eGFP

G$_5$-eGFP-LPETG-His$_6$ (SEQ ID NO: 165) (50 µM) was circularized by treatment with sortase A (50 µM) in sortase reaction buffer (50 Tris, pH 7.5, 150 mM NaCl, 10 mM CaCl$_2$) for 24 h at 37° C. The reaction was run on a 750-µl scale. The entire reaction was then diluted into 10 ml of 20 mM Tris, 500 mM NaCl, and 20 mm imidazole, pH 8.0. This solution was then applied to a column consisting of 2 ml of Ni-NTA-agarose (Qiagen) pre-equilibrated with 20 mM Tris, 500 mM NaCl, and 20 mM imidazole, pH 8.0. The flow-through was then concentrated and buffer exchanged in 20 mM Tris, 150 mM NaCl, pH 8.0, using a NAP™ 5 Sephadex™ column (GE Healthcare). The concentrations of circular eGFP and linear G$_5$-eGFP-LPETG-His$_6$ (SEQ ID NO: 165) were estimated by UV-visible spectroscopy using the absorbance of eGFP at 488 nm (extinction coefficient 55,900 M$^{-1}$ cm$^{-1}$) (26). Circular and linear eGFP (40 µl of 18 µm solutions) was placed in 1.5-ml microcentrifuge tubes and denatured by heating to 90° C. for 5 min. Samples were then incubated at room temperature in the dark for the times indicated. Fluorescent images were acquired using a UV gel documentation system (UVP Laboratory Products).

Reaction of Cyclic UCHL3 with Activity-based Ubiquitin Probe

UCHL3 (30 µM) was incubated with sortase A (150 µm) in sortase reaction buffer (50 mM Tris, pH 7.5, 150 mM NaCl, 10 mM CaCl$_2$) in the presence or absence of 90 mM GGG peptide (Sigma) on a 25-µl scale at 37° C. for 3 h. Ten microliters was withdrawn and diluted with 10 µl of labeling buffer (100 mM Tris, pH 7.5, 150 mM NaCl). Hemagglutinin epitope-tagged ubiquitin vinyl methyl ester (4 µg) was added as well as 1 mM dithiothreitol and incubated at room temperature for 1 h. Reactions were then separated on an SDS-polyacrylamide gel and visualized by Coomassie staining or α-HA immunoblot (supplemental Fig. S4). Hemagglutinin epitope-tagged ubiquitin vinyl methyl ester was prepared following published protocols (27).

MS/MS Sequencing of Proteolytic Fragments from Circular Proteins

Prior to MS/MS analysis, circular eGFP and Cre were separated from sortase A by RP-HPLC using an Agilent 1100 Series HPLC system equipped with a Waters Delta Pak 5 μm, 100 Å C18 column (3.9×150 mm, MeCN:H$_2$O gradient mobile phase containing 0.1% trifluoroacetic acid, 1 ml/min). Fractions containing the circular proteins were pooled and subjected to trypsin digestion. Crude transpeptidation reactions containing circular UCHL3 were separated by SDS-PAGE followed by Coomassie staining. The band corresponding to circular UCHL3 was excised and digested with Glu-C. Crude transpeptidation reactions containing dimeric p97 were separated by SDS-PAGE followed by Coomassie staining. The transpeptidation reaction used for this purpose was incubated for only 2 h and therefore contains less oligomerization than that seen after an overnight incubation (see supplemental Fig. S6). The band corresponding to dimeric p97 was excised and digested with chymotrypsin. For all protein substrates, the peptides generated from proteolytic digestion were extracted and concentrated for analysis by RP-HPLC and tandem mass spectrometry. RP-HPLC was carried out on a Waters NanoAcquity HPLC system with a flow rate of 250 nl/min and mobile phases of 0.1% formic acid in water and 0.1% formic acid in acetonitrile. The gradient used was isocratic 1% acetonitrile for 1 min followed by 2% acetonitrile per min to 40% acetonitrile. The analytical column was 0.075 μm×10 cm with the tip pulled to 0.005 μm and self-packed with 3 μm Jupiter C18 (Phenomenex). The column was interfaced to a Thermo LTQ linear ion trap mass spectrometer in a nanospray configuration, and data were collected in full scan mode followed by MS/MS analysis in a data-dependent manner. The mass spectral data were data base searched using SEQUEST.

Construction of Molecular Models

Molecular models were generated from published crystal structures (PDB codes 1kbu, 1gfl, 1xd3, and 3cf1) (28-31). N- and C-terminal residues were added using Coot 0.5 (32). Protein termini were repositioned using the Auto Sculpting function in MacPyMOL (DeLano Scientific LLC). Residues visible in the published crystal structures were not moved during positioning of the extended N and C termini. All protein images in this study were generated using MacPyMOL.

Results

Cre Recombinase.

Figure 26A:
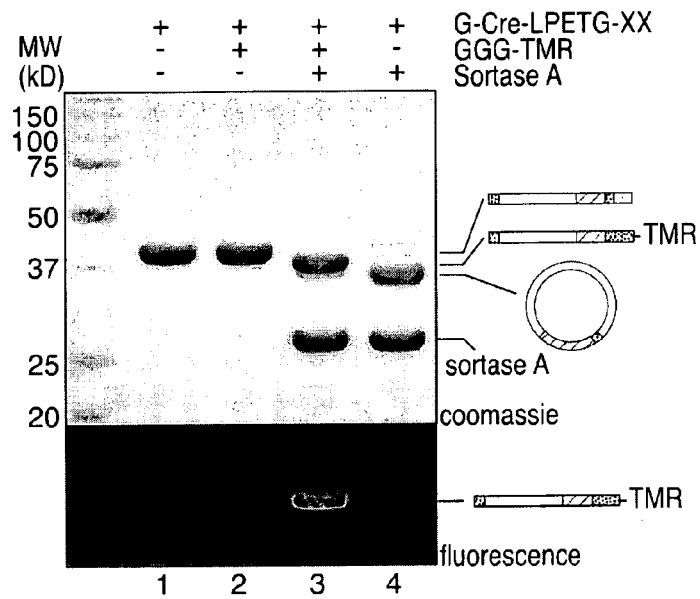
FIG. 26 illustrates cyclization of Cre recombinase. A, G-Cre-LPETG-His6 (SEQ ID NO: 51, 50 μm) was incubated with sortase A (50 μm) in the presence or absence of fluorescent GGG-TMR (10 mm) in sortase reaction buffer (50 mm Tris, pH 7.5, 150 mm NaCl, 10 mm CaCl2) for 21.5 h at 37° C. SDS-PAGE revealed the expected C-terminal transpeptidation product when GGG-TMR was included, whereas omission of the triglycine nucleophile resulted in clean conversion to a unique protein species with a lower apparent molecular weight. Schematic representations to the right of the gel indicate the topology of the protein species produced by transpeptidation. B, ESI-MS of linear G-Cre-LPETG-His6 (SEQ ID NO: 51) and circular Cre formed by intramolecular transpeptidation. C, MS/MS spectrum of a tryptic fragment of circular Cre showing the ligation of the N-terminal residues (GEFAPK, SEQ ID NO: 52) to the C-terminal LPET (SEQ ID NO: 53) motif. Expected masses for y and b ions are listed above and below the peptide sequence. Ions that were positively identified in the MS/MS spectrum are highlighted in blue or red. Only the most prominent daughter ions have been labeled in the MS/MS spectrum. LPETG-XX—SEQ ID NO: 192.
Figure 26B:
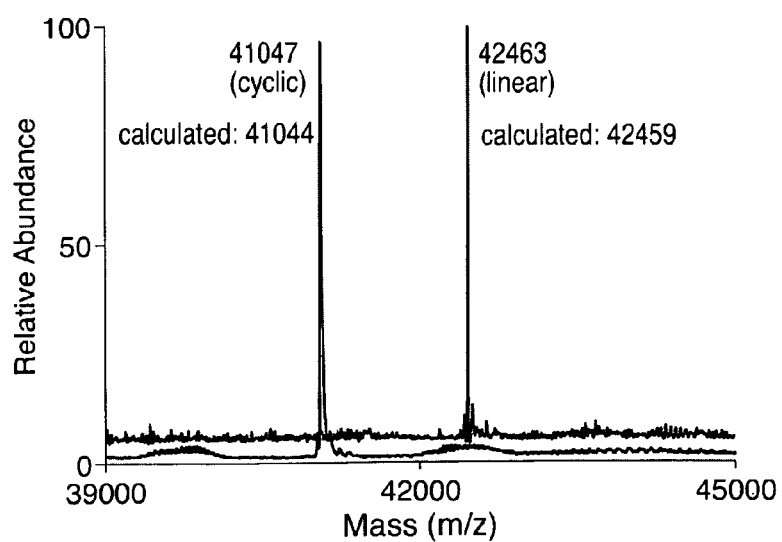
Figure 26C:
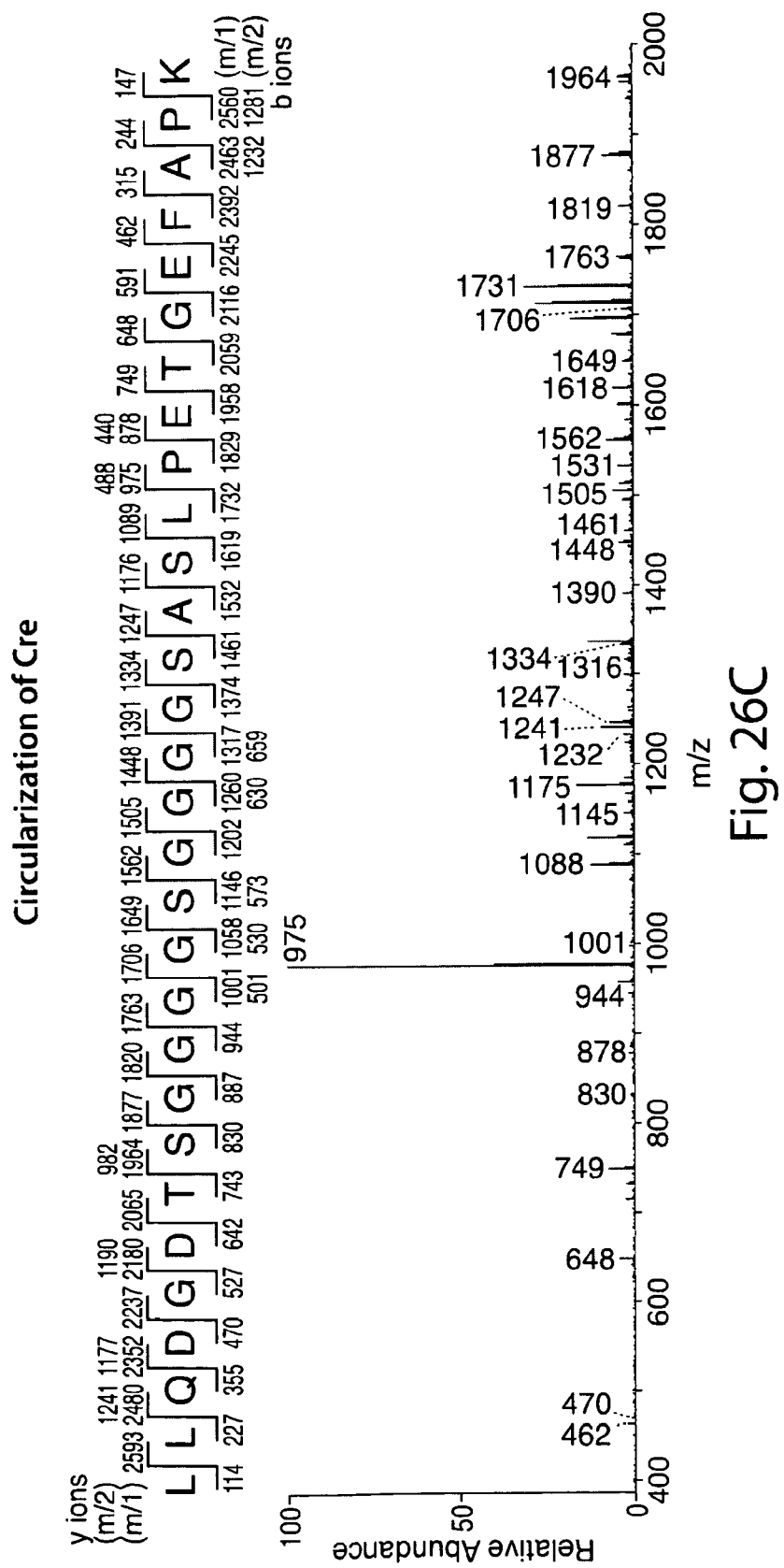
Figure 27A:
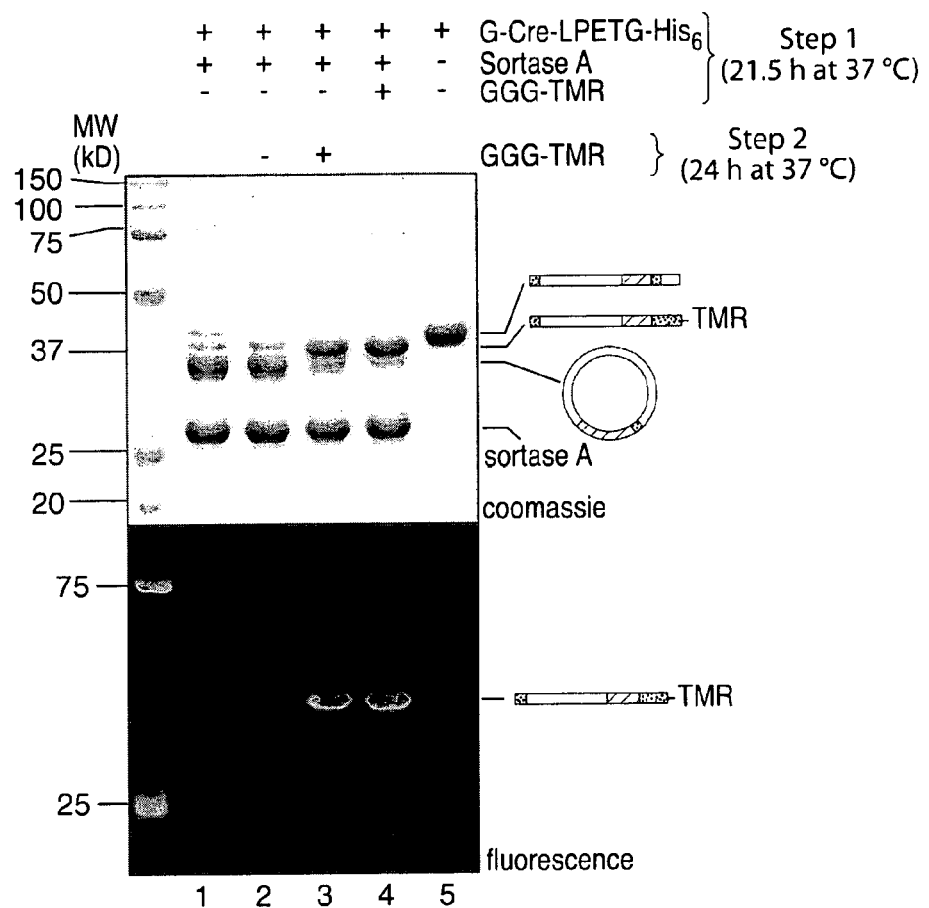
FIG. 27. Cyclization of Cre is reversible. A, G-Cre-LPETG-His6 (SEQ ID NO: 51, 50 μm) was circularized by treatment with sortase A (50 μm) in sortase reaction buffer (50 mm Tris, pH 7.5, 150 mm NaCl, 10 mm CaCl2) for 21.5 h at 37° C. (lane 1). This reaction mixture was then treated with 10 mm GGG-TMR (lane 3) or simply incubated for an additional 24 h at 37° C. (lane 2). All reactions were analyzed by SDS-PAGE with visualization by Coomassie staining or in-gel fluorescence. For comparison, a C-terminal labeling reaction performed using 10 mm GGG-TMR without prior cyclization of the Cre substrate (lane 4) and a sample of linear G-Cre-LPETG-His6 (SEQ ID NO: 51) incubated without sortase A or nucleophile (lane 5) are included. B, molecular model of Cre recombinase monomer (generated from PDB code 1kbu) (29) showing the proximity relationship between the N and C termini. The N-terminal glycine residue is highlighted in red, and the C-terminal LPET (SEQ ID NO: 53) residues are shown in green.
Figure 27B:
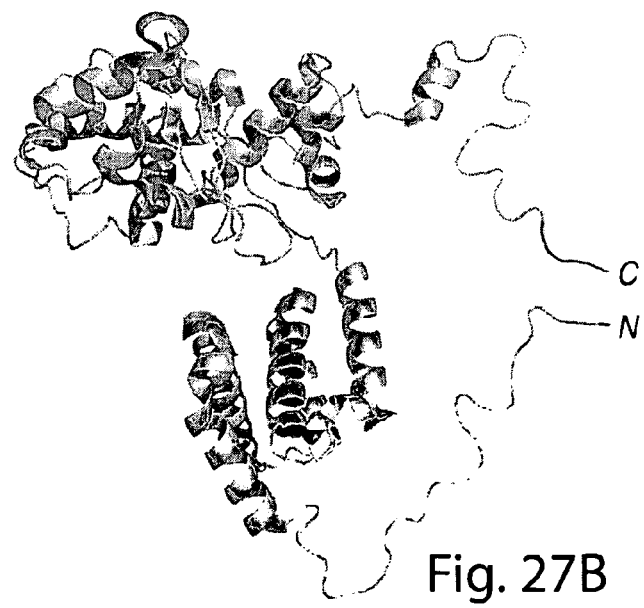

We first noticed the presence of a circular protein product when installing a C-terminal modification onto a nonfunctional mutant of Cre recombinase containing a single N-terminal glycine residue and an LPETG (SEQ ID NO: 55) sequence near the C terminus. The LPETG (SEQ ID NO: 55) motif was separated from the native protein by a flexible amino acid linker (GGGGSGGGGS (SEQ ID NO: 167)). Whereas installation of the label at the Cre C terminus proceeded efficiently when a triglycine nucleophile containing tetramethylrhodamine (GGG-TMR) was included, we observed a product that migrated more rapidly on SDS-PAGE when nucleophile was omitted from the reaction mixture (FIG. 26). Hydrolysis of the sortase acyl enzyme is known to proceed slowly in the absence of glycine nucleophiles (19, 33, 34). However, when reaction mixtures were analyzed by ESI-MS, we consistently observed a protein species that differed from the mass expected for hydrolysis by approximately −18 Da (FIG. 2B). This mass was consistent with intramolecular nucleophilic attack, suggesting that the single N-terminal glycine residue was serving as the nucleophile in this transformation. Ultimately, MS/MS on tryptic digests of this species showed unequivocally that it consisted of a covalently closed circular product of Cre, with the N-terminal glycine fused exactly at the LPETG (SEQ ID NO: 55) cleavage site in the expected position (FIG. 26C). Recognizing that the LPETG (SEQ ID NO: 55) motif is maintained in the cyclized Cre product, we suspected that sortase should be capable of cleaving the circular protein at this site, thus producing an equilibrium between circular and linear forms of Cre. To demonstrate this point, Cre was first incubated with sortase in the presence or absence of triglycine nucleophile (FIG. 27A). A portion of the cyclized reaction mixture (FIG. 27A, lane 1) was then treated with a large molar excess of triglycine nucleophile or left alone for a further 24 h (FIG. 27A, lanes 2 and 3). Remarkably, upon treatment with exogenous nucleophile, the pre-cyclized material yielded a reaction mixture that was nearly identical to the result obtained when nucleophile was included from the very beginning of the experiment (FIG. 27A, compare lanes 3 and 4). This result provided further evidence that cyclized Cre indeed contains the expected LPETG (SEQ ID NO: 55) motif at the site of covalent closure. In addition, it suggested that hydrolysis of the acyl enzyme intermediate does not effectively compete during cyclization, because the hydrolyzed material should be unable to participate in the transpeptidation reaction. The circularization reaction observed for Cre proceeded with remarkable efficiency. Conversion was estimated to be >90% by SDS-PAGE. By taking an existing crystal structure (29) of the Cre protein and modeling in those residues not visible in the structure, it was clear that the N and C termini were located in sufficiently close proximity to permit closure without significant perturbation of the native structure (FIG. 27B). We assume that these regions possess considerable flexibility because they are not resolved in the crystal structure.

eGFP.

Figure 28A:
FIG. 28. Circularization of eGFP. A, molecular model of eGFP (generated from PDB code 1gfl) (31) showing the proximity relationship between the N and C termini. The N-terminal glycine residue is highlighted in red, and the C-terminal LPET (SEQ ID NO: 53) residues are shown in green. B, G5-eGFP-LPETG-His6 (SEQ ID NO: 54, 50 μm) was circularized by treatment with sortase A (50 μm) in sortase reaction buffer (50 mm Tris, pH 7.5, 150 mm NaCl, 10 mm CaCl2) for 24 h at 37° C. Schematic representations to the right of the gel indicate the topology of the protein species produced by transpeptidation. C, circular eGFP (C) recovers fluorescence more rapidly than linear G5-eGFP-LPETG-His6 (SEQ ID NO: 54, L) following thermal denaturation for 5 min at 90° C. SDS-PAGE analysis confirmed the purity and concentration of the circular eGFP (C) and linear G5-eGFP-LPETG-His6 (SEQ ID NO: 54, L) samples used for refolding.

Having verified the cyclization of Cre recombinase, we sought to explore the generality of this technique. To this end we generated a derivative of eGFP containing the LPETG (SEQ ID NO: 55) sequence and five N-terminal glycine residues. This construct was of particular interest because inspection of the x-ray crystal structure (31) revealed that the N and C termini were positioned on the same end of the β-barrel, suggesting that this substrate should be ideal for cyclization (FIG. 28A). Furthermore, in one of the earliest reports on the use of sortase for protein engineering, a similar eGFP substrate was described and reported to cyclize in the presence of sortase (16). In this instance, cyclization only proceeded in modest yield, and the putative cyclized product was produced as a mixture with higher molecular weight species assigned as oligomers of eGFP formed by intermolecular transpeptidation. Thus, to explore potential complications caused by intermolecular reactions, we studied the reaction of our eGFP construct in the presence of sortase.

Figure 28B:
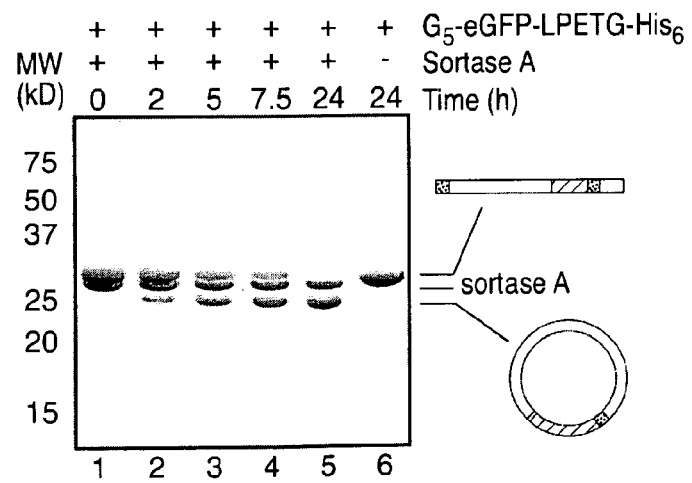

In our hands, we observed clean conversion to a lower molecular weight species (>90% estimated conversion) with little to no evidence for oligomerization (FIG. 28B). A higher molecular weight polypeptide was observed at early time points and may represent a covalent eGFP dimer that is generated transiently over the course of the reaction. Higher molecular species, however, were only observed in trace quantities in the final reaction mixture. As in the case of Cre, evidence for circularization was provided by mass spectral characterization of the intact circular protein and MS/MS sequencing of tryptic peptides (supplemental Fig. S1). As an additional control to demonstrate that the N-terminal glycine residue was the only nucleophile participating in intramolecular transpeptidation, we analyzed the behavior of an eGFP derivative that lacked an N-terminal glycine. In this case, ESI-MS revealed products consistent with hydrolysis of the acyl enzyme intermediate, rather than intramolecular nucleophilic attack (supplemental Fig. S1).

Figure 28C:
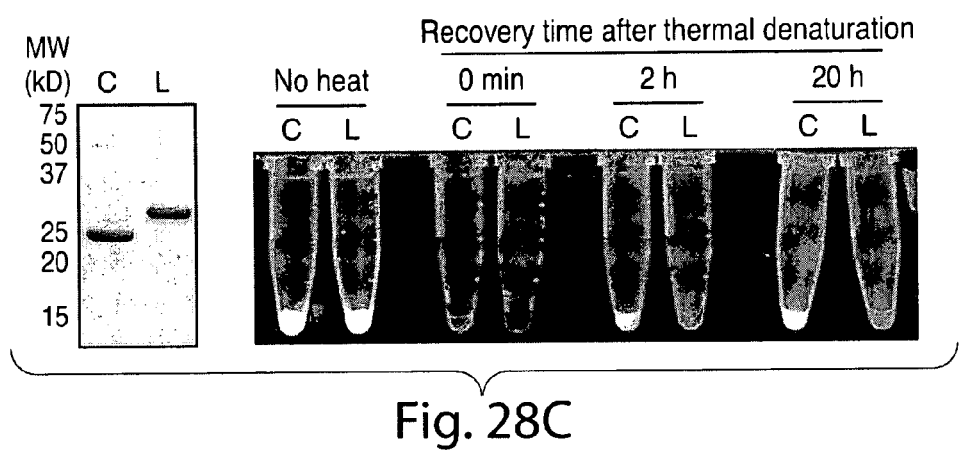

Circularization has been shown to confer unique properties onto proteins when compared with the linear form (35-37). In the case of GFP circularized using intein-based methods, these properties include a reduced rate of unfolding when exposed to denaturants, as well as an enhanced rate of refolding following denaturation (35). We observed a similar phenomenon for eGFP circularized using sortase (FIG. 28C). Circular eGFP was first separated from residual sortase A using Ni-NTA resin. This material retained fluorescence suggesting that covalent ligation of the N and C termini had minimal impact on the structure of this substrate. Circular and linear eGFP were then subjected to simple thermal denaturation, followed by recovery at room temperature. As shown in FIG. 28C, circular eGFP regained fluorescence more rapidly than linear eGFP.

UCHL3.

Figure 29A:
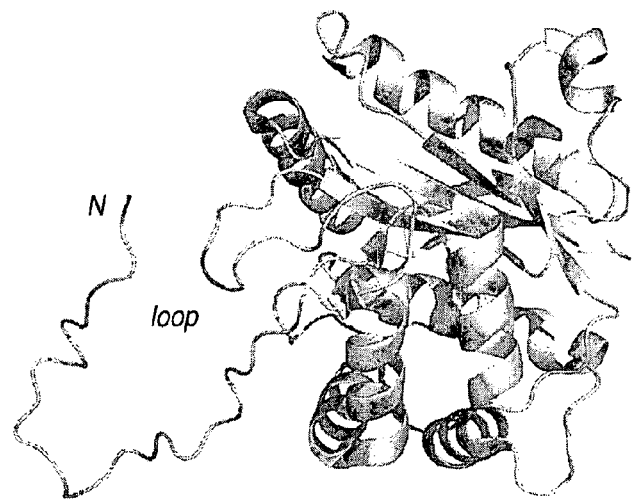
FIG. 29. UCHL3 with an internally positioned LPETG (SEQ ID NO: 55) motif is circularized by sortase A. A, molecular model of human UCHL3 (generated from PDB code 1xd3) (30) showing the active site crossover loop bearing an LPETG (SEQ ID NO: 55) substitution (LPET (SEQ ID NO: 53) residues shown in green and Gly residue shown in red). The N-terminal glycine residue that serves as the nucleophile for intramolecular transpeptidation is highlighted in red. B, UCHL3 (30 μm) bearing an LPETG (SEQ ID NO: 55) substitution in the active site crossover loop was incubated with sortase A (150 μm) in the absence or presence of GGG nucleophile (90 mm) in sortase reaction buffer (50 mm Tris, pH 7.5, 150 mm NaCl, 10 mm CaCl2) for the indicated times at 37° C. and analyzed by SDS-PAGE, followed by Coomassie staining. Schematic representations to the right of the gel indicate the topology of the protein species produced by transpeptidation. LPETG-XX—SEQ ID NO: 193; His6—SEQ ID NO: 174.

Even an internally positioned LPXTG (SEQ ID NO: 45) motif was sufficient to effectuate a circularization reaction. We installed a sortase recognition site in the crossover loop of the ubiquitin C-terminal hydrolase UCHL3, and we demonstrated that the continuity of the polypeptide backbone can be disrupted with concomitant installation of a covalent modification that reports on the accuracy of cleavage and transpeptidation (25). This reaction proceeds without complete loss of activity of UCHL3, indicating that even the cleaved form of UCHL3 retains its structural integrity to a significant degree (25). This UCHL3 construct was prepared with an N-terminal glycine residue, and examination of the crystal structure of UCHL3 (30) clearly showed the close apposition of the N terminus and the crossover loop, suggesting that cyclization to yield a circular fragment containing the N-terminal portion of UCHL3 should be readily observable (FIG. 29A).

Figure 29B:
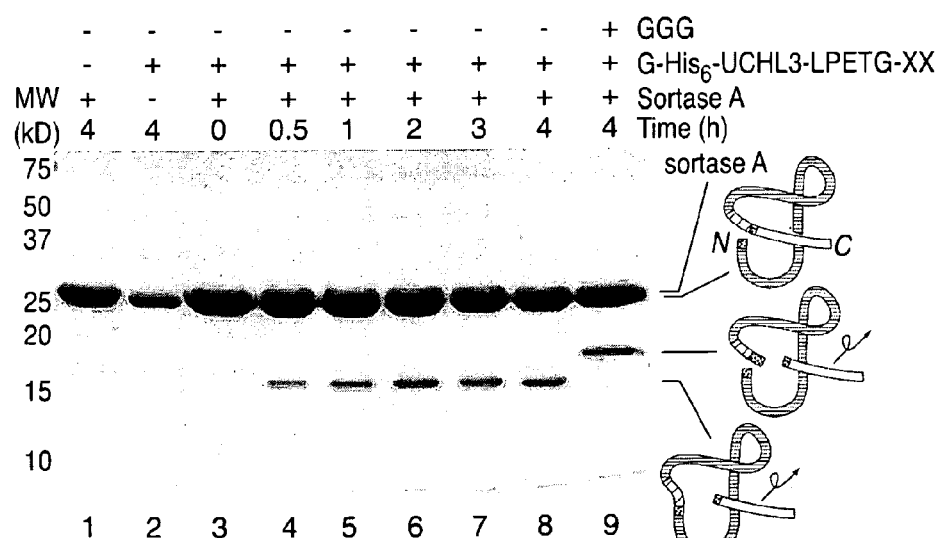

As expected, in the absence of added nucleophile, the N-terminal glycine serves as a highly efficient nucleophile to yield a circular fragment that contains the N-terminal portion of UCHL3 (FIG. 29B). The identity of the circular polypeptide was confirmed by MS/MS of the peptide containing the expected fusion of the N-terminal glycine residue with the new C terminus released from the crossover loop (see supplemental Fig. S2). Cyclization was efficiently blocked if a high concentration of triglycine (GGG) was included in the reaction, generating instead the N-terminal fragment of UCHL3 transacylated onto the triglycine nucleophile (FIG. 29B, lane 9, and supplemental Fig. S3). Cyclization could also be reversed by adding an excess of triglycine to reaction mixtures preincubated with sortase to allow cyclization. This reopening reaction was observed by both SDS-PAGE and ESI-MS (supplemental Fig. S3).

To test the functional properties of cyclic UCHL3, we incubated reaction mixtures with an activity-based probe consisting of ubiquitin equipped with an electrophilic vinyl methyl ester moiety at the C terminus (supplemental Fig. S4). Probes of this nature are able to specifically alkylate active site cysteine residues in ubiquitin-specific hydrolases such as UCHL3 (25, 27, 38). Following circularization, the active site cysteine (Cys-95) of UCHL3 is located in the circular N-terminal fragment, and indeed we observed covalent labeling of this fragment with a corresponding shift in apparent molecular weight consistent with the attachment of ubiquitin. This result suggests that despite cleavage of the polypeptide backbone, the circular N-terminal fragment of UCHL3 and the C-terminal portion released during transpeptidation remain associated and preserve the affinity of UCHL3 for ubiquitin. This result is consistent with previous observations from our laboratory demonstrating that covalent closure of the UCHL3 crossover loop is dispensable for enzyme activity (25).

p97.

Figure 30A:
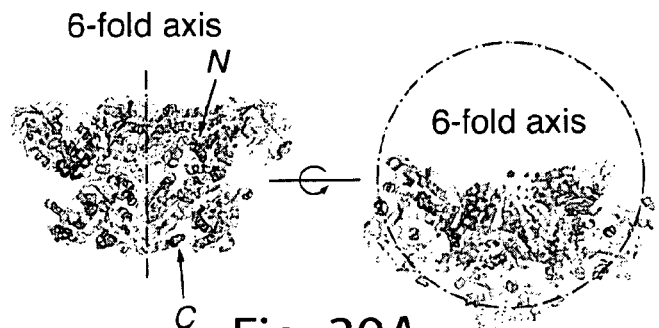
FIG. 30. Positions of the N and C termini in the p97 hexamer are suitable for intermolecular cross-linking through sortase-catalyzed transpeptidation. A, molecular model of p97 trimer (generated from PDB code 3cf1) (28) showing the relative position of p97 monomers in the hexameric ring. The visible N and C termini from the published p97 trimer structure are indicated in red and green, respectively. B, molecular model of G-His6-p97-LPSTG-XX (SEQ ID NO: 56) showing the proximity relationship between N and C termini in adjacent p97 monomers. N- and C-terminal residues not visible in the published crystal structure have been modeled onto the existing structure. N-terminal glycine residues are shown in red, and the C-terminal LPST (SEQ ID NO: 57) residues are shown in green. For clarity, the C-terminal domains of the outer monomers are hidden, as is the N-terminal domain of the central monomer. C, G-His6-p97-LPSTG-XX (SEQ ID NO: 56, 1.5 mg/ml) was incubated with sortase A (30 μm) in sortase reaction buffer (50 mm Tris, pH 7.5, 150 mm NaCl, 10 mm CaCl2) for the times indicated at 37° C. After 22 h, diglycine (GG) was added (100 mm final concentration), resulting in disappearance of the covalent oligomers (lane 5). For comparison, a control reaction containing 100 mm diglycine peptide from the outset of the experiment is shown in lane 6.
Figure 30B:
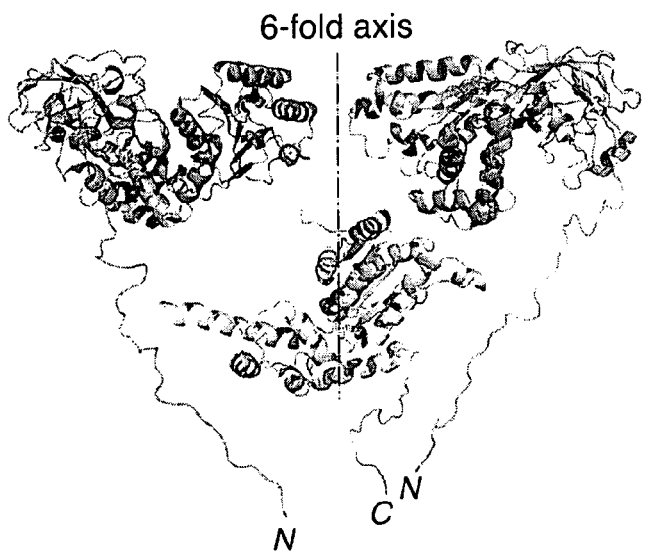
Figure 30C:
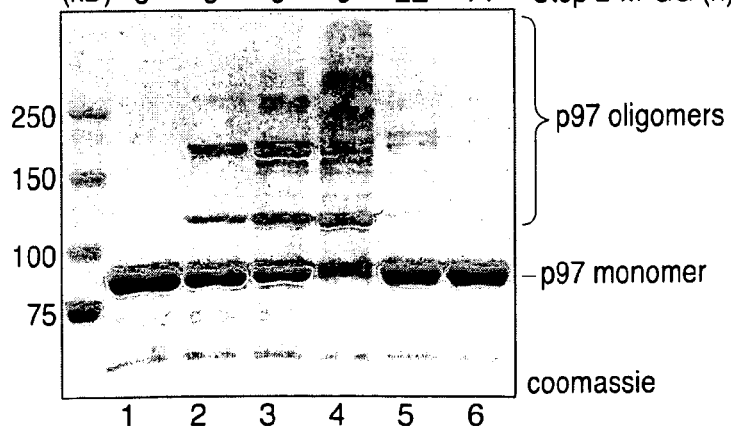
Figure 31:
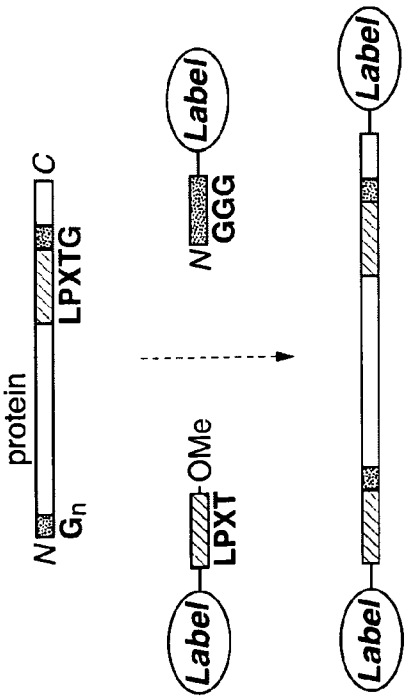
FIG. 31. Overview of orthogonal labeling strategies using multiple sortases with distinct recognition motifs (recognition motifs described in Pallen, M. J.; Lam, A. C.; Antonio, M.; Dunbar, K. Trends in Microbiology 2001, 9(3), 97-101). LPXTG—SEQ ID NO: 194; NPQTN—SEQ ID NO: 195; NPKTG—SEQ ID NO: 196; LAXTG—SEQ ID NO: 197; LPXTG—SEQ ID NO: 198.

The examples described above in this Example concern single chain proteins whose termini are sufficiently close to allow covalent closure by means of the sortase-mediated transacylation reaction. Similar proximity relationships between protein termini should also be present on separate polypeptides that assemble into defined oligomeric structures. As an example, we examined p97, a hexameric AAA-ATPase. We generated a derivative of p97 (G-His$_6$-p97-LPSTG-XX (SEQ ID NO: 166)) containing an LPSTG (SEQ ID NO: 168) motif near the C terminus, and a hexahistidine tag capped by two serine residues and a single glycine at the N terminus. The structure of a p97 trimer in the presence of ADP has been solved at 3.5 Å resolution (28), with several residues from the N and C termini not visible (FIG. 30A). When all the residues present in our modified version of p97 were modeled onto the published trimer of p97, it was evident that the N and C termini of adjacent p97 units were sufficiently close to permit covalent cross-linking (FIG. 30B). G-His$_6$-p97-LPSTG-XX (SEQ ID NO: 166) was expressed in *E. coli* and yielded the hexameric p97 ring, as assessed by gel filtration. As expected, this derivative of p97 was an excellent substrate for transpeptidation at its C terminus, allowing efficient installation of a label when incubated in the presence of sortase and GGG-TMR (supplemental Fig. S5). In contrast, a variant of p97 lacking the LPSTG (SEQ ID NO: 168) sequence showed no labeling (supplemental Fig. S5). When G-His$_6$-p97-LPSTG-XX (SEQ ID NO: 166) was treated with sortase A in the absence of added nucleophile, we observed formation of an SDS-resistant ladder of polypeptides, as would be expected for intermolecular cross-linking of p97 monomers (FIG. 30C). We were confident that these species arise from head-to-tail ligation of p97 because introduction of excess diglycine peptide after oligomerization caused collapse of the higher molecular weight structures back to monomeric p97 (FIG. 30C, lane 5). This suggested that the higher order aggregates are held together by newly formed LPSTG units formed from the C-terminal LPST (SEQ ID NO: 169) residues of one p97 monomer and the N-terminal glycine residue of a neighboring monomer. The banding pattern observed for reopening was also nearly identical to that seen when diglycine was included from the very beginning of the experiment, a scenario where installation of diglycine at the C terminus of each p97 subunit is presumed to be the major reaction pathway (FIG. 30C, lane 6). We have also been able to identify peptides consistent with intermolecular cross-linking of p97 subunits by MS/MS (supplemental Fig. S6).

In this Example we have explored transpeptidation reactions using four structurally diverse protein substrates. Cyclization has been confirmed for three proteins, including an example (UCHL3) utilizing an LPXTG (SEQ ID NO: 55) sequence positioned in a flexible internal loop rather than near the C terminus of the protein. Cyclization and oligomerization via sortase-mediated transpeptidation have been previously suggested to occur for an eGFP construct modified in a manner similar to that used here (16), and for a by-product from a protein purification system where the substrate circularized appears to be sortase A itself (20). In both cases, the identity of the circular products was not rigorously confirmed. Our data identify the circular or oligomeric products unambiguously by MS/MS for all substrates studied. We also find that our eGFP derivative strongly favors cyclization over oligomerization, showing little evidence for the formation of higher order structures that might be expected by the head-to-tail ligation of termini from separate eGFP monomers. Subtle differences in the structure of the eGFP constructs cannot be overlooked as a potential cause for the observed results. For example, our eGFP is extended at the N terminus by only five glycine residues, whereas the construct studied by Parthasarathy et al. (16) contains an additional 17 residues, including 3 N-terminal glycines. Future work will be required to thoroughly characterize the effect of distance relationships between protein termini on favoring intra-versus intermolecular transpeptidation.

With respect to protein cyclization, sortase-mediated circularization is efficient despite the potential for competing reaction pathways. In the absence of added oligoglycine nucleophile, these include hydrolysis of the acyl enzyme intermediate, reattachment of the C-terminal protein fragment that is lost upon initial cleavage of the protein substrate by sortase, or, as mentioned above, oligomerization of protein monomers in head-to-tail fashion. Even when oligoglycine nucleophile is added with the intent of blocking the cyclization pathway, millimolar concentrations are necessary to efficiently compete with cyclization. One factor that certainly must contribute to this observed preference for cyclization is the distance between protein termini. Inspection of the data base of PDB shows that nearly one-third of proteins with known structures have their termini in rather close apposition (within 20 Å) (40). The LPXTG (SEQ ID NO: 45) sequence itself spans roughly 15 Å in an extended conformation, suggesting that circularization via sortase-catalyzed transpeptidation might be amenable to a significant fraction of proteins using the LPXTG (SEQ ID NO: 45) sequence alone to bridge the gap between N and C termini. Larger distances could simply be covered by inserting flexible amino acid spacers at either termini. We also consider it likely that the circularized version of a protein will show more restricted mobility in the segment that corresponds to the newly established LPXTG (SEQ ID NO: 45) connection between its termini. This fact alone may render the circular product a comparatively worse substrate for sortase and therefore assist in driving the transpeptidation reaction toward cyclization. As evidence for this point, we have observed previously that sortase fails to cleave LPXTG (SEQ ID NO: 45) motifs placed in structured loops of class I major histocompatibility complex molecules (14).

The sortase-catalyzed approach also provides additional levels of control over the ensuing transpeptidation reaction. This may be particularly useful for oligomeric species, such as the p97 example described here. Specifically, our modified p97 protein (G-His$_6$-p97-LPSTG-xx (SEQ ID NO: 166)) is produced in a form that is by itself unreactive. This allows protein expression and the subsequent assembly and purification of the hexamer to be completed first, without complications caused by premature covalent oligomerization. Cross-linking is then induced by the addition of sortase after the individual subunits have been correctly positioned in the hexameric ring. The extent of transpeptidation can be further controlled by inclusion of synthetic oligoglycine nucleophiles, either during the transpeptidation reaction or after transpeptidation is complete. The latter scenario even allows cyclization to be completely reversed. Incubating circular protein products with sortase in the presence of an oligoglycine nucleophile restores linearity to the protein product, because in the course of the initial cyclization reaction, the LPxTG (SEQ ID NO: 45) motif is restored. An equilibrium between closed and open forms is thus established and can be driven toward the linear state by adding a large excess of the oligoglycine nucleophile.

Example 4

Dual Modification Using Distinct Sortases

Materials and Methods.
SrtAstrep.
The expression plasmid for SrtAstrep (residues 82-249) including an N-terminal His$_6$ (SEQ ID NO: 174) tag has been described.[3] The construct was transformed into *E. coli* BL-21. Cells were grown in 2 L of sterile LB containing kanamycin (30 µg/mL) to an optical density of ~0.7 at 600 nm. Cells were induced with IPTG (1 mM) for 3 h at 37° C. Cells were harvested by centrifugation and the pellet was stored overnight at −20° C. The pellet was thawed and resuspended in 70 mL of 50 mM Tris pH 8.0, 150 mM NaCl, 20 mM imidazole and 10% glycerol. Cells were then treated with 300 L of DNAse I (10 mg/mL in PBS), 500 L of lysozyme (50 mg/mL in PBS), and 10 L of MgCl2 (1 M in PBS). The lysis reaction was incubated for 1 h at 4° C. The cells were then sonicated and centrifuged to remove insoluble material. The clarified lysate was then applied to a Ni-NTA column consisting of 5.0 mL of commercial Ni-NTA slurry (Qiagen) equilibrated with 50 mM Tris pH 8.0, 150 mM NaCl, 20 mM imidazole, and 10% glycerol. The column was washed with 80 mL of 50 mM Tris pH 8.0, 150 mM NaCl, 20 mM imidazole, and 10% glycerol. Protein was eluted with five 5 mL portions of 50 mM Tris pH 8.0, 150 mM NaCl, 300 mM imidazole, and 10% glycerol. Fractions containing SrtAstrep were pooled and further purified by size exclusion chromatography on a HiLoad 16/60 Superdex 75 column (Amersham), eluting with 20 mM Tris pH 8.0, 150 mM NaCl at a flow rate of 1 mL/min. Fractions containing SrtAstrep were pooled and subjected to a second round of Ni-affinity chromatography. Purified SrtAstrep was then dialyzed against 50 mM Tris pH 8.0, 150 mM NaCl, and 10% glycerol. These solutions were stored at −80° C. until further use. Protein concentration was estimated by Bradford assay.

SrtAstaph.
Recombinant SrtAstaph (residues 26-206) containing an N-terminal His$_6$ (SEQ ID NO: 174) tag was produced in *E. coli* as previously described.[4] SrtAstaph does not contain an N-terminal glycine residue (retains initiator methionine). Purified SrtAstaph was stored in 10% (w/v) glycerol, 50 mM Tris pH 8.0, 150 NaCl at −80° C. until further use. Protein concentration was estimated by Bradford assay.

Δ59-SrtAstaph.
Recombinant Δ59-SrtAstaph (residues 60-206) containing an N-terminal His$_6$ (SEQ ID NO: 174) tag was cloned into pET28a+. 59-SrtAstaph does not contain an N-terminal glycine residue (retains initiator methionine). Expression of Δ59-SrtAstaph was achieved following the protocol described above for SrtAstrep. Purification by size exclusion chromatography was not necessary because Δ59-SrtAstaph was sufficiently pure following Ni-affinity chromatography.

CtxB.
The template for construction of G1-CtxB, G3-CtxB, G5-CtxB (SEQ ID NO: 162), and AG4-CtxB (SEQ ID NO: 178) consisted of the B-subunit of cholera toxin fused at its N terminus to the signal peptide sequence of *E. coli* heat labile enterotoxin LTIIb.[5] This targets the expressed protein to the periplasm where the signal peptide is removed. Glycine and/or alanine residues were inserted between the signal sequence and CtxB via Quickchange® II Site-Directed Mutagenesis (Stratagene). Plasmids were transformed into *E. coli* BL21. Cells were grown in 1 L of sterile LB containing chloramphenicol (34 µg/mL) to an optical density of ~0.5-1.0 at 600 nm. Cells were induced with arabinose (0.25% w/v) for 3 h at 37° C. Cells were harvested by centrifugation and the pellet was stored overnight at −20° C. The pellet was thawed and resuspended in 30 mL of 50 mM Tris pH 8.0 and 300 mM NaCl. This suspension was then treated with 3 mL of polymixin B solution (5 mg/mL freshly made in water). This was mixture was gently stirred at room temperature for 1 h and then centrifuged. The clarified lysate was treated with 2.5 mL of Ni-NTA slurry (Qiagen). CtxB has a naturally affinity for Ni-NTA although it does not possess a $His_6$ (SEQ ID NO: 174) tag. The Ni-NTA mixture was incubated at 4° C. for 1 h and then poured into a fritted plastic column (Bio-Rad). The resin was washed with 40 mL of 50 mM Tris pH 8.0 and 300 mM NaCl. Protein was eluted with two 10 mL portions of 50 mM Tris pH 8.0, 300 mM NaCl, and 300 mM imidazole. Purified CtxB was buffer exchanged into 20 mM Tris pH 8.0 and 150 mM NaCl. Solutions were stored at 4° C. Protein concentration was estimated by Bradford assay.

G5-eGFP_(SEQ ID NO: 177) and Dual Labeling eGFP Substrate.

G5-eGFP (SEQ ID NO: 177) (containing a C-terminal $His_6$ (SEQ ID NO: 174) tag) and the eGFP dual labeling substrate (containing an N-terminal thrombin cleavage site and a C-terminal LPETG (SEQ ID NO: 55) motif followed by a $His_6$ (SEQ ID NO: 174) tag) and were prepared in pET28a+ (Novagen) using a Quickchange® II Site-Directed Mutagenesis Kit (Stratagene). The template plasmid used for mutagenesis has been described.[6] Plasmids were then transformed into *E. coli* BL-21. In a typical experiment, cells were grown in sterile LB containing kanamycin (30 µg/mL) to an optical density of ~0.6-0.9 at 600 nm. Cells were induced with IPTG (1 mM) for 3 h at 37° C. Cells were harvested by centrifugation and the pellet was stored overnight at −20° C. The pellet was thawed and resuspended in 20 mM Tris pH 8.0, 150 mM NaCl, 20 mM imidazole and 1% NP-40. The cell suspension was then lysed by French press and centrifuged. The clarified lysate was then applied to a Ni-NTA column consisting of 5.0 mL of commercial Ni-NTA slurry (Qiagen) equilibrated with 20 mM Tris pH 8.0, 150 mM NaCl, 20 mM imidazole and 1% NP-40. The column was washed with 40 mL of 20 mM Tris pH 8.0, 150 mM NaCl, 20 mM imidazole and 1% NP-40, followed by 40 mL of 20 mM Tris pH 8.0, 150 mM NaCl, and 20 mM imidazole. Protein was eluted with 20 mM Tris pH 8.0, 150 mM NaCl, and 300 mM imidazole until the characteristic green color was fully removed from the column. This material was concentrated and further purified by size exclusion chromatography on a HiLoad 16/60 Superdex 75 column (Amersham), eluting with 20 mM Tris pH 8.0, 150 mM NaCl at a flow rate of 1 mL/min. Fractions containing eGFP were pooled and subjected to a second round of Ni-affinity chromatography. Purified eGFP was then buffer exchanged into 20 mM Tris pH 8.0, 150 mM NaCl using a PD-10 Sephadex™ column (GE Healthcare), concentrated, and treated with glycerol (10% v/v final concentration). These solutions were stored at −80° C. until further use. Protein concentration was estimated by UV-vis spectroscopy using the absorbance of eGFP at 488 nm (extinction coefficient 55,900 $M^{-1}$ $cm^{-1}$).[7]

UCHL3 and Dual Labeling UCHL3 Substrate.

UCHL3 containing a single N-terminal glycine residue was produced in *E. coli* as described previously.[8] This construct (in pET28a+, Novagen) was then used to prepare the dual labeling UCHL3 substrate. Synthetic 5'-phosphorylated oligonucleotide duplexes containing appropriate sticky ends were designed to achieve insertion of an N-terminal thrombin site and a C-terminal LPETG (SEQ ID NO: 55) sequence separated from UCHL3 by a GGGGSGGGGS (SEQ ID NO: 167) spacer in two sequential cloning steps. Duplexes were annealed before ligation into the parent vector. The C-terminal insertion was performed first using the PstI and XhoI restriction sites. The result of using the XhoI site was the addition of a $His_6$ (SEQ ID NO: 174)-tag after the LPETG (SEQ ID NO: 55) sequence. The N-terminal insertion was then achieved using the XbaI and NdeI restriction sites. This plasmid was then transformed into *E. coli* BL21. Cells were grown in sterile LB containing kanamycin (30 µg/mL) to an optical density of ~0.6-0.9 at 600 nm.

Cells were induced with IPTG (1 mM) for 3 h at 37° C. Bacteria were then harvested by centrifugation and the pellet was stored overnight at −20° C. The pellet was thawed and resuspended in 20 mM Tris pH 8.0, 150 mM NaCl, 20 mM imidazole and 1% NP-40. The cell suspension was then lysed by French press and centrifuged. The clarified lysate was then applied to a Ni-NTA column consisting of 5.0 mL of commercial Ni-NTA slurry (Qiagen) equilibrated with 20 mM Tris pH 8.0, 150 mM NaCl, 20 mM imidazole and 1% NP-40. The column was washed with 40 mL of 20 mM Tris pH 8.0, 150 mM NaCl, 20 mM imidazole and 1% NP-40, followed by 40 mL of 20 mM Tris pH 8.0, 150 mM NaCl, and 20 mM imidazole. Protein was eluted with 20 mM Tris pH 8.0, 150 mM NaCl, and 300 mM imidazole. This material was then purified by anion-exchange chromatography on a Mono Q 5/50 GL column (Amersham) [Buffer A (50 mM Tris pH 7.5, 5 mM DTT, 0.5 mM EDTA), Buffer B (50 mM Tris pH 7.5, 5 mM DTT, 0.5 mM EDTA, 500 mM NaCl), 1.5 mL/min, gradient: 100% Buffer A (0-15 mL), 0% Buffer B→50% Buffer B (15-45 mL), 50% Buffer B (45-50 mL)]. Fractions containing UCHL3 were pooled and further purified by size exclusion chromatography on a HiLoad 16/60 Superdex 75 column (Amersham), eluting with 20 mM Tris pH 8.0, 150 mM NaCl at a flow rate of 1 mL/min. Fractions containing UCHL3 were pooled and subjected to a final purification step by anion-exchange chromatography on a Mono Q 5/50 GL column (Amersham) [Buffer A (50 mM phosphate pH 6.0), Buffer B (50 mM phosphate pH 6.0, 500 mM NaCl), 1.5 mL/min, gradient: 100% Buffer A (0-15 mL), 0% Buffer B→50% Buffer B (15-45 mL), 50% Buffer B (45-50 mL)]. The dual labeling UCHL3 substrate was buffer exchanged into 20 mM Tris pH 8.0, 150 NaCl and protein concentration was estimated by Bradford assay.

N-Terminal Labeling.

N-terminal transpeptidation reactions were performed by combining the necessary proteins/reagents at the specified concentrations in the presence of SrtAstaph or Δ59-SrtAstaph in sortase reaction buffer (50 mM Tris pH 7.5, 150 mM NaCl, 10 mM CaCl2) and incubating at 37° C. for the times indicated. Reactions were either diluted with 2× reducing Laemmli sample buffer for SDSPAGE analysis or diluted with water (~50 fold) for ESI-MS analysis. Gels were visualized by staining with coomassie blue. Fluorescence was visualized on a Typhoon 9200 Imager (GE Healthcare). For detection of biotinylation, proteins were separated by SDS-PAGE and transferred to a nitrocellulose membrane. The membrane was then probed with a streptavidin-horseradish peroxidase conjugate (GE Healthcare) and visualized by chemiluminescence. ESI-MS was performed on a Micromass LCT mass spectrometer (Micromass® MS Technologies, USA) and a Paradigm MG4 HPLC system equipped with a HTC PAL autosampler (Michrom BioResources, USA) and a Waters Symmetry 5 m C8 column (2.1×50 mm, MeCN:H$_2$O (0.1% formic acid) gradient mobile phase, 150 L/min).

Dual labeling of eGFP.

Immediately prior to starting the dual labeling sequence, the eGFP stock was thawed and again purified by affinity chromatography over commercial Ni-NTA resin. After binding eGFP to the resin, the column was washed with 20 mM Tris pH 8.0, 150 mM NaCl, and 20 mM imidazole. The protein was eluted with 20 mM Tris pH 8.0, 150 mM NaCl, and 300 mM imidazole. This material was buffer exchanged into 20 mM Tris pH 8.0, 150 mM NaCl using a NAP™ 5 Sephadex™ column (GE Healthcare) and concentrated. The concentration was estimated to be 84 M by UV-vis spectroscopy using eGFP absorbance at 488 nm (extinction coefficient 55,900 M$^{-1}$ cm$^{-1}$).[7]

C-Terminal Modification of eGFP with 3 and SrtAstrep.

400 L of the freshly purified eGFP solution was then treated with SrtAstrep (87 L of a 140 M stock solution) and 3 (4.9 L of a 100 mM stock solution) [Note: SrtAstrep does not require Ca$^{2+}$ for activity].[3] The reaction was incubated for 7 h at 37° C. ESIMS analysis of the crude reaction mixture revealed excellent conversion to the desired product (Supporting Figure S6a). The reaction was then treated with [2-(trimethylammonium)ethyl] methane thiosulfonate bromide (MTSET) (2.5 L of a 500 mM solution in 1:1 DMSO/H2O) for 10 min at room temperature to quench SrtAstrep. The entire reaction was then diluted with 5 mL of 20 mM Tris pH 8.0, 500 mM NaCl, and 20 mM imidazole. This solution was then passed over a 1.5 mL column of Ni-NTA that been equilibrated with 20 mM Tris pH 8.0, 500 mM NaCl, and 20 mM imidazole. The column was then washed with 1.5 mL of 20 mM Tris pH 8.0, 500 mM NaCl, and 20 mM imidazole. His6 (SEQ ID NO: 174)-tagged SrtAstrep was bound by Ni-NTA while the eGFP product (which lost its His6 (SEQ ID NO: 174) tag during the course of transpeptidation) was not retained. The eGFP solution was then concentrated and passed over a PD-10 Sephadex™ desalting column (equilibrated with 20 mM Tris pH 8.0, 150 mM NaCl) to remove excess 3. This material was concentrated to ~800 L and subjected to thrombin cleavage.

Thrombin cleavage of eGFP.

Figure 35A:
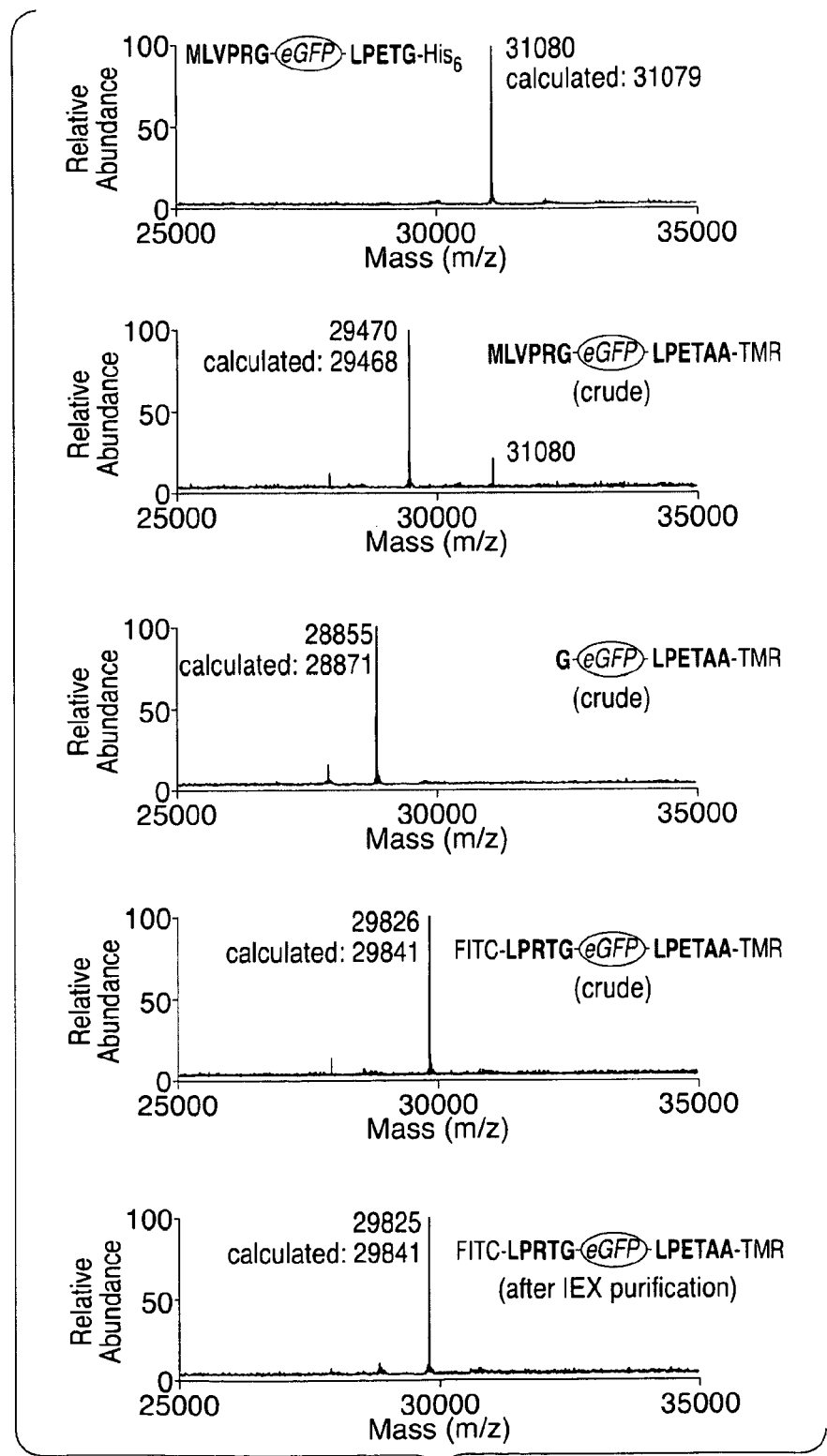
FIG. 35. Site-specific labeling at the N and C termini of eGFP and UCHL3. (a) ESI-MS spectra for all intermediates generated during the double labeling procedure. From top to bottom, this includes the eGFP starting material (m/z=31080 Da), the intermediate formed after C-terminal modification with 3 mediated by SrtAstrep (m/z=29470 Da), the product of thrombin cleavage (m/z=28855 Da), crude dual labeled eGFP (m/z=29726 Da), and dual labeled eGFP after anion exchange chromatography (m/z=29725 Da). (b) ESI-MS spectra for all intermediates generated during double labeling of UCHL3. From top to bottom, this includes the UCHL3 starting material (m/z=29252 Da), the intermediate formed after C-terminal modification with 3 mediated by SrtAstrep (m/z=29050 Da), the product of thrombin cleavage (m/z=28458 Da), crude dual labeled UCHL3 (m/z=29412 Da), and dual labeled UCHL3 after anion exchange chromatography (m/z=29412 Da). The MTSET reagent used to quench SrtAstrep also modifies the active site cysteine of UCHL3 creating an extra +118 Da signal in the mass spectrum. This modification is easily removed from the final product by brief treatment with DTT. MLVPRG—SEQ ID NO: 201; LPETG-His6—SEQ ID NO: 205; LPRTG—SEQ ID NO: 199; LPETAA—SEQ ID NO: 206.
Figure 35B:
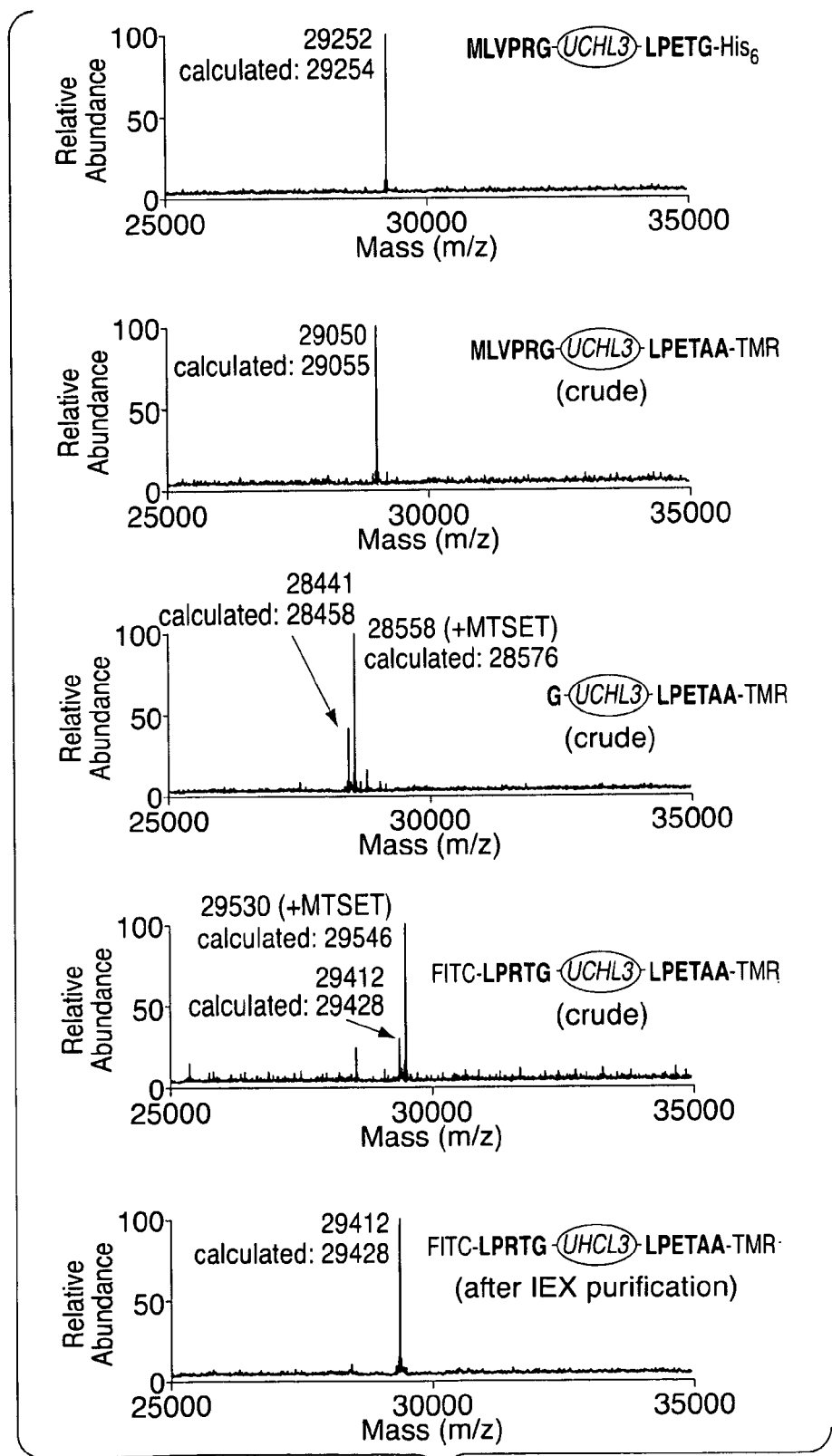
Figure 36:
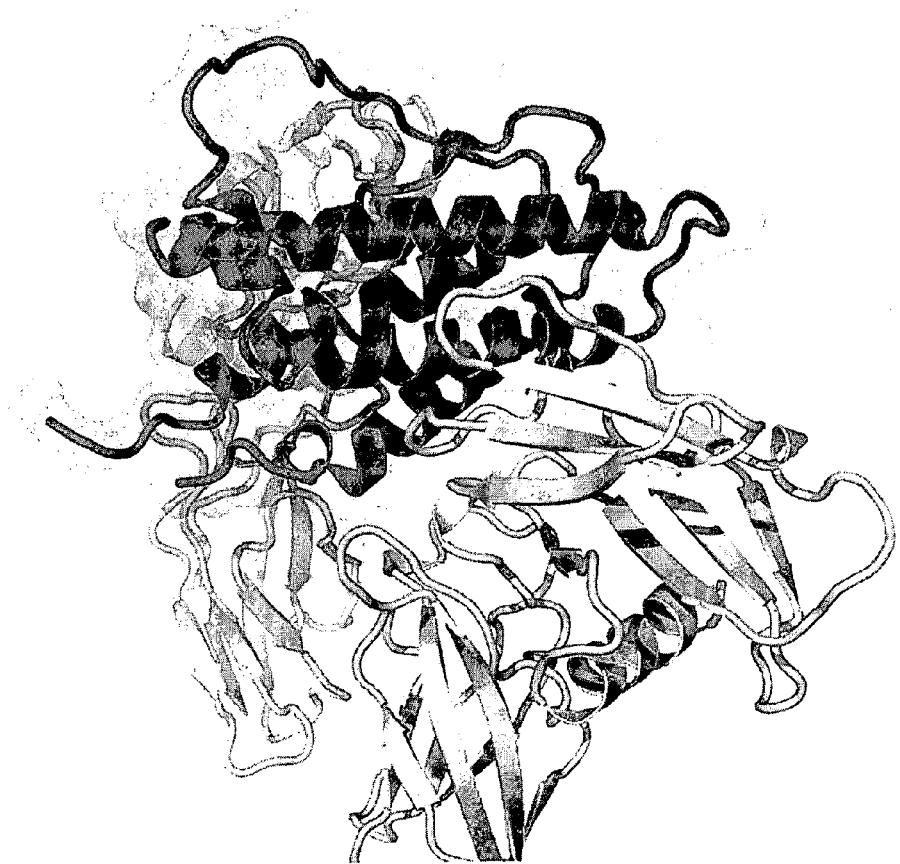
FIG. 36 shows a ribbon structure of a representative four helix bundle cytokine (erythropoietin) and its receptor, showing that the N and C termini are located away from the receptor binding domain and in close proximity to each other.
Figure 37:
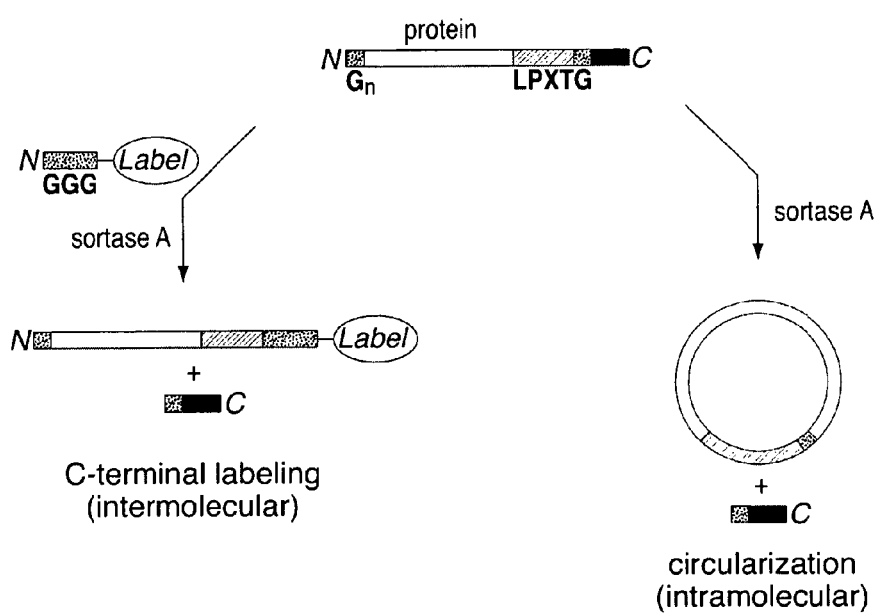
FIG. 37 shows a scheme for C terminal modification or circularization. LPXTG—SEQ ID NO: 45.

All 800 uL of the solution described above was combined with 100 L of 10× cleavage buffer and 100 L of thrombin agarose beads (from Thrombin CleanCleave™ Kit, Sigma). This mixture was incubated for 1 h at 37° C., and then checked by ESI-MS to ensure quantitative cleavage (FIG. 35). The reaction was then filtered to remove the thrombin beads.

N-terminal labeling of eGFP with 1 and 59-SrtAstaph.

389 L of the thrombin cleaved material was combined with 1 (25 L of a 10 mM DMSO solution), 59-SrtAstaph (36 L of a 700 M stock solution), and 10× sortase reaction buffer (50 L of 500 mM Tris pH 8.0, 1.5 M NaCl, 100 mM CaCl2). The reaction was incubated for 75 min at 37° C. ESI-MS of the crude reaction mixture showed clean formation of the dual labeled product as the major reaction product (Supporting Figure S6a). The reaction was then diluted with 5 mL of 20 mM Tris pH 8.0, 500 mM NaCl, and 20 mM imidazole. This solution was passed over a 1.5 mL column of Ni-NTA that been equilibrated with 20 mM Tris pH 8.0, 500 mM NaCl, and 20 mM imidazole in order to remove His$_6$ (SEQ ID NO: 174)-tagged 59-SrtAstaph. 2.5 mL of this eluate was then passed over a PD-10 Sephadex™ desalting column (equilibrated with 20 mM Tris pH 8.0). This material was then purified by anion-exchange chromatography on a Mono Q 5/50 GL column (Amersham) [Buffer A (20 mM Tris pH 8.0), Buffer B (20 mM Tris pH 8.0, 1 M NaCl), 1.5 mL/min, gradient: 100% Buffer A (0-15 mL), 0% Buffer B→50% Buffer B (15-45 mL), 50% Buffer B (45-50 mL)]. Fractions containing dual labeled eGFP were pooled and analyzed by SDS-PAGE and ESI-MS. Coomassie stained gels were imaged using a CanoScan 8600F scanner. Protein purity was estimated from these images using ImageJ 1.42q densitometry software.

Dual labeling of UCHL3

C-terminal modification of UCHL3 with 3 and SrtAstrep.

UCHL3 (350 L of a 65 M stock solution) was treated with SrtAstrep (76 L of a 140 M stock solution) and 3 (4.3 L of a 100 mM stock solution) [Note: SrtAstrep does not require Ca$^{2+}$ for activity].[3] The reaction was incubated for 15 h at 37° C. ESIMS analysis of the crude reaction mixture revealed excellent conversion to the desired product (Supporting Figure S6b). The entire reaction was then diluted with 5 mL of 20 mM Tris pH 8.0, 500 mM NaCl, and 20 mM imidazole. This solution was then treated with [2-(trimethylammonium)ethyl] methane thiosulfonate bromide (MTSET) (5.0 L of a 500 mM solution in 1:1 DMSO/H2O) for 10 min at room temperature to quench SrtAstrep. [Note: UCHL3 contains an active site cysteine residue and is therefore modified by MTSET. The resulting modification is disulfide linked, and is easily removed by treatment with DTT following completion of the dual labeling procedure]. The diluted reaction solution was then passed over a 1.5 mL column of Ni-NTA that been equilibrated with 20 mM Tris pH 8.0, 500 mM NaCl, and 20 mM imidazole. The column was then washed with 1.5 mL of 20 mM Tris pH 8.0, 500 mM NaCl, and 20 mM imidazole. The UCHL3 solution was then concentrated and passed over a PD-10 Sephadex™ desalting column (equilibrated with 20 mM Tris pH 8.0, 150 mM NaCl) to remove excess 3. This material was concentrated to 1 mL and subjected to thrombin cleavage.

Thrombin Cleavage of UCHL3.

All 1 mL of the solution described above was combined with 100 L of 10× cleavage buffer and 100 L of thrombin agarose beads (from Thrombin CleanCleave™ Kit, Sigma). This mixture was incubated for 1 h at 37 degrees C., and then checked by ESI-MS to ensure quantitative cleavage (FIG. 35). The reaction was then filtered to remove the thrombin beads.

N-Terminal Labeling of UCHL3 with 1 and 59-SrtAstaph.

778 L of the thrombin cleaved material was combined with 1 (50 L of a 10 mM DMSO solution), 59-SrtAstaph (72 L of a 700 M stock solution), and 10× sortase reaction buffer (100 L of 500 mM Tris pH 8.0, 1.5 M NaCl, 100 mM CaCl2). The reaction was incubated for 60 min at 37° C. ESI-MS of the crude reaction mixture showed clean formation of the dual labeled product as the major reaction product (Supporting Figure S6b). The reaction was then diluted with 5 mL of 20 mM Tris pH 8.0, 500 mM NaCl, and 20 mM imidazole. This solution was passed over a 1.5 mL column of Ni-NTA that been equilibrated with 20 mM Tris pH 8.0, 500 mM NaCl, and 20 mM imidazole in order to remove His$_6$ (SEQ ID NO: 174)-tagged 59-SrtAstaph. The column was then washed with 2.0 mL of 20 mM Tris pH 8.0, 500 mM NaCl, and 20 mM imidazole. The eluate was then desalted using PD-10 Sephadex™ columns (equilibrated with 20 mM Tris pH 8.0). This material was then purified by anion-exchange chromatography on a Mono Q 5/50 GL column (Amersham) [Buffer A (20 mM Tris pH 8.0), Buffer B (20 mM Tris pH 8.0, 1 M NaCl), 1.5 mL/min, gradient: 100% Buffer A (0-15 mL), 0% Buffer B→50% Buffer B (15-45 mL), 50% Buffer B (45-50 mL)]. Fractions containing dual labeled UCHL3 were pooled and analyzed by SDS-PAGE and ESI-MS. Prior to ESIMS, dual labeled UCHL3 was treated with 10 mM DTT for 10 min at RT to remove the MTSET modification on the active site cysteine residue. Coomassie stained gels were imaged using a CanoScan 8600F scanner. Protein purity was estimated from these images using ImageJ 1.42q densitometry software.

Results

Figure 32A:
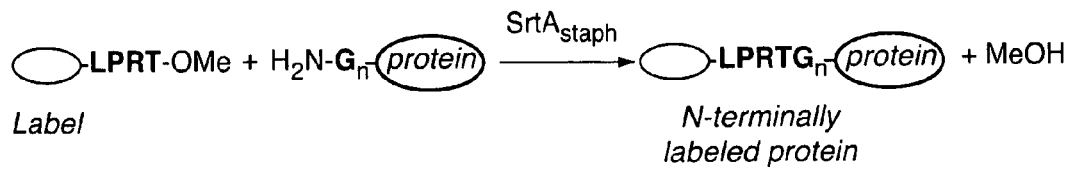
FIG. 32. N-terminal labeling using SrtA$_{staph}$. (a) SrtA$_{staph}$ catalyzes a transacylation reaction using labeled LPRT (SEQ ID NO: 50) methyl esters as substrates. The labeled LPRT (SEQ ID NO: 50) fragment is transferred to proteins containing N-terminal glycines in a site-specific fashion. (b) FITC (1) and biotin (2) LPRT (SEQ ID NO: 50) methyl esters for N-terminal transacylation. (c) CtxB derivatives (50 µM) were treated with 500 µM 1 and 50 µM SrtA$_{staph}$ for 2 h at 37° C. in 50 mM Tris (pH 7.5), 150 mM NaCl, and 10 mM CaCl$_2$. Reactions were analyzed by SDS-PAGE with visualization by coomassie staining and fluorescent gel scanning. LPRTG—SEQ ID NO: 199; GGGGG—SEQ ID NO: 162; AGGGG—SEQ ID NO: 200.
Figure 32B:
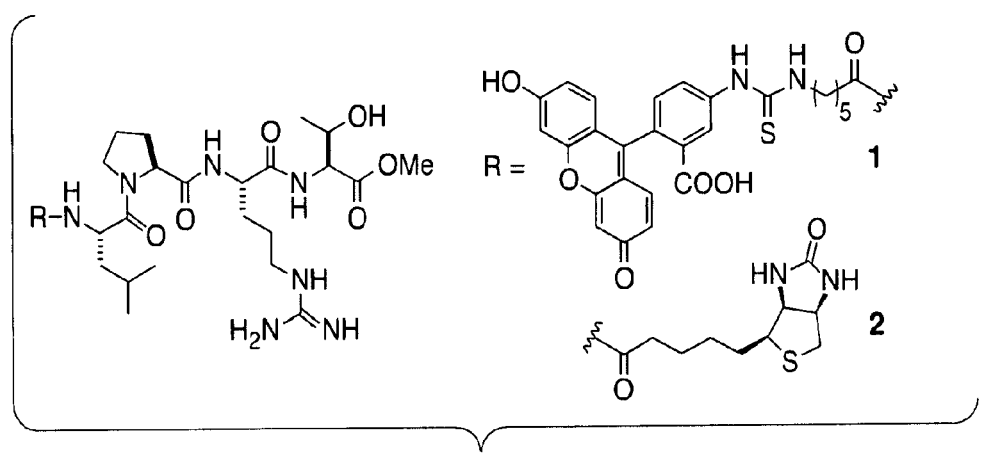
Figure 32C:
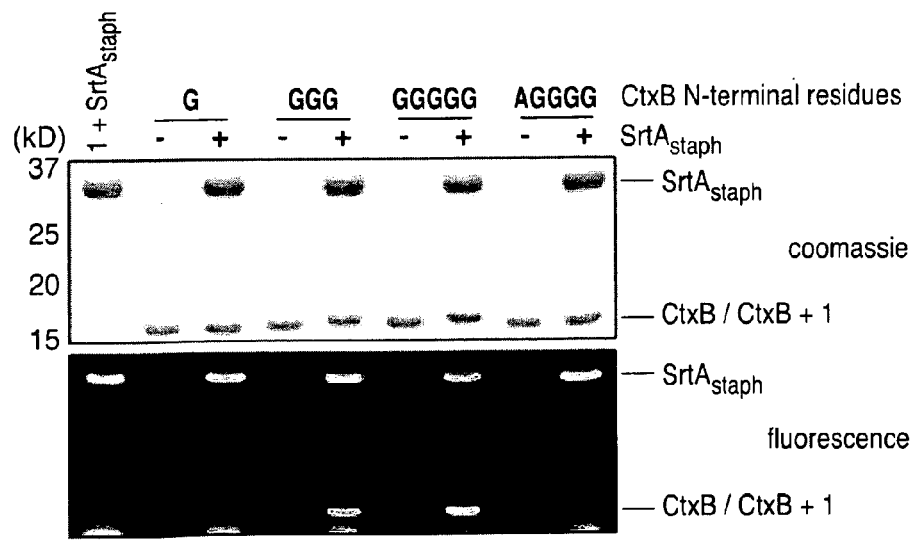

We synthesized FITC (1) and biotin (2) derivatives of an LPRT peptide in which the glycine of the normal LPXTG (SEQ ID NO: 45) motif was replaced by a methyl ester (FIG. 32; see also Example 2). With the ability of SrtA$_{staph}$ to append labels at either terminus, as described herein (see, e.g., Example 2), we pursued the possibility of installing two modifications within the same protein. Attempts to execute this type of transformation using SrtA$_{staph}$ alone failed to yield desired levels of product, due to intramolecular transpeptidation between N-terminal glycines and the C-terminal LPXTG (SEQ ID NO: 45) motif that occurred in most cases. Therefore, we considered the possibility of using a second, distinct sortase. We initially sought to use sortase B (SrtB) from either *Staph. aureus* or *Bacillus anthracis* as enzymes with recognition sequences (NPQTN (SEQ ID NO: 104) and NPKTG (SEQ ID NO: 104), respectively) orthogonal to that of SrtA$_{staph}$.(9, 10). Both SrtB enzymes were easily produced in *Escherichia coli* and purified to homogeneity. We reproduced the reported in vitro enzyme activity using a FRET-based assay to measure cleavage of short peptides substrates (9, 10). However, we did not obtain transpeptidation with either SrtB on protein substrates modified with the appropriate recognition sequences on a time scale or with yields that compare favorably with SrtA$_{staph}$ (data not shown).

Figure 33A:
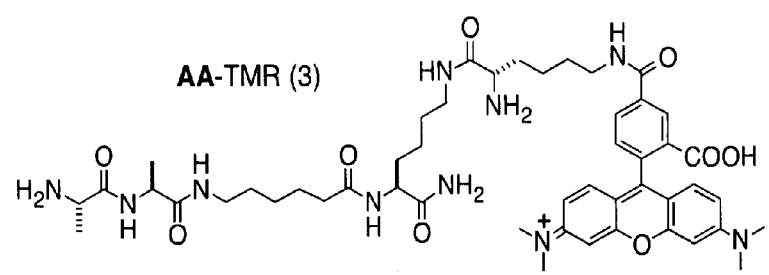
FIG. 33. Site-specific N- and C-terminal labeling using multiple sortases. (a) Tetramethylrhodamine-labeled dialanine nucleophile (3) for SrtAstrep-mediated transpeptidation. (b) Strategy for the installation of discrete labels at both termini of the same protein using Δ59-SrtAstaph and SrtAstrep. (c, d) SDS-PAGE characterization with fluorescent gel scanning of dual-labeled (c) eGFP and (d) UCHL3. MLVPRG—SEQ ID NO: 201; LPXTG-His6—SEQ ID NO: 202; LPRTG—SEQ ID NO: 199; LPXTAA—SEQ ID NO: 203.
Figure 33B:
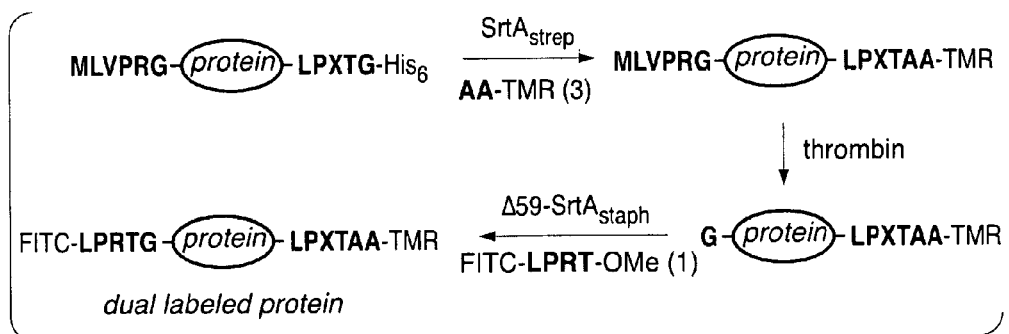
Figure 33C:
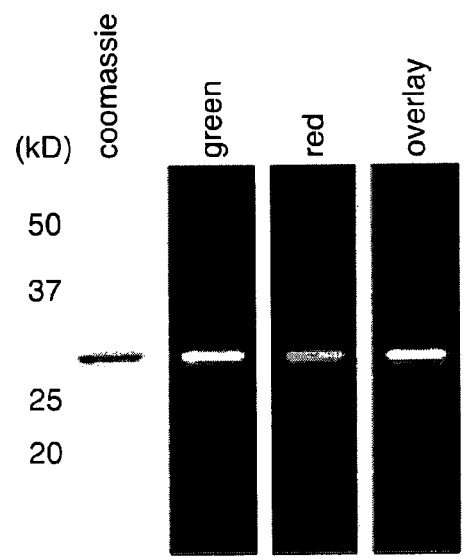
Figure 33D:
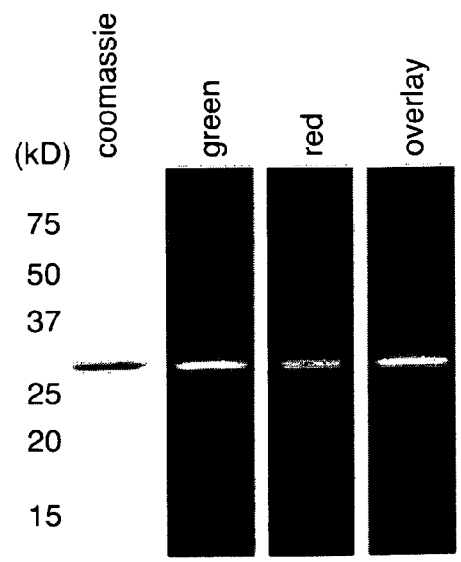
Figure 34:
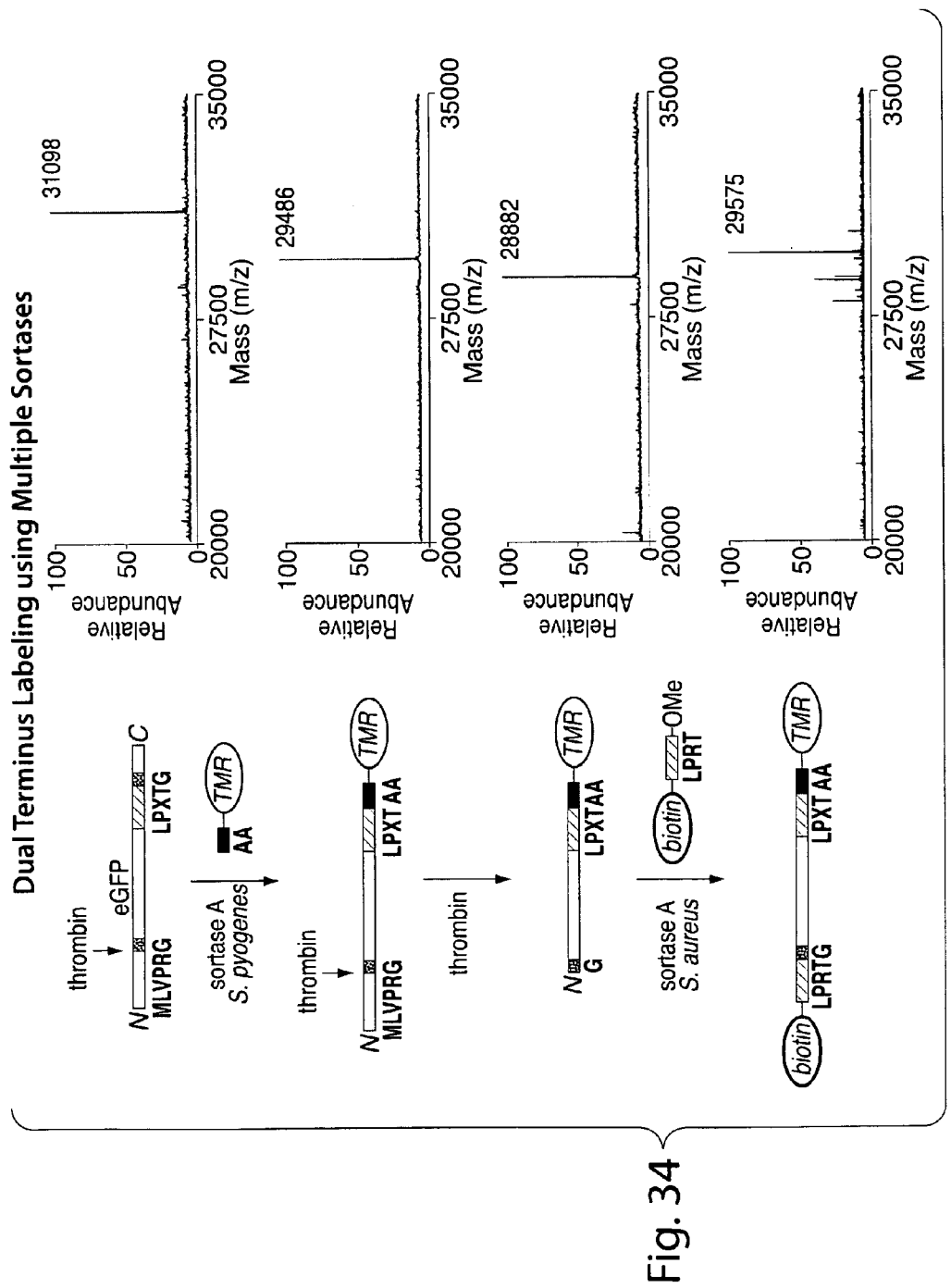
FIG. 34. Scheme for site-specific N- and C-terminal labeling using multiple sortases. Starting materials, intermediates, and products may be analyzed using ESI-MS. MLVPRG—SEQ ID NO: 201; LPXTG—SEQ ID NO: 45; LPRTG—SEQ ID NO: 199; LPRT—SEQ ID NO: 204; LPXTAA—SEQ ID NO: 203.

We ultimately arrived at a more successful orthogonal strategy using SrtA$_{strep}$, which recognizes the same LPXTG (SEQ ID NO: 45) sequence used by SrtA$_{staph}$ but can accept alanine-based nucleophiles (11) This leads to the formation of an LPXTA (SEQ ID NO: 110) sequence at the site of ligation, a motif refractory to cleavage by SrtA$_{staph}$.(12) This allows SrtA$_{staph}$ to act on the N terminus without affecting the C-terminal modification installed with SrtA$_{strep}$. An exemplary strategy for dual-terminus labeling is outlined in FIGS. 33b and 34. We first synthesized a tetramethylrhodamine-labeled peptide (3) containing two N-terminal alanine residues to serve as the nucleophile for SrtA$_{strep}$-mediated protein ligation (FIG. 33a). We prepared two model substrates (eGFP and UCHL3) containing masked N-terminal glycines that are exposed only upon thrombin cleavage. Masking was required because SrtA$_{strep}$ was observed to ligate both glycine and alanine nucleophiles (data not shown). Substrates also contained an LPXTG (SEQ ID NO: 45) motif at the C terminus to allow a first round of labeling with SrtA$_{strep}$. For both eGFP and UCHL3, C-terminal labeling using 3 and SrtA$_{strep}$ resulted in >90% conversion to the desired adduct, as revealed by ESI-MS (FIG. 35). SrtA$_{strep}$ was quenched by the addition of MTSET followed by removal of His$_6$ (SEQ ID NO: 174)-tagged SrtA$_{strep}$ using Ni-NTA. Residual 3 was then removed using a disposable desalting column. Thrombin cleavage proceeded in quantitative fashion using commercial thrombin agarose resin (FIG. 35). The exposed N-terminal glycines were then labeled by treatment with 500 μM 1 and 50 μM Δ59-SrtA$_{staph}$(13) for ~1 h at 37° C. ESI-MS of crude reaction mixtures showed the dual-labeled material as the major component, with only minor amounts of byproduct (FIG. 35). A final separation by anion-exchange chromatography yielded dual-labeled eGFP and UCHL3 with excellent purity, as determined by both SDS-PAGE and ESI-MS (FIG. 34 and FIG. 35). In the case of UCHL3, we observed some additional low-intensity bands in the fluorescent gel scan (FIG. 33). However, quantitative densitometric analysis of coomassie-stained gels indicated purity in excess of 95% for both dual-labeled eGFP and UCHL3.

References for Example 4

(1) Zumbuehl, A.; Jeannerat, D.; Martin, S. E.; Sohrmann, M.; Stano, P.; Vigassy, T.; Clark, D. D.; Hussey, S. L.; Peter, M.; Peterson, B. R.; Pretsch, E.; Walde, P.; Carreira, E. M. *Angew Chem Int Ed Engl* 2004, 43, 5181-5.

(2) Kottani, R.; Valiulin, R. A.; Kutateladze, A. G. *Proc Natl Acad Sci USA* 2006, 103, 13917-21.

(3) Race, P. R.; Bentley, M. L.; Melvin, J. A.; Crow, A.; Hughes, R. K.; Smith, W. D.; Sessions, R. B.; Kehoe, M. A.; McCafferty, D. G.; Banfield, M. J. *J Biol Chem* 2009, 284, 6924-33.

(4) Ton-That, H.; Liu, G.; Mazmanian, S. K.; Faull, K. F.; Schneewind, O. *Proc. Natl. Acad. Sci. U.S.A.* 1999, 96, 12424-9.

(5) Jobling, M. G.; Palmer, L. M.; Erbe, J. L.; Holmes, R. K. *Plasmid* 1997, 38, 158-73.

(6) Antos, J. M.; Miller, G. M.; Grotenbreg, G. M.; Ploegh, H. L. *J Am Chem Soc* 2008, 130, 16338-43.

(7) Tsien, R. Y. *Annu. Rev. Biochem.* 1998, 67, 509-544.

(8) Popp, M. W.; Artavanis-Tsakonas, K.; Ploegh, H. L. *Journal of Biological Chemistry* 2008, 284, 3593-3602.

(9) Maresso, A. W., Chapa, T. J. and Schneewind, O. *J. Bacteriol.* 2006, 188, 8145-8152

(10) Mazmanian, S. K., Ton-That, H., Su, K. and Schneewind, O. *Proc. Natl. Acad. Sci. U.S.A.* 2002, 99, 2293-2298

(11) Race, P. R., Bentley, M. L., Melvin, J. A., Crow, A., Hughes, R. K., Smith, W. D., Sessions, R. B., Kehoe, M. A., McCafferty, D. G. and Banfield, M. J. *J. Biol. Chem.* 2009, 284, 6924-6933

(12) Kruger, R. G., Otvos, B., Frankel, B. A., Bentley, M., Dostal, P. and McCafferty, D. G. *Biochemistry* 2004, 43, 1541-1551

(13) Δ59-SrtA$_{staph}$ is a truncated form of SrtA$_{staph}$ that has identical reactivity Example 5

Site-Specific PEGylation Using SrtA$_{staph}$

Figure 39A:
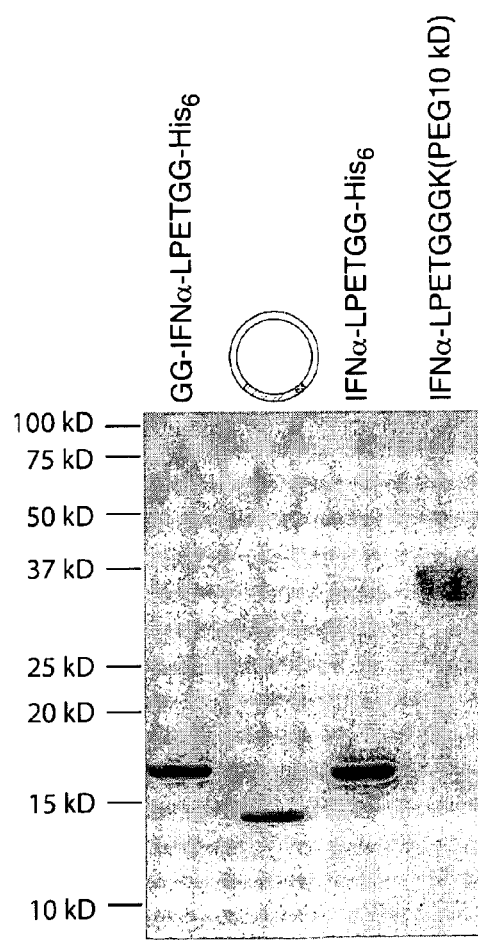
FIG. 39A shows a Coomassie gel of purified Interferon α (IFNα) variants. The IFNα variant contain two additional G residues at the C terminus that were introduced during cloning and are not depicted in the legend. Cyclization results in removal of GGHis6 (SEQ ID NO: 175) so that the circularized version contains an additional GGLPETGG (SEQ ID NO: 60) relative to native IFNα positioned as follows: -Xaa$_C$-GGLPETGG-Xaa$_N$- (SEQ ID NO: 61), where Xaa$_C$ and Xaa$_N$ represent the C-terminal and N-terminal amino acids, respectively, of native IFNα. LPETGG-His6—SEQ ID NO: 207; LPETGGGK—SEQ ID NO: 209.

This example describes PEGylation of the four-helix bundle cytokine interferon α at the C-terminus using sortase and demonstrates that the PEGylated version retains activity and has enhanced in vivo circulating time. We cloned into the pET28a+ vector (Novagen) a version of interferon alpha lacking the leader sequence and fused to LPETGG (SEQ ID NO: 170), the SrtA$_{staph}$ recognition site, separated from the body of the protein by two glycines (FIG. 39A). For purification, we added a 6-His tag following the SrtA$_{staph}$ cleavage site; this tag is lost upon transpeptidation. We expressed this protein in Rosetta-gami(DE3)pLysS cells (Novagen) and purified soluble protein by Ni-NTA IMAC chromatography (Qiagen), followed by size exclusion chromatography on a Superdex 75 column (GE) at pH 5.0.

We constructed a Gly$_3$K-PEG (SEQ ID NO: 171)(10 kDa) nucleophile compatible with SrtA$_{staph}$. The Gly$_3$K (SEQ ID NO: 172) peptide scaffold was constructed by standard Fluorenylmethoxycarbonyl (Fmoc) solid phase peptide chemistry on rink amide resin. Fmoc protected peptide was liberated from the resin by treatment with 95% TFA/3% TIPS/2% H$_2$O, precipitated with cold ether and lyophilized. Methyl-capped 10 kDa PEG succinimidyl ester (1 equivalent, Nanocs) was mixed with peptide (2 equivalents), 1 equivalent N-hydroxysuccinimide (NHS, Sigma) and 1 equivalent 1-ethyl-3-(3-dimethylaminopropyl) carbodiimide (EDC, Pierce) in N-Methylpyrrolidone (NMP, Fluka) for 24 hours at room temperature, followed by precipitation in cold ether. The resulting solid was resuspended in 20% piperidine/NMP for 30 minutes, followed by re-precipitation in cold ether. This material was resuspended in $H_2O$ and dialyzed extensively against $H_2O$ to remove free peptide.

Sortase labeling was conducted as described previously (see, e.g., other Examples herein). PEGylated protein was purified by cation exchange chromatography on a Mono-S column (GE) at pH 5.0 or 4.5. Protein concentrations were measured by the Bradford method.

To compare in-vitro activity of interferon alpha conjugates, a standard Daudi cell proliferation inhibition assay was used. The site-specifically PEGylated interferon alpha conjugate is extremely potent in inhibiting Daudi cell proliferation (FIG. 40, Table C), despite conjugation to the large 10 kDa PEG chain. The PEG moiety, positioned away from the receptor binding site prolongs the time the interferon alpha conjugate spends in circulation, as assessed by ELISA performed on mice injected with 10 µg of interferon alpha, followed by retro-orbital collection of serum at different time points (FIG. 41). Thus, by PEGylating interferon alpha at a site distant from the receptor binding site, we can extend the circulating half-life with minimal sacrifice in potency.

TABLE C*

Inhibition of Daudi cell proliferation by IFNα and IFNα variants

| IFNα2 Variant | IC50 (pg/mL) | LogIC50 Standard Error |
|---|---|---|
| Standard | 15.51 | 0.0378 |
| +GG | 9.969 | 0.0553 |
| Circular | 4.918 | 0.0639 |
| delGG | 7.098 | 0.0411 |
| PEGylated | 21.67 | 0.0488 |

Figure 40:
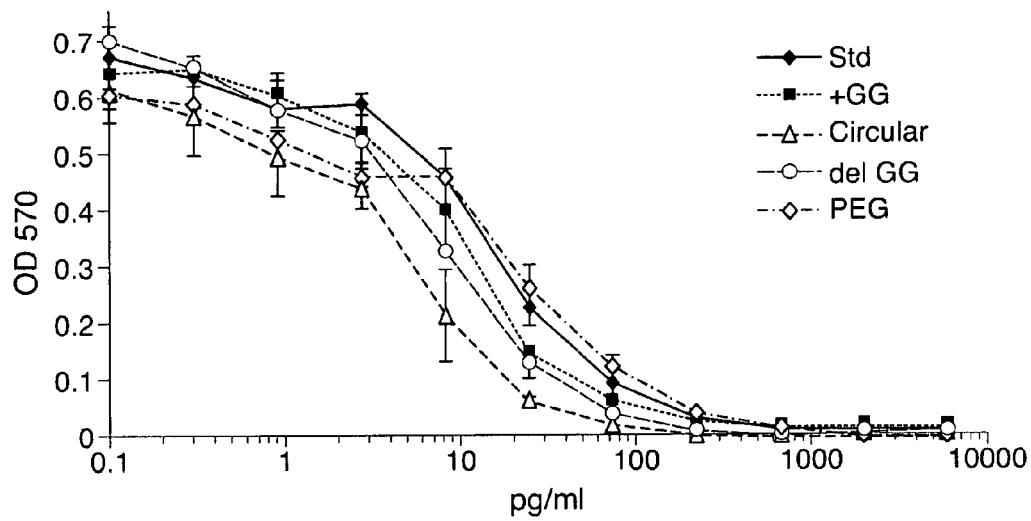
FIG. 40 shows results of a Daudi cell proliferation inhibition assay demonstrating that IFNα variants retain biological activity equivalent to the original protein. IFNα variants are as shown in FIG. 39. Legend: standard: commercially available IFNα; +GG: GG-IFNα-LPETGG-His6 (SEQ ID NO: 62); circular: (see description of FIG. 39); delGG: IFNα-LPETGG-His6 (SEQ ID NO: 63); PEG: IFNα-LPETGGGK-PEG (SEQ ID NO: 64).
Figure 41:
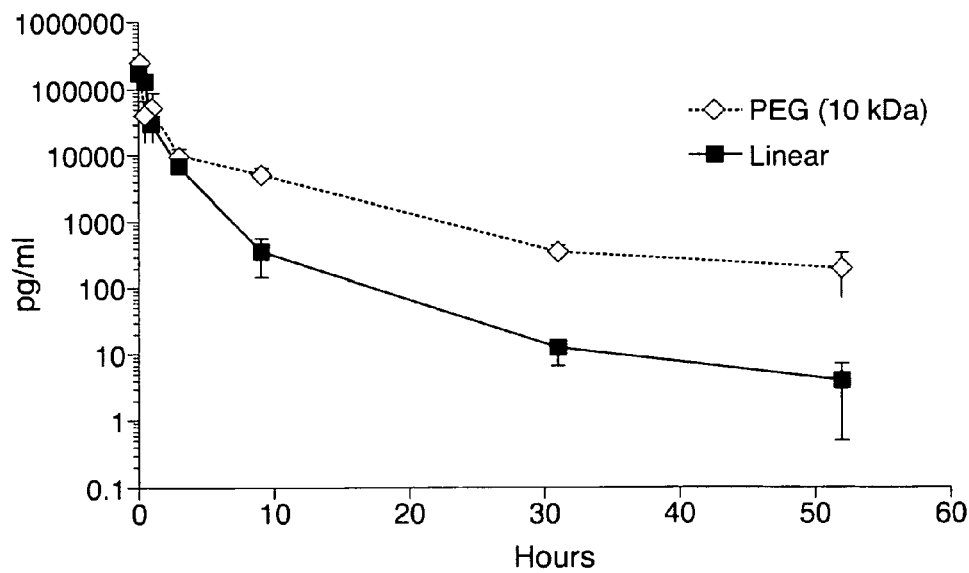
FIG. 41 shows serum half life ELISA results for PEGylated vs. linear IFNα demonstrating that PEGylation significantly prolongs the half-life. The linear IFNα variant tested in this experiment is the delGG variant (which comprises an LPETGG-His6 (SEQ ID NO: 65) moiety at the C-terminus).

*See FIGS. 39 and 40 legend for details regarding the IFNα2 sequences

Figure 47A:
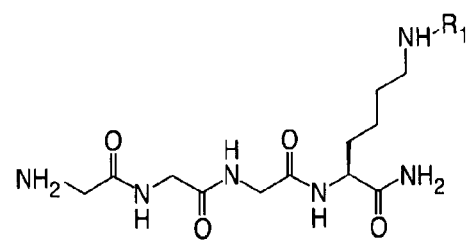
FIG. 47 shows (A) exemplary C-terminal probe. (B) exemplary N-terminal probe. (C) exemplary C-terminal masked probe. Representative R1 groups: (1) PEG; (2) biotin; (3) tetramethylrhodamine.
Figure 47B:
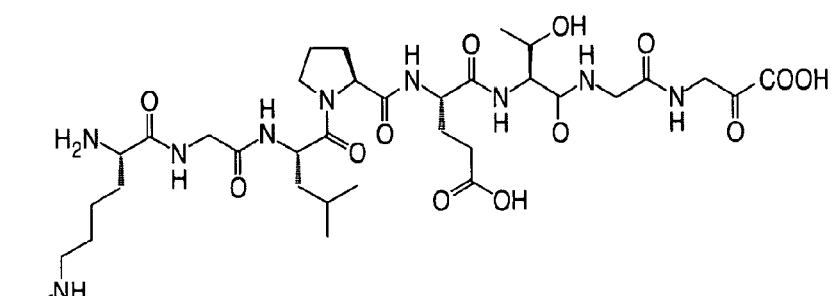
Figure 47C:
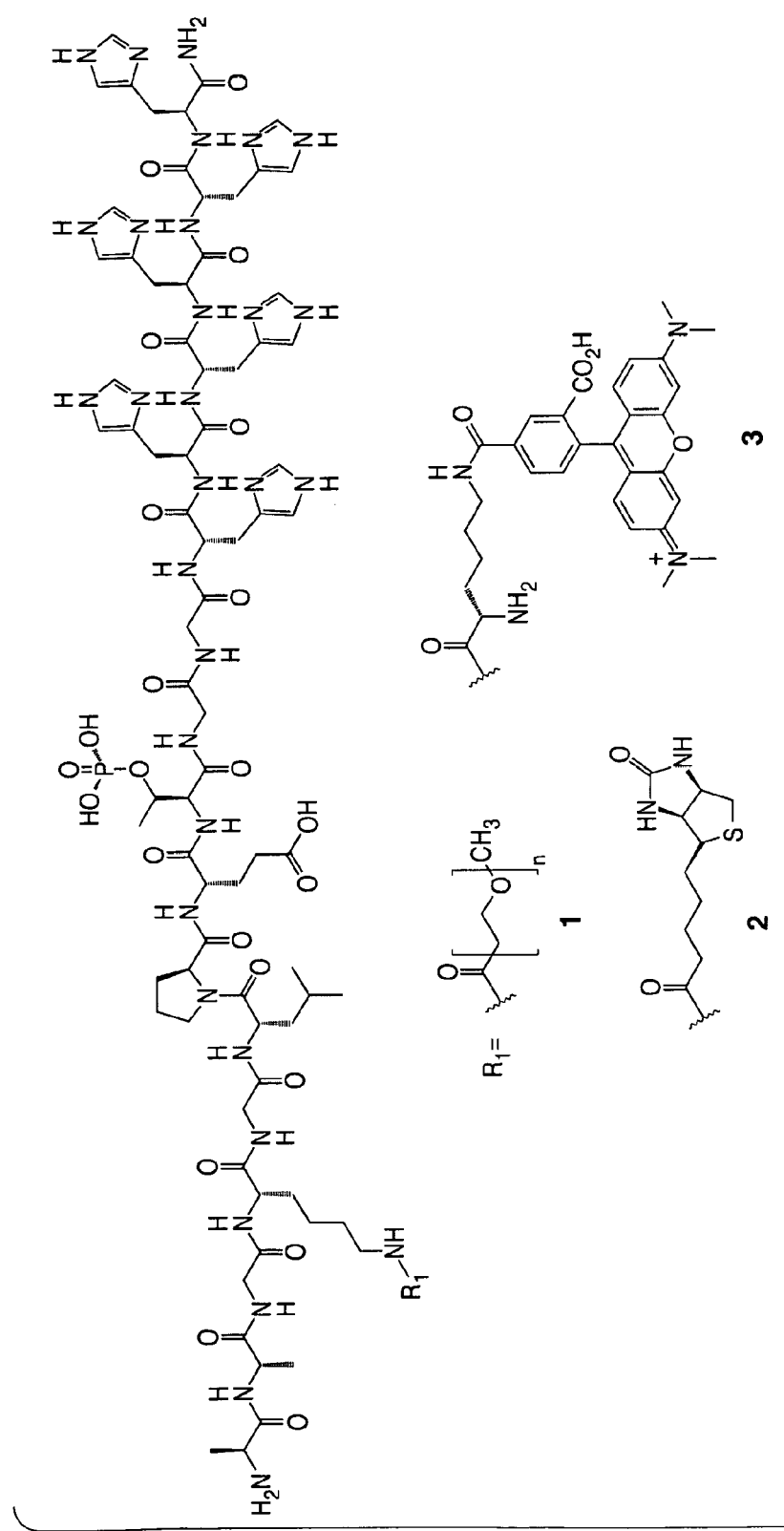

As described herein, we have extended the sortase methodology to N-terminal labeling. Since the N-terminus lies in close proximity to the C-terminus in four-helix bundle cytokines, we expect PEG conjugation using N-terminal probes (e.g., FIG. 47) to yield similar results.

Example 6

Sortase-Mediated Circularization of IFNα

We have shown that proteins bearing an LPXTG (SEQ ID NO: 45) motif at the C-terminus and an N-terminal glycine can be covalently cyclized after incubation with sortase A, provided that the N and C terminus are in close apposition to one another, as they are in the four helix bundle cytokines. We constructed an interferon alpha variant by inserting two glycine residues between the initiating methionine and the body of the interferon alpha sequence used for PEGylation (FIG. 39A). When incubated with sortase, this protein cyclizes, as shown unambiguously by MS/MS sequence identification of the junction peptide between the N and C-termini following chymotrypsin digestion (FIG. 39B). The circular interferon alpha was purified by cation exchange chromatography and tested in the cell based interferon alpha activity assay. Again, the engineered protein is as potent as the recombinant standard (FIG. 40, Table C).

Figure 42:
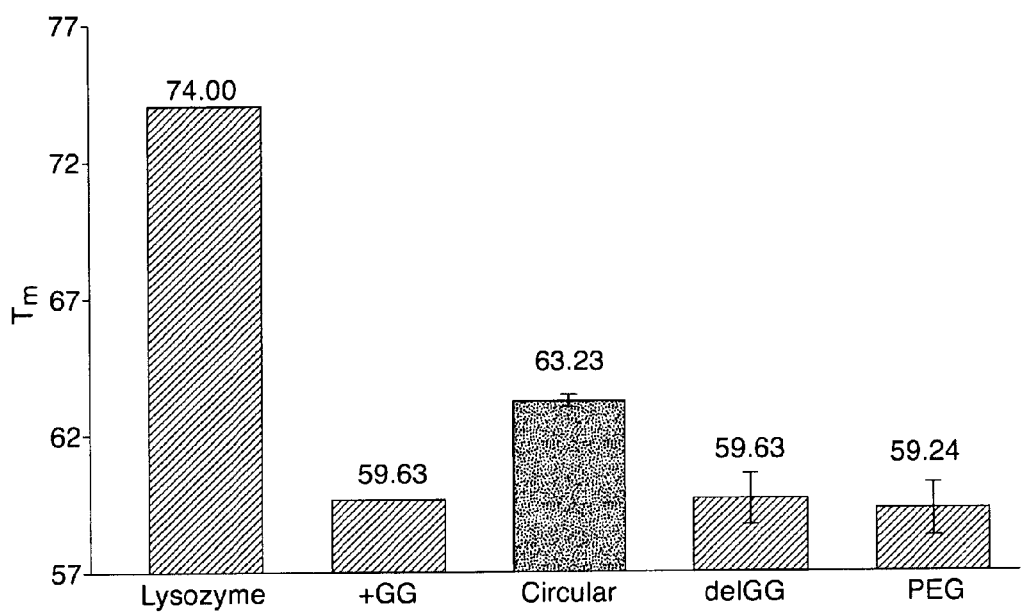
FIG. 42 shows Tm's for a thermal denaturation assay performed on IFNα variants with lysozyme as a control and shows that the circular variant exhibits significantly enhanced thermal stability relative to the other variants.

To test the thermal stability of the circular protein, we turned to a dye-based thermal denaturation assay, Thermofluor. When denatured, proteins expose hydrophobic residues that bind to and increase fluorescence of the dye Sypro Orange (Invitrogen). The circular interferon alpha has a significantly higher $T_m$ than any other variant tested (FIG. 42).

We conclude that covalently clamping the termini of interferon alpha together stabilizes the protein by preventing premature fraying of the ends, without sacrificing activity.

Example 7

Circular Site-Specifically PEGylated Proteins

Combining the insertion of a non-genetically encoded PEG moiety at the terminus of interferon alpha and subsequently joining the resulting termini will impart both increased circulating half-life and thermal stability. This is accomplished by two subsequent transacylation steps (FIG. 43), the first joining a peptide bearing the PEG moiety as well as another distinct sortase recognition element to the candidate protein. The second transacylation step is accomplished by a different sortase and results in covalent closure of the protein. However, because the sortase reactions are equilibrium reactions and the sortases $SrtA_{strep}$ and $SrtA_{staph}$ are orthogonal in one direction only ($SrtA_{strep}$ cleaves both LPXTG (SEQ ID NO: 45) and LPXTA (SEQ ID NO: 110) sites but $SrtA_{staph}$ attacks only LPXTG (SEQ ID NO: 45)), we sought to render the sortase cleavage site on the nucleophile refractory to cleavage during the initial installation of the probe. To that end, we have generated a nucleophile bearing an LPXtG (SEQ ID NO: 45) sequence, where t is a phosphorylated threonine residue. Based on the crystal structures of $SrtA_{staph}$ and $SrtA_{strep}$, phosphothreonine will not fit into the substrate recognition groove. Thus, the first transpeptidation step can be accomplished without premature cleavage of the $SrtA_{staph}$ site on the PEG nucleophile. The resulting conjugate can then be dephosphorylated and incubated with $SrtA_{staph}$ (which will not cleave the LPETAA (SEQ ID NO: 173) junction between the protein and nucleophile) to join the termini.

Our experiments demonstrate the feasibility of this scheme. We installed a peptide bearing an N-terminal AA sequence (compatible with $SrtA_{strep}$) followed by a lysine for conjugating to a non-genetically encoded moiety of choice, an LPEtG (SEQ ID NO: 55) $SrtA_{staph}$ cleavage site, and a hexahistidine epitope tag onto interferon alpha (FIG. 43). The reaction product was confirmed by LC ESI-MS. We then dephosphorylated the protein by incubating with Antarctic phosphatase (NEB), exposing the $SrtA_{staph}$ cleavage site. This site is competent to undergo the second transacylation step; we installed a triglycine nucleophile onto this site by incubating with $SrtA_{staph}$ and $Gly_3$ peptide (Sigma) (FIG. 44). Thus, we can accomplish two successive transacylation steps by controlling the accessibility of two orthogonal sortase enzymes to their respective cleavage sites.

Example 8

Sortase-Mediated Installation of a Non-Genetically Encoded Element Between Two Proteins The strategy described in Example 7 can be used to install a non-genetically encoded element between two proteins or protein domains as shown, e.g., in FIG. 45. A specific example is the construction of a cytokine variant joined to the Fc region of an antibody, with a non-genetically encoded moiety in the intervening region. Genetic fusions of cytokines to Fc regions can be delivered non-invasively into the bloodstream by Fc receptor bearing epithelial cells in the lungs, after which the half-life of the molecule is prolonged. Implicit in this mechanism is the requirement for an Fc region that is able to bind to its cognate Fc receptor, and thus chemical conjugation of a molecule to the C-terminus or an internal lysine of the Fc portion would likely decrease binding capacity. Using two transacylation steps, we will install a PEG moiety onto the C-terminus of the cytokine portion, followed by installation of an unhindered Fc region. Such a conjugate may show even greater gains in half-life relative to the genetic Fc fusion, as kidney filtration of the molecule is predicted to be further reduced. Other applications include installing a detectable label, e.g., for diagnostic purposes or to monitor the distribution or elimination of the molecule in vivo.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method of ligation comprising the step of contacting an acyl donor compound of formula:

wherein
the transamidase recognition sequence is LPXT, wherein the X of the recognition sequence is any natural or unnatural amino acid;
X is —O— or —S—;
R is hydrogen, substituted or unsubstituted aliphatic, or substituted or unsubstituted heteroaliphatic;
$A^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;
$R^1$ is acyl, substituted or unsubstituted aliphatic, substituted or unsubstituted heteroaliphatic, substituted or unsubstituted aryl, or substituted or unsubstituted heteroaryl; and
with a nucleophilic compound of formula:

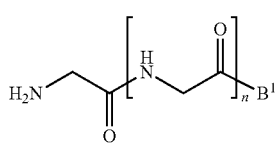

wherein
$B^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and
n is an integer from 0 to 6, inclusive;
in the presence of a transamidase enzyme under suitable conditions to form a compound of formula:

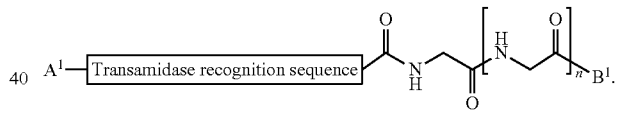

2. The method of claim 1, wherein X is —O—.

3. The method of claim 1, wherein the recognition sequence is LPXT, wherein the X of the recognition sequence is D, E, A, N, Q, K, or R.

4. The method of claim 1, wherein the transamidase is sortase A.

5. The method of ligation of claim 1 comprising the step of contacting an acyl donor compound of formula:

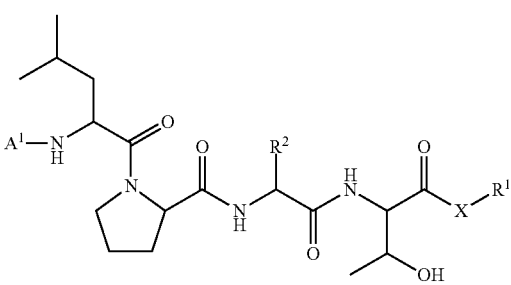

wherein
$A^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;

X is —O— or —S—;

R is hydrogen, substituted or unsubstituted aliphatic, or substituted or unsubstituted heteroaliphatic;

$R^1$ is acyl, substituted or unsubstituted aliphatic, substituted or unsubstituted heteroaliphatic, substituted or unsubstituted aryl, or substituted or unsubstituted heteroaryl; and $R^2$ is a natural or unnatural amino acid side chain;

with a nucleophilic compound of formula:

$$H_2N-CH_2-C(O)-[NH-CH_2-C(O)]_n-B^1$$

wherein $B^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and n is an integer from 0 to 100, inclusive;

in the presence of a transamidase enzyme under suitable conditions to form a compound of formula:

$$A^1-NH-Leu-Pro-NH-CH(R^2)-NH-CH(CH(OH)CH_3)-C(O)-NH-CH_2-C(O)-[NH-CH_2-C(O)]_n-B^1$$

6. A method of ligation comprising the step of contacting an acyl donor compound of formula:

$$A^1-\boxed{\text{Transamidase recognition sequence}}-C(O)-XR^1$$

wherein the transamidase recognition sequence is selected from LPXT, SPXT, LAXT, LSXT, NPXT, VPXT, IPXT, and YPXR wherein the X of the recognition sequence is a natural or unnatural amino acid;

X is —O— or —S—;

R is hydrogen, substituted or unsubstituted aliphatic, or substituted or unsubstituted heteroaliphatic;

$A^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;

$R^1$ is acyl, substituted or unsubstituted aliphatic, substituted or unsubstituted heteroaliphatic, substituted or unsubstituted aryl, or substituted or unsubstituted heteroaryl; and with a nucleophilic compound of formula:

$$H_2N-CH_2-C(O)-[NH-CH_2-C(O)]_n-B^1$$

wherein $B^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and n is an integer from 0 to 6, inclusive;

in the presence of a transamidase enzyme under suitable conditions to form a compound of formula:

$$A^1-\boxed{\text{Transamidase recognition sequence}}-C(O)-NH-CH_2-C(O)-[NH-CH_2-C(O)]_n-B^1.$$

7. The method of claim 6, wherein X is —O—.

8. The method of claim 6, wherein the X of the recognition sequence is D, E, A, N, Q, K, or R.

9. The method of claim 6, wherein the transamidase is sortase A.

10. The method of claim 6, wherein the transamidase is sortase B.

11. The method of claim 6 comprising the step of contacting an acyl donor compound of formula:

$$A^1-NH-Leu-Pro-NH-CH(R^2)-NH-CH(CH(OH)CH_3)-C(O)-X-R^1$$

wherein $A^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;

X is —O— or —S—;

R is hydrogen, substituted or unsubstituted aliphatic, or substituted or unsubstituted heteroaliphatic;

R¹ is acyl, substituted or unsubstituted aliphatic, substituted or unsubstituted heteroaliphatic, substituted or unsubstituted aryl, or substituted or unsubstituted heteroaryl; and R² is a natural or unnatural amino acid side chain;

with a nucleophilic compound of formula:

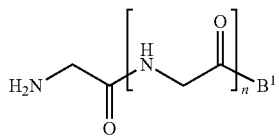

wherein
B¹ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and n is an integer from 0 to 100, inclusive;

in the presence of a transamidase enzyme under suitable conditions to form a compound of formula:

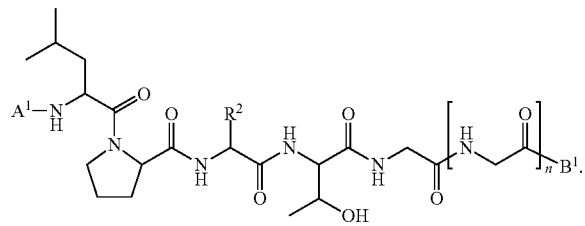

12. A method of ligation comprising the step of contacting an acyl donor compound of formula:

wherein
the transamidase recognition sequence is selected from: LPKT (SEQ ID NO: 69), LPIT (SEQ ID NO: 70), LPDT (SEQ ID NO: 71), SPKT (SEQ ID NO: 72), LAET (SEQ ID NO: 73), LAAT (SEQ ID NO: 74), LAET (SEQ ID NO: 75), LAST (SEQ ID NO: 76), LAET (SEQ ID NO: 77), LPLT (SEQ ID NO: 78), LSRT (SEQ ID NO: 79), LPET (SEQ ID NO: 53), VPDT (SEQ ID NO: 80), IPQT (SEQ ID NO: 81), YPRR (SEQ ID NO: 82), LPMT (SEQ ID NO: 83), LPLT (SEQ ID NO: 84), LAFT (SEQ ID NO: 85), LPQT (SEQ ID NO: 86), NSKT (SEQ ID NO: 87), NPQT (SEQ ID NO: 88), NAKT (SEQ ID NO: 89), and NPQS (SEQ ID NO: 90);

X is —O— or —S—;

R is hydrogen, substituted or unsubstituted aliphatic, or substituted or unsubstituted heteroaliphatic;

A¹ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;

R¹ is acyl, substituted or unsubstituted aliphatic, substituted or unsubstituted heteroaliphatic, substituted or unsubstituted aryl, or substituted or unsubstituted heteroaryl; and with a nucleophilic compound of formula:

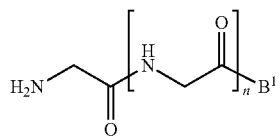

wherein
B¹ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and n is an integer from 0 to 6, inclusive;

in the presence of a transamidase enzyme under suitable conditions to form a compound of formula:

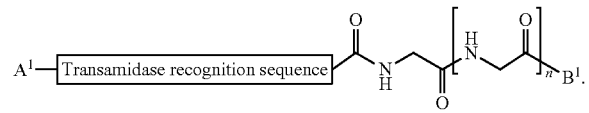

13. The method of claim 12, wherein X is —O—.

14. The method of claim 12, wherein the transamidase is sortase A.

15. The method of claim 12, wherein the transamidase is sortase B.

16. The method of claim 12 comprising the step of contacting an acyl donor compound of formula:

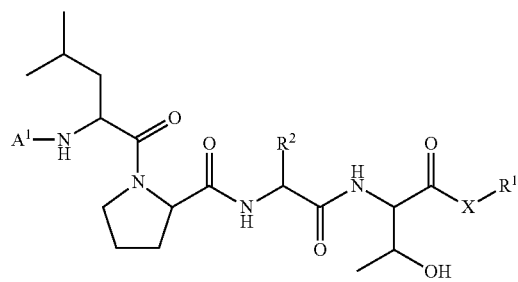

wherein
A¹ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;

X is —O— or —S—;

R is hydrogen, substituted or unsubstituted aliphatic, or substituted or unsubstituted heteroaliphatic;

$R^1$ is acyl, substituted or unsubstituted aliphatic, substituted or unsubstituted heteroaliphatic, substituted or unsubstituted aryl, or substituted or unsubstituted heteroaryl; and $R^2$ is a natural or unnatural amino acid side chain;

with a nucleophilic compound of formula:

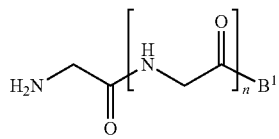

wherein
$B^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and
n is an integer from 0 to 100, inclusive;

in the presence of a transamidase enzyme under suitable conditions to form a compound of formula:

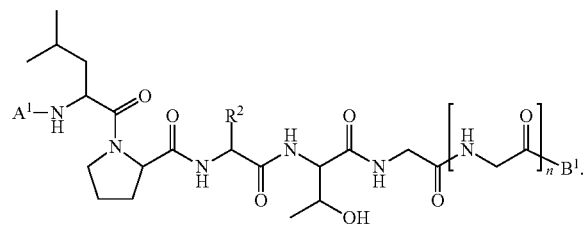

17. A method of ligation comprising the step of contacting an acyl donor compound of formula:

wherein
the transamidase recognition sequence is $X_1PX_2X_3$, where $X_1$ is leucine, isoleucine, valine or methionine; $X_2$ is any amino acid; $X_3$ is threonine, serine or alanine; P is proline;

X is —O— or —S—;

R is hydrogen, substituted or unsubstituted aliphatic, or substituted or unsubstituted heteroaliphatic;

$A^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;

$R^1$ is acyl, substituted or unsubstituted aliphatic, substituted or unsubstituted heteroaliphatic, substituted or unsubstituted aryl, or substituted or unsubstituted heteroaryl; and with a nucleophilic compound of formula:

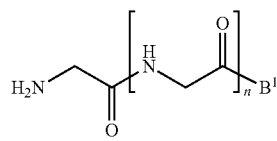

wherein
$B^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and
n is an integer from 0 to 6, inclusive;

in the presence of a transamidase enzyme under suitable conditions to form a compound of formula:

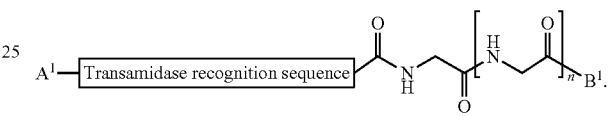

18. The method of claim 17, wherein X is —O—.

19. The method of claim 17, wherein the transamidase is sortase A.

20. The method of claim 17, wherein the transamidase is sortase B.

21. The method of claim 17 comprising the step of contacting an acyl donor compound of formula:

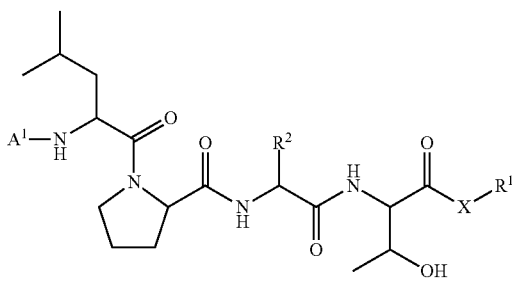

wherein
$A^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label;

X is —O— or —S—;

R is hydrogen, substituted or unsubstituted aliphatic, or substituted or unsubstituted heteroaliphatic;

$R^1$ is acyl, substituted or unsubstituted aliphatic, substituted or unsubstituted heteroaliphatic, substituted or unsubstituted aryl, or substituted or unsubstituted heteroaryl; and $R^2$ is a natural or unnatural amino acid side chain;

with a nucleophilic compound of formula:

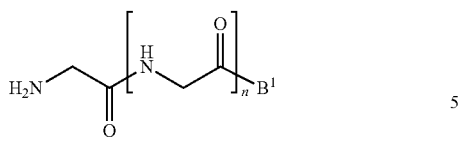

wherein
- $B^1$ is acyl, substituted or unsubstituted aliphatic, substituted or unsubstituted heteroaliphatic, substituted or unsubstituted aryl, substituted or unsubstituted heteroaryl, a peptide, a protein, a polynucleotide, a carbohydrate, a tag, a metal atom, a contrast agent, a catalyst, a non-polypeptide polymer, a recognition element, a small molecule, a lipid, or a label; and
- n is an integer from 0 to 100, inclusive;

in the presence of a transamidase enzyme under suitable conditions to form a compound of formula:

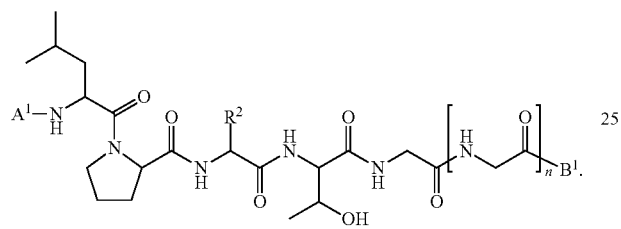

* * * * *